(12) United States Patent
Clarke et al.

(10) Patent No.: US 8,563,697 B2
(45) Date of Patent: Oct. 22, 2013

(54) ANTI-IL-12/IL-23 ANTIBODIES

(75) Inventors: Adam William Clarke, Five Dock (AU); Anthony Gerard Doyle, Drummoyne (AU); Philip Anthony Jennings, Warrawee (AU); Lynn Dorothy Poulton, Beecroft (AU); Bernadette Wai, Winston Hills (AU); Andrew James Pow, St. Kilda (AU); George Kopsidas, Preston (AU)

(73) Assignee: Cephalon Australia Pty. Ltd., New South Wales (AU)

( * ) Notice: Subject to any disclaimer, the term of this patent is extended or adjusted under 35 U.S.C. 154(b) by 0 days.

(21) Appl. No.: 13/058,914

(22) PCT Filed: Aug. 14, 2009

(86) PCT No.: PCT/AU2009/001047
§ 371 (c)(1),
(2), (4) Date: Jul. 8, 2011

(87) PCT Pub. No.: WO2010/017598
PCT Pub. Date: Feb. 18, 2010

(65) Prior Publication Data
US 2011/0262445 A1   Oct. 27, 2011

Related U.S. Application Data

(60) Provisional application No. 61/089,028, filed on Aug. 14, 2008.

(30) Foreign Application Priority Data

Aug. 14, 2008   (AU) ................. 2008904178

(51) Int. Cl.
C07K 16/24    (2006.01)
C12P 21/08    (2006.01)
(52) U.S. Cl.
USPC ............... 530/388.23; 530/387.3; 530/388.1; 530/391.1; 530/351
(58) Field of Classification Search
None
See application file for complete search history.

(56) References Cited

U.S. PATENT DOCUMENTS

| | | |
|---|---|---|
| 4,172,124 A | 10/1979 | Koprowski et al. |
| 4,239,754 A | 12/1980 | Sache et al. |
| 4,309,989 A | 1/1982 | Fahim |
| 4,399,216 A | 8/1983 | Axel et al. |
| 4,634,665 A | 1/1987 | Axel et al. |
| 4,656,134 A | 4/1987 | Ringold |
| 4,668,218 A | 5/1987 | Virtanen |
| 4,676,980 A | 6/1987 | Segal et al. |
| 4,683,195 A | 7/1987 | Mullis et al. |
| 4,683,202 A | 7/1987 | Mullis |
| 4,704,692 A | 11/1987 | Ladner |
| 4,766,067 A | 8/1988 | Biswas |
| 4,767,402 A | 8/1988 | Kost et al. |
| 4,795,699 A | 1/1989 | Tabor et al. |
| 4,800,159 A | 1/1989 | Mullis et al. |
| 4,873,316 A | 10/1989 | Meade et al. |
| 4,889,818 A | 12/1989 | Gelfand et al. |
| 4,921,794 A | 5/1990 | Tabor et al. |
| 4,925,673 A | 5/1990 | Steiner et al. |
| 4,939,666 A | 7/1990 | Hardman |
| 4,946,778 A | 8/1990 | Ladner et al. |
| 4,956,288 A | 9/1990 | Barsoum |
| 4,965,188 A | 10/1990 | Mullis et al. |
| 4,994,370 A | 2/1991 | Silver et al. |
| 5,066,584 A | 11/1991 | Gyllensten et al. |
| 5,091,310 A | 2/1992 | Innis |
| 5,122,464 A | 6/1992 | Wilson et al. |
| 5,130,238 A | 7/1992 | Malek et al. |
| 5,142,033 A | 8/1992 | Innis |
| 5,149,636 A | 9/1992 | Axel et al. |
| 5,168,062 A | 12/1992 | Stinski |
| 5,179,017 A | 1/1993 | Axel et al. |
| 5,223,409 A | 6/1993 | Ladner et al. |
| 5,225,539 A | 7/1993 | Winter |
| 5,256,648 A | 10/1993 | Gasparro et al. |
| 5,260,203 A | 11/1993 | Ladner et al. |
| 5,266,491 A | 11/1993 | Nagata et al. |
| 5,304,489 A | 4/1994 | Rosen |

(Continued)

FOREIGN PATENT DOCUMENTS

| | | |
|---|---|---|
| EP | 237507 | 9/1987 |
| EP | 0368684 | 5/1990 |
| EP | 0550400 | 7/1993 |
| EP | 0710719 | 5/1996 |
| WO | WO 88/06630 | 9/1988 |
| WO | WO 89/00999 | 2/1989 |
| WO | WO 89/06283 | 7/1989 |
| WO | WO 90/03809 | 4/1990 |
| WO | WO 90/04036 | 4/1990 |
| WO | WO 90/14424 | 11/1990 |

(Continued)

OTHER PUBLICATIONS

Pascalis et al. J. Immunol. 2002, 169:3076-3084.*
Paul, Fundamenta.l Immunology, 3rd Edition, 1993, pp. 292-295.*
Desmet et al. Humanization by Resurfacing. Antibody Engineering vol. 1, pp. 341-353 (R. Kontermann and S. Dubel (eds.), Antibody Engineering vol. 1, Springer-Verlag Berlin Heidelberg 2010).*

(Continued)

*Primary Examiner* — Dong Jiang
(74) *Attorney, Agent, or Firm* — Woodcock Washburn LLP

(57) ABSTRACT

The present invention provides an antibody comprising an antigen binding domain which binds to human IL-12 and human IL-23. The antibody binds human IL-12p40 existing as a monomer (human IL-12p40) and as a homodimer (human IL-12p80) and the antibody inhibits the binding of human IL-12 to human IL-12R β2 and human IL-23 to human IL-23R but does not inhibit the binding of human IL-12 or human IL-23 or human IL-12p40 or human IL-12p80 to human IL-12Rβ1.

11 Claims, 31 Drawing Sheets

(56) References Cited

U.S. PATENT DOCUMENTS

| | | |
|---|---|---|
| 5,385,839 A | 1/1995 | Stinski |
| 5,403,484 A | 4/1995 | Ladner et al. |
| 5,404,871 A | 4/1995 | Goodman et al. |
| 5,427,908 A | 6/1995 | Dower et al. |
| 5,455,030 A | 10/1995 | Ladner et al. |
| 5,458,135 A | 10/1995 | Patton et al. |
| 5,484,908 A | 1/1996 | Froehler et al. |
| 5,514,670 A | 5/1996 | Friedman et al. |
| 5,518,889 A | 5/1996 | Ladner et al. |
| 5,534,621 A | 7/1996 | Ladner et al. |
| 5,543,507 A | 8/1996 | Cook et al. |
| 5,545,806 A | 8/1996 | Lonberg et al. |
| 5,545,807 A | 8/1996 | Surani et al. |
| 5,565,362 A | 10/1996 | Rosen |
| 5,569,825 A | 10/1996 | Lonberg et al. |
| 5,571,698 A | 11/1996 | Ladner et al. |
| 5,576,195 A | 11/1996 | Robinson et al. |
| 5,580,717 A | 12/1996 | Dower et al. |
| 5,580,734 A | 12/1996 | Treco et al. |
| 5,595,898 A | 1/1997 | Robinson et al. |
| 5,618,920 A | 4/1997 | Robinson et al. |
| 5,625,126 A | 4/1997 | Lonberg et al. |
| 5,625,825 A | 4/1997 | Rostoker et al. |
| 5,627,052 A | 5/1997 | Schrader |
| 5,633,425 A | 5/1997 | Lonberg et al. |
| 5,641,670 A | 6/1997 | Treco et al. |
| 5,643,768 A | 7/1997 | Kawasaki |
| 5,656,730 A | 8/1997 | Lee |
| 5,658,754 A | 8/1997 | Kawasaki |
| 5,661,016 A | 8/1997 | Lonberg et al. |
| 5,672,593 A | 9/1997 | Michejda et al. |
| 5,681,941 A | 10/1997 | Cook et al. |
| 5,693,493 A | 12/1997 | Robinson et al. |
| 5,693,761 A | 12/1997 | Queen et al. |
| 5,698,417 A | 12/1997 | Robinson et al. |
| 5,698,435 A | 12/1997 | Robinson et al. |
| 5,723,323 A | 3/1998 | Kauffman et al. |
| 5,733,761 A | 3/1998 | Treco et al. |
| 5,750,373 A | 5/1998 | Garrard et al. |
| 5,763,192 A | 6/1998 | Kauffman et al. |
| 5,763,733 A | 6/1998 | Whitlow et al. |
| 5,767,260 A | 6/1998 | Whitlow et al. |
| 5,770,222 A | 6/1998 | Unger et al. |
| 5,770,359 A | 6/1998 | Wilson et al. |
| 5,770,428 A | 6/1998 | Boris-Lawrie |
| 5,789,650 A | 8/1998 | Lonberg et al. |
| 5,814,476 A | 9/1998 | Kauffman et al. |
| 5,814,599 A | 9/1998 | Mitragotri et al. |
| 5,817,483 A | 10/1998 | Kauffman et al. |
| 5,824,514 A | 10/1998 | Kauffman et al. |
| 5,827,690 A | 10/1998 | Meade et al. |
| 5,827,739 A | 10/1998 | Wilson et al. |
| 5,837,500 A | 11/1998 | Ladner et al. |
| 5,839,446 A | 11/1998 | Waner et al. |
| 5,849,695 A | 12/1998 | Cohen et al. |
| 5,849,992 A | 12/1998 | Meade et al. |
| 5,851,198 A | 12/1998 | Castellano et al. |
| 5,856,456 A | 1/1999 | Whitlow et al. |
| 5,871,753 A | 2/1999 | Crabtree et al. |
| 5,879,681 A | 3/1999 | Leone-Bay et al. |
| 5,885,793 A | 3/1999 | Griffiths et al. |
| 5,939,598 A | 8/1999 | Kucherlapati et al. |
| 5,962,255 A | 10/1999 | Griffiths et al. |
| 5,969,108 A | 10/1999 | McCafferty et al. |
| 5,976,862 A | 11/1999 | Kauffman et al. |
| 5,994,616 A | 11/1999 | Rosen |
| 6,914,128 B1 | 7/2005 | Salfeld et al. |
| 7,041,870 B2 | 5/2006 | Tomizuka et al. |
| 7,247,711 B2 | 7/2007 | Benson et al. |
| 7,306,907 B2 | 12/2007 | Winter et al. |
| 2003/0039649 A1 | 2/2003 | Foote |

FOREIGN PATENT DOCUMENTS

| | | |
|---|---|---|
| WO | WO 90/14430 | 11/1990 |
| WO | WO 90/14443 | 11/1990 |
| WO | WO 91/00360 | 1/1991 |
| WO | WO 91/10741 | 7/1991 |
| WO | WO 91/17271 | 11/1991 |
| WO | WO 91/18980 | 12/1991 |
| WO | WO 91/19818 | 12/1991 |
| WO | WO 92/00373 | 1/1992 |
| WO | WO 92/01047 | 1/1992 |
| WO | WO 92/03918 | 3/1992 |
| WO | WO 92/05258 | 4/1992 |
| WO | WO 92/06204 | 4/1992 |
| WO | WO 92/07076 | 4/1992 |
| WO | WO 92/14843 | 9/1992 |
| WO | WO 92/16221 | 10/1992 |
| WO | WO 92/18619 | 10/1992 |
| WO | WO 92/20791 | 11/1992 |
| WO | WO 93/06213 | 4/1993 |
| WO | WO 93/08278 | 4/1993 |
| WO | WO 93/08829 | 5/1993 |
| WO | WO 93/11236 | 6/1993 |
| WO | WO 93/19172 | 9/1993 |
| WO | WO 94/06498 | 3/1994 |
| WO | WO 94/08552 | 4/1994 |
| WO | WO 94/16970 | 8/1994 |
| WO | WO 94/18219 | 8/1994 |
| WO | WO 94/25585 | 11/1994 |
| WO | WO 95/01438 | 1/1995 |
| WO | WO 95/15388 | 6/1995 |
| WO | WO 95/16027 | 6/1995 |
| WO | WO 96/07754 | 3/1996 |
| WO | WO 96/13583 | 5/1996 |
| WO | WO 96/34096 | 10/1996 |
| WO | WO 97/08320 | 3/1997 |
| WO | WO 97/13852 | 4/1997 |
| WO | WO 97/15327 | 5/1997 |
| WO | WO 97/20078 | 6/1997 |
| WO | WO 97/22376 | 6/1997 |
| WO | WO 97/25086 | 7/1997 |
| WO | WO 98/01757 | 1/1998 |
| WO | WO 98/24884 | 6/1998 |
| WO | WO 98/24893 | 6/1998 |
| WO | WO 98/35888 | 8/1998 |
| WO | WO 98/50433 | 11/1998 |
| WO | WO 99/37682 | 7/1999 |
| WO | WO 02/097048 | 12/2002 |
| WO | WO 2004/006955 | 1/2004 |
| WO | WO 2004/101750 | 11/2004 |
| WO | WO 2006/069036 | 6/2006 |
| WO | WO 2007/005608 | 1/2007 |
| WO | WO 2007/027714 | 3/2007 |
| WO | WO 2010/017598 | 2/2010 |

OTHER PUBLICATIONS

Azzazy et al., "Phage display technology: clinical applications and recent innovations", Clinical Biochemistry, 2002, 35, 425-445.

Babcook et al., "A novel Strategy for generating monoclonal antibodies from single, isolated lymphocytes producing antibodies of defined specificities", Prc. Natl. Acad. Sci. USA. Jul. 1996, 93, 7843-7848.

Bird et al., "Single-Chain Antigen-Binding Proteins", Science, Oct. 1988, 242, 423-426.

Brown et al., "Anti-Tac-H, a humanized antibody to the interleukin 2 receptor, prolongs primate cardiac allograft survival", Proc. Natl. Acad. Sci. USA, Immunology, Apr. 1991, 88, 2663-2667.

Camoglio et al., "Contrasting roles of IL-12p40 and IL-12p35 in the development of hapten-induces induces colitis", Eur. J. Immunol. 2002, 32, 261-269.

Capellas et al., "Enzymatic condensation of cholecystokinin CCK-8 (4-6) and CCK-8 (7-8) peptide fragments in organic media", Biotechnology and Bioengineering, Nov. 1997, 56(4), 456-463.

Carter et al., "Humanization of an anti-p185$^{HER2}$ antibody for human cancer therapy", Proc. Natl. Acad. USA, Immunology, May 1992, 89, 4285-4289.

(56) References Cited

OTHER PUBLICATIONS

Carter, "Potent antibody therapeutics by design", Nature Reviews Immunology, May 2006, 6, 343-357.
Caspary et al., "A new therapeutic approach to treat psoriasis by inhibition of fatty acid oxidation by Etomoxir", Clinical and Laboratory Investigations, British Journal of Dermatology, 2005, 153, 937-944.
Chen et al., "Distinct Regulation of Interleukin-17 in Human T Helper Lymphocytes", Arthritis & Rheumatism, Sep. 2007, 56(9), 2936-2946.
Chizzontie et al., "IL-12 Receptor, I. Characterization of the Recptor on Phytohemagglutinin-Activated Human Lymphoblasts", The Journal of Immunology, May 1992, 148(10), 3117-3124.
Chothia et al., "Canonical Structures for the Hypervariable Regions of Immunoglobulins", J. Mol. Biol. 1987, 196, 901-917.
Chothia et al., "Conformations of immunoglobulin hypervariable regions", Nature, Dec. 1989, 342, 877-883.
Chothia et al., "Structural repertoire of the human VH segments", J. Mol. Biol., 1992, 227(3), 799-817.
Chua et al., "Expression Cloning of Human Il-12 Receptor Component—A New Member of the Cytokine Receptor Superfamily with Strong Homology to gp130", The Journal of Immunology, 1994, 153(1), 128-136.
Clackson et al., "Making antibody fragments using phage display libraries", Nature, Aug. 1991, 352, 624-628.
Conrad et al., "Compartment-specific accumulation of recombinant immunoglobullins in plant cells: an essential tool for antibody production and iummunomodulation of physiological functions and pathogen activity", Plant Molecular Biology, Sep. 1998, 38(1-2), 101-109.
Cooper et al., "IL-12p40: an inherently agonistic sytokine", TRENDS in Immunology, 2007, 28(1), 33-38.
Corcoran et al., "Characterizing of ligand binding by the human p55 tumour-necrosis-factor receptor Involvement of individual cysteine-rich repeats", Eur. J. Biochem., Mar. 1994, 223, 831-840.
Cramer et al., "Transgenic plants for therapeutic proteins: linking upstream and downstream strategies", Current topics in microbiology and immunology, 1999, 240, 95-118.
Cua et al., "Interleukin-23 rather than interleukin-12 is the critical cytokine for autoimmune inflammation of the brain", Nature, Feb. 2003, 421, 744-748.
Cunningham et al., "High-Resolution Epitope Mapping of hGH-Receptor Interactions by Alanine-Scanning Mutagenesis", Science, Jun. 1989, 244, 1081-1085.
D'Andrea et al., "Production of Natural Killer Cell Stimulatory Factor (Interleukin 12) by Periphera Blood Mononuclear Cells", J. Exp. Med., Nov. 1992, 176, 1387-1398.
De Rie, "Interleukin 12 and Psoriasis", Dermatology, 1999, 199, 101.
De Vos et al., "Human Growth Hormone and Extracelluar Domain of Its Receptor: Crystal Structure of the Complex", Science, 1992, 255, 306-312.
Devergne et al., "Expression of Epstein-Barr Virus-Induced Gene 3, an Interleukin-12 p40-Related Molecule, Throughout Human Pregnancy", Amer J. Path, Nov. 2001, 159, 1763-1776.
Ding et al., "ABT-874, a fully human monoclonal anti-IL-12/IL-23 antibody for the potential treatment of autoimmune disease", Current Opinion in Investigational Drugs, Drug Profile, Apr. 25, 2008, 9(5), 515-522.
Dong, "$T_H17$ cells in development: an updated view of their molecular identity and genetic programming", Nature Reviews Immunology, May 2008, 8, 337-348.
Durocher et al., "High-level and high-throughput recombinant protein production by transient transfection of suspension-growing human 293-EBNA1 cells", Nucleic Acids Research, Jul. 2002, 30(2), 9 pages.
Elliott et al., "Repeated therapy with monoclonal antibody to tumor necrosis factor α (cA2) in patients with rheumatoid", The Lancet, Oct. 1994, 344, 1125-1127.
Engelmann et al., "Two Tumor Necrosis Factor-binding Proteins Purified from Human Urin", The Journal of Biological Chemistry, Jan. 1990, 265(3), 1531-1536.
Fassbender et al., "Increased release of interleukin- 12p40 in MS: association with interacerebral inflammation", Neurology, Sep. 1998, 51(3), 753-758.
Fisch et al., "Site-specific modification of a fragment of a chimeric monoclonal antibody using reverse proteolysis", Bioconjugate Chemistry, Mar. 1992, 3(2), 147-153.
Fishwild et al., "High-avidity human igG? monoclonal antibodies from a novel strain of minilocus transgenic mice", Nature Biotechnology, Jul. 1996, 14(7), 845-851.
Foote et al., "Antibody Framework Residues Affecting the Conformation of the Hypervariable Loops", J. Mol. Biol. 1992, 224, 487-499.
Galfre et al., "Antibodies to major histocompatibility antigens produced by hybrid cell line" Nature Publishing Group, Apr. 1977, 266(5602), 550-552.
Gately et al., "Interleukin-12 antagonist activity of mouse interleukin-12 p40 homodimer in vitro and in vivo", Annal. NY Academy of Science, Oct. 1996, 795, 1-12.
Gavilondo et al., "Antibody engineering at the millennium", Bio Techniques, Jul. 2000, 29(1), 128-132.
Gillessen et al., "Mouse interleukin-12 (IL-12) p40 homodimer:a potent IL-12 antagonist", European Journal of Immunology, Jan. 1995, 25(1), 200-206.
Gordon et al., "The pathophysiologic rationale of biological therapies in inflammatory bowel disease", Current Opinion in Gastroenterology, Jul. 2005, 21(4), 431-437.
Gray et al., "Secretion capture and report web: use of affinity derivatized agarose microdroplets for the selection of hybridoma cells", Journal of Immunological Methods, 1995, 182, 155-163.
Green et al., "Antigen-specific human monoclonal antibodies from mice engineered with Ig heavy and light chain YACs", Nature Genetics, May 1994, 7(1), 13-21.
Griffiths et al., "Human anti-self antibodies with high specifity from phage display libraries", The EMBO Journal, 1993, 12(2), 725-734.
Gustafsson et al., "SPAM-8, a mouse-human heteromyeloma fusion partner in the production of human monoclonal antibodies. Establishment of a human monoclonal antibody against sytomegalovirus", Human antibodies and hybridomas, Jan. 1991, 2(1), 26-32.
Hanes et al., "In vitro selection and evolution of functional proteins by using ribosome display", Proc. Natl. acad. Sci. USA., May 1997, 4937-4942.
Hanes et al., "Ribosome display efficiently selects and evolves high-affinity antibodies in vitro from immune libraries", Proc. Natl. Acad. Sci. USA., Nov. 1998, 95, 14130-14135.
Holliger et al., "Diabodies": Small bivalent and bispecific antibody fragments, Proc. Natl. Acad. Sci. USA., Biophysics, Jul. 1993, 90, 6444-6448.
Hood et al. "Molecular Farming of Industrial Proteins from Transgenic Maize", Adv. In experimental medicine and biology, 1999, 127-147.
Hoogenboom et al., "Natural and designer binding sites made by phage display technology", Immunology Today, Aug. 2000, 21(8), 371-378.
Hoogenboom, "Designing and optimizing library selection strategies for generating high-affinity antibodies", TIBTECH, Feb. 1997, 15, 62-70.
Huston et al., "Protein engineering of antibody binding sites: Recovery of specific activity in an anti-digoxin single-chain Fv analogue produced in *Escherichia coli*", Proc. Natl. Acad. Sci. USA. Aug. 1988, 85, 5879-5883.
Johnson et al., "Human antibody engineering", Current Opinion Structural Biology, 1993, 3, 564-571.
Jones et al., "Replacing the complementarity-determining regions in a human antibody with those from a mouse" Nature, 1986, 321(6069), 522-525.
Junghans et al., "Anti-Tac-H, a Humanized Antibody to the Interleukin 2 Receptor with New Features for Immunotherapy in Malignant and Immune Disorders", Cancer Research 50, Mar. 1990, 1495-1502.

(56) References Cited

OTHER PUBLICATIONS

Kabat et al., "Attempts to locate complementarity-determining residues in the variable pos", Ann N Y Acad. Sci., 1971, 190, 382-393.
Katsube et al., "Analysis of kappa light chain contribution to anti-DNA antibody activity of a human VH4-21-21-encoded monoclonal antibody (NE-1) by antibody-phage display technique", International Journal of molecular medicine, May 1998, 1(5), 863-868.
Kenney et al., "Production of Monoclonal Antibodies Using a Secretion Capture Report Web", Bio/Technology, Aug. 1995, 13(8), 787-790.
Khader et al., Interleukin 12p40 is required for dendritic cell migration and T cell priming after *Mycobacterium tuberculosis* infection, JEM, Jul. 2006, 203, 1805-1815.
Kim et al., "The role of Il-12 in inflammatory activity of patients with rheumatoid arthritis (RA)", Clin Exp Immunol, 2000, 119, 175-181.
Kipriyanov et al., "Recombinant Single-Chain Ev Fragments Carrying C-Terminal Cyseine Residues: Production of Bivalent and Biotinylated Miniantibodies", Molecular Immunology, 1994, 31(14), 1047-1058.
Kipriyanov et al., "Single-chain antibody streptavidin fusions: teramric bifunctional scFv-complexes with biotin bindinf activity and enhanced affinity to antigen", Human antibodies and hybridomas, 1995, 6(3), 93-101.
Knorre et al., "Reactive oligonucleotide derivatives and sequence-specific modification of nucleic acids", Biochimie, 1985, 67, 785-789.
Kohler et al., Derivation of specific antibody-producing tissue culture and tumor lines by cell fusion, European Journal of Immunology, Jul. 1976, 6(7), 511-519.
Kohler, "Continuous cultures of fused cells secreting antibody of predefined specificity", Nature, Aug. 1975, 256, 495-497.
Kumaran et al., "Conformationally driven protease-catalyzed splicing peptide segments: V8 protease-mediated synthesis of fragments derived from thermolysin and ribonuclease A", Protein Sci., 1997, 6, 2233-2241.
Laman et al., "Expression of accessory molecules and cytolines in avute EAE in marmoset monkeys (*Callithrix jacchus*)" Journal of Neuroimmunology, 1998, 86, 30-45.
Lazar et al., "Engineered antibody Fc variants with enhanced effector function", Proc. Natl. Acad. Sci. USA., Mar. 2006, 103(11), 4005-4010.
Lee et al., "Increased Expression of Interleukin 23 p19 and p40 in Lesional Skin of Patients with Psoriasis Vulgaris", J. Exp. Med., Jan. 2004, 199(1), 125-130.
Lee et al., "Interaction of Psoralen-Derivatized Oligodeoxyribonucleoside Methylphosphonates with Single-Stranded DNA", Biochemistry, 1988, 27, 3197-3203.
Leonard et al., Regulation of the inflammatory response in animal models of multiple sclerosis by interleukin-12, Critical reviews in immunology, 1997, 17(5-6), 545-553.
Leung et al., "Combined Effects of IL-12 and IL-18 on the Induction of Collagen-Induced Arthritis", The Journal of immunology, 2000, 6495-6502.
Li et al., "Optimization of humanized igGs in glycoengineered pichia pastoris", Nature biotechnology, Feb. 2006, 24(2), 210-215.
Little et al., "Of mice and men: hybridoma and recombinant antibodies", Immunology Today, Aug. 2000, 21(8), 364-370.
Loetscher et al., "Molecular Cloning and Expression of the Human 55 kd Tumor Necrosis Factor Receptor", Cell, Apr. 1990, 61, 351-359.
Lonberg et al., "Antigen-specific human antibodies from mice comprising four distinct genetic modifications", Nature, Apr. 1994, 368, 856-859.
Lonberg et al., "Human antibodies from transgenic mice", Int. Rev. Immunol., 1995, 13(1), 65-93.
Ma et al., "Immunotherapeutic potential of antibodies produced in plants", TIBTECH, Dec. 1995, 13, 522-527.
Ma et al., "Plant Antibodies for Immunotherapy", Plant Physiol, 1995, 109, 341-346.
Marchalonis et al., "Evolutionary factors in the emergence of the combinatorial germline antibody repertoire", Advances in experimental medicine and biology, 2001, 484, 13-30.
Marks et al., "By passing Immunization, Human Antibodies from V-gene Libraries Displayed on Phage", J. Mol. Biol. 1991, 222, 581-597.
Marks et al., "By-Passing Immunization: Building High Affinity Human Antibodies by Chain Shuffling", Nature Bio/Technology, Jul. 1992, 10, 779-783.
Mattner et al., "The interleukin-12 subunit p40 specifically inhibits effects of the interleukin-12 heterodimer", European Journal of Immunology, Sep. 1993, 23(9), 2202-2208.
Mattner et al., "Treatment with Homodimeric Interleukin-12 (IL-12) p40 Protects Mice from IL-12-Dependent Shock but Not from Tumor Necrosis Factor Alpha-Dependent Shock", Infect. Immun., Nov. 1997, 65(11), 4734-4737.
Mendez et al., "Functional transplant of megabase human immunoglobulin loci recapitulates human antibody response in mice", Nature Genetics, Feb. 1997, 15(2), 146-156.
Meyers et al., "Development of monoclonal antibody imaging of metastatic prostatic carcinoma", The Prostate, 1989, 14(3), 209-220.
Milstein et al., "Hybrid hybridomas and their use in immunohistochemistry", Nature, 1983, 305(5943), 537-540.
Neurath et al., "Antibodies to Interleukin 12 Abrogate Established Experimental Colitis in Mice", The Journal of Experimental Medicine, Nov. 1995, 182, 1281-1290.
Neurath et al., "IL-23: a master regulator in Crohn disease—Three studies should shift thinking about the cause of inflammatory bowel disease. It seems that researchers have been focusing on the wrong cytokine as a driving force", Nature Medicine, Jan. 2007, 13(1), 26-28.
Nguyen et al., "Production of human monoclonal antibodies in SCID mouse", Microbiology and Immunology, 1997, 41(12), 901-907.
Niedbala et al., "Il-35 is a novel cytokine with therapeutic effects against collagen-induced arthritis through the expansion of regulatory T cells and suppression of Th17 cells", Eur. J. Immunol. 2007, 37, 3021-3029.
Nils et al., "Antigen-specific human antibodies from mice comprising four distinct genetic modifications", Nature Publishing Group, Apr. 1994, 368(6474, 856-859.
Oppmann et al., "Novel p19 Protein Engages IL-12p40 to Form a Cytokine, IL-23, with Biological Activities Similar as Well as Distinct form IL-12", Immunity, 2000, 13, 715-725.
Papp et al., "Efficacy of ISA247 in plague psoriasis: a randomized, multicentre, double-blind, placebo-controlled phase III study", The Lancet, Apr. 2008, 371, 1337-1342.
Parham et al., "A Receptor for the Heterodimeric Cytokine IL-23 is Composed of Il-12Rβ1 and a Novel Cytokine Receptor Subunit, IL-23R[1]" The Journal of Immunology, 2002, 68, 5699-5708.
Powell et al., "Gel Microdroplets and Flow Cytometry: Rapid Determination of Antibody Secretion by Individual Cells Within a Cell Population", Bio/Technology, Apr. 1990, 8(4), 333-337.
Presky et a., "Evidence for Multiple Sites of Interaction between IL-12 and Its Receptor", Annals New York Academy of Sciences, 1996, 390-393.
Presky et al., "A functional interleukin 12 receptor complex is composed of two β-type cytokine receptor subunits", Proc. Natl. Acad. Sci. USA. Nov. 1996, Proc. Natl. Acad. Sci. USA. Nov. 1996, 93, 14002-14007.
Presta et al., "Humanization of an Antibody Directed Against IgE", The Journal of Immunology, 1993, 151(5), 2623-2632.
Presta, "Engineering of therapeutic antibodies to minimize immunogenicity and optimize function" Adv. Drug Delivery Reviews, 2006, 58, 640-656.
Qiu et al., "Small antibody mimetics comprising two complementarity-determining regions and a framework region for tumor targeting", Nature Biotechnology, Aug. 2007, 25(8), 921-929.
Quinones et al., "Preformed Membrane-associated Stores of Interleukin (IL) -12 are a Previously Unrecognized Source of Bioactive IL-12 That is Mobilized within Minutes of Contact with an Intercellular Parasite", J. Exp. Med., Aug. 2000, 192(4), 507-515.

(56) References Cited

OTHER PUBLICATIONS

Reddy et al., "Modulation of CLA, IL-12R, CD4OL, and IL-2Rα expression and inhibition of IL-12-and IL-23-induced cytokine secretion by CNTO 1275", Cellular Immunology, 2007, 247(1), 1-11.
Riechmann et al., "Reshaping human antibodies for therapy", Nature, Mar. 1988, 332, 323-327.
Rogge et al., "Selective Expression of an Interleukin-12 Receptor Component by Human T Helper 1 Cells", J. Exp Med., Mar. 1997, 185,(5), 825-831.
Russell et al., "IL-12 p40 Homodimer-Dependent Macrophage Chemotaxis and Respiratory Viral Inflammation Are Mediated Through IL-12 Receptor β1¹" The Journal of Immunolgy, 2003, 185, 6866-6874.
Sandhu et al., "The use SCID mice in biotechnology and as a model for human disease", Critical Reviews in Biotechnology, 1996, 16(1), 95-118.
Schell et al., "Molecular Cloning and Expression of a Receptor for Human Tumor Necrosis Factor", Cell, Apr. 1990, 61, 361-370.
Schuster et al., "In vivo glycol-engineered antibody with improved lytic potential produced by an innovative non-mammalian expression system", Biotechnology Journal, Jun. 2007, 2(6), 700-708.
Shaker et al., "The role of interleukin-12 in the pathogenesis of psoriasis", Clinical Biochemistry, 2006, 39, 119-125.
Shapiro et al., "DNA target motifs of somatic mutagenesis in antibody genes", Critical reviews in immunology, 2002, 2293), 183-200.
Shields et al., "High Resolution Mapping of the Binding Site on Human IgG1 for FcγRI, FcγRII, FcγIII, and FcRn and Design of IgG1 Variants with Improved Binding to the FcγR*", The Journal of Biological Chemistry, Mar. 2001, 276(9), 6591-6604.
Shimozato et al., "The Secreted form of the p40 subunit of interleukin (IL)-12 inhibits IL-23 functions and abrogates IL-23-mediated antiumour effects", Immunology, 2005, 117, 22-28.
Simpson et al., "T Cell-mediated Pathology in Two Models of Experimental Colitis Depends Predominantly on the Interleukin 12/Signal Transducer and activator of Transcript (Stat)-4 Pathway, but is not Conditional on Interferon γ Expression by T Cells", J. Exp. Med., Apr. 1998, 187(8), 1225-1234.
Sims et al., "A Humanized CD18 Antibody Can Block Function without Cell Destruction", The Journal of Immunology, Aug. 1993, 151(4), 2296-2308.
Smith et al., "Human Interleukin 4, The Solution Structure of a Four-helix Bundle Protein", J. Mol. Biol. 1992, 899-904.
Sprague et al., "Expression of a Recombinant DNA Gene Coding for the Vesicular Stomatitis Virus Nucleocapsid Protein", Journal of Virology, Feb. 1983, 45(2), 773-781.
Steenbakkers et al., "Efficient generation of monoclonal antibodies from preselected antigen-specific B cells", Molecular Biology Reports, 1994, 19, 125-134.
Suresh et al. "Bispecific Monoclonal Antibodies from Hybrid Hybridomas", Methods in Enzymology, 1986, 121,210-228.
Taylor et al., "A transgenic mouse that expresses a diversity of human sequence heavy and light chain immunoglobulins", Nucleic Acids Research, Aug. 1992, 20(23), 6287-6295.
Taylor et al., "Human Immunoglobulin transgenes undergo rearrangement, somatic mutation and class switching in mice that lack endogenous IgM", International Immunology, Apr. 1994, 6(4), 579-591.
Torti et al., "Interleukin-12, interleukin-23, and psoriasis; Current prospects", J. Am. Acad. Dermatol, Dec. 2007, 1059-1068.
Traunecker et al., "Bispecific single chain molecules (Janusins) target cytotoxic lymphocytes on HIV infected cells", The EMBO Journal, 10(12), 1991, 3655-3659.
Trinchieri et al., "The IL-12 Family of Heterodimeric Cytokines: New Players in the Regulation of T Cell Responses", Immunity, Nov. 2003, 19, 641-644.
Trinchieri, "Interleukin-12 and the regulation of innate resistance and adaptive immunity", Nature Reviews Immunology, Feb. 2003, 3(2), 133-146.
Tuaillon et al., "Human immunoglobulin heavy-chain minilocus recombination in transgenic mice: Gene-segment use in μ and γ transcripts", Proc. Natl. Acad. Sci. USA., Apr. 1993, 90, 3720-3724.
Verhoeyen et al., "Reshaping Human Antibodies: Grafting an Antilysozyme Activity", Science, 1988, 239, 1534-1536.
Verreck et al., "Human IL-23-producing type 1 macrophages promote but IL-10-producing type 2 macrophages subvert immunity to (myco)bacteria", Proc. Natl. Acad. Sci. USA., Mar. 2004, 101(13), 4560-4565.
Vlassov et al., "Complementary addressed modification and cleavage of a single stranded DNA fragment with alkylating oligonucleotide derivatives", Nucleic Acids Research, Jan. 1986, 14(10), 4065-4076.
Vogel et al., "Direct binding of IL-12 to human and murine B lymphocytes", International immunology, 1996, 8(12), 1955-1962.
Wang et al., "Characterization of mouse interleukin-12 p40 homodimer binding to the interleukin-12 receptor subunits", Eur. J. Immunol., 1999, 29, 2007-2013.
Ward et al., "Binding activities of a repertoire of single immunoglobulin variable domains secreted from *Escherichia coli*, Nature, Oct. 1989, 341, 544-546.
Waterhouse et al., "Combinatorial infection and in vivo recombination: a strategy for making large phage antibody repertoires", Nucleic Acids Research, 1993, 21(9), 2265-2266.
Watford et al., "Signaling by IL-12 and Il-23 and the immunoregulatory roles of STAT4", Immunological Reviews, 2004, 202, 139-156.
Webb et al., "Hybridization triggered cross-linking of deoxyoligonucleotides", Nucleic Acids Research, May 1986, 14(19), 7661-7674.
Wen et al., "Limiting dilution assay for human B cells based on their activation by mutant EL4 thymoma cells: total and antimalaria responder B cell frequencies", European Journal of Immunology, Jun. 1987, 17(6), 887-892.
Werlen et al., "Site-specific conjugation of an enzyme and an antibody fragment", Bioconjugate Chemistry, Sep. 1994, 5(5), 411-417.
Whitelam et al., "Antibody production in transgenic plants", Biochem Soc. Transactions, 1994, 940-944.
Wrone-Smith et al., "Dermal Injection of Immunocytes Induces Psoriasis", The Pathogenicity of immunocytes in Psoriasis, Oct. 1996, 9,(8), 1878-1887.
Yamane-Ohnuki et al., "Establishment of FUT8 knockout Chinese hamster ovary cells: An ideal host cell line for producing completely defucosylated antibodies with enhanced antibody-dependent cellular cytotoxicity", Biotechnology and Bioengineering, Sep. 2004, 87(5), 614-622.
Yao et al., "Direct Interaction of STAT4 with the IL-12 Receptor", Archives of Biochemistry and Biophysics, Aug. 1999, 368(1), 147-155.
Yawalkar et al., "Expression of interleukin-12 is increased in psoriatic skin", Journal of Investigative Dermatology, Dec. 1998, 111(6), 1053-1057.
Yoon et al., "Charged residues dominate a unique interlocking topography in the heterodimeric sytokin interleukin-12", The EMBO Journal, 2000, 19(14), 3530-3541.
Zanella et al., "New heteromyeloma cell lines for the production of human monoclonal antibodies", Journal of Immunology Methods, 1992, 156, 205-215.
Zhou et al., "IL-6 programs $T_H$-17 cell differentiation by promoting sequential engagement of the IL-21 and Il-23 pathways", Nature Immunology, Sep. 2007, 8(9), 967-974.
Zou et al., "Differential Associations between the Cytoplasmic Regions of the Interleukin-12 Receptor Subunits β1 β2 and JAK Kinases*", The Journal of Biological Chemistry, Feb. 1997, 272(9), 6073-6077.

* cited by examiner

SEQUENCE LISTING

<160> NUMBER OF SEQ ID NOS: 395

<210> SEQ ID NO 1
<211> LENGTH: 306
<212> TYPE: PRT
<213> ORGANISM: Homo sapiens

<400> SEQUENCE: 1

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285
```

```
Gln Asp Arg Tyr Tyr Ser Ser Trp Ser Glu Trp Ala Ser Val Pro
    290                 295                 300

Cys Ser
305

<210> SEQ ID NO 2
<211> LENGTH: 197
<212> TYPE: PRT
<213> ORGANISM: Homo sapiens

<400> SEQUENCE: 2

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195

<210> SEQ ID NO 3
<211> LENGTH: 170
<212> TYPE: PRT
<213> ORGANISM: Homo sapiens

<400> SEQUENCE: 3

Arg Ala Val Pro Gly Gly Ser Ser Pro Ala Trp Thr Gln Cys Gln Gln
1               5                   10                  15

Leu Ser Gln Lys Leu Cys Thr Leu Ala Trp Ser Ala His Pro Leu Val
            20                  25                  30

Gly His Met Asp Leu Arg Glu Glu Gly Asp Glu Glu Thr Thr Asn Asp
        35                  40                  45

Val Pro His Ile Gln Cys Gly Asp Gly Cys Asp Pro Gln Gly Leu Arg
    50                  55                  60

Asp Asn Ser Gln Phe Cys Leu Gln Arg Ile His Gln Gly Leu Ile Phe
65                  70                  75                  80

Tyr Glu Lys Leu Leu Gly Ser Asp Ile Phe Thr Gly Glu Pro Ser Leu
                85                  90                  95
```

-continued

Leu Pro Asp Ser Pro Val Gly Gln Leu His Ala Ser Leu Leu Gly Leu
                100                 105                 110

Ser Gln Leu Gln Pro Glu Gly His His Trp Glu Thr Gln Gln Ile
        115                 120                 125

Pro Ser Leu Ser Pro Ser Gln Pro Trp Gln Arg Leu Leu Leu Arg Phe
    130                 135                 140

Lys Ile Leu Arg Ser Leu Gln Ala Phe Val Ala Val Ala Ala Arg Val
145                 150                 155                 160

Phe Ala His Gly Ala Ala Thr Leu Ser Pro
                165                 170

<210> SEQ ID NO 4
<211> LENGTH: 121
<212> TYPE: PRT
<213> ORGANISM: Mus musculus

<400> SEQUENCE: 4

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Phe Lys Asn Glu Asp Thr Ala Thr Tyr Phe Cys
                85                  90                  95

Ala Arg Ser Leu Ser Thr Met Ile Thr Thr Phe Ala Tyr Trp Gly
            100                 105                 110

Gln Gly Thr Leu Val Thr Val Ser Ser
            115                 120

<210> SEQ ID NO 5
<211> LENGTH: 108
<212> TYPE: PRT
<213> ORGANISM: Mus musculus

<400> SEQUENCE: 5

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys Arg
            100                 105

<210> SEQ ID NO 6
<211> LENGTH: 118
<212> TYPE: PRT

<213> ORGANISM: Mus musculus

<400> SEQUENCE: 6

```
Glu Val Gln Leu Gln Gln Ser Gly Ala Asp Leu Val Arg Ser Gly Ala
1               5                   10                  15

Ser Ile Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Cys Lys Glu Leu Arg Tyr Phe Asp Val Trp Gly Ala Gly Thr
            100                 105                 110

Thr Val Thr Val Ser Ser
            115
```

<210> SEQ ID NO 7
<211> LENGTH: 108
<212> TYPE: PRT
<213> ORGANISM: Mus musculus

<400> SEQUENCE: 7

```
Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Ile Asn
            20                  25                  30

Leu His Trp Tyr Gln Gln Lys Ser His Glu Ser Pro Arg Leu Leu Ile
        35                  40                  45

Lys Phe Ala Ser Gln Ser Ile Ser Gly Ile Pro Ser Arg Phe Ser Gly
    50                  55                  60

Tyr Gly Ser Gly Thr Asp Phe Thr Leu Ser Ile Asn Ser Val Glu Thr
65                  70                  75                  80

Glu Asp Phe Gly Arg Tyr Phe Cys Gln Gln Ser Asn Ser Trp Pro Leu
                85                  90                  95

Thr Phe Gly Ala Gly Thr Lys Leu Glu Leu Lys Arg
            100                 105
```

<210> SEQ ID NO 8
<211> LENGTH: 330
<212> TYPE: PRT
<213> ORGANISM: Homo sapiens

<400> SEQUENCE: 8

```
Ala Ser Thr Lys Asn Pro Asp Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                 85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 9
<211> LENGTH: 106
<212> TYPE: PRT
<213> ORGANISM: Homo sapiens

<400> SEQUENCE: 9

Thr Val Ala Ala Pro Ser Val Phe Ile Phe Pro Pro Ser Asp Glu Gln
1               5                   10                  15
Leu Lys Ser Gly Thr Ala Ser Val Val Cys Leu Leu Asn Asn Phe Tyr
            20                  25                  30
Pro Arg Glu Ala Lys Val Gln Trp Lys Val Asp Asn Ala Leu Gln Ser
        35                  40                  45
Gly Asn Ser Gln Glu Ser Val Thr Glu Gln Asp Ser Lys Asp Ser Thr
    50                  55                  60
Tyr Ser Leu Ser Ser Thr Leu Thr Leu Ser Lys Ala Asp Tyr Glu Lys
65                  70                  75                  80
His Lys Val Tyr Ala Cys Glu Val Thr His Gln Gly Leu Ser Ser Pro
                85                  90                  95
Val Thr Lys Ser Phe Asn Arg Gly Glu Cys
            100                 105

<210> SEQ ID NO 10
<211> LENGTH: 451
```

<212> TYPE: PRT
<213> ORGANISM: Artificial Sequence
<220> FEATURE:
<223> OTHER INFORMATION: Synthetic

<400> SEQUENCE: 10

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Phe Lys Asn Glu Asp Thr Ala Thr Tyr Phe Cys
                85                  90                  95

Ala Arg Ser Leu Ser Thr Met Ile Thr Thr Phe Ala Tyr Trp Gly
            100                 105                 110

Gln Gly Thr Leu Val Thr Val Ser Ala Ser Thr Lys Asn Pro Asp
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
```

```
                385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 11
<211> LENGTH: 214
<212> TYPE: PRT
<213> ORGANISM: Artificial Sequence
<220> FEATURE:
<223> OTHER INFORMATION: Synthetic

<400> SEQUENCE: 11

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
                20                  25                  30

Val Ala Trp Tyr Gln Gln Lys Pro Gly Gln Ser Pro Lys Leu Leu Ile
            35                  40                  45

Tyr Tyr Ala Ser Asn Arg Tyr Thr Gly Val Pro Asp Arg Phe Thr Gly
50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 448
<212> TYPE: PRT
<213> ORGANISM: Artificial Sequence
<220> FEATURE:
<223> OTHER INFORMATION: Synthetic

<400> SEQUENCE: 12

Glu Val Gln Leu Gln Gln Ser Gly Ala Asp Leu Val Arg Ser Gly Ala
1               5                   10                  15

Ser Ile Lys Leu Ser Cys Thr Ala Ser Gly Phe Asn Ile Lys Asp Tyr
```

```
                    20                  25                  30
Tyr Met His Trp Val Lys Gln Arg Pro Glu Gln Gly Leu Glu Trp Ile
         35                  40                  45
Gly Trp Ile Asp Pro Glu Asn Gly Asp Thr Glu Tyr Ala Pro Lys Phe
 50                  55                  60
Gln Gly Lys Ala Thr Met Thr Ala Asp Thr Ser Ser Asn Thr Ala Tyr
 65                  70                  75                  80
Leu Gln Leu Ser Ser Leu Thr Ser Glu Asp Thr Ala Val Tyr Tyr Cys
                 85                  90                  95
Asn Ala Cys Lys Glu Leu Arg Tyr Phe Asp Val Trp Gly Ala Gly Thr
                100                 105                 110
Thr Val Thr Val Ser Ser Ala Ser Thr Lys Asn Pro Asp Val Phe Pro
             115                 120                 125
Leu Ala Pro Ser Ser Lys Ser Thr Ser Gly Gly Thr Ala Ala Leu Gly
         130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445
```

<210> SEQ ID NO 13
<211> LENGTH: 214
<212> TYPE: PRT
<213> ORGANISM: Artificial Sequence
<220> FEATURE:
<223> OTHER INFORMATION: Synthetic

<400> SEQUENCE: 13

```
Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Ile Asn
            20                  25                  30

Leu His Trp Tyr Gln Gln Lys Ser His Glu Ser Pro Arg Leu Leu Ile
        35                  40                  45

Lys Phe Ala Ser Gln Ser Ile Ser Gly Ile Pro Ser Arg Phe Ser Gly
    50                  55                  60

Tyr Gly Ser Gly Thr Asp Phe Thr Leu Ser Ile Asn Ser Val Glu Thr
65                  70                  75                  80

Glu Asp Phe Gly Arg Tyr Phe Cys Gln Gln Ser Asn Ser Trp Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 14
<211> LENGTH: 521
<212> TYPE: PRT
<213> ORGANISM: Homo sapiens

<400> SEQUENCE: 14

```
Arg Thr Ser Glu Cys Cys Phe Gln Asp Pro Pro Tyr Pro Asp Ala Asp
1               5                   10                  15

Ser Gly Ser Ala Ser Gly Pro Arg Asp Leu Arg Cys Tyr Arg Ile Ser
            20                  25                  30

Ser Asp Arg Tyr Glu Cys Ser Trp Gln Tyr Glu Gly Pro Thr Ala Gly
        35                  40                  45

Val Ser His Phe Leu Arg Cys Cys Leu Ser Ser Gly Arg Cys Cys Tyr
    50                  55                  60

Phe Ala Ala Gly Ser Ala Thr Arg Leu Gln Phe Ser Asp Gln Ala Gly
65                  70                  75                  80

Val Ser Val Leu Tyr Thr Val Thr Leu Trp Val Glu Ser Trp Ala Arg
                85                  90                  95

Asn Gln Thr Glu Lys Ser Pro Glu Val Thr Leu Gln Leu Tyr Asn Ser
            100                 105                 110
```

-continued

```
Val Lys Tyr Glu Pro Pro Leu Gly Asp Ile Lys Val Ser Lys Leu Ala
        115                 120                 125
Gly Gln Leu Arg Met Glu Trp Glu Thr Pro Asp Asn Gln Val Gly Ala
        130                 135                 140
Glu Val Gln Phe Arg His Arg Thr Pro Ser Ser Pro Trp Lys Leu Gly
145                 150                 155                 160
Asp Cys Gly Pro Gln Asp Asp Thr Glu Ser Cys Leu Cys Pro Leu
                165                 170                 175
Glu Met Asn Val Ala Gln Glu Phe Gln Leu Arg Arg Arg Gln Leu Gly
                180                 185                 190
Ser Gln Gly Ser Ser Trp Ser Lys Trp Ser Pro Val Cys Val Pro
        195                 200                 205
Pro Glu Asn Pro Pro Gln Pro Gln Val Arg Phe Ser Val Glu Gln Leu
        210                 215                 220
Gly Gln Asp Gly Arg Arg Arg Leu Thr Leu Lys Glu Gln Pro Thr Gln
225                 230                 235                 240
Leu Glu Leu Pro Glu Gly Cys Gln Gly Leu Ala Pro Gly Thr Glu Val
                245                 250                 255
Thr Tyr Arg Leu Gln Leu His Met Leu Ser Cys Pro Cys Lys Ala Lys
                260                 265                 270
Ala Thr Arg Thr Leu His Leu Gly Lys Met Pro Tyr Leu Ser Gly Ala
        275                 280                 285
Ala Tyr Asn Val Ala Val Ile Ser Ser Asn Gln Phe Gly Pro Gly Leu
        290                 295                 300
Asn Gln Thr Trp His Ile Pro Ala Asp Thr His Thr Glu Pro Val Ala
305                 310                 315                 320
Leu Asn Ile Ser Val Gly Thr Asn Gly Thr Thr Met Tyr Trp Pro Ala
                325                 330                 335
Arg Ala Gln Ser Met Thr Tyr Cys Ile Glu Trp Gln Pro Val Gly Gln
                340                 345                 350
Asp Gly Gly Leu Ala Thr Cys Ser Leu Thr Ala Pro Gln Asp Pro Asp
        355                 360                 365
Pro Ala Gly Met Ala Thr Tyr Ser Trp Ser Arg Glu Ser Gly Ala Met
        370                 375                 380
Gly Gln Glu Lys Cys Tyr Tyr Ile Thr Ile Phe Ala Ser Ala His Pro
385                 390                 395                 400
Glu Lys Leu Thr Leu Trp Ser Thr Val Leu Ser Thr Tyr His Phe Gly
                405                 410                 415
Gly Asn Ala Ser Ala Ala Gly Thr Pro His His Val Ser Val Lys Asn
                420                 425                 430
His Ser Leu Asp Ser Val Ser Val Asp Trp Ala Pro Ser Leu Leu Ser
        435                 440                 445
Thr Cys Pro Gly Val Leu Lys Glu Tyr Val Val Arg Cys Arg Asp Glu
450                 455                 460
Asp Ser Lys Gln Val Ser Glu His Pro Val Gln Pro Thr Glu Thr Gln
465                 470                 475                 480
Val Thr Leu Ser Gly Leu Arg Ala Gly Val Ala Tyr Thr Val Gln Val
                485                 490                 495
Arg Ala Asp Thr Ala Trp Leu Arg Gly Val Trp Ser Gln Pro Gln Arg
                500                 505                 510
Phe Ser Ile Glu Val Gln Val Ser Asp
        515                 520
```

-continued

```
<210> SEQ ID NO 15
<211> LENGTH: 599
<212> TYPE: PRT
<213> ORGANISM: Homo sapiens

<400> SEQUENCE: 15

Lys Ile Asp Ala Cys Lys Arg Gly Asp Val Thr Val Lys Pro Ser His
1               5                   10                  15

Val Ile Leu Leu Gly Ser Thr Val Asn Ile Thr Cys Ser Leu Lys Pro
                20                  25                  30

Arg Gln Gly Cys Phe His Tyr Ser Arg Arg Asn Lys Leu Ile Leu Tyr
            35                  40                  45

Lys Phe Asp Arg Arg Ile Asn Phe His His Gly His Ser Leu Asn Ser
        50                  55                  60

Gln Val Thr Gly Leu Pro Leu Gly Thr Thr Leu Phe Val Cys Lys Leu
65                  70                  75                  80

Ala Cys Ile Asn Ser Asp Glu Ile Gln Ile Cys Gly Ala Glu Ile Phe
                85                  90                  95

Val Gly Val Ala Pro Glu Gln Pro Gln Asn Leu Ser Cys Ile Gln Lys
            100                 105                 110

Gly Glu Gln Gly Thr Val Ala Cys Thr Trp Glu Arg Gly Arg Asp Thr
        115                 120                 125

His Leu Tyr Thr Glu Tyr Thr Leu Gln Leu Ser Gly Pro Lys Asn Leu
130                 135                 140

Thr Trp Gln Lys Gln Cys Lys Asp Ile Tyr Cys Asp Tyr Leu Asp Phe
145                 150                 155                 160

Gly Ile Asn Leu Thr Pro Glu Ser Pro Glu Ser Asn Phe Thr Ala Lys
                165                 170                 175

Val Thr Ala Val Asn Ser Leu Gly Ser Ser Ser Ser Leu Pro Ser Thr
            180                 185                 190

Phe Thr Phe Leu Asp Ile Val Arg Pro Leu Pro Pro Trp Asp Ile Arg
        195                 200                 205

Ile Lys Phe Gln Lys Ala Ser Val Ser Arg Cys Thr Leu Tyr Trp Arg
        210                 215                 220

Asp Glu Gly Leu Val Leu Leu Asn Arg Leu Arg Tyr Arg Pro Ser Asn
225                 230                 235                 240

Ser Arg Leu Trp Asn Met Val Asn Val Thr Lys Ala Lys Gly Arg His
                245                 250                 255

Asp Leu Leu Asp Leu Lys Pro Phe Thr Glu Tyr Glu Phe Gln Ile Ser
            260                 265                 270

Ser Lys Leu His Leu Tyr Lys Gly Ser Trp Ser Asp Trp Ser Glu Ser
        275                 280                 285

Leu Arg Ala Gln Thr Pro Glu Glu Pro Thr Gly Met Leu Asp Val
        290                 295                 300

Trp Tyr Met Lys Arg His Ile Asp Tyr Ser Arg Gln Gln Ile Ser Leu
305                 310                 315                 320

Phe Trp Lys Asn Leu Ser Val Ser Glu Ala Arg Gly Lys Ile Leu His
                325                 330                 335

Tyr Gln Val Thr Leu Gln Glu Leu Thr Gly Gly Lys Ala Met Thr Gln
            340                 345                 350

Asn Ile Thr Gly His Thr Ser Trp Thr Val Ile Pro Arg Thr Gly
        355                 360                 365

Asn Trp Ala Val Ala Val Ser Ala Ala Asn Ser Lys Gly Ser Ser Leu
        370                 375                 380

Pro Thr Arg Ile Asn Ile Met Asn Leu Cys Glu Ala Gly Leu Leu Ala
```

-continued

```
                385                 390                 395                 400
Pro Arg Gln Val Ser Ala Asn Ser Glu Gly Met Asp Asn Ile Leu Val
                        405                 410                 415
Thr Trp Gln Pro Pro Arg Lys Asp Pro Ser Ala Val Gln Glu Tyr Val
                        420                 425                 430
Val Glu Trp Arg Glu Leu His Pro Gly Gly Asp Thr Gln Val Pro Leu
                        435                 440                 445
Asn Trp Leu Arg Ser Arg Pro Tyr Asn Val Ser Ala Leu Ile Ser Glu
                450                 455                 460
Asn Ile Lys Ser Tyr Ile Cys Tyr Glu Ile Arg Val Tyr Ala Leu Ser
465                 470                 475                 480
Gly Asp Gln Gly Gly Cys Ser Ser Ile Leu Gly Asn Ser Lys His Lys
                        485                 490                 495
Ala Pro Leu Ser Gly Pro His Ile Asn Ala Ile Thr Glu Glu Lys Gly
                        500                 505                 510
Ser Ile Leu Ile Ser Trp Asn Ser Ile Pro Val Gln Glu Gln Met Gly
                        515                 520                 525
Cys Leu Leu His Tyr Arg Ile Tyr Trp Lys Glu Arg Asp Ser Asn Ser
                530                 535                 540
Gln Pro Gln Leu Cys Glu Ile Pro Tyr Arg Val Ser Gln Asn Ser His
545                 550                 555                 560
Pro Ile Asn Ser Leu Gln Pro Arg Val Thr Tyr Val Leu Trp Met Thr
                        565                 570                 575
Ala Leu Thr Ala Ala Gly Glu Ser Ser His Gly Asn Glu Arg Glu Phe
                        580                 585                 590
Cys Leu Gln Gly Lys Ala Asn
                        595

<210> SEQ ID NO 16
<211> LENGTH: 332
<212> TYPE: PRT
<213> ORGANISM: Homo sapiens

<400> SEQUENCE: 16

Gly Ile Thr Asn Ile Asn Cys Ser Gly His Ile Trp Val Glu Pro Ala
1               5                   10                  15
Thr Ile Phe Lys Met Gly Met Asn Ile Ser Ile Tyr Cys Gln Ala Ala
                20                  25                  30
Ile Lys Asn Cys Gln Pro Arg Lys Leu His Phe Tyr Lys Asn Gly Ile
                35                  40                  45
Lys Glu Arg Phe Gln Ile Thr Arg Ile Asn Lys Thr Thr Ala Arg Leu
        50                  55                  60
Trp Tyr Lys Asn Phe Leu Glu Pro His Ala Ser Met Tyr Cys Thr Ala
65                  70                  75                  80
Glu Cys Pro Lys His Phe Gln Glu Thr Leu Ile Cys Gly Lys Asp Ile
                85                  90                  95
Ser Ser Gly Tyr Pro Pro Asp Ile Pro Asp Glu Val Thr Cys Val Ile
                        100                 105                 110
Tyr Glu Tyr Ser Gly Asn Met Thr Cys Thr Trp Asn Ala Gly Lys Leu
                115                 120                 125
Thr Tyr Ile Asp Thr Lys Tyr Val Val His Val Lys Ser Leu Glu Thr
        130                 135                 140
Glu Glu Glu Gln Gln Tyr Leu Thr Ser Ser Tyr Ile Asn Ile Ser Thr
145                 150                 155                 160
Asp Ser Leu Gln Gly Gly Lys Lys Tyr Leu Val Trp Val Gln Ala Ala
```

```
                            165                 170                 175
Asn Ala Leu Gly Met Glu Glu Ser Lys Gln Leu Gln Ile His Leu Asp
                180                 185                 190

Asp Ile Val Ile Pro Ser Ala Ala Val Ile Ser Arg Ala Glu Thr Ile
            195                 200                 205

Asn Ala Thr Val Pro Lys Thr Ile Ile Tyr Trp Asp Ser Gln Thr Thr
        210                 215                 220

Ile Glu Lys Val Ser Cys Glu Met Arg Tyr Lys Ala Thr Thr Asn Gln
225                 230                 235                 240

Thr Trp Asn Val Lys Glu Phe Asp Thr Asn Phe Thr Tyr Val Gln Gln
                245                 250                 255

Ser Glu Phe Tyr Leu Glu Pro Asn Ile Lys Tyr Val Phe Gln Val Arg
            260                 265                 270

Cys Gln Glu Thr Gly Lys Arg Tyr Trp Gln Pro Trp Ser Ser Pro Phe
        275                 280                 285

Phe His Lys Thr Pro Glu Thr Val Pro Gln Val Thr Ser Lys Ala Phe
    290                 295                 300

Gln His Asp Thr Trp Asn Ser Gly Leu Thr Val Ala Ser Ile Ser Thr
305                 310                 315                 320

Gly His Leu Thr Ser Asp Asn Arg Gly Asp Ile Gly
                325                 330

<210> SEQ ID NO 17
<211> LENGTH: 98
<212> TYPE: PRT
<213> ORGANISM: Homo sapiens

<400> SEQUENCE: 17

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr

<210> SEQ ID NO 18
<211> LENGTH: 98
<212> TYPE: PRT
<213> ORGANISM: Homo sapiens

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60
```

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr

<210> SEQ ID NO 19
<211> LENGTH: 98
<212> TYPE: PRT
<213> ORGANISM: Homo sapiens

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg

<210> SEQ ID NO 20
<211> LENGTH: 15
<212> TYPE: PRT
<213> ORGANISM: Homo sapiens

<400> SEQUENCE: 20

Ala Phe Asp Val Trp Gly Gln Gly Thr Met Val Thr Val Ser Ser
1               5                   10                  15

<210> SEQ ID NO 21
<211> LENGTH: 95
<212> TYPE: PRT
<213> ORGANISM: Homo sapiens

<400> SEQUENCE: 21

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
                20                  25                  30

Leu His Trp Tyr Gln Gln Lys Pro Asp Gln Ser Pro Lys Leu Leu Ile
            35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro
                85                  90                  95

<210> SEQ ID NO 22
<211> LENGTH: 95
<212> TYPE: PRT
<213> ORGANISM: Homo sapiens

<400> SEQUENCE: 22

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
                35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95
```

<210> SEQ ID NO 23
<211> LENGTH: 95
<212> TYPE: PRT
<213> ORGANISM: Homo sapiens

<400> SEQUENCE: 23

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
                35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95
```

<210> SEQ ID NO 24
<211> LENGTH: 13
<212> TYPE: PRT
<213> ORGANISM: Homo sapiens

<400> SEQUENCE: 24

```
Leu Thr Phe Gly Gly Gly Thr Lys Val Glu Ile Lys Arg
1               5                   10
```

<210> SEQ ID NO 25
<211> LENGTH: 119
<212> TYPE: PRT
<213> ORGANISM: Homo sapiens

<400> SEQUENCE: 25

```
Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Asp Phe
            20                  25                  30

Tyr Met Tyr Trp Val Arg Gln Ala Pro Gly Lys Gly Leu Glu Trp Met
                35                  40                  45

Gly Leu Ile Asp Pro Asp Ala Asp Thr Met Tyr Ala Glu Lys Phe
    50                  55                  60

Arg Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
```

```
                     85                  90                  95
Ala Ala Asp Pro Trp Glu Leu Asn Ala Phe Asn Val Trp Gly Gln Gly
            100                 105                 110

Thr Leu Val Ser Val Ser Ser
        115

<210> SEQ ID NO 26
<211> LENGTH: 107
<212> TYPE: PRT
<213> ORGANISM: Homo sapiens

<400> SEQUENCE: 26

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Thr Trp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Ser Leu Thr Ile Asn Ser Leu Gln Pro
65                  70                  75                  80

Glu Asp Phe Ala Thr Tyr Tyr Cys Gln Gln Ala Asn Ser Phe Phe Thr
                85                  90                  95

Phe Gly Gly Gly Thr Lys Val Glu Ile Lys Arg
            100                 105

<210> SEQ ID NO 27
<211> LENGTH: 241
<212> TYPE: PRT
<213> ORGANISM: Artificial Sequence
<220> FEATURE:
<223> OTHER INFORMATION: Synthetic

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Gln Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Thr
            100                 105                 110

Met Val Thr Val Ser Ser Gly Gly Gly Gly Ser Gly Gly Gly Gly Ser
        115                 120                 125

Gly Gly Gly Ala Ser Glu Ile Val Met Thr Gln Ser Pro Ala Thr Leu
    130                 135                 140

Ser Val Ser Pro Gly Glu Arg Ala Thr Leu Ser Cys Arg Ala Ser Gln
145                 150                 155                 160

Ser Ile Ser Ile Asn Leu His Trp Tyr Gln Gln Lys Pro Gly Gln Ala
                165                 170                 175
```

```
Pro Arg Leu Leu Ile Tyr Phe Ala Ser Gln Ser Ile Ser Gly Ile Pro
            180                 185                 190
Ala Arg Phe Ser Gly Ser Gly Ser Gly Thr Glu Phe Thr Leu Thr Ile
        195                 200                 205
Ser Ser Leu Gln Ser Glu Asp Phe Ala Val Tyr Tyr Cys Gln Gln Ser
210                 215                 220
Asn Ser Phe Pro Leu Thr Phe Gly Gly Gly Thr Lys Val Glu Ile Lys
225                 230                 235                 240
Arg

<210> SEQ ID NO 28
<211> LENGTH: 118
<212> TYPE: PRT
<213> ORGANISM: Artificial Sequence
<220> FEATURE:
<223> OTHER INFORMATION: Synthetic

<400> SEQUENCE: 28

Gln Val Gln Leu Val Gln Ser Gly Ala Glu Val Lys Lys Pro Gly Ala
1               5                   10                  15
Ser Val Lys Val Ser Cys Lys Ala Ser Gly Cys Thr Phe Thr Asp Tyr
            20                  25                  30
Tyr Leu His Trp Val Arg Gln Ala Pro Gly Gln Gly Leu Glu Trp Met
        35                  40                  45
Gly Trp Ile Asp Pro Glu Asn Gly Asp Thr Glu Tyr Ala Pro Lys Phe
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Asn Ala Asn Lys Glu Leu Arg Tyr Phe Asp Val Trp Gly Gln Gly Thr
            100                 105                 110
Met Val Thr Val Ser Ser
        115

<210> SEQ ID NO 29
<211> LENGTH: 118
<212> TYPE: PRT
<213> ORGANISM: Artificial Sequence
<220> FEATURE:
<223> OTHER INFORMATION: Synthetic

<400> SEQUENCE: 29

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
            20                  25                  30
Tyr Leu His Trp Val Arg Gln Ala Pro Gly Gln Gly Leu Glu Trp Met
        35                  40                  45
Gly Trp Ile Asp Pro Glu Asn Gly Asp Thr Glu Tyr Ala Pro Lys Phe
    50                  55                  60
Gln Gly Arg Val Thr Val Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Asn Ala Asn Lys Glu Leu Arg Tyr Phe Asp Val Trp Gly Gln Gly Thr
            100                 105                 110
Met Val Thr Val Ser Ser
```

<210> SEQ ID NO 30
<211> LENGTH: 118
<212> TYPE: PRT
<213> ORGANISM: Artificial Sequence
<220> FEATURE:
<223> OTHER INFORMATION: Synthetic

<400> SEQUENCE: 30

```
Gln Val Gln Leu Val Gln Ser Gly Ala Gln Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Gln Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Thr
            100                 105                 110

Met Val Thr Val Ser Ser
        115
```

<210> SEQ ID NO 31
<211> LENGTH: 118
<212> TYPE: PRT
<213> ORGANISM: Artificial Sequence
<220> FEATURE:
<223> OTHER INFORMATION: Synthetic

<400> SEQUENCE: 31

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Asp Tyr
            20                  25                  30

Tyr Leu His Trp Val Arg Gln Ala Pro Gly Gln Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Ala
            100                 105                 110

Met Val Thr Val Ser Ser
        115
```

<210> SEQ ID NO 32
<211> LENGTH: 108
<212> TYPE: PRT
<213> ORGANISM: Artificial Sequence
<220> FEATURE:
<223> OTHER INFORMATION: Synthetic

<400> SEQUENCE: 32

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ile Asn
            20                  25                  30

Leu His Trp Tyr Gln Gln Lys Pro Gly Gln Ala Pro Arg Leu Leu Ile
        35                  40                  45

Tyr Phe Ala Ser Gln Ser Ile Ser Gly Ile Pro Ala Arg Phe Phe Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Asn Ser Phe Pro Leu
                85                  90                  95

Thr Phe Gly Gly Gly Thr Lys Val Glu Ile Lys Arg
            100                 105

<210> SEQ ID NO 33
<211> LENGTH: 118
<212> TYPE: PRT
<213> ORGANISM: Artificial Sequence
<220> FEATURE:
<223> OTHER INFORMATION: Synthetic

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Gln Gly Leu Glu Trp Met
        35                  40                  45

Gly Trp Ile Asp Pro Glu Asn Gly Asp Thr Glu His Ala Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Asn Ala Asn Lys Glu Leu Arg Tyr Phe Asp Val Trp Gly Gln Gly Thr
            100                 105                 110

Met Val Thr Val Ser Ser
        115

<210> SEQ ID NO 34
<211> LENGTH: 118
<212> TYPE: PRT
<213> ORGANISM: Artificial Sequence
<220> FEATURE:
<223> OTHER INFORMATION: Synthetic

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Gln Gly Leu Glu Trp Met
        35                  40                  45

Gly Trp Ile Asp Pro Glu Asn Gly Asp Thr Glu Ser Ala Pro Lys Phe
    50                  55                  60

Gln Gly Arg Val Thr Met Thr Thr Asp Thr Ser Thr Ser Thr Ala Tyr
65                  70                  75                  80

-continued

```
Met Glu Leu Arg Ser Leu Arg Ser Asp Asp Thr Ala Val Tyr Tyr Cys
            85                  90                  95

Asn Ala Asn Lys Glu Leu Arg Tyr Phe Asp Val Trp Gly Gln Gly Thr
            100                 105                 110

Met Val Thr Val Ser Ser
            115

<210> SEQ ID NO 35
<211> LENGTH: 118
<212> TYPE: PRT
<213> ORGANISM: Artificial Sequence
<220> FEATURE:
<223> OTHER INFORMATION: Synthetic

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Gln Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
            85                  90                  95

Asn Ala Asn Lys Glu Leu Arg Tyr Phe Asp Val Trp Gly Gln Gly Thr
            100                 105                 110

Met Val Thr Val Ser Ser
            115

<210> SEQ ID NO 36
<211> LENGTH: 118
<212> TYPE: PRT
<213> ORGANISM: Artificial Sequence
<220> FEATURE:
<223> OTHER INFORMATION: Synthetic

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Gln Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Asn Ala Asn Lys Glu Leu Arg Tyr Phe Asp Val Trp Gly Gln Gly Thr
            100                 105                 110

Met Val Thr Val Pro Ser
            115

<210> SEQ ID NO 37
<211> LENGTH: 108
```

```
<212> TYPE: PRT
<213> ORGANISM: Artificial Sequence
<220> FEATURE:
<223> OTHER INFORMATION: Synthetic

<400> SEQUENCE: 37

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ile Asn
            20                  25                  30

Leu His Trp Tyr Gln Gln Lys Pro Gly Gln Ala Pro Arg Leu Leu Ile
        35                  40                  45

Tyr Phe Ala Ser Gln Ser Ile Ser Gly Ile Pro Ala Arg Phe Ser Gly
    50                  55                  60

Ser Gly Ser Gly Thr Glu Phe Thr Leu Thr Ser Ser Leu Gln Ser
65                  70                  75                  80

Glu Asp Phe Ala Val Tyr Tyr Cys Gln Gln Ser Asn Ser Phe Pro Leu
                85                  90                  95

Thr Phe Gly Gly Gly Thr Lys Val Glu Ile Lys Arg
            100                 105

<210> SEQ ID NO 38
<211> LENGTH: 118
<212> TYPE: PRT
<213> ORGANISM: Artificial Sequence
<220> FEATURE:
<223> OTHER INFORMATION: Synthetic

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Asp Tyr
            20                  25                  30

Tyr Leu His Trp Val Arg Gln Ala Pro Gly Gln Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Thr
            100                 105                 110

Met Val Thr Val Ser Ser
        115

<210> SEQ ID NO 39
<211> LENGTH: 118
<212> TYPE: PRT
<213> ORGANISM: Artificial Sequence
<220> FEATURE:
<223> OTHER INFORMATION: Synthetic

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45
```

Gly Trp Ile Asp Pro Glu Asn Gly Asp Thr Glu Tyr Ala Pro Lys Phe
            50                  55                  60

Gln Gly Arg Val Thr Met Thr Thr Asp Thr Ser Ser Thr Ala Tyr
 65                  70                  75                  80

Met Glu Leu Arg Ser Leu Arg Ser Asp Asp Thr Ala Val Tyr Tyr Cys
                 85                  90                  95

Asn Ala Asn Lys Glu Leu Arg Tyr Phe Asp Val Trp Gly Gln Gly Thr
                100                 105                 110

Met Val Thr Val Ser Ser
        115

<210> SEQ ID NO 40
<211> LENGTH: 118
<212> TYPE: PRT
<213> ORGANISM: Artificial Sequence
<220> FEATURE:
<223> OTHER INFORMATION: Synthetic

<400> SEQUENCE: 40

Gln Val Gln Leu Val Gln Ser Gly Ala Glu Val Glu Lys Pro Gly Ala
  1               5                  10                  15

Ser Val Lys Val Ser Cys Lys Ala Ser Gly Tyr Thr Phe Thr Asp Tyr
                 20                  25                  30

Tyr Leu His Trp Val Arg Gln Ala Pro Gly Gln Gly Leu Glu Trp Met
             35                  40                  45

Gly Trp Ile Asp Pro Glu Asn Gly Asp Thr Glu Tyr Ala Pro Lys Phe
         50                  55                  60

Gln Gly Gly Val Thr Met Thr Thr Asp Thr Ser Ser Thr Ala Tyr
 65                  70                  75                  80

Met Glu Leu Arg Ser Leu Arg Ser Asp Asp Thr Ala Val Tyr Tyr Cys
                 85                  90                  95

Asn Ala Asn Lys Glu Leu Arg Tyr Phe Asp Val Trp Gly Gln Gly Thr
                100                 105                 110

Met Val Thr Val Ser Ser
        115

<210> SEQ ID NO 41
<211> LENGTH: 118
<212> TYPE: PRT
<213> ORGANISM: Artificial Sequence
<220> FEATURE:
<223> OTHER INFORMATION: Synthetic

<400> SEQUENCE: 41

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asp Tyr
                 20                  25                  30

Tyr Leu His Trp Val Arg Gln Ala Pro Gly Arg Gly Leu Glu Trp Met
             35                  40                  45

Gly Trp Ile Asp Pro Glu Asn Gly Asp Thr Glu Tyr Ala Pro Lys Phe
         50                  55                  60

Gln Gly Arg Val Thr Met Thr Thr Asp Thr Ser Ser Thr Ala Tyr
 65                  70                  75                  80

Met Glu Leu Arg Ser Leu Arg Ser Asp Asp Thr Ala Val Tyr Tyr Cys
                 85                  90                  95

Asn Ala Asn Lys Glu Leu Arg Tyr Phe Asp Val Trp Gly Gln Gly Thr
                100                 105                 110

```
Met Val Thr Val Ser Ser
        115

<210> SEQ ID NO 42
<211> LENGTH: 108
<212> TYPE: PRT
<213> ORGANISM: Artificial Sequence
<220> FEATURE:
<223> OTHER INFORMATION: Synthetic

<400> SEQUENCE: 42

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ile Asn
            20                  25                  30

Leu His Trp Tyr Gln Gln Lys Pro Gly Gln Ala Pro Arg Leu Leu Ile
        35                  40                  45

Tyr Phe Ala Ser Gln Ser Thr Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Asn Ser Phe Pro Leu
                85                  90                  95

Thr Phe Gly Gly Gly Thr Lys Val Glu Ile Lys Arg
            100                 105

<210> SEQ ID NO 43
<211> LENGTH: 118
<212> TYPE: PRT
<213> ORGANISM: Artificial Sequence
<220> FEATURE:
<223> OTHER INFORMATION: Synthetic

<400> SEQUENCE: 43

Gln Val Gln Leu Leu Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Gln Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Thr
            100                 105                 110

Met Val Thr Val Ser Ser
        115

<210> SEQ ID NO 44
<211> LENGTH: 118
<212> TYPE: PRT
<213> ORGANISM: Artificial Sequence
<220> FEATURE:
<223> OTHER INFORMATION: Synthetic

<400> SEQUENCE: 44

Gln Val Gln Leu Val Gln Ser Gly Ala Glu Val Lys Lys Pro Gly Ala
```

```
                1               5                   10                  15
Ser Val Lys Val Ser Cys Lys Ala Ser Gly Tyr Ala Phe Thr Asp Tyr
                20                  25                  30

Tyr Leu His Trp Val Arg Gln Ala Pro Gly Gln Gly Leu Glu Trp Met
                35                  40                  45

Gly Trp Ile Asp Pro Glu Asn Gly Asp Thr Glu Tyr Ala Pro Lys Phe
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Thr
                100                 105                 110

Met Val Thr Val Ser Ser
            115
```

<210> SEQ ID NO 45
<211> LENGTH: 118
<212> TYPE: PRT
<213> ORGANISM: Artificial Sequence
<220> FEATURE:
<223> OTHER INFORMATION: Synthetic

<400> SEQUENCE: 45

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asp Tyr
                20                  25                  30

Tyr Leu His Trp Val Arg Gln Ala Pro Gly Gln Gly Leu Glu Trp Met
                35                  40                  45

Gly Trp Ile Asp Pro Glu Asn Gly Asp Thr Glu Tyr Ala Pro Lys Phe
        50                  55                  60

Gln Gly Arg Val Ser Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Thr
                100                 105                 110

Met Val Thr Val Ser Ser
            115
```

<210> SEQ ID NO 46
<211> LENGTH: 108
<212> TYPE: PRT
<213> ORGANISM: Artificial Sequence
<220> FEATURE:
<223> OTHER INFORMATION: Synthetic

<400> SEQUENCE: 46

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ile Asn
                20                  25                  30

Leu His Trp Tyr Gln Gln Lys Pro Gly Gln Ala Pro Arg Leu Leu Ile
                35                  40                  45

Tyr Phe Ala Ser Gln Ser Ile Ser Gly Ile Pro Ala Arg Phe Ser Gly
        50                  55                  60

Ser Gly Ser Gly Thr Glu Phe Thr Leu Thr Ile Ser Ser Leu Gln Ser
```

```
                65                  70                  75                  80
Glu Asp Phe Ala Val His Tyr Cys Gln Gln Ser Asn Ser Phe Pro Leu
                    85                  90                  95

Thr Phe Gly Gly Gly Thr Lys Val Glu Ile Lys Arg
                100                 105

<210> SEQ ID NO 47
<211> LENGTH: 108
<212> TYPE: PRT
<213> ORGANISM: Artificial Sequence
<220> FEATURE:
<223> OTHER INFORMATION: Synthetic

<400> SEQUENCE: 47

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ile Asn
                20                  25                  30

Leu His Trp Tyr Gln Gln Lys Pro Gly Gln Ala Pro Arg Leu Leu Ile
            35                  40                  45

Tyr Phe Ala Arg Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Asn Ser Phe Pro Leu
                85                  90                  95

Thr Phe Gly Gly Gly Thr Lys Val Glu Ile Lys Arg
                100                 105

<210> SEQ ID NO 48
<211> LENGTH: 108
<212> TYPE: PRT
<213> ORGANISM: Artificial Sequence
<220> FEATURE:
<223> OTHER INFORMATION: Synthetic

<400> SEQUENCE: 48

Glu Ile Val Met Thr Gln Ser Pro Ala Thr Leu Ser Met Ser Pro Gly
1               5                   10                  15

Glu Arg Ala Thr Leu Ser Cys Arg Ala Ser Gln Ser Ile Ser Ile Asn
                20                  25                  30

Leu His Trp Tyr Gln Gln Lys Pro Gly Gln Ala Pro Arg Leu Leu Ile
            35                  40                  45

Tyr Phe Ala Ser Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Asn Ser Phe Pro Leu
                85                  90                  95

Thr Phe Gly Gly Gly Thr Lys Val Glu Ile Lys Arg
                100                 105

<210> SEQ ID NO 49
<211> LENGTH: 108
<212> TYPE: PRT
<213> ORGANISM: Artificial Sequence
<220> FEATURE:
<223> OTHER INFORMATION: Synthetic

<400> SEQUENCE: 49
```

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ile Asn
            20                  25                  30

Leu His Trp Tyr Gln Gln Lys Pro Gly Gln Ala Pro Arg Leu Leu Ile
        35                  40                  45

Tyr Phe Ala Ser Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Gly Phe Ala Val Tyr Tyr Cys Gln Gln Ser Asn Ser Phe Pro Leu
                85                  90                  95

Thr Phe Gly Gly Gly Thr Lys Val Glu Ile Lys Arg
            100                 105
```

<210> SEQ ID NO 50
<211> LENGTH: 108
<212> TYPE: PRT
<213> ORGANISM: Artificial Sequence
<220> FEATURE:
<223> OTHER INFORMATION: Synthetic

<400> SEQUENCE: 50

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ile Asn
            20                  25                  30

Leu His Trp Tyr Gln Gln Lys Pro Gly Gln Ala Pro Arg Leu Leu Ile
        35                  40                  45

Tyr Phe Ala Ser Gln Ser Ile Ser Gly Ile Pro Ala Arg Phe Ser Ser
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Asn Ser Phe Pro Leu
                85                  90                  95

Thr Phe Gly Gly Gly Thr Lys Val Glu Ile Lys Arg
            100                 105
```

<210> SEQ ID NO 51
<211> LENGTH: 108
<212> TYPE: PRT
<213> ORGANISM: Artificial Sequence
<220> FEATURE:
<223> OTHER INFORMATION: Synthetic

<400> SEQUENCE: 51

```
Glu Ile Val Met Thr Gln Ser Pro Ala Thr Leu Ser Val Ser Pro Gly
1               5                   10                  15

Glu Arg Ala Thr Leu Ser Cys Arg Ala Pro Gln Ser Ile Ser Ile Asn
            20                  25                  30

Leu His Trp Tyr Gln Gln Lys Pro Gly Gln Ala Pro Arg Leu Leu Ile
        35                  40                  45

Tyr Phe Ala Ser Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Asn Ser Phe Pro Leu
                85                  90                  95
```

Thr Phe Gly Gly Gly Thr Lys Val Glu Ile Lys Arg
            100                 105

<210> SEQ ID NO 52
<211> LENGTH: 108
<212> TYPE: PRT
<213> ORGANISM: Artificial Sequence
<220> FEATURE:
<223> OTHER INFORMATION: Synthetic

<400> SEQUENCE: 52

Glu Ile Val Met Thr Gln Ser Pro Ala Thr Leu Ser Val Ser Pro Gly
1               5                   10                  15

Glu Arg Ala Thr Leu Ser Cys Arg Ala Ser Arg Ser Ile Ser Ile Asn
            20                  25                  30

Leu His Trp Tyr Gln Gln Lys Pro Gly Gln Ala Pro Arg Leu Leu Ile
        35                  40                  45

Tyr Phe Ala Ser Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Asn Ser Phe Pro Leu
                85                  90                  95

Thr Phe Gly Gly Gly Thr Lys Val Glu Ile Lys Arg
            100                 105

<210> SEQ ID NO 53
<211> LENGTH: 118
<212> TYPE: PRT
<213> ORGANISM: Artificial Sequence
<220> FEATURE:
<223> OTHER INFORMATION: Synthetic

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Arg Gly Leu Glu Trp Met
        35                  40                  45

Gly Trp Ile Asp Pro Glu Asn Gly Asp Thr Glu His Ala Pro Lys Phe
    50                  55                  60

Gln Gly Arg Val Thr Met Thr Arg Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Thr
            100                 105                 110

Met Val Thr Val Ser Ser
        115

<210> SEQ ID NO 54
<211> LENGTH: 118
<212> TYPE: PRT
<213> ORGANISM: Artificial Sequence
<220> FEATURE:
<223> OTHER INFORMATION: Synthetic

<400> SEQUENCE: 54

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Ala Phe Thr Asp Tyr
            20                  25                  30

Tyr Leu His Trp Val Arg Gln Ala Pro Gly Gln Gly Leu Glu Trp Met
        35                  40                  45

Gly Trp Ile Asp Pro Glu Asn Gly Asp Thr Glu Ser Ala Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Thr
                100                 105                 110

Met Val Thr Val Ser Ser
            115

<210> SEQ ID NO 55
<211> LENGTH: 118
<212> TYPE: PRT
<213> ORGANISM: Artificial Sequence
<220> FEATURE:
<223> OTHER INFORMATION: Synthetic

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asp Tyr
            20                  25                  30

Tyr Leu His Trp Val Arg Gln Ala Pro Gly Gln Gly Leu Glu Trp Met
        35                  40                  45

Gly Trp Ile Asp Pro Glu Asn Gly Asp Thr Glu His Ala Pro Lys Phe
    50                  55                  60

Gln Gly Arg Val Ser Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Thr
                100                 105                 110

Met Val Thr Val Ser Ser
            115

<210> SEQ ID NO 56
<211> LENGTH: 118
<212> TYPE: PRT
<213> ORGANISM: Artificial Sequence
<220> FEATURE:
<223> OTHER INFORMATION: Synthetic

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Asp Tyr
            20                  25                  30

Tyr Leu His Trp Val Arg Gln Ala Pro Gly Gln Gly Leu Glu Trp Met
        35                  40                  45

Gly Trp Ile Asp Pro Glu Asn Gly Asp Thr Glu His Ala Pro Lys Phe
    50                  55                  60

Gln Gly Arg Val Thr Met Thr Thr Asp Thr Ser Thr Ser Thr Ala Tyr
65                  70                  75                  80
```

```
Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Thr
            100                 105                 110

Met Val Thr Val Ser Ser
        115

<210> SEQ ID NO 57
<211> LENGTH: 118
<212> TYPE: PRT
<213> ORGANISM: Artificial Sequence
<220> FEATURE:
<223> OTHER INFORMATION: Synthetic

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Asp Tyr
            20                  25                  30

Tyr Leu His Trp Val Arg Gln Ala Pro Gly Gln Gly Leu Glu Trp Met
        35                  40                  45

Gly Trp Ile Asp Pro Glu Asn Gly Asp Thr Glu Ser Ala Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Thr
            100                 105                 110

Met Val Thr Val Ser Ser
        115

<210> SEQ ID NO 58
<211> LENGTH: 118
<212> TYPE: PRT
<213> ORGANISM: Artificial Sequence
<220> FEATURE:
<223> OTHER INFORMATION: Synthetic

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Arg Gly Leu Glu Trp Met
        35                  40                  45

Gly Trp Ile Asp Pro Glu Asn Gly Asp Thr Glu Ser Ala Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Thr
            100                 105                 110

Met Val Thr Val Ser Ser
        115

<210> SEQ ID NO 59
```

```
<211> LENGTH: 118
<212> TYPE: PRT
<213> ORGANISM: Artificial Sequence
<220> FEATURE:
<223> OTHER INFORMATION: Synthetic

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asp Tyr
            20                  25                  30

Tyr Leu His Trp Val Arg Gln Ala Pro Gly Gln Gly Leu Glu Trp Met
        35                  40                  45

Gly Trp Ile Asp Pro Glu Asn Gly Asp Thr Glu His Ala Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Thr
            100                 105                 110

Met Val Thr Val Ser Ser
        115

<210> SEQ ID NO 60
<211> LENGTH: 118
<212> TYPE: PRT
<213> ORGANISM: Artificial Sequence
<220> FEATURE:
<223> OTHER INFORMATION: Synthetic

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asp Tyr
            20                  25                  30

Tyr Leu His Trp Val Arg Gln Ala Pro Gly Gln Gly Leu Glu Trp Met
        35                  40                  45

Gly Trp Ile Asp Pro Glu Asn Gly Asp Thr Glu Ser Ala Pro Lys Phe
    50                  55                  60

Gln Gly Arg Val Ser Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Thr
            100                 105                 110

Met Val Thr Val Ser Ser
        115

<210> SEQ ID NO 61
<211> LENGTH: 118
<212> TYPE: PRT
<213> ORGANISM: Artificial Sequence
<220> FEATURE:
<223> OTHER INFORMATION: Synthetic

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asp Tyr
```

```
                    20                  25                  30

Tyr Leu His Trp Val Arg Gln Ala Pro Gly Arg Gly Leu Glu Trp Met
            35                  40                  45

Gly Trp Ile Asp Pro Glu Asn Gly Asp Thr Glu Tyr Ala Pro Lys Phe
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Thr
            100                 105                 110

Met Val Thr Val Ser Ser
            115

<210> SEQ ID NO 62
<211> LENGTH: 118
<212> TYPE: PRT
<213> ORGANISM: Artificial Sequence
<220> FEATURE:
<223> OTHER INFORMATION: Synthetic

<400> SEQUENCE: 62

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Leu Thr Asp Tyr
                20                  25                  30

Tyr Leu His Trp Val Arg Gln Ala Pro Gly Arg Gly Leu Glu Trp Met
            35                  40                  45

Gly Trp Ile Asp Pro Glu Asn Gly Asp Thr Glu Tyr Ala Pro Lys Phe
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Thr
            100                 105                 110

Met Val Thr Val Ser Ser
            115

<210> SEQ ID NO 63
<211> LENGTH: 568
<212> TYPE: PRT
<213> ORGANISM: Artificial Sequence
<220> FEATURE:
<223> OTHER INFORMATION: Synthetic

<400> SEQUENCE: 63

Ile Trp Glu Leu Lys Lys Asp Val Tyr Val Val Glu Leu Asp Trp Tyr
1               5                  10                  15

Pro Asp Ala Pro Gly Glu Met Val Val Leu Thr Cys Asp Thr Pro Glu
                20                  25                  30

Glu Asp Gly Ile Thr Trp Thr Leu Asp Gln Ser Ser Glu Val Leu Gly
            35                  40                  45

Ser Gly Lys Thr Leu Thr Ile Gln Val Lys Glu Phe Gly Asp Ala Gly
        50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
```

-continued

```
                85                  90                  95
Asp Gln Lys Glu Pro Lys Asn Lys Thr Phe Leu Arg Cys Glu Ala Lys
            100                 105                 110
Asn Tyr Ser Gly Arg Phe Thr Cys Trp Trp Leu Thr Thr Ile Ser Thr
        115                 120                 125
Asp Leu Thr Phe Ser Val Lys Ser Ser Arg Gly Ser Ser Asp Pro Gln
    130                 135                 140
Gly Val Thr Cys Gly Ala Ala Thr Leu Ser Ala Glu Arg Val Arg Gly
145                 150                 155                 160
Asp Asn Lys Glu Tyr Glu Tyr Ser Val Glu Cys Gln Glu Asp Ser Ala
                165                 170                 175
Cys Pro Ala Ala Glu Glu Ser Leu Pro Ile Glu Val Met Val Asp Ala
            180                 185                 190
Val His Lys Leu Lys Tyr Glu Asn Tyr Thr Ser Ser Phe Phe Ile Arg
        195                 200                 205
Asp Ile Ile Lys Pro Asp Pro Pro Lys Asn Leu Gln Leu Lys Pro Leu
    210                 215                 220
Lys Asn Ser Arg Gln Val Glu Val Ser Trp Glu Tyr Pro Asp Thr Trp
225                 230                 235                 240
Ser Thr Pro His Ser Tyr Phe Ser Leu Thr Phe Cys Val Gln Val Gln
                245                 250                 255
Gly Lys Ser Lys Arg Glu Lys Lys Asp Arg Val Phe Thr Asp Lys Thr
            260                 265                 270
Ser Ala Thr Val Ile Cys Arg Lys Asn Ala Ser Ile Ser Val Arg Ala
        275                 280                 285
Gln Asp Arg Tyr Tyr Ser Ser Ser Trp Ser Glu Trp Ala Ser Val Pro
    290                 295                 300
Cys Ser Gly Ser Gly Ser Ser Arg Gly Gly Ser Gly Gly Gly Gly Ser
305                 310                 315                 320
Gly Gly Gly Gly Ser Lys Leu Arg Val Ile Pro Val Ser Gly Pro Ala
                325                 330                 335
Arg Cys Leu Ser Gln Ser Arg Asn Leu Leu Lys Thr Thr Asp Asp Met
            340                 345                 350
Val Lys Thr Ala Arg Glu Lys Leu Lys His Tyr Ser Cys Thr Ala Glu
        355                 360                 365
Asp Ile Asp His Glu Asp Ile Thr Arg Asp Gln Thr Ser Thr Leu Lys
    370                 375                 380
Thr Cys Leu Pro Leu Glu Leu His Lys Asn Glu Ser Cys Leu Ala Thr
385                 390                 395                 400
Arg Glu Thr Ser Ser Thr Thr Arg Gly Ser Cys Leu Pro Pro Gln Lys
                405                 410                 415
Thr Ser Leu Met Met Thr Leu Cys Leu Gly Ser Ile Tyr Glu Asp Leu
            420                 425                 430
Lys Met Tyr Gln Thr Glu Phe Gln Ala Ile Asn Ala Ala Leu Gln Asn
        435                 440                 445
His Asn His Gln Gln Ile Ile Leu Asp Lys Gly Met Leu Val Ala Ile
    450                 455                 460
Asp Glu Leu Met Gln Ser Leu Asn His Asn Gly Glu Thr Leu Arg Gln
465                 470                 475                 480
Lys Pro Pro Val Gly Glu Ala Asp Pro Tyr Arg Val Lys Met Lys Leu
                485                 490                 495
Cys Ile Leu Leu His Ala Phe Ser Thr Arg Val Val Thr Ile Asn Arg
            500                 505                 510
```

```
Val Met Gly Tyr Leu Ser Ser Ala Gly Ser Leu Val Pro Arg Gly Ser
        515                 520                 525

Ser Gly Asp Tyr Lys Asp His Asp Gly Asp Tyr Lys Asp His Asp Ile
530                 535                 540

Asp Tyr Lys Asp His Asp His His His His His His His His Glu Gln
545                 550                 555                 560

Lys Leu Ile Ser Glu Glu Asp Leu
                565

<210> SEQ ID NO 64
<211> LENGTH: 306
<212> TYPE: PRT
<213> ORGANISM: Artificial Sequence
<220> FEATURE:
<223> OTHER INFORMATION: Synthetic

<400> SEQUENCE: 64

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Arg Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
```

```
<210> SEQ ID NO 65
<211> LENGTH: 34
<212> TYPE: PRT
<213> ORGANISM: Homo sapiens

<400> SEQUENCE: 65
```

Val Gln Val Gln Gly Lys Ser Lys Arg Glu Lys Lys Asp Arg Val Phe
1               5                   10                  15

Thr Asp Lys Thr Ser Ala Thr Val Ile Cys Arg Lys Asn Ala Ser Ile
            20                  25                  30

Ser Val

```
<210> SEQ ID NO 66
<211> LENGTH: 497
<212> TYPE: PRT
<213> ORGANISM: Artificial Sequence
<220> FEATURE:
<223> OTHER INFORMATION: Synthetic

<400> SEQUENCE: 66
```

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala

```
                   275                 280                 285
Gln Asp Arg Tyr Tyr Ser Ser Trp Ser Glu Trp Ala Ser Val Pro
290                 295                 300

Cys Ser Gly Ser Gly Ser Arg Gly Gly Ser Gly Ser Gly Gly Ser
305                 310                 315                 320

Gly Gly Gly Gly Ser Lys Leu Arg Ala Val Pro Gly Gly Ser Ser Pro
                325                 330                 335

Ala Trp Thr Gln Cys Gln Gln Leu Ser Gln Lys Leu Cys Thr Leu Ala
                340                 345                 350

Trp Ser Ala His Pro Leu Val Gly His Met Asp Leu Arg Glu Glu Gly
                355                 360                 365

Asp Glu Glu Thr Thr Asn Asp Val Pro His Ile Gln Cys Gly Asp Gly
                370                 375                 380

Cys Asp Pro Gln Gly Leu Arg Asp Asn Ser Gln Phe Cys Leu Gln Arg
385                 390                 395                 400

Ile His Gln Gly Leu Ile Phe Tyr Glu Lys Leu Leu Gly Ser Asp Ile
                405                 410                 415

Phe Thr Gly Glu Pro Ser Leu Leu Pro Asp Ser Pro Val Gly Gln Leu
                420                 425                 430

His Ala Ser Leu Leu Gly Leu Ser Gln Leu Leu Gln Pro Glu Gly His
                435                 440                 445

His Trp Glu Thr Gln Gln Ile Pro Ser Leu Ser Pro Ser Gln Pro Trp
                450                 455                 460

Gln Arg Leu Leu Leu Arg Phe Lys Ile Leu Arg Ser Leu Gln Ala Phe
465                 470                 475                 480

Val Ala Val Ala Ala Arg Val Phe Ala His Gly Ala Ala Thr Leu Ser
                485                 490                 495

Pro

<210> SEQ ID NO 67
<211> LENGTH: 497
<212> TYPE: PRT
<213> ORGANISM: Artificial Sequence
<220> FEATURE:
<223> OTHER INFORMATION: Synthetic

<400> SEQUENCE: 67

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
                20                  25                  30

Glu Asp Gly Ile Thr Trp Thr Leu Asp Gln Ser Ser Glu Val Leu Gly
            35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
                100                 105                 110

Asn Tyr Ser Gly Arg Phe Thr Cys Trp Trp Leu Thr Thr Ile Ser Thr
            115                 120                 125

Asp Leu Thr Phe Ser Val Lys Ser Ser Arg Gly Ser Ser Asp Pro Gln
    130                 135                 140
```

```
Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
            165                 170                 175

Cys Pro Ala Ala Glu Glu Ser Leu Pro Ile Glu Val Met Val Asp Ala
        180                 185                 190

Val His Lys Leu Lys Tyr Glu Asn Tyr Thr Ser Ser Phe Phe Ile Arg
    195                 200                 205

Asp Ile Ile Lys Pro Asp Pro Pro Lys Asn Leu Gln Leu Lys Pro Leu
210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Ala Val Gln
            245                 250                 255

Gly Lys Ser Lys Arg Glu Lys Lys Asp Arg Val Phe Thr Asp Lys Thr
        260                 265                 270

Ser Ala Thr Val Ile Cys Arg Lys Asn Ala Ser Ile Ser Val Arg Ala
    275                 280                 285

Gln Asp Arg Tyr Tyr Ser Ser Ser Trp Ser Glu Trp Ala Ser Val Pro
290                 295                 300

Cys Ser Gly Ser Gly Ser Ser Arg Gly Gly Ser Gly Ser Gly Gly Ser
305                 310                 315                 320

Gly Gly Gly Gly Ser Lys Leu Arg Ala Val Pro Gly Gly Ser Ser Pro
            325                 330                 335

Ala Trp Thr Gln Cys Gln Gln Leu Ser Gln Lys Leu Cys Thr Leu Ala
        340                 345                 350

Trp Ser Ala His Pro Leu Val Gly His Met Asp Leu Arg Glu Glu Gly
    355                 360                 365

Asp Glu Glu Thr Thr Asn Asp Val Pro His Ile Gln Cys Gly Asp Gly
370                 375                 380

Cys Asp Pro Gln Gly Leu Arg Asp Asn Ser Gln Phe Cys Leu Gln Arg
385                 390                 395                 400

Ile His Gln Gly Leu Ile Phe Tyr Glu Lys Leu Leu Gly Ser Asp Ile
            405                 410                 415

Phe Thr Gly Glu Pro Ser Leu Leu Pro Asp Ser Pro Val Gly Gln Leu
        420                 425                 430

His Ala Ser Leu Leu Gly Leu Ser Gln Leu Leu Gln Pro Glu Gly His
    435                 440                 445

His Trp Glu Thr Gln Gln Ile Pro Ser Leu Ser Pro Ser Gln Pro Trp
450                 455                 460

Gln Arg Leu Leu Leu Arg Phe Lys Ile Leu Arg Ser Leu Gln Ala Phe
465                 470                 475                 480

Val Ala Val Ala Ala Arg Val Phe Ala His Gly Ala Ala Thr Leu Ser
            485                 490                 495

Pro

<210> SEQ ID NO 68
<211> LENGTH: 497
<212> TYPE: PRT
<213> ORGANISM: Artificial Sequence
<220> FEATURE:
<223> OTHER INFORMATION: Synthetic

<400> SEQUENCE: 68

Ile Trp Glu Leu Lys Lys Asp Val Tyr Val Val Glu Leu Asp Trp Tyr
1               5                   10                  15
```

-continued

Pro Asp Ala Pro Gly Glu Met Val Val Leu Thr Cys Asp Thr Pro Glu
                20                  25                  30

Glu Asp Gly Ile Thr Trp Thr Leu Asp Gln Ser Ser Glu Val Leu Gly
                35                  40                  45

Ser Gly Lys Thr Leu Thr Ile Gln Val Lys Glu Phe Gly Asp Ala Gly
        50                  55                  60

Gln Tyr Thr Cys His Lys Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
                100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
        130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
        180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
        210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Ala Gln
                245                 250                 255

Gly Lys Ser Lys Arg Glu Lys Lys Asp Arg Val Phe Thr Asp Lys Thr
                260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
        290                 295                 300

Cys Ser Gly Ser Gly Ser Ser Arg Gly Gly Ser Gly Ser Gly Gly Ser
305                 310                 315                 320

Gly Gly Gly Gly Ser Lys Leu Arg Ala Val Pro Gly Gly Ser Ser Pro
                325                 330                 335

Ala Trp Thr Gln Cys Gln Gln Leu Ser Gln Lys Leu Cys Thr Leu Ala
                340                 345                 350

Trp Ser Ala His Pro Leu Val Gly His Met Asp Leu Arg Glu Glu Gly
        355                 360                 365

Asp Glu Glu Thr Thr Asn Asp Val Pro His Ile Gln Cys Gly Asp Gly
        370                 375                 380

Cys Asp Pro Gln Gly Leu Arg Asp Asn Ser Gln Phe Cys Leu Gln Arg
385                 390                 395                 400

Ile His Gln Gly Leu Ile Phe Tyr Glu Lys Leu Leu Gly Ser Asp Ile
                405                 410                 415

Phe Thr Gly Glu Pro Ser Leu Leu Pro Asp Ser Pro Val Gly Gln Leu
        420                 425                 430

His Ala Ser Leu Leu Gly Leu Ser Gln Leu Leu Gln Pro Glu Gly His

```
                    435              440                 445
His Trp Glu Thr Gln Gln Ile Pro Ser Leu Ser Pro Ser Gln Pro Trp
                450              455                 460

Gln Arg Leu Leu Leu Arg Phe Lys Ile Leu Arg Ser Leu Gln Ala Phe
465              470                 475                 480

Val Ala Val Ala Ala Arg Val Phe Ala His Gly Ala Ala Thr Leu Ser
                    485                 490                 495

Pro

<210> SEQ ID NO 69
<211> LENGTH: 497
<212> TYPE: PRT
<213> ORGANISM: Artificial Sequence
<220> FEATURE:
<223> OTHER INFORMATION: Synthetic

<400> SEQUENCE: 69

Ile Trp Glu Leu Lys Lys Asp Val Tyr Val Glu Leu Asp Trp Tyr
1               5                   10                  15

Pro Asp Ala Pro Gly Glu Met Val Val Leu Thr Cys Asp Thr Pro Glu
                20                  25                  30

Glu Asp Gly Ile Thr Trp Thr Leu Asp Gln Ser Ser Glu Val Leu Gly
            35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Ala Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
290                 295                 300
```

```
Cys Ser Gly Ser Gly Ser Ser Arg Gly Gly Ser Gly Ser Gly Gly Ser
305                 310                 315                 320

Gly Gly Gly Gly Ser Lys Leu Arg Ala Val Pro Gly Gly Ser Ser Pro
            325                 330                 335

Ala Trp Thr Gln Cys Gln Gln Leu Ser Gln Lys Leu Cys Thr Leu Ala
        340                 345                 350

Trp Ser Ala His Pro Leu Val Gly His Met Asp Leu Arg Glu Glu Gly
        355                 360                 365

Asp Glu Glu Thr Thr Asn Asp Val Pro His Ile Gln Cys Gly Asp Gly
        370                 375                 380

Cys Asp Pro Gln Gly Leu Arg Asp Asn Ser Gln Phe Cys Leu Gln Arg
385                 390                 395                 400

Ile His Gln Gly Leu Ile Phe Tyr Glu Lys Leu Leu Gly Ser Asp Ile
                405                 410                 415

Phe Thr Gly Glu Pro Ser Leu Leu Pro Asp Ser Pro Val Gly Gln Leu
                420                 425                 430

His Ala Ser Leu Leu Gly Leu Ser Gln Leu Leu Gln Pro Glu Gly His
            435                 440                 445

His Trp Glu Thr Gln Gln Ile Pro Ser Leu Ser Pro Ser Gln Pro Trp
        450                 455                 460

Gln Arg Leu Leu Leu Arg Phe Lys Ile Leu Arg Ser Leu Gln Ala Phe
465                 470                 475                 480

Val Ala Val Ala Ala Arg Val Phe Ala His Gly Ala Ala Thr Leu Ser
                485                 490                 495

Pro

<210> SEQ ID NO 70
<211> LENGTH: 497
<212> TYPE: PRT
<213> ORGANISM: Artificial Sequence
<220> FEATURE:
<223> OTHER INFORMATION: Synthetic

<400> SEQUENCE: 70

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175
```

```
Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ala Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Ser Gly Ser Ser Arg Gly Gly Ser Gly Ser Gly Gly Ser
305                 310                 315                 320

Gly Gly Gly Gly Ser Lys Leu Arg Ala Val Pro Gly Gly Ser Ser Pro
                325                 330                 335

Ala Trp Thr Gln Cys Gln Gln Leu Ser Gln Lys Leu Cys Thr Leu Ala
            340                 345                 350

Trp Ser Ala His Pro Leu Val Gly His Met Asp Leu Arg Glu Glu Gly
        355                 360                 365

Asp Glu Glu Thr Thr Asn Asp Val Pro His Ile Gln Cys Gly Asp Gly
    370                 375                 380

Cys Asp Pro Gln Gly Leu Arg Asp Asn Ser Gln Phe Cys Leu Gln Arg
385                 390                 395                 400

Ile His Gln Gly Leu Ile Phe Tyr Glu Lys Leu Leu Gly Ser Asp Ile
                405                 410                 415

Phe Thr Gly Glu Pro Ser Leu Leu Pro Asp Ser Pro Val Gly Gln Leu
            420                 425                 430

His Ala Ser Leu Leu Gly Leu Ser Gln Leu Leu Gln Pro Glu Gly His
        435                 440                 445

His Trp Glu Thr Gln Gln Ile Pro Ser Leu Ser Pro Ser Gln Pro Trp
    450                 455                 460

Gln Arg Leu Leu Leu Arg Phe Lys Ile Leu Arg Ser Leu Gln Ala Phe
465                 470                 475                 480

Val Ala Val Ala Ala Arg Val Phe Ala His Gly Ala Ala Thr Leu Ser
                485                 490                 495

Pro

<210> SEQ ID NO 71
<211> LENGTH: 497
<212> TYPE: PRT
<213> ORGANISM: Artificial Sequence
<220> FEATURE:
<223> OTHER INFORMATION: Synthetic

<400> SEQUENCE: 71

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
```

```
                35                  40                  45
Ser Gly Lys Thr Leu Thr Ile Gln Val Lys Glu Phe Gly Asp Ala Gly
 50                  55                  60

Gln Tyr Thr Cys His Lys Gly Glu Val Leu Ser His Ser Leu Leu
 65                  70                  75                  80

Leu Leu His Lys Lys Glu Asp Gly Ile Trp Ser Thr Asp Ile Leu Lys
                 85                  90                  95

Asp Gln Lys Glu Pro Lys Asn Lys Thr Phe Leu Arg Cys Glu Ala Lys
                100                 105                 110

Asn Tyr Ser Gly Arg Phe Thr Cys Trp Trp Leu Thr Thr Ile Ser Thr
                115                 120                 125

Asp Leu Thr Phe Ser Val Lys Ser Ser Arg Gly Ser Ser Asp Pro Gln
                130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
                180                 185                 190

Val His Lys Leu Lys Tyr Glu Asn Tyr Thr Ser Ser Phe Phe Ile Arg
                195                 200                 205

Asp Ile Ile Lys Pro Asp Pro Pro Lys Asn Leu Gln Leu Lys Pro Leu
                210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Ala Arg Glu Lys Lys Asp Arg Val Phe Thr Asp Lys Thr
                260                 265                 270

Ser Ala Thr Val Ile Cys Arg Lys Asn Ala Ser Ile Ser Val Arg Ala
                275                 280                 285

Gln Asp Arg Tyr Tyr Ser Ser Ser Trp Ser Glu Trp Ala Ser Val Pro
290                 295                 300

Cys Ser Gly Ser Gly Ser Ser Arg Gly Gly Ser Gly Ser Gly Gly Ser
305                 310                 315                 320

Gly Gly Gly Gly Ser Lys Leu Arg Ala Val Pro Gly Gly Ser Ser Pro
                325                 330                 335

Ala Trp Thr Gln Cys Gln Gln Leu Ser Gln Lys Leu Cys Thr Leu Ala
                340                 345                 350

Trp Ser Ala His Pro Leu Val Gly His Met Asp Leu Arg Glu Glu Gly
                355                 360                 365

Asp Glu Glu Thr Thr Asn Asp Val Pro His Ile Gln Cys Gly Asp Gly
                370                 375                 380

Cys Asp Pro Gln Gly Leu Arg Asp Asn Ser Gln Phe Cys Leu Gln Arg
385                 390                 395                 400

Ile His Gln Gly Leu Ile Phe Tyr Glu Lys Leu Leu Gly Ser Asp Ile
                405                 410                 415

Phe Thr Gly Glu Pro Ser Leu Leu Pro Asp Ser Pro Val Gly Gln Leu
                420                 425                 430

His Ala Ser Leu Leu Gly Leu Ser Gln Leu Leu Gln Pro Glu Gly His
                435                 440                 445

His Trp Glu Thr Gln Gln Ile Pro Ser Leu Ser Pro Ser Gln Pro Trp
                450                 455                 460
```

```
Gln Arg Leu Leu Leu Arg Phe Lys Ile Leu Arg Ser Leu Gln Ala Phe
465                 470                 475                 480

Val Ala Val Ala Ala Arg Val Phe Ala His Gly Ala Ala Thr Leu Ser
                485                 490                 495

Pro

<210> SEQ ID NO 72
<211> LENGTH: 497
<212> TYPE: PRT
<213> ORGANISM: Artificial Sequence
<220> FEATURE:
<223> OTHER INFORMATION: Synthetic

<400> SEQUENCE: 72

Ile Trp Glu Leu Lys Lys Asp Val Tyr Val Glu Leu Asp Trp Tyr
1               5                   10                  15

Pro Asp Ala Pro Gly Glu Met Val Val Leu Thr Cys Asp Thr Pro Glu
                20                  25                  30

Glu Asp Gly Ile Thr Trp Thr Leu Asp Gln Ser Ser Glu Val Leu Gly
                35                  40                  45

Ser Gly Lys Thr Leu Thr Ile Gln Val Lys Glu Phe Gly Asp Ala Gly
50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
                100                 105                 110

Asn Tyr Ser Gly Arg Phe Thr Cys Trp Trp Leu Thr Thr Ile Ser Thr
            115                 120                 125

Asp Leu Thr Phe Ser Val Lys Ser Ser Arg Gly Ser Ser Asp Pro Gln
130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Ala Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Ser Gly Ser Arg Gly Gly Ser Gly Ser Gly Gly Ser
305                 310                 315                 320

Gly Gly Gly Gly Ser Lys Leu Arg Ala Val Pro Gly Ser Ser Pro
                325                 330                 335
```

```
Ala Trp Thr Gln Cys Gln Gln Leu Ser Gln Lys Leu Cys Thr Leu Ala
            340                 345                 350

Trp Ser Ala His Pro Leu Val Gly His Met Asp Leu Arg Glu Glu Gly
        355                 360                 365

Asp Glu Glu Thr Thr Asn Asp Val Pro His Ile Gln Cys Gly Asp Gly
    370                 375                 380

Cys Asp Pro Gln Gly Leu Arg Asp Asn Ser Gln Phe Cys Leu Gln Arg
385                 390                 395                 400

Ile His Gln Gly Leu Ile Phe Tyr Glu Lys Leu Leu Gly Ser Asp Ile
                405                 410                 415

Phe Thr Gly Glu Pro Ser Leu Leu Pro Asp Ser Pro Val Gly Gln Leu
            420                 425                 430

His Ala Ser Leu Leu Gly Leu Ser Gln Leu Leu Gln Pro Glu Gly His
        435                 440                 445

His Trp Glu Thr Gln Gln Ile Pro Ser Leu Ser Pro Ser Gln Pro Trp
    450                 455                 460

Gln Arg Leu Leu Leu Arg Phe Lys Ile Leu Arg Ser Leu Gln Ala Phe
465                 470                 475                 480

Val Ala Val Ala Ala Arg Val Phe Ala His Gly Ala Ala Thr Leu Ser
                485                 490                 495

Pro

<210> SEQ ID NO 73
<211> LENGTH: 497
<212> TYPE: PRT
<213> ORGANISM: Artificial Sequence
<220> FEATURE:
<223> OTHER INFORMATION: Synthetic

<400> SEQUENCE: 73

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
```

```
            195                 200                 205
Asp Ile Ile Lys Pro Asp Pro Pro Lys Asn Leu Gln Leu Lys Pro Leu
210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                    245                 250                 255

Gly Lys Ser Lys Arg Ala Lys Lys Asp Arg Val Phe Thr Asp Lys Thr
                260                 265                 270

Ser Ala Thr Val Ile Cys Arg Lys Asn Ala Ser Ile Ser Val Arg Ala
                275                 280                 285

Gln Asp Arg Tyr Tyr Ser Ser Ser Trp Ser Glu Trp Ala Ser Val Pro
290                 295                 300

Cys Ser Gly Ser Gly Ser Ser Arg Gly Gly Ser Gly Gly Gly Ser
305                 310                 315                 320

Gly Gly Gly Gly Ser Lys Leu Arg Ala Val Pro Gly Gly Ser Ser Pro
                325                 330                 335

Ala Trp Thr Gln Cys Gln Gln Leu Ser Gln Lys Leu Cys Thr Leu Ala
                340                 345                 350

Trp Ser Ala His Pro Leu Val Gly His Met Asp Leu Arg Glu Glu Gly
                355                 360                 365

Asp Glu Glu Thr Thr Asn Asp Val Pro His Ile Gln Cys Gly Asp Gly
370                 375                 380

Cys Asp Pro Gln Gly Leu Arg Asp Asn Ser Gln Phe Cys Leu Gln Arg
385                 390                 395                 400

Ile His Gln Gly Leu Ile Phe Tyr Glu Lys Leu Leu Gly Ser Asp Ile
                405                 410                 415

Phe Thr Gly Glu Pro Ser Leu Leu Pro Asp Ser Pro Val Gly Gln Leu
                420                 425                 430

His Ala Ser Leu Leu Gly Leu Ser Gln Leu Leu Gln Pro Glu Gly His
                435                 440                 445

His Trp Glu Thr Gln Gln Ile Pro Ser Leu Ser Pro Ser Gln Pro Trp
                450                 455                 460

Gln Arg Leu Leu Leu Arg Phe Lys Ile Leu Arg Ser Leu Gln Ala Phe
465                 470                 475                 480

Val Ala Val Ala Ala Arg Val Phe Ala His Gly Ala Ala Thr Leu Ser
                485                 490                 495

Pro

<210> SEQ ID NO 74
<211> LENGTH: 497
<212> TYPE: PRT
<213> ORGANISM: Artificial Sequence
<220> FEATURE:
<223> OTHER INFORMATION: Synthetic

<400> SEQUENCE: 74

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
                20                  25                  30

Glu Asp Gly Ile Thr Trp Thr Leu Asp Gln Ser Ser Glu Val Leu Gly
                35                  40                  45

Ser Gly Lys Thr Leu Thr Ile Gln Val Lys Glu Phe Gly Asp Ala Gly
50                  55                  60
```

```
Gln Tyr Thr Cys His Lys Gly Gly Glu Val Leu Ser His Ser Leu Leu
 65                  70                  75                  80

Leu Leu His Lys Lys Glu Asp Gly Ile Trp Ser Thr Asp Ile Leu Lys
                 85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Ala Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Ser Gly Ser Ser Arg Gly Gly Ser Gly Gly Gly Gly Ser
305                 310                 315                 320

Gly Gly Gly Gly Ser Lys Leu Arg Ala Val Pro Gly Gly Ser Ser Pro
                325                 330                 335

Ala Trp Thr Gln Cys Gln Gln Leu Ser Gln Lys Leu Cys Thr Leu Ala
            340                 345                 350

Trp Ser Ala His Pro Leu Val Gly His Met Asp Leu Arg Glu Glu Gly
        355                 360                 365

Asp Glu Glu Thr Thr Asn Asp Val Pro His Ile Gln Cys Gly Asp Gly
    370                 375                 380

Cys Asp Pro Gln Gly Leu Arg Asp Asn Ser Gln Phe Cys Leu Gln Arg
385                 390                 395                 400

Ile His Gln Gly Leu Ile Phe Tyr Glu Lys Leu Leu Gly Ser Asp Ile
                405                 410                 415

Phe Thr Gly Glu Pro Ser Leu Leu Pro Asp Ser Pro Val Gly Gln Leu
            420                 425                 430

His Ala Ser Leu Leu Gly Leu Ser Gln Leu Leu Gln Pro Glu Gly His
        435                 440                 445

His Trp Glu Thr Gln Gln Ile Pro Ser Leu Ser Pro Ser Gln Pro Trp
    450                 455                 460

Gln Arg Leu Leu Leu Arg Phe Lys Ile Leu Arg Ser Leu Gln Ala Phe
465                 470                 475                 480

Val Ala Val Ala Ala Arg Val Phe Ala His Gly Ala Ala Thr Leu Ser
                485                 490                 495
```

Pro

<210> SEQ ID NO 75
<211> LENGTH: 497
<212> TYPE: PRT
<213> ORGANISM: Artificial Sequence
<220> FEATURE:
<223> OTHER INFORMATION: Synthetic

<400> SEQUENCE: 75

```
Ile Trp Glu Leu Lys Lys Asp Val Tyr Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Ala Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Ser Gly Ser Ser Arg Gly Gly Ser Gly Ser Gly Gly Ser
305                 310                 315                 320

Gly Gly Gly Gly Ser Lys Leu Arg Ala Val Pro Gly Gly Ser Ser Pro
                325                 330                 335

Ala Trp Thr Gln Cys Gln Gln Leu Ser Gln Lys Leu Cys Thr Leu Ala
            340                 345                 350

Trp Ser Ala His Pro Leu Val Gly His Met Asp Leu Arg Glu Glu Gly
```

```
                     355                 360                 365
Asp Glu Glu Thr Thr Asn Asp Val Pro His Ile Gln Cys Gly Asp Gly
        370                 375                 380

Cys Asp Pro Gln Gly Leu Arg Asp Asn Ser Gln Phe Cys Leu Gln Arg
385                 390                 395                 400

Ile His Gln Gly Leu Ile Phe Tyr Glu Lys Leu Leu Gly Ser Asp Ile
                405                 410                 415

Phe Thr Gly Glu Pro Ser Leu Leu Pro Asp Ser Pro Val Gly Gln Leu
            420                 425                 430

His Ala Ser Leu Leu Gly Leu Ser Gln Leu Leu Gln Pro Glu Gly His
        435                 440                 445

His Trp Glu Thr Gln Gln Ile Pro Ser Leu Ser Pro Ser Gln Pro Trp
    450                 455                 460

Gln Arg Leu Leu Leu Arg Phe Lys Ile Leu Arg Ser Leu Gln Ala Phe
465                 470                 475                 480

Val Ala Val Ala Ala Arg Val Phe Ala His Gly Ala Ala Thr Leu Ser
                485                 490                 495

Pro

<210> SEQ ID NO 76
<211> LENGTH: 497
<212> TYPE: PRT
<213> ORGANISM: Artificial Sequence
<220> FEATURE:
<223> OTHER INFORMATION: Synthetic

<400> SEQUENCE: 76

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220
```

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
            245                 250                 255

Gly Lys Ser Lys Arg Glu Lys Lys Asp Ala Val Phe Thr Asp Lys Thr
        260                 265                 270

Ser Ala Thr Val Ile Cys Arg Lys Asn Ala Ser Ile Ser Val Arg Ala
    275                 280                 285

Gln Asp Arg Tyr Tyr Ser Ser Trp Ser Glu Trp Ala Ser Val Pro
290                 295                 300

Cys Ser Gly Ser Gly Ser Arg Gly Gly Ser Gly Gly Gly Ser
305                 310                 315                 320

Gly Gly Gly Gly Ser Lys Leu Arg Ala Val Pro Gly Gly Ser Ser Pro
                325                 330                 335

Ala Trp Thr Gln Cys Gln Gln Leu Ser Gln Lys Leu Cys Thr Leu Ala
                340                 345                 350

Trp Ser Ala His Pro Leu Val Gly His Met Asp Leu Arg Glu Glu Gly
                355                 360                 365

Asp Glu Glu Thr Thr Asn Asp Val Pro His Ile Gln Cys Gly Asp Gly
370                 375                 380

Cys Asp Pro Gln Gly Leu Arg Asp Asn Ser Gln Phe Cys Leu Gln Arg
385                 390                 395                 400

Ile His Gln Gly Leu Ile Phe Tyr Glu Lys Leu Leu Gly Ser Asp Ile
                405                 410                 415

Phe Thr Gly Glu Pro Ser Leu Leu Pro Asp Ser Pro Val Gly Gln Leu
                420                 425                 430

His Ala Ser Leu Leu Gly Leu Ser Gln Leu Leu Gln Pro Glu Gly His
            435                 440                 445

His Trp Glu Thr Gln Gln Ile Pro Ser Leu Ser Pro Ser Gln Pro Trp
        450                 455                 460

Gln Arg Leu Leu Leu Arg Phe Lys Ile Leu Arg Ser Leu Gln Ala Phe
465                 470                 475                 480

Val Ala Val Ala Ala Arg Val Phe Ala His Gly Ala Ala Thr Leu Ser
                485                 490                 495

Pro

<210> SEQ ID NO 77
<211> LENGTH: 497
<212> TYPE: PRT
<213> ORGANISM: Artificial Sequence
<220> FEATURE:
<223> OTHER INFORMATION: Synthetic

<400> SEQUENCE: 77

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
                20                  25                  30

Glu Asp Gly Ile Thr Trp Thr Leu Asp Gln Ser Ser Glu Val Leu Gly
            35                  40                  45

Ser Gly Lys Thr Leu Thr Ile Gln Val Lys Glu Phe Gly Asp Ala Gly
        50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

```
Asp Gln Lys Glu Pro Lys Asn Lys Thr Phe Leu Arg Cys Glu Ala Lys
                100                 105                 110
Asn Tyr Ser Gly Arg Phe Thr Cys Trp Trp Leu Thr Thr Ile Ser Thr
            115                 120                 125
Asp Leu Thr Phe Ser Val Lys Ser Ser Arg Gly Ser Ser Asp Pro Gln
        130                 135                 140
Gly Val Thr Cys Gly Ala Ala Thr Leu Ser Ala Glu Arg Val Arg Gly
145                 150                 155                 160
Asp Asn Lys Glu Tyr Glu Tyr Ser Val Glu Cys Gln Glu Asp Ser Ala
                165                 170                 175
Cys Pro Ala Ala Glu Glu Ser Leu Pro Ile Glu Val Met Val Asp Ala
            180                 185                 190
Val His Lys Leu Lys Tyr Glu Asn Tyr Thr Ser Ser Phe Phe Ile Arg
        195                 200                 205
Asp Ile Ile Lys Pro Asp Pro Pro Lys Asn Leu Gln Leu Lys Pro Leu
210                 215                 220
Lys Asn Ser Arg Gln Val Glu Val Ser Trp Glu Tyr Pro Asp Thr Trp
225                 230                 235                 240
Ser Thr Pro His Ser Tyr Phe Ser Leu Thr Phe Cys Val Gln Val Gln
                245                 250                 255
Gly Lys Ser Lys Arg Glu Lys Lys Asp Arg Ala Phe Thr Asp Lys Thr
            260                 265                 270
Ser Ala Thr Val Ile Cys Arg Lys Asn Ala Ser Ile Ser Val Arg Ala
        275                 280                 285
Gln Asp Arg Tyr Tyr Ser Ser Ser Trp Ser Glu Trp Ala Ser Val Pro
        290                 295                 300
Cys Ser Gly Ser Gly Ser Ser Arg Gly Gly Ser Gly Ser Gly Gly Ser
305                 310                 315                 320
Gly Gly Gly Gly Ser Lys Leu Arg Ala Val Pro Gly Gly Ser Ser Pro
                325                 330                 335
Ala Trp Thr Gln Cys Gln Gln Leu Ser Gln Lys Leu Cys Thr Leu Ala
            340                 345                 350
Trp Ser Ala His Pro Leu Val Gly His Met Asp Leu Arg Glu Glu Gly
        355                 360                 365
Asp Glu Glu Thr Thr Asn Asp Val Pro His Ile Gln Cys Gly Asp Gly
        370                 375                 380
Cys Asp Pro Gln Gly Leu Arg Asp Asn Ser Gln Phe Cys Leu Gln Arg
385                 390                 395                 400
Ile His Gln Gly Leu Ile Phe Tyr Glu Lys Leu Leu Gly Ser Asp Ile
                405                 410                 415
Phe Thr Gly Glu Pro Ser Leu Leu Pro Asp Ser Pro Val Gly Gln Leu
            420                 425                 430
His Ala Ser Leu Leu Gly Leu Ser Gln Leu Leu Gln Pro Glu Gly His
        435                 440                 445
His Trp Glu Thr Gln Gln Ile Pro Ser Leu Ser Pro Ser Gln Pro Trp
        450                 455                 460
Gln Arg Leu Leu Leu Arg Phe Lys Ile Leu Arg Ser Leu Gln Ala Phe
465                 470                 475                 480
Val Ala Val Ala Ala Arg Val Phe Ala His Gly Ala Ala Thr Leu Ser
                485                 490                 495
Pro

<210> SEQ ID NO 78
```

<211> LENGTH: 497
<212> TYPE: PRT
<213> ORGANISM: Artificial Sequence
<220> FEATURE:
<223> OTHER INFORMATION: Synthetic

<400> SEQUENCE: 78

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Ala Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Ser Gly Ser Ser Arg Gly Gly Ser Gly Ser Gly Gly Ser
305                 310                 315                 320

Gly Gly Gly Gly Ser Lys Leu Arg Ala Val Pro Gly Gly Ser Ser Pro
                325                 330                 335

Ala Trp Thr Gln Cys Gln Gln Leu Ser Gln Lys Leu Cys Thr Leu Ala
            340                 345                 350

Trp Ser Ala His Pro Leu Val Gly His Met Asp Leu Arg Glu Glu Gly
        355                 360                 365

Asp Glu Glu Thr Thr Asn Asp Val Pro His Ile Gln Cys Gly Asp Gly
    370                 375                 380
```

-continued

```
Cys Asp Pro Gln Gly Leu Arg Asp Asn Ser Gln Phe Cys Leu Gln Arg
385                 390                 395                 400

Ile His Gln Gly Leu Ile Phe Tyr Glu Lys Leu Leu Gly Ser Asp Ile
            405                 410                 415

Phe Thr Gly Glu Pro Ser Leu Leu Pro Asp Ser Pro Val Gly Gln Leu
            420                 425                 430

His Ala Ser Leu Leu Gly Leu Ser Gln Leu Leu Gln Pro Glu Gly His
            435                 440                 445

His Trp Glu Thr Gln Gln Ile Pro Ser Leu Ser Pro Ser Gln Pro Trp
            450                 455                 460

Gln Arg Leu Leu Leu Arg Phe Lys Ile Leu Arg Ser Leu Gln Ala Phe
465                 470                 475                 480

Val Ala Val Ala Ala Arg Val Phe Ala His Gly Ala Ala Thr Leu Ser
            485                 490                 495

Pro
```

<210> SEQ ID NO 79
<211> LENGTH: 497
<212> TYPE: PRT
<213> ORGANISM: Artificial Sequence
<220> FEATURE:
<223> OTHER INFORMATION: Synthetic

<400> SEQUENCE: 79

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
            35                  40                  45

Ser Gly Lys Thr Leu Thr Ile Gln Val Lys Glu Phe Gly Asp Ala Gly
        50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
            115                 120                 125

Asp Leu Thr Phe Ser Val Lys Ser Ser Arg Gly Ser Ser Asp Pro Gln
130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
            195                 200                 205

Asp Ile Ile Lys Pro Asp Pro Pro Lys Asn Leu Gln Leu Lys Pro Leu
        210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255
```

```
Gly Lys Ser Lys Arg Glu Lys Lys Asp Arg Val Phe Ala Asp Lys Thr
            260                 265                 270
Ser Ala Thr Val Ile Cys Arg Lys Asn Ala Ser Ile Ser Val Arg Ala
            275                 280                 285
Gln Asp Arg Tyr Tyr Ser Ser Ser Trp Ser Glu Trp Ala Ser Val Pro
    290                 295                 300
Cys Ser Gly Ser Gly Ser Ser Arg Gly Gly Ser Gly Ser Gly Gly Ser
305                 310                 315                 320
Gly Gly Gly Gly Ser Lys Leu Arg Ala Val Pro Gly Gly Ser Ser Pro
                325                 330                 335
Ala Trp Thr Gln Cys Gln Gln Leu Ser Gln Lys Leu Cys Thr Leu Ala
            340                 345                 350
Trp Ser Ala His Pro Leu Val Gly His Met Asp Leu Arg Glu Glu Gly
            355                 360                 365
Asp Glu Glu Thr Thr Asn Asp Val Pro His Ile Gln Cys Gly Asp Gly
    370                 375                 380
Cys Asp Pro Gln Gly Leu Arg Asp Asn Ser Gln Phe Cys Leu Gln Arg
385                 390                 395                 400
Ile His Gln Gly Leu Ile Phe Tyr Glu Lys Leu Leu Gly Ser Asp Ile
                405                 410                 415
Phe Thr Gly Glu Pro Ser Leu Leu Pro Asp Ser Pro Val Gly Gln Leu
            420                 425                 430
His Ala Ser Leu Leu Gly Leu Ser Gln Leu Leu Gln Pro Glu Gly His
            435                 440                 445
His Trp Glu Thr Gln Gln Ile Pro Ser Leu Ser Pro Ser Gln Pro Trp
            450                 455                 460
Gln Arg Leu Leu Leu Arg Phe Lys Ile Leu Arg Ser Leu Gln Ala Phe
465                 470                 475                 480
Val Ala Val Ala Ala Arg Val Phe Ala His Gly Ala Ala Thr Leu Ser
                485                 490                 495
Pro

<210> SEQ ID NO 80
<211> LENGTH: 497
<212> TYPE: PRT
<213> ORGANISM: Artificial Sequence
<220> FEATURE:
<223> OTHER INFORMATION: Synthetic

<400> SEQUENCE: 80

Ile Trp Glu Leu Lys Lys Asp Val Tyr Val Val Glu Leu Asp Trp Tyr
1               5                   10                  15
Pro Asp Ala Pro Gly Glu Met Val Val Leu Thr Cys Asp Thr Pro Glu
            20                  25                  30
Glu Asp Gly Ile Thr Trp Thr Leu Asp Gln Ser Ser Glu Val Leu Gly
        35                  40                  45
Ser Gly Lys Thr Leu Thr Ile Gln Val Lys Glu Phe Gly Asp Ala Gly
    50                  55                  60
Gln Tyr Thr Cys His Lys Gly Gly Glu Val Leu Ser His Ser Leu Leu
65              70                  75                  80
Leu Leu His Lys Lys Glu Asp Gly Ile Trp Ser Thr Asp Ile Leu Lys
                85                  90                  95
Asp Gln Lys Glu Pro Lys Asn Lys Thr Phe Leu Arg Cys Glu Ala Lys
            100                 105                 110
Asn Tyr Ser Gly Arg Phe Thr Cys Trp Trp Leu Thr Thr Ile Ser Thr
```

```
                115                 120                 125
Asp Leu Thr Phe Ser Val Lys Ser Ser Arg Gly Ser Ser Asp Pro Gln
130                 135                 140
Gly Val Thr Cys Gly Ala Ala Thr Leu Ser Ala Glu Arg Val Arg Gly
145                 150                 155                 160
Asp Asn Lys Glu Tyr Glu Tyr Ser Val Glu Cys Gln Glu Asp Ser Ala
                165                 170                 175
Cys Pro Ala Ala Glu Glu Ser Leu Pro Ile Glu Val Met Val Asp Ala
                180                 185                 190
Val His Lys Leu Lys Tyr Glu Asn Tyr Thr Ser Ser Phe Phe Ile Arg
                195                 200                 205
Asp Ile Ile Lys Pro Asp Pro Pro Lys Asn Leu Gln Leu Lys Pro Leu
210                 215                 220
Lys Asn Ser Arg Gln Val Glu Val Ser Trp Glu Tyr Pro Asp Thr Trp
225                 230                 235                 240
Ser Thr Pro His Ser Tyr Phe Ser Leu Thr Phe Cys Val Gln Val Gln
                245                 250                 255
Gly Lys Ser Lys Arg Glu Lys Lys Asp Arg Val Phe Thr Ala Lys Thr
                260                 265                 270
Ser Ala Thr Val Ile Cys Arg Lys Asn Ala Ser Ile Ser Val Arg Ala
                275                 280                 285
Gln Asp Arg Tyr Tyr Ser Ser Ser Trp Ser Glu Trp Ala Ser Val Pro
                290                 295                 300
Cys Ser Gly Ser Gly Ser Ser Arg Gly Gly Ser Gly Ser Gly Gly Ser
305                 310                 315                 320
Gly Gly Gly Gly Ser Lys Leu Arg Ala Val Pro Gly Gly Ser Ser Pro
                325                 330                 335
Ala Trp Thr Gln Cys Gln Gln Leu Ser Gln Lys Leu Cys Thr Leu Ala
                340                 345                 350
Trp Ser Ala His Pro Leu Val Gly His Met Asp Leu Arg Glu Glu Gly
                355                 360                 365
Asp Glu Glu Thr Thr Asn Asp Val Pro His Ile Gln Cys Gly Asp Gly
370                 375                 380
Cys Asp Pro Gln Gly Leu Arg Asp Asn Ser Gln Phe Cys Leu Gln Arg
385                 390                 395                 400
Ile His Gln Gly Leu Ile Phe Tyr Glu Lys Leu Leu Gly Ser Asp Ile
                405                 410                 415
Phe Thr Gly Glu Pro Ser Leu Leu Pro Asp Ser Pro Val Gly Gln Leu
                420                 425                 430
His Ala Ser Leu Leu Gly Leu Ser Gln Leu Leu Gln Pro Glu Gly His
                435                 440                 445
His Trp Glu Thr Gln Gln Ile Pro Ser Leu Ser Pro Ser Gln Pro Trp
                450                 455                 460
Gln Arg Leu Leu Leu Arg Phe Lys Ile Leu Arg Ser Leu Gln Ala Phe
465                 470                 475                 480
Val Ala Val Ala Ala Arg Val Phe Ala His Gly Ala Ala Thr Leu Ser
                485                 490                 495
Pro

<210> SEQ ID NO 81
<211> LENGTH: 497
<212> TYPE: PRT
<213> ORGANISM: Artificial Sequence
<220> FEATURE:
<223> OTHER INFORMATION: Synthetic
```

<400> SEQUENCE: 81

```
Ile Trp Glu Leu Lys Lys Asp Val Tyr Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Ala Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Ser Gly Ser Ser Arg Gly Gly Ser Gly Ser Gly Gly Ser
305                 310                 315                 320

Gly Gly Gly Gly Ser Lys Leu Arg Ala Val Pro Gly Gly Ser Ser Pro
                325                 330                 335

Ala Trp Thr Gln Cys Gln Gln Leu Ser Gln Lys Leu Cys Thr Leu Ala
            340                 345                 350

Trp Ser Ala His Pro Leu Val Gly His Met Asp Leu Arg Glu Glu Gly
        355                 360                 365

Asp Glu Glu Thr Thr Asn Asp Val Pro His Ile Gln Cys Gly Asp Gly
    370                 375                 380

Cys Asp Pro Gln Gly Leu Arg Asp Asn Ser Gln Phe Cys Leu Gln Arg
385                 390                 395                 400

Ile His Gln Gly Leu Ile Phe Tyr Glu Lys Leu Leu Gly Ser Asp Ile
                405                 410                 415
```

```
Phe Thr Gly Glu Pro Ser Leu Leu Pro Asp Ser Pro Val Gly Gln Leu
            420                 425                 430

His Ala Ser Leu Leu Gly Leu Ser Gln Leu Leu Gln Pro Glu Gly His
            435                 440                 445

His Trp Glu Thr Gln Gln Ile Pro Ser Leu Ser Pro Ser Gln Pro Trp
            450                 455                 460

Gln Arg Leu Leu Arg Phe Lys Ile Leu Arg Ser Leu Gln Ala Phe
465                 470                 475                 480

Val Ala Val Ala Ala Arg Val Phe Ala His Gly Ala Ala Thr Leu Ser
                    485                 490                 495

Pro

<210> SEQ ID NO 82
<211> LENGTH: 497
<212> TYPE: PRT
<213> ORGANISM: Artificial Sequence
<220> FEATURE:
<223> OTHER INFORMATION: Synthetic

<400> SEQUENCE: 82

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ala Cys Arg Lys Asn Ala Ser Ile Ser Val Arg Ala
```

```
                275                 280                 285
Gln Asp Arg Tyr Tyr Ser Ser Trp Ser Glu Trp Ala Ser Val Pro
290                 295                 300

Cys Ser Gly Ser Ser Ser Arg Gly Gly Ser Gly Ser Gly Gly Ser
305                 310                 315                 320

Gly Gly Gly Gly Ser Lys Leu Arg Ala Val Pro Gly Gly Ser Ser Pro
        325                 330                 335

Ala Trp Thr Gln Cys Gln Gln Leu Ser Gln Lys Leu Cys Thr Leu Ala
            340                 345                 350

Trp Ser Ala His Pro Leu Val Gly His Met Asp Leu Arg Glu Glu Gly
        355                 360                 365

Asp Glu Glu Thr Thr Asn Asp Val Pro His Ile Gln Cys Gly Asp Gly
    370                 375                 380

Cys Asp Pro Gln Gly Leu Arg Asp Asn Ser Gln Phe Cys Leu Gln Arg
385                 390                 395                 400

Ile His Gln Gly Leu Ile Phe Tyr Glu Lys Leu Leu Gly Ser Asp Ile
                405                 410                 415

Phe Thr Gly Glu Pro Ser Leu Leu Pro Asp Ser Pro Val Gly Gln Leu
            420                 425                 430

His Ala Ser Leu Leu Gly Leu Ser Gln Leu Leu Gln Pro Glu Gly His
        435                 440                 445

His Trp Glu Thr Gln Gln Ile Pro Ser Leu Ser Pro Ser Gln Pro Trp
    450                 455                 460

Gln Arg Leu Leu Leu Arg Phe Lys Ile Leu Arg Ser Leu Gln Ala Phe
465                 470                 475                 480

Val Ala Val Ala Ala Arg Val Phe Ala His Gly Ala Ala Thr Leu Ser
                485                 490                 495

Pro

<210> SEQ ID NO 83
<211> LENGTH: 497
<212> TYPE: PRT
<213> ORGANISM: Artificial Sequence
<220> FEATURE:
<223> OTHER INFORMATION: Synthetic

<400> SEQUENCE: 83

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140
```

-continued

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
            165                 170                 175

Cys Pro Ala Ala Glu Glu Ser Leu Pro Ile Glu Val Met Val Asp Ala
        180                 185                 190

Val His Lys Leu Lys Tyr Glu Asn Tyr Thr Ser Ser Phe Phe Ile Arg
    195                 200                 205

Asp Ile Ile Lys Pro Asp Pro Pro Lys Asn Leu Gln Leu Lys Pro Leu
210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Ala Lys Asn Ala Ser Ile Ser Val Arg Ala
        275                 280                 285

Gln Asp Arg Tyr Tyr Ser Ser Trp Ser Glu Trp Ala Ser Val Pro
    290                 295                 300

Cys Ser Gly Ser Gly Ser Ser Arg Gly Gly Ser Gly Ser Gly Gly Ser
305                 310                 315                 320

Gly Gly Gly Gly Ser Lys Leu Arg Ala Val Pro Gly Gly Ser Ser Pro
                325                 330                 335

Ala Trp Thr Gln Cys Gln Gln Leu Ser Gln Lys Leu Cys Thr Leu Ala
            340                 345                 350

Trp Ser Ala His Pro Leu Val Gly His Met Asp Leu Arg Glu Glu Gly
        355                 360                 365

Asp Glu Glu Thr Thr Asn Asp Val Pro His Ile Gln Cys Gly Asp Gly
    370                 375                 380

Cys Asp Pro Gln Gly Leu Arg Asp Asn Ser Gln Phe Cys Leu Gln Arg
385                 390                 395                 400

Ile His Gln Gly Leu Ile Phe Tyr Glu Lys Leu Leu Gly Ser Asp Ile
                405                 410                 415

Phe Thr Gly Glu Pro Ser Leu Leu Pro Asp Ser Pro Val Gly Gln Leu
            420                 425                 430

His Ala Ser Leu Leu Gly Leu Ser Gln Leu Leu Gln Pro Glu Gly His
        435                 440                 445

His Trp Glu Thr Gln Gln Ile Pro Ser Leu Ser Pro Ser Gln Pro Trp
    450                 455                 460

Gln Arg Leu Leu Leu Arg Phe Lys Ile Leu Arg Ser Leu Gln Ala Phe
465                 470                 475                 480

Val Ala Val Ala Ala Arg Val Phe Ala His Gly Ala Ala Thr Leu Ser
                485                 490                 495

Pro

<210> SEQ ID NO 84
<211> LENGTH: 497
<212> TYPE: PRT
<213> ORGANISM: Artificial Sequence
<220> FEATURE:
<223> OTHER INFORMATION: Synthetic

<400> SEQUENCE: 84

Ile Trp Glu Leu Lys Lys Asp Val Tyr Val Val Glu Leu Asp Trp Tyr
1               5                   10                  15

-continued

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
            35                  40                  45

Ser Gly Lys Thr Leu Thr Ile Gln Val Lys Glu Phe Gly Asp Ala Gly
50                      55                  60

Gln Tyr Thr Cys His Lys Gly Gly Val Leu Ser His Ser Leu Leu
65                      70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
            115                 120                 125

Asp Leu Thr Phe Ser Val Lys Ser Ser Arg Gly Ser Ser Asp Pro Gln
        130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
            165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
        210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
            245                 250                 255

Gly Lys Ser Lys Arg Glu Lys Lys Asp Arg Val Phe Thr Asp Lys Thr
            260                 265                 270

Ser Ala Thr Val Ile Cys Arg Lys Ala Ala Ser Ile Ser Val Arg Ala
        275                 280                 285

Gln Asp Arg Tyr Tyr Ser Ser Ser Trp Ser Glu Trp Ala Ser Val Pro
290                 295                 300

Cys Ser Gly Ser Gly Ser Ser Arg Gly Gly Ser Gly Ser Gly Gly Ser
305                 310                 315                 320

Gly Gly Gly Gly Ser Lys Leu Arg Ala Val Pro Gly Gly Ser Ser Pro
            325                 330                 335

Ala Trp Thr Gln Cys Gln Gln Leu Ser Gln Lys Leu Cys Thr Leu Ala
            340                 345                 350

Trp Ser Ala His Pro Leu Val Gly His Met Asp Leu Arg Glu Glu Gly
        355                 360                 365

Asp Glu Glu Thr Thr Asn Asp Val Pro His Ile Gln Cys Gly Asp Gly
        370                 375                 380

Cys Asp Pro Gln Gly Leu Arg Asp Asn Ser Gln Phe Cys Leu Gln Arg
385                 390                 395                 400

Ile His Gln Gly Leu Ile Phe Tyr Glu Lys Leu Leu Gly Ser Asp Ile
            405                 410                 415

Phe Thr Gly Glu Pro Ser Leu Leu Pro Asp Ser Pro Val Gly Gln Leu
            420                 425                 430

His Ala Ser Leu Leu Gly Leu Ser Gln Leu Leu Gln Pro Glu Gly His

```
                                 435                 440                 445
        His Trp Glu Thr Gln Gln Ile Pro Ser Leu Ser Pro Ser Gln Pro Trp
                            450                 455                 460

Gln Arg Leu Leu Leu Arg Phe Lys Ile Leu Arg Ser Leu Gln Ala Phe
        465                 470                 475                 480

Val Ala Val Ala Ala Arg Val Phe Ala His Gly Ala Ala Thr Leu Ser
                            485                 490                 495

Pro

<210> SEQ ID NO 85
<211> LENGTH: 497
<212> TYPE: PRT
<213> ORGANISM: Artificial Sequence
<220> FEATURE:
<223> OTHER INFORMATION: Synthetic

<400> SEQUENCE: 85

Ile Trp Glu Leu Lys Lys Asp Val Tyr Val Val Glu Leu Asp Trp Tyr
        1               5                   10                  15

Pro Asp Ala Pro Gly Glu Met Val Val Leu Thr Cys Asp Thr Pro Glu
                        20                  25                  30

Glu Asp Gly Ile Thr Trp Thr Leu Asp Gln Ser Ser Glu Val Leu Gly
                    35                  40                  45

Ser Gly Lys Thr Leu Thr Ile Gln Val Lys Glu Phe Gly Asp Ala Gly
        50                  55                  60

Gln Tyr Thr Cys His Lys Gly Gly Glu Val Leu Ser His Ser Leu Leu
        65                  70                  75                  80

Leu Leu His Lys Lys Glu Asp Gly Ile Trp Ser Thr Asp Ile Leu Lys
                        85                  90                  95

Asp Gln Lys Glu Pro Lys Asn Lys Thr Phe Leu Arg Cys Glu Ala Lys
                    100                 105                 110

Asn Tyr Ser Gly Arg Phe Thr Cys Trp Trp Leu Thr Thr Ile Ser Thr
                115                 120                 125

Asp Leu Thr Phe Ser Val Lys Ser Ser Arg Gly Ser Ser Asp Pro Gln
        130                 135                 140

Gly Val Thr Cys Gly Ala Ala Thr Leu Ser Ala Glu Arg Val Arg Gly
        145                 150                 155                 160

Asp Asn Lys Glu Tyr Glu Tyr Ser Val Glu Cys Gln Glu Asp Ser Ala
                        165                 170                 175

Cys Pro Ala Ala Glu Glu Ser Leu Pro Ile Glu Val Met Val Asp Ala
                    180                 185                 190

Val His Lys Leu Lys Tyr Glu Asn Tyr Thr Ser Ser Phe Phe Ile Arg
                195                 200                 205

Asp Ile Ile Lys Pro Asp Pro Pro Lys Asn Leu Gln Leu Lys Pro Leu
        210                 215                 220

Lys Asn Ser Arg Gln Val Glu Val Ser Trp Glu Tyr Pro Asp Thr Trp
        225                 230                 235                 240

Ser Thr Pro His Ser Tyr Phe Ser Leu Thr Phe Cys Val Gln Val Gln
                        245                 250                 255

Gly Lys Ser Lys Arg Glu Lys Lys Asp Arg Val Phe Thr Asp Lys Thr
                    260                 265                 270

Ser Ala Thr Val Ile Cys Arg Lys Asn Ala Ala Ile Ser Val Arg Ala
                275                 280                 285

Gln Asp Arg Tyr Tyr Ser Ser Ser Trp Ser Glu Trp Ala Ser Val Pro
        290                 295                 300
```

```
Cys Ser Gly Ser Gly Ser Ser Arg Gly Gly Ser Gly Ser Gly Gly Ser
305                 310                 315                 320

Gly Gly Gly Gly Ser Lys Leu Arg Ala Val Pro Gly Gly Ser Ser Pro
            325                 330                 335

Ala Trp Thr Gln Cys Gln Gln Leu Ser Gln Lys Leu Cys Thr Leu Ala
            340                 345                 350

Trp Ser Ala His Pro Leu Val Gly His Met Asp Leu Arg Glu Glu Gly
        355                 360                 365

Asp Glu Glu Thr Thr Asn Asp Val Pro His Ile Gln Cys Gly Asp Gly
        370                 375                 380

Cys Asp Pro Gln Gly Leu Arg Asp Asn Ser Gln Phe Cys Leu Gln Arg
385                 390                 395                 400

Ile His Gln Gly Leu Ile Phe Tyr Glu Lys Leu Leu Gly Ser Asp Ile
                405                 410                 415

Phe Thr Gly Glu Pro Ser Leu Leu Pro Asp Ser Pro Val Gly Gln Leu
            420                 425                 430

His Ala Ser Leu Leu Gly Leu Ser Gln Leu Leu Gln Pro Glu Gly His
        435                 440                 445

His Trp Glu Thr Gln Gln Ile Pro Ser Leu Ser Pro Ser Gln Pro Trp
        450                 455                 460

Gln Arg Leu Leu Leu Arg Phe Lys Ile Leu Arg Ser Leu Gln Ala Phe
465                 470                 475                 480

Val Ala Val Ala Ala Arg Val Phe Ala His Gly Ala Ala Thr Leu Ser
                485                 490                 495

Pro

<210> SEQ ID NO 86
<211> LENGTH: 497
<212> TYPE: PRT
<213> ORGANISM: Artificial Sequence
<220> FEATURE:
<223> OTHER INFORMATION: Synthetic

<400> SEQUENCE: 86

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175
```

Cys Pro Ala Ala Glu Glu Ser Leu Pro Ile Glu Val Met Val Asp Ala
              180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ala Val Arg Ala
        275                 280                 285

Gln Asp Arg Tyr Tyr Ser Ser Ser Trp Ser Glu Trp Ala Ser Val Pro
    290                 295                 300

Cys Ser Gly Ser Gly Ser Ser Arg Gly Gly Ser Gly Ser Gly Gly Ser
305                 310                 315                 320

Gly Gly Gly Gly Ser Lys Leu Arg Ala Val Pro Gly Gly Ser Ser Pro
                325                 330                 335

Ala Trp Thr Gln Cys Gln Gln Leu Ser Gln Lys Leu Cys Thr Leu Ala
                340                 345                 350

Trp Ser Ala His Pro Leu Val Gly His Met Asp Leu Arg Glu Glu Gly
            355                 360                 365

Asp Glu Glu Thr Thr Asn Asp Val Pro His Ile Gln Cys Gly Asp Gly
        370                 375                 380

Cys Asp Pro Gln Gly Leu Arg Asp Asn Ser Gln Phe Cys Leu Gln Arg
385                 390                 395                 400

Ile His Gln Gly Leu Ile Phe Tyr Glu Lys Leu Leu Gly Ser Asp Ile
                405                 410                 415

Phe Thr Gly Glu Pro Ser Leu Leu Pro Asp Ser Pro Val Gly Gln Leu
            420                 425                 430

His Ala Ser Leu Leu Gly Leu Ser Gln Leu Leu Gln Pro Glu Gly His
        435                 440                 445

His Trp Glu Thr Gln Gln Ile Pro Ser Leu Ser Pro Ser Gln Pro Trp
    450                 455                 460

Gln Arg Leu Leu Leu Arg Phe Lys Ile Leu Arg Ser Leu Gln Ala Phe
465                 470                 475                 480

Val Ala Val Ala Ala Arg Val Phe Ala His Gly Ala Ala Thr Leu Ser
                485                 490                 495

Pro

<210> SEQ ID NO 87
<211> LENGTH: 118
<212> TYPE: PRT
<213> ORGANISM: Artificial Sequence
<220> FEATURE:
<223> OTHER INFORMATION: Synthetic

<400> SEQUENCE: 87

Glu Val Gln Leu Gln Gln Ser Gly Ala Asp Leu Val Arg Ser Gly Ala
1               5                   10                  15

Ser Ile Lys Leu Ser Cys Thr Ala Ser Gly Phe Asn Ile Lys Asp Tyr
            20                  25                  30

Tyr Leu His Trp Val Lys Gln Arg Pro Glu Gln Gly Leu Glu Trp Ile

```
                35                  40                  45
Gly Trp Ile Asp Pro Glu Asn Gly Asp Thr Glu Tyr Ala Pro Lys Phe
 50                  55                  60

Gln Gly Lys Ala Thr Met Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Asn Ala Cys Lys Glu Leu Arg Tyr Phe Asp Val Trp Gly Ala Gly Thr
                100                 105                 110

Thr Val Thr Val Ser Ser
            115

<210> SEQ ID NO 88
<211> LENGTH: 118
<212> TYPE: PRT
<213> ORGANISM: Artificial Sequence
<220> FEATURE:
<223> OTHER INFORMATION: Synthetic

<400> SEQUENCE: 88

Glu Val Gln Leu Gln Gln Ser Gly Ala Asp Leu Val Arg Ser Gly Ala
  1               5                  10                  15

Ser Ile Lys Leu Ser Cys Thr Ala Ser Gly Phe Asn Ile Lys Asp Tyr
                 20                  25                  30

Tyr Met His Trp Val Lys Gln Arg Pro Glu Gln Gly Leu Glu Trp Ile
                 35                  40                  45

Gly Trp Ile Asp Pro Glu Asn Gly Asp Thr Glu Tyr Ala Pro Lys Phe
 50                  55                  60

Gln Gly Lys Ala Thr Met Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Asn Ala Ala Lys Glu Leu Arg Tyr Phe Asp Val Trp Gly Ala Gly Thr
                100                 105                 110

Thr Val Thr Val Ser Ser
            115

<210> SEQ ID NO 89
<211> LENGTH: 118
<212> TYPE: PRT
<213> ORGANISM: Artificial Sequence
<220> FEATURE:
<223> OTHER INFORMATION: Synthetic

<400> SEQUENCE: 89

Glu Val Gln Leu Gln Gln Ser Gly Ala Asp Leu Val Arg Ser Gly Ala
  1               5                  10                  15

Ser Ile Lys Leu Ser Cys Thr Ala Ser Gly Phe Asn Ile Lys Asp Tyr
                 20                  25                  30

Tyr Met His Trp Val Lys Gln Arg Pro Glu Gln Gly Leu Glu Trp Ile
                 35                  40                  45

Gly Trp Ile Asp Pro Glu Asn Gly Asp Thr Glu Tyr Ala Pro Lys Phe
 50                  55                  60

Gln Gly Lys Ala Thr Met Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Asn Ala Arg Lys Glu Leu Arg Tyr Phe Asp Val Trp Gly Ala Gly Thr
```

Thr Val Thr Val Ser Ser
        115

<210> SEQ ID NO 90
<211> LENGTH: 118
<212> TYPE: PRT
<213> ORGANISM: Artificial Sequence
<220> FEATURE:
<223> OTHER INFORMATION: Synthetic

<400> SEQUENCE: 90

Glu Val Gln Leu Gln Gln Ser Gly Ala Asp Leu Val Arg Ser Gly Ala
1               5                   10                  15

Ser Ile Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Asn Lys Glu Leu Arg Tyr Phe Asp Val Trp Gly Ala Gly Thr
            100                 105                 110

Thr Val Thr Val Ser Ser
        115

<210> SEQ ID NO 91
<211> LENGTH: 118
<212> TYPE: PRT
<213> ORGANISM: Artificial Sequence
<220> FEATURE:
<223> OTHER INFORMATION: Synthetic

<400> SEQUENCE: 91

Glu Val Gln Leu Gln Gln Ser Gly Ala Asp Leu Val Arg Ser Gly Ala
1               5                   10                  15

Ser Ile Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Asp Lys Glu Leu Arg Tyr Phe Asp Val Trp Gly Ala Gly Thr
            100                 105                 110

Thr Val Thr Val Ser Ser
        115

<210> SEQ ID NO 92
<211> LENGTH: 118
<212> TYPE: PRT
<213> ORGANISM: Artificial Sequence
<220> FEATURE:
<223> OTHER INFORMATION: Synthetic

```
<400> SEQUENCE: 92

Glu Val Gln Leu Gln Gln Ser Gly Ala Asp Leu Val Arg Ser Gly Ala
1               5                   10                  15

Ser Ile Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Glu Lys Glu Leu Arg Tyr Phe Asp Val Trp Gly Ala Gly Thr
            100                 105                 110

Thr Val Thr Val Ser Ser
        115

<210> SEQ ID NO 93
<211> LENGTH: 118
<212> TYPE: PRT
<213> ORGANISM: Artificial Sequence
<220> FEATURE:
<223> OTHER INFORMATION: Synthetic

<400> SEQUENCE: 93

Glu Val Gln Leu Gln Gln Ser Gly Ala Asp Leu Val Arg Ser Gly Ala
1               5                   10                  15

Ser Ile Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Gln Lys Glu Leu Arg Tyr Phe Asp Val Trp Gly Ala Gly Thr
            100                 105                 110

Thr Val Thr Val Ser Ser
        115

<210> SEQ ID NO 94
<211> LENGTH: 118
<212> TYPE: PRT
<213> ORGANISM: Artificial Sequence
<220> FEATURE:
<223> OTHER INFORMATION: Synthetic

<400> SEQUENCE: 94

Glu Val Gln Leu Gln Gln Ser Gly Ala Asp Leu Val Arg Ser Gly Ala
1               5                   10                  15

Ser Ile Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45
```

Gly Trp Ile Asp Pro Glu Asn Gly Asp Thr Glu Tyr Ala Pro Lys Phe
            50                  55                  60

Gln Gly Lys Ala Thr Met Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Asn Ala Gly Lys Glu Leu Arg Tyr Phe Asp Val Trp Gly Ala Gly Thr
            100                 105                 110

Thr Val Thr Val Ser Ser
            115

<210> SEQ ID NO 95
<211> LENGTH: 118
<212> TYPE: PRT
<213> ORGANISM: Artificial Sequence
<220> FEATURE:
<223> OTHER INFORMATION: Synthetic

<400> SEQUENCE: 95

Glu Val Gln Leu Gln Gln Ser Gly Ala Asp Leu Val Arg Ser Gly Ala
1               5                   10                  15

Ser Ile Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala His Lys Glu Leu Arg Tyr Phe Asp Val Trp Gly Ala Gly Thr
            100                 105                 110

Thr Val Thr Val Ser Ser
            115

<210> SEQ ID NO 96
<211> LENGTH: 118
<212> TYPE: PRT
<213> ORGANISM: Artificial Sequence
<220> FEATURE:
<223> OTHER INFORMATION: Synthetic

<400> SEQUENCE: 96

Glu Val Gln Leu Gln Gln Ser Gly Ala Asp Leu Val Arg Ser Gly Ala
1               5                   10                  15

Ser Ile Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Ile Lys Glu Leu Arg Tyr Phe Asp Val Trp Gly Ala Gly Thr
            100                 105                 110

Thr Val Thr Val Ser Ser
        115

<210> SEQ ID NO 97
<211> LENGTH: 118
<212> TYPE: PRT
<213> ORGANISM: Artificial Sequence
<220> FEATURE:
<223> OTHER INFORMATION: Synthetic

<400> SEQUENCE: 97

Glu Val Gln Leu Gln Gln Ser Gly Ala Asp Leu Val Arg Ser Gly Ala
1               5                   10                  15

Ser Ile Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Leu Lys Glu Leu Arg Tyr Phe Asp Val Trp Gly Ala Gly Thr
            100                 105                 110

Thr Val Thr Val Ser Ser
        115

<210> SEQ ID NO 98
<211> LENGTH: 118
<212> TYPE: PRT
<213> ORGANISM: Artificial Sequence
<220> FEATURE:
<223> OTHER INFORMATION: Synthetic

<400> SEQUENCE: 98

Glu Val Gln Leu Gln Gln Ser Gly Ala Asp Leu Val Arg Ser Gly Ala
1               5                   10                  15

Ser Ile Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Lys Lys Glu Leu Arg Tyr Phe Asp Val Trp Gly Ala Gly Thr
            100                 105                 110

Thr Val Thr Val Ser Ser
        115

<210> SEQ ID NO 99
<211> LENGTH: 118
<212> TYPE: PRT
<213> ORGANISM: Artificial Sequence
<220> FEATURE:
<223> OTHER INFORMATION: Synthetic

<400> SEQUENCE: 99

Glu Val Gln Leu Gln Gln Ser Gly Ala Asp Leu Val Arg Ser Gly Ala
1               5                   10                  15

Ser Ile Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Met Lys Glu Leu Arg Tyr Phe Asp Val Trp Gly Ala Gly Thr
            100                 105                 110

Thr Val Thr Val Ser Ser
        115

<210> SEQ ID NO 100
<211> LENGTH: 118
<212> TYPE: PRT
<213> ORGANISM: Artificial Sequence
<220> FEATURE:
<223> OTHER INFORMATION: Synthetic

<400> SEQUENCE: 100

Glu Val Gln Leu Gln Gln Ser Gly Ala Asp Leu Val Arg Ser Gly Ala
1               5                   10                  15

Ser Ile Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Phe Lys Glu Leu Arg Tyr Phe Asp Val Trp Gly Ala Gly Thr
            100                 105                 110

Thr Val Thr Val Ser Ser
        115

<210> SEQ ID NO 101
<211> LENGTH: 118
<212> TYPE: PRT
<213> ORGANISM: Artificial Sequence
<220> FEATURE:
<223> OTHER INFORMATION: Synthetic

<400> SEQUENCE: 101

Glu Val Gln Leu Gln Gln Ser Gly Ala Asp Leu Val Arg Ser Gly Ala
1               5                   10                  15

Ser Ile Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Pro Lys Glu Leu Arg Tyr Phe Asp Val Trp Gly Ala Gly Thr
            100                 105                 110

Thr Val Thr Val Ser Ser
        115

<210> SEQ ID NO 102
<211> LENGTH: 118
<212> TYPE: PRT
<213> ORGANISM: Artificial Sequence
<220> FEATURE:
<223> OTHER INFORMATION: Synthetic

<400> SEQUENCE: 102

Glu Val Gln Leu Gln Gln Ser Gly Ala Asp Leu Val Arg Ser Gly Ala
1               5                   10                  15

Ser Ile Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Ser Lys Glu Leu Arg Tyr Phe Asp Val Trp Gly Ala Gly Thr
            100                 105                 110

Thr Val Thr Val Ser Ser
        115

<210> SEQ ID NO 103
<211> LENGTH: 118
<212> TYPE: PRT
<213> ORGANISM: Artificial Sequence
<220> FEATURE:
<223> OTHER INFORMATION: Synthetic

<400> SEQUENCE: 103

Glu Val Gln Leu Gln Gln Ser Gly Ala Asp Leu Val Arg Ser Gly Ala
1               5                   10                  15

Ser Ile Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Thr Lys Glu Leu Arg Tyr Phe Asp Val Trp Gly Ala Gly Thr
            100                 105                 110

Thr Val Thr Val Ser Ser
        115

-continued

<210> SEQ ID NO 104
<211> LENGTH: 118
<212> TYPE: PRT
<213> ORGANISM: Artificial Sequence
<220> FEATURE:
<223> OTHER INFORMATION: Synthetic

<400> SEQUENCE: 104

Glu Val Gln Leu Gln Gln Ser Gly Ala Asp Leu Val Arg Ser Gly Ala
1               5                   10                  15

Ser Ile Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Tyr Lys Glu Leu Arg Tyr Phe Asp Val Trp Gly Ala Gly Thr
            100                 105                 110

Thr Val Thr Val Ser Ser
        115

<210> SEQ ID NO 105
<211> LENGTH: 118
<212> TYPE: PRT
<213> ORGANISM: Artificial Sequence
<220> FEATURE:
<223> OTHER INFORMATION: Synthetic

<400> SEQUENCE: 105

Glu Val Gln Leu Gln Gln Ser Gly Ala Asp Leu Val Arg Ser Gly Ala
1               5                   10                  15

Ser Ile Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Val Lys Glu Leu Arg Tyr Phe Asp Val Trp Gly Ala Gly Thr
            100                 105                 110

Thr Val Thr Val Ser Ser
        115

<210> SEQ ID NO 106
<211> LENGTH: 118
<212> TYPE: PRT
<213> ORGANISM: Artificial Sequence
<220> FEATURE:
<223> OTHER INFORMATION: Synthetic

<400> SEQUENCE: 106

Glu Val Gln Leu Val Gln Ser Gly Ala Glu Val Lys Lys Pro Gly Ala

```
                1               5                   10                  15
            Thr Val Lys Ile Ser Cys Lys Val Ser Gly Tyr Thr Phe Thr Asp Tyr
                            20                  25                  30

Tyr Met His Trp Val Gln Gln Ala Pro Gly Lys Gly Leu Glu Trp Met
                        35                  40                  45

Gly Trp Ile Asp Pro Glu Asn Gly Asp Thr Glu Tyr Ala Pro Lys Phe
                    50                  55                  60

Gln Gly Arg Val Thr Ile Thr Ala Asp Thr Ser Thr Asp Thr Ala Tyr
             65                 70                  75                  80

Met Glu Leu Ser Ser Leu Arg Ser Glu Asp Thr Ala Val Tyr Tyr Cys
                            85                  90                  95

Asn Ala Cys Lys Glu Leu Arg Tyr Phe Asp Val Trp Gly Gln Gly Thr
                            100                 105                 110

Met Val Thr Val Ser Ser
                            115

<210> SEQ ID NO 107
<211> LENGTH: 118
<212> TYPE: PRT
<213> ORGANISM: Artificial Sequence
<220> FEATURE:
<223> OTHER INFORMATION: Synthetic

<400> SEQUENCE: 107

Gln Val Gln Leu Val Gln Ser Gly Ala Glu Val Lys Lys Pro Gly Ala
 1               5                   10                  15

Ser Val Lys Val Ser Cys Lys Val Ser Gly Tyr Thr Leu Thr Asp Tyr
                20                  25                  30

Tyr Met His Trp Val Arg Gln Ala Pro Gly Lys Gly Leu Glu Trp Met
            35                  40                  45

Gly Trp Ile Asp Pro Glu Asn Gly Asp Thr Glu Tyr Ala Pro Lys Phe
        50                  55                  60

Gln Gly Arg Val Thr Met Thr Glu Asp Thr Ser Thr Asp Thr Ala Tyr
 65                 70                  75                  80

Met Glu Leu Ser Ser Leu Arg Ser Glu Asp Thr Ala Val Tyr Tyr Cys
                85                  90                  95

Asn Ala Cys Lys Glu Leu Arg Tyr Phe Asp Val Trp Gly Gln Gly Thr
                100                 105                 110

Met Val Thr Val Ser Ser
                115

<210> SEQ ID NO 108
<211> LENGTH: 118
<212> TYPE: PRT
<213> ORGANISM: Artificial Sequence
<220> FEATURE:
<223> OTHER INFORMATION: Synthetic

<400> SEQUENCE: 108

Gln Val Gln Leu Val Gln Ser Gly Ala Glu Val Lys Lys Pro Gly Ala
 1               5                   10                  15

Ser Val Lys Val Ser Cys Lys Ala Ser Gly Tyr Thr Phe Thr Asp Tyr
                20                  25                  30

Tyr Met His Trp Val Arg Gln Ala Pro Gly Gln Gly Leu Glu Trp Met
            35                  40                  45

Gly Trp Ile Asp Pro Glu Asn Gly Asp Thr Glu Tyr Ala Pro Lys Phe
        50                  55                  60

Gln Gly Arg Val Thr Met Thr Thr Asp Thr Ser Thr Ser Thr Ala Tyr
```

```
                65                  70                  75                  80
Met Glu Leu Arg Ser Leu Arg Ser Asp Asp Thr Ala Val Tyr Tyr Cys
                    85                  90                  95

Asn Ala Cys Lys Glu Leu Arg Tyr Phe Asp Val Trp Gly Gln Gly Thr
                100                 105                 110

Met Val Thr Val Ser Ser
            115

<210> SEQ ID NO 109
<211> LENGTH: 118
<212> TYPE: PRT
<213> ORGANISM: Artificial Sequence
<220> FEATURE:
<223> OTHER INFORMATION: Synthetic

<400> SEQUENCE: 109

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
                20                  25                  30

Tyr Met His Trp Val Gln Gln Ala Pro Gly Lys Gly Leu Glu Trp Met
            35                  40                  45

Gly Trp Ile Asp Pro Glu Asn Gly Asp Thr Glu Tyr Ala Pro Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Cys Lys Glu Leu Arg Tyr Phe Asp Val Trp Gly Gln Gly Thr
                100                 105                 110

Met Val Thr Val Ser Ser
            115

<210> SEQ ID NO 110
<211> LENGTH: 118
<212> TYPE: PRT
<213> ORGANISM: Artificial Sequence
<220> FEATURE:
<223> OTHER INFORMATION: Synthetic

<400> SEQUENCE: 110

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asp Tyr
                20                  25                  30

Tyr Met His Trp Val Arg Gln Ala Pro Gly Lys Gly Leu Glu Trp Met
            35                  40                  45

Gly Trp Ile Asp Pro Glu Asn Gly Asp Thr Glu Tyr Ala Pro Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Cys Lys Glu Leu Arg Tyr Phe Asp Val Trp Gly Gln Gly Thr
                100                 105                 110

Met Val Thr Val Ser Ser
            115
```

```
<210> SEQ ID NO 111
<211> LENGTH: 118
<212> TYPE: PRT
<213> ORGANISM: Artificial Sequence
<220> FEATURE:
<223> OTHER INFORMATION: Synthetic

<400> SEQUENCE: 111

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Met His Trp Val Arg Gln Ala Pro Gly Gln Gly Leu Glu Trp Met
            35                  40                  45

Gly Trp Ile Asp Pro Glu Asn Gly Asp Thr Glu Tyr Ala Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Cys Lys Glu Leu Arg Tyr Phe Asp Val Trp Gly Gln Gly Thr
            100                 105                 110

Met Val Thr Val Ser Ser
        115

<210> SEQ ID NO 112
<211> LENGTH: 118
<212> TYPE: PRT
<213> ORGANISM: Artificial Sequence
<220> FEATURE:
<223> OTHER INFORMATION: Synthetic

<400> SEQUENCE: 112

Glu Val Gln Leu Gln Gln Ser Gly Ala Asp Leu Val Arg Ser Gly Ala
1               5                   10                  15

Ser Ile Lys Leu Ser Cys Thr Ala Ser Gly Phe Asn Ile Lys Asp Tyr
                20                  25                  30

Tyr Leu His Trp Val Lys Gln Arg Pro Glu Gln Gly Leu Glu Trp Ile
            35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Asn Lys Glu Leu Arg Tyr Phe Asp Val Trp Gly Ala Gly Thr
            100                 105                 110

Thr Val Thr Val Ser Ser
        115

<210> SEQ ID NO 113
<211> LENGTH: 118
<212> TYPE: PRT
<213> ORGANISM: Artificial Sequence
<220> FEATURE:
<223> OTHER INFORMATION: Synthetic

<400> SEQUENCE: 113

Glu Val Gln Leu Val Gln Ser Gly Ala Glu Val Lys Lys Pro Gly Ala
1               5                   10                  15
```

```
Thr Val Lys Ile Ser Cys Lys Ala Ser Gly Tyr Thr Phe Ser Asp Tyr
            20                  25                  30

Tyr Leu His Trp Val Arg Gln Ala Pro Gly Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
            115

<210> SEQ ID NO 114
<211> LENGTH: 118
<212> TYPE: PRT
<213> ORGANISM: Artificial Sequence
<220> FEATURE:
<223> OTHER INFORMATION: Synthetic

<400> SEQUENCE: 114

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Asp Tyr
            20                  25                  30

Tyr Leu His Trp Val Arg Gln Arg Pro Gly Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
            115

<210> SEQ ID NO 115
<211> LENGTH: 118
<212> TYPE: PRT
<213> ORGANISM: Artificial Sequence
<220> FEATURE:
<223> OTHER INFORMATION: Synthetic

<400> SEQUENCE: 115

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Asp Tyr
            20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Ala Asp Thr Ser Thr Asp Thr Gly Tyr
65                  70                  75                  80
```

```
Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
        115

<210> SEQ ID NO 116
<211> LENGTH: 118
<212> TYPE: PRT
<213> ORGANISM: Artificial Sequence
<220> FEATURE:
<223> OTHER INFORMATION: Synthetic

<400> SEQUENCE: 116

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Asp Tyr
            20                  25                  30

Tyr Leu His Trp Val Arg Gln Ala Pro Gly Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Lys Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
        115

<210> SEQ ID NO 117
<211> LENGTH: 118
<212> TYPE: PRT
<213> ORGANISM: Artificial Sequence
<220> FEATURE:
<223> OTHER INFORMATION: Synthetic

<400> SEQUENCE: 117

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Asp Tyr
            20                  25                  30

Tyr Leu His Trp Val Arg Gln Arg Pro Glu Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Lys Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
        115

<210> SEQ ID NO 118
<211> LENGTH: 118
```

```
<212> TYPE: PRT
<213> ORGANISM: Artificial Sequence
<220> FEATURE:
<223> OTHER INFORMATION: Synthetic

<400> SEQUENCE: 118

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Leu His Trp Val Gln Gln Ala Pro Gly Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
            85                  90                  95

Asn Ala Asn Lys Glu Leu Arg Tyr Phe Asp Val Trp Gly Gln Gly Thr
            100                 105                 110

Met Val Thr Val Ser Ser
        115

<210> SEQ ID NO 119
<211> LENGTH: 118
<212> TYPE: PRT
<213> ORGANISM: Artificial Sequence
<220> FEATURE:
<223> OTHER INFORMATION: Synthetic

<400> SEQUENCE: 119

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Gln Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Asn Ala Asn Lys Glu Leu Arg Tyr Phe Asp Val Trp Gly Gln Gly Thr
            100                 105                 110

Met Val Thr Val Ser Ser
        115

<210> SEQ ID NO 120
<211> LENGTH: 118
<212> TYPE: PRT
<213> ORGANISM: Artificial Sequence
<220> FEATURE:
<223> OTHER INFORMATION: Synthetic

<400> SEQUENCE: 120

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asp Tyr
            20                  25                  30
```

Tyr Leu His Trp Val Arg Gln Ala Pro Gly Lys Gly Leu Glu Trp Met
            35                  40                  45

Gly Trp Ile Asp Pro Glu Asn Gly Asp Thr Glu Tyr Ala Pro Lys Phe
     50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asn Lys Glu Leu Arg Tyr Phe Asp Val Trp Gly Gln Gly Thr
            100                 105                 110

Met Val Thr Val Ser Ser
            115

<210> SEQ ID NO 121
<211> LENGTH: 118
<212> TYPE: PRT
<213> ORGANISM: Artificial Sequence
<220> FEATURE:
<223> OTHER INFORMATION: Synthetic

<400> SEQUENCE: 121

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Asp Tyr
            20                  25                  30

Tyr Leu His Trp Val Arg Gln Ala Pro Glu Lys Gly Leu Glu Trp Met
            35                  40                  45

Gly Trp Ile Asp Pro Glu Asn Gly Asp Thr Glu Tyr Ala Pro Lys Phe
     50                  55                  60

Gln Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Arg Asn Lys Glu Leu Arg Tyr Phe Asp Val Trp Gly Gln Gly Thr
            100                 105                 110

Leu Val Thr Val Ser Ser
            115

<210> SEQ ID NO 122
<211> LENGTH: 118
<212> TYPE: PRT
<213> ORGANISM: Artificial Sequence
<220> FEATURE:
<223> OTHER INFORMATION: Synthetic

<400> SEQUENCE: 122

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Asp Tyr
            20                  25                  30

Tyr Leu His Trp Val Arg Gln Ala Pro Glu Lys Gly Leu Glu Trp Met
            35                  40                  45

Gly Trp Ile Asp Pro Glu Asn Gly Asp Thr Glu Tyr Ala Pro Lys Phe
     50                  55                  60

Gln Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

```
Asn Ala Asn Lys Glu Leu Arg Tyr Phe Asp Val Trp Gly Gln Gly Thr
            100                 105                 110
Leu Val Thr Val Ser Ser
        115

<210> SEQ ID NO 123
<211> LENGTH: 118
<212> TYPE: PRT
<213> ORGANISM: Artificial Sequence
<220> FEATURE:
<223> OTHER INFORMATION: Synthetic

<400> SEQUENCE: 123

Glu Val Gln Leu Val Gln Ser Gly Ala Glu Val Lys Lys Pro Gly Ala
1               5                   10                  15
Thr Val Lys Ile Ser Cys Lys Ala Ser Gly Tyr Thr Phe Ser Asp Tyr
            20                  25                  30
Tyr Leu His Trp Val Arg Gln Ala Pro Glu Lys Gly Leu Glu Trp Met
        35                  40                  45
Gly Trp Ile Asp Pro Glu Asn Gly Asp Thr Glu Tyr Ala Pro Lys Phe
    50                  55                  60
Gln Gly Arg Val Thr Ile Thr Ala Asp Thr Ser Thr Asp Thr Gly Tyr
65                  70                  75                  80
Leu Glu Leu Ser Ser Leu Arg Ser Glu Asp Thr Ala Val Tyr Tyr Cys
                85                  90                  95
Asn Arg Asn Lys Glu Leu Arg Tyr Phe Asp Val Trp Gly Gln Gly Thr
            100                 105                 110
Leu Val Thr Val Ser Ser
        115

<210> SEQ ID NO 124
<211> LENGTH: 118
<212> TYPE: PRT
<213> ORGANISM: Artificial Sequence
<220> FEATURE:
<223> OTHER INFORMATION: Synthetic

<400> SEQUENCE: 124

Gln Val Gln Leu Val Gln Ser Gly Ala Glu Val Lys Lys Pro Gly Ala
1               5                   10                  15
Thr Val Lys Ile Ser Cys Lys Ala Ser Gly Tyr Thr Phe Ser Asp Tyr
            20                  25                  30
Tyr Leu His Trp Val Arg Gln Ala Pro Glu Lys Gly Leu Glu Trp Met
        35                  40                  45
Gly Trp Ile Asp Pro Glu Asn Gly Asp Thr Glu Tyr Ala Pro Lys Phe
    50                  55                  60
Gln Gly Arg Val Thr Ile Thr Ala Asp Thr Ser Thr Asp Thr Gly Tyr
65                  70                  75                  80
Leu Glu Leu Ser Ser Leu Arg Ser Glu Asp Thr Ala Val Tyr Tyr Cys
                85                  90                  95
Ala Ala Asn Lys Glu Leu Arg Tyr Phe Asp Val Trp Gly Gln Gly Thr
            100                 105                 110
Leu Val Thr Val Ser Ser
        115

<210> SEQ ID NO 125
<211> LENGTH: 118
<212> TYPE: PRT
<213> ORGANISM: Artificial Sequence
```

```
<220> FEATURE:
<223> OTHER INFORMATION: Synthetic

<400> SEQUENCE: 125

Glu Val Gln Leu Gln Gln Ser Gly Ala Glu Val Lys Lys Pro Gly Ala
1               5                   10                  15

Thr Val Lys Ile Ser Cys Lys Ala Ser Gly Tyr Thr Phe Ser Asp Tyr
            20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
        115

<210> SEQ ID NO 126
<211> LENGTH: 118
<212> TYPE: PRT
<213> ORGANISM: Artificial Sequence
<220> FEATURE:
<223> OTHER INFORMATION: Synthetic

<400> SEQUENCE: 126

Glu Val Gln Leu Val Gln Ser Gly Ala Asp Val Lys Lys Pro Gly Ala
1               5                   10                  15

Thr Val Lys Ile Ser Cys Lys Ala Ser Gly Tyr Thr Phe Ser Asp Tyr
            20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
        115

<210> SEQ ID NO 127
<211> LENGTH: 118
<212> TYPE: PRT
<213> ORGANISM: Artificial Sequence
<220> FEATURE:
<223> OTHER INFORMATION: Synthetic

<400> SEQUENCE: 127

Glu Val Gln Leu Val Gln Ser Gly Ala Glu Leu Lys Lys Pro Gly Ala
1               5                   10                  15

Thr Val Lys Ile Ser Cys Lys Ala Ser Gly Tyr Thr Phe Ser Asp Tyr
            20                  25                  30

Tyr Leu His Trp Val Arg Gln Ala Pro Glu Lys Gly Leu Glu Trp Met
```

```
                35                  40                  45
Gly Trp Ile Asp Pro Glu Asn Gly Asp Thr Glu Tyr Ala Pro Lys Phe
 50                  55                  60

Gln Gly Arg Val Thr Ile Thr Ala Asp Thr Ser Thr Asp Thr Gly Tyr
 65                  70                  75                  80

Leu Glu Leu Ser Ser Leu Arg Ser Glu Asp Thr Ala Val Tyr Tyr Cys
                 85                  90                  95

Ala Ala Asn Lys Glu Leu Arg Tyr Phe Asp Val Trp Gly Gln Gly Thr
                100                 105                 110

Leu Val Thr Val Ser Ser
        115

<210> SEQ ID NO 128
<211> LENGTH: 118
<212> TYPE: PRT
<213> ORGANISM: Artificial Sequence
<220> FEATURE:
<223> OTHER INFORMATION: Synthetic

<400> SEQUENCE: 128

Glu Val Gln Leu Val Gln Ser Gly Ala Glu Val Val Lys Pro Gly Ala
 1               5                  10                  15

Thr Val Lys Ile Ser Cys Lys Ala Ser Gly Tyr Thr Phe Ser Asp Tyr
                 20                  25                  30

Tyr Leu His Trp Val Arg Gln Ala Pro Glu Lys Gly Leu Glu Trp Met
                 35                  40                  45

Gly Trp Ile Asp Pro Glu Asn Gly Asp Thr Glu Tyr Ala Pro Lys Phe
 50                  55                  60

Gln Gly Arg Val Thr Ile Thr Ala Asp Thr Ser Thr Asp Thr Gly Tyr
 65                  70                  75                  80

Leu Glu Leu Ser Ser Leu Arg Ser Glu Asp Thr Ala Val Tyr Tyr Cys
                 85                  90                  95

Ala Ala Asn Lys Glu Leu Arg Tyr Phe Asp Val Trp Gly Gln Gly Thr
                100                 105                 110

Leu Val Thr Val Ser Ser
        115

<210> SEQ ID NO 129
<211> LENGTH: 118
<212> TYPE: PRT
<213> ORGANISM: Artificial Sequence
<220> FEATURE:
<223> OTHER INFORMATION: Synthetic

<400> SEQUENCE: 129

Glu Val Gln Leu Val Gln Ser Gly Ala Glu Val Lys Arg Pro Gly Ala
 1               5                  10                  15

Thr Val Lys Ile Ser Cys Lys Ala Ser Gly Tyr Thr Phe Ser Asp Tyr
                 20                  25                  30

Tyr Leu His Trp Val Arg Gln Ala Pro Glu Lys Gly Leu Glu Trp Met
                 35                  40                  45

Gly Trp Ile Asp Pro Glu Asn Gly Asp Thr Glu Tyr Ala Pro Lys Phe
 50                  55                  60

Gln Gly Arg Val Thr Ile Thr Ala Asp Thr Ser Thr Asp Thr Gly Tyr
 65                  70                  75                  80

Leu Glu Leu Ser Ser Leu Arg Ser Glu Asp Thr Ala Val Tyr Tyr Cys
                 85                  90                  95

Ala Ala Asn Lys Glu Leu Arg Tyr Phe Asp Val Trp Gly Gln Gly Thr
```

-continued

<210> SEQ ID NO 130
<211> LENGTH: 118
<212> TYPE: PRT
<213> ORGANISM: Artificial Sequence
<220> FEATURE:
<223> OTHER INFORMATION: Synthetic

<400> SEQUENCE: 130

Glu Val Gln Leu Val Gln Ser Gly Ala Glu Val Lys Lys Ser Gly Ala
1               5                   10                  15

Thr Val Lys Ile Ser Cys Lys Ala Ser Gly Tyr Thr Phe Ser Asp Tyr
            20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
        115

<210> SEQ ID NO 131
<211> LENGTH: 118
<212> TYPE: PRT
<213> ORGANISM: Artificial Sequence
<220> FEATURE:
<223> OTHER INFORMATION: Synthetic

<400> SEQUENCE: 131

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Ser Asp Tyr
            20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
        115

<210> SEQ ID NO 132
<211> LENGTH: 118
<212> TYPE: PRT
<213> ORGANISM: Artificial Sequence
<220> FEATURE:
<223> OTHER INFORMATION: Synthetic

```
<400> SEQUENCE: 132

Glu Val Gln Leu Val Gln Ser Gly Ala Glu Val Lys Lys Pro Gly Ala
1               5                   10                  15

Thr Ile Lys Ile Ser Cys Lys Ala Ser Gly Tyr Thr Phe Ser Asp Tyr
            20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
                100                 105                 110

Leu Val Thr Val Ser Ser
        115

<210> SEQ ID NO 133
<211> LENGTH: 118
<212> TYPE: PRT
<213> ORGANISM: Artificial Sequence
<220> FEATURE:
<223> OTHER INFORMATION: Synthetic

<400> SEQUENCE: 133

Glu Val Gln Leu Val Gln Ser Gly Ala Glu Val Lys Lys Pro Gly Ala
1               5                   10                  15

Thr Val Lys Leu Ser Cys Lys Ala Ser Gly Tyr Thr Phe Ser Asp Tyr
            20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
                100                 105                 110

Leu Val Thr Val Ser Ser
        115

<210> SEQ ID NO 134
<211> LENGTH: 118
<212> TYPE: PRT
<213> ORGANISM: Artificial Sequence
<220> FEATURE:
<223> OTHER INFORMATION: Synthetic

<400> SEQUENCE: 134

Glu Val Gln Leu Val Gln Ser Gly Ala Glu Val Lys Lys Pro Gly Ala
1               5                   10                  15

Thr Val Lys Ile Ser Cys Thr Ala Ser Gly Tyr Thr Phe Ser Asp Tyr
            20                  25                  30

Tyr Leu His Trp Val Arg Gln Ala Pro Glu Lys Gly Leu Glu Trp Met
        35                  40                  45
```

Gly Trp Ile Asp Pro Glu Asn Gly Asp Thr Glu Tyr Ala Pro Lys Phe
            50                  55                  60

Gln Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                    85                  90                  95

Ala Ala Asn Lys Glu Leu Arg Tyr Phe Asp Val Trp Gly Gln Gly Thr
                100                 105                 110

Leu Val Thr Val Ser Ser
            115

<210> SEQ ID NO 135
<211> LENGTH: 118
<212> TYPE: PRT
<213> ORGANISM: Artificial Sequence
<220> FEATURE:
<223> OTHER INFORMATION: Synthetic

<400> SEQUENCE: 135

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Thr Phe Ser Asp Tyr
                20                  25                  30

Tyr Leu His Trp Val Arg Gln Ala Pro Glu Lys Gly Leu Glu Trp Met
            35                  40                  45

Gly Trp Ile Asp Pro Glu Asn Gly Asp Thr Glu Tyr Ala Pro Lys Phe
        50                  55                  60

Gln Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                    85                  90                  95

Ala Ala Asn Lys Glu Leu Arg Tyr Phe Asp Val Trp Gly Gln Gly Thr
                100                 105                 110

Leu Val Thr Val Ser Ser
            115

<210> SEQ ID NO 136
<211> LENGTH: 118
<212> TYPE: PRT
<213> ORGANISM: Artificial Sequence
<220> FEATURE:
<223> OTHER INFORMATION: Synthetic

<400> SEQUENCE: 136

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Asn Phe Ser Asp Tyr
                20                  25                  30

Tyr Leu His Trp Val Arg Gln Ala Pro Glu Lys Gly Leu Glu Trp Met
            35                  40                  45

Gly Trp Ile Asp Pro Glu Asn Gly Asp Thr Glu Tyr Ala Pro Lys Phe
        50                  55                  60

Gln Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                    85                  90                  95

Ala Ala Asn Lys Glu Leu Arg Tyr Phe Asp Val Trp Gly Gln Gly Thr
                100                 105                 110

```
Leu Val Thr Val Ser Ser
        115

<210> SEQ ID NO 137
<211> LENGTH: 118
<212> TYPE: PRT
<213> ORGANISM: Artificial Sequence
<220> FEATURE:
<223> OTHER INFORMATION: Synthetic

<400> SEQUENCE: 137

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Ile Ser Asp Tyr
            20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
        115

<210> SEQ ID NO 138
<211> LENGTH: 118
<212> TYPE: PRT
<213> ORGANISM: Artificial Sequence
<220> FEATURE:
<223> OTHER INFORMATION: Synthetic

<400> SEQUENCE: 138

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Lys Asp Tyr
            20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
        115

<210> SEQ ID NO 139
<211> LENGTH: 118
<212> TYPE: PRT
<213> ORGANISM: Artificial Sequence
<220> FEATURE:
<223> OTHER INFORMATION: Synthetic

<400> SEQUENCE: 139
```

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Asp Tyr
            20                  25                  30

Tyr Leu His Trp Val Lys Gln Ala Pro Glu Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
                100                 105                 110

Leu Val Thr Val Ser Ser
        115

<210> SEQ ID NO 140
<211> LENGTH: 118
<212> TYPE: PRT
<213> ORGANISM: Artificial Sequence
<220> FEATURE:
<223> OTHER INFORMATION: Synthetic

<400> SEQUENCE: 140

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Asp Tyr
            20                  25                  30

Tyr Leu His Trp Val Arg Gln Ala Pro Glu Lys Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
                100                 105                 110

Leu Val Thr Val Ser Ser
        115

<210> SEQ ID NO 141
<211> LENGTH: 118
<212> TYPE: PRT
<213> ORGANISM: Artificial Sequence
<220> FEATURE:
<223> OTHER INFORMATION: Synthetic

<400> SEQUENCE: 141

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Asp Tyr
            20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Tyr Ala Pro Lys Phe
    50                  55                  60

```
Gln Gly Arg Ala Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
        115

<210> SEQ ID NO 142
<211> LENGTH: 118
<212> TYPE: PRT
<213> ORGANISM: Artificial Sequence
<220> FEATURE:
<223> OTHER INFORMATION: Synthetic

<400> SEQUENCE: 142

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Asp Tyr
            20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Met Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
        115

<210> SEQ ID NO 143
<211> LENGTH: 118
<212> TYPE: PRT
<213> ORGANISM: Artificial Sequence
<220> FEATURE:
<223> OTHER INFORMATION: Synthetic

<400> SEQUENCE: 143

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Asp Tyr
            20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
        115
```

```
<210> SEQ ID NO 144
<211> LENGTH: 118
<212> TYPE: PRT
<213> ORGANISM: Artificial Sequence
<220> FEATURE:
<223> OTHER INFORMATION: Synthetic

<400> SEQUENCE: 144

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Asp Tyr
            20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Ala Asp Thr Ser Ser Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
        115

<210> SEQ ID NO 145
<211> LENGTH: 118
<212> TYPE: PRT
<213> ORGANISM: Artificial Sequence
<220> FEATURE:
<223> OTHER INFORMATION: Synthetic

<400> SEQUENCE: 145

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Asp Tyr
            20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Ala Asp Thr Ser Thr Asn Thr Gly Tyr
65                  70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
        115

<210> SEQ ID NO 146
<211> LENGTH: 118
<212> TYPE: PRT
<213> ORGANISM: Artificial Sequence
<220> FEATURE:
<223> OTHER INFORMATION: Synthetic

<400> SEQUENCE: 146

Glu Val Gln Leu Val Gln Ser Gly Ala Glu Val Lys Lys Pro Gly Ala
```

```
                1               5                   10                  15
Thr Val Lys Ile Ser Cys Lys Ala Ser Gly Tyr Thr Phe Ser Asp Tyr
        20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Tyr Ala Pro Lys Phe
        50                  55                  60

Gln Gly Arg Val Thr Ile Thr Ala Asp Thr Ser Thr Asp Thr Ala Tyr
65                      70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
            115

<210> SEQ ID NO 147
<211> LENGTH: 118
<212> TYPE: PRT
<213> ORGANISM: Artificial Sequence
<220> FEATURE:
<223> OTHER INFORMATION: Synthetic

<400> SEQUENCE: 147

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Asp Tyr
        20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Tyr Ala Pro Lys Phe
        50                  55                  60

Gln Gly Arg Val Thr Ile Thr Ala Asp Thr Ser Thr Asp Thr Gly Tyr
65                      70                  75                  80

Met Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
            115

<210> SEQ ID NO 148
<211> LENGTH: 118
<212> TYPE: PRT
<213> ORGANISM: Artificial Sequence
<220> FEATURE:
<223> OTHER INFORMATION: Synthetic

<400> SEQUENCE: 148

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Asp Tyr
        20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Tyr Ala Pro Lys Phe
        50                  55                  60

Gln Gly Arg Val Thr Ile Thr Ala Asp Thr Ser Thr Asp Thr Gly Tyr
```

```
                65                  70                  75                  80
Leu Gln Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
        115

<210> SEQ ID NO 149
<211> LENGTH: 118
<212> TYPE: PRT
<213> ORGANISM: Artificial Sequence
<220> FEATURE:
<223> OTHER INFORMATION: Synthetic

<400> SEQUENCE: 149

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Asp Tyr
            20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Ala Asp Thr Ser Thr Asp Thr Gly Tyr
65                  70                  75                  80

Leu Glu Leu Arg Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
        115

<210> SEQ ID NO 150
<211> LENGTH: 118
<212> TYPE: PRT
<213> ORGANISM: Artificial Sequence
<220> FEATURE:
<223> OTHER INFORMATION: Synthetic

<400> SEQUENCE: 150

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Asp Tyr
            20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Ala Asp Thr Ser Thr Asp Thr Gly Tyr
65                  70                  75                  80

Leu Glu Leu Ser Ser Leu Thr Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
        115
```

```
<210> SEQ ID NO 151
<211> LENGTH: 118
<212> TYPE: PRT
<213> ORGANISM: Artificial Sequence
<220> FEATURE:
<223> OTHER INFORMATION: Synthetic

<400> SEQUENCE: 151

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Asp Tyr
            20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Ala Asp Thr Ser Thr Asp Thr Gly Tyr
65                  70                  75                  80

Leu Glu Leu Ser Ser Leu Arg Ser Asp Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
        115

<210> SEQ ID NO 152
<211> LENGTH: 118
<212> TYPE: PRT
<213> ORGANISM: Artificial Sequence
<220> FEATURE:
<223> OTHER INFORMATION: Synthetic

<400> SEQUENCE: 152

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Asp Tyr
            20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Ala Gly Thr
            100                 105                 110

Leu Val Thr Val Ser Ser
        115

<210> SEQ ID NO 153
<211> LENGTH: 118
<212> TYPE: PRT
<213> ORGANISM: Artificial Sequence
<220> FEATURE:
<223> OTHER INFORMATION: Synthetic

<400> SEQUENCE: 153

Glu Val Gln Leu Val Gln Ser Gly Ala Glu Val Lys Lys Pro Gly Ala
1               5                   10                  15
```

```
Thr Val Lys Ile Ser Cys Lys Ala Ser Gly Tyr Ala Phe Ser Asp Tyr
            20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Tyr Ala Pro Lys Phe
 50                  55                  60

Gln Gly Arg Val Thr Ile Thr Ala Asp Thr Ser Thr Asp Thr Gly Tyr
 65                  70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
        115

<210> SEQ ID NO 154
<211> LENGTH: 118
<212> TYPE: PRT
<213> ORGANISM: Artificial Sequence
<220> FEATURE:
<223> OTHER INFORMATION: Synthetic

<400> SEQUENCE: 154

Glu Val Gln Leu Val Gln Ser Gly Ala Glu Val Lys Lys Pro Gly Ala
  1               5                  10                  15

Thr Val Lys Ile Ser Cys Lys Ala Ser Gly Tyr Thr Leu Ser Asp Tyr
            20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Tyr Ala Pro Lys Phe
 50                  55                  60

Gln Gly Arg Val Thr Ile Thr Ala Asp Thr Ser Thr Asp Thr Gly Tyr
 65                  70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
        115

<210> SEQ ID NO 155
<211> LENGTH: 118
<212> TYPE: PRT
<213> ORGANISM: Artificial Sequence
<220> FEATURE:
<223> OTHER INFORMATION: Synthetic

<400> SEQUENCE: 155

Glu Val Gln Leu Val Gln Ser Gly Ala Glu Val Lys Lys Pro Gly Ala
  1               5                  10                  15

Thr Val Lys Ile Ser Cys Lys Ala Ser Gly Tyr Thr Phe Ser Asp Tyr
            20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Ser Ala Pro Lys Phe
 50                  55                  60

Gln Gly Arg Val Thr Ile Thr Ala Asp Thr Ser Thr Asp Thr Gly Tyr
 65                  70                  75                  80
```

```
Leu Glu Leu Ser Ser Leu Arg Ser Glu Asp Thr Ala Val Tyr Tyr Cys
            85                  90                  95

Ala Ala Asn Lys Glu Leu Arg Tyr Phe Asp Val Trp Gly Gln Gly Thr
            100                 105                 110

Leu Val Thr Val Ser Ser
            115

<210> SEQ ID NO 156
<211> LENGTH: 118
<212> TYPE: PRT
<213> ORGANISM: Artificial Sequence
<220> FEATURE:
<223> OTHER INFORMATION: Synthetic

<400> SEQUENCE: 156

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Ala Leu Ser Asp Tyr
            20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
            85                  90                  95

Ala Ala Asn Lys Glu Leu Arg Tyr Phe Asp Val Trp Gly Gln Gly Thr
            100                 105                 110

Leu Val Thr Val Ser Ser
            115

<210> SEQ ID NO 157
<211> LENGTH: 118
<212> TYPE: PRT
<213> ORGANISM: Artificial Sequence
<220> FEATURE:
<223> OTHER INFORMATION: Synthetic

<400> SEQUENCE: 157

Glu Val Gln Leu Val Gln Ser Gly Ala Gln Val Lys Lys Pro Gly Ala
1               5                   10                  15

Thr Val Lys Ile Ser Cys Lys Ala Ser Gly Tyr Thr Leu Ser Asp Tyr
            20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
            85                  90                  95

Ala Ala Asn Lys Glu Leu Arg Tyr Phe Asp Val Trp Gly Gln Gly Thr
            100                 105                 110

Leu Val Thr Val Ser Ser
            115

<210> SEQ ID NO 158
<211> LENGTH: 118
```

```
<212> TYPE: PRT
<213> ORGANISM: Artificial Sequence
<220> FEATURE:
<223> OTHER INFORMATION: Synthetic

<400> SEQUENCE: 158

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Leu Ser Asp Tyr
            20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu Ser Ala Pro Lys Phe
    50                  55                  60

Gln Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
        115

<210> SEQ ID NO 159
<211> LENGTH: 118
<212> TYPE: PRT
<213> ORGANISM: Artificial Sequence
<220> FEATURE:
<223> OTHER INFORMATION: Synthetic

<400> SEQUENCE: 159

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Asp Tyr
            20                  25                  30

Tyr Leu His Trp Val Arg Gln Ala Pro Glu Lys Gly Leu Glu Trp Met
        35                  40                  45

Gly Trp Ile Asp Pro Glu Asn Gly Asp Thr Glu His Ala Pro Lys Phe
    50                  55                  60

Gln Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
        115

<210> SEQ ID NO 160
<211> LENGTH: 118
<212> TYPE: PRT
<213> ORGANISM: Artificial Sequence
<220> FEATURE:
<223> OTHER INFORMATION: Synthetic

<400> SEQUENCE: 160

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Leu Ser Asp Tyr
            20                  25                  30
```

Tyr Leu His Trp Val Arg Gln Ala Pro Glu Lys Gly Leu Glu Trp Met
            35                  40                  45

Gly Trp Ile Asp Pro Glu Asn Gly Asp Thr Glu His Ala Pro Lys Phe
 50                  55                  60

Gln Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Leu Val Thr Val Ser Ser
            115

<210> SEQ ID NO 161
<211> LENGTH: 118
<212> TYPE: PRT
<213> ORGANISM: Artificial Sequence
<220> FEATURE:
<223> OTHER INFORMATION: Synthetic

<400> SEQUENCE: 161

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Gln Gly Leu Glu Trp Met
            35                  40                  45

Gly Trp Ile Asp Pro Glu Asn Gly Asp Thr Glu Tyr Ala Pro Lys Phe
 50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Met Val Thr Val Ser Ser
            115

<210> SEQ ID NO 162
<211> LENGTH: 118
<212> TYPE: PRT
<213> ORGANISM: Artificial Sequence
<220> FEATURE:
<223> OTHER INFORMATION: Synthetic

<400> SEQUENCE: 162

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Asp Tyr
            20                  25                  30

Tyr Leu His Trp Val Arg Gln Ala Pro Gly Gln Gly Leu Glu Trp Met
            35                  40                  45

Gly Trp Ile Asp Pro Glu Asn Gly Asp Thr Glu Tyr Ala Pro Lys Phe
 50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Met Val Thr Val Ser Ser
        115

<210> SEQ ID NO 163
<211> LENGTH: 118
<212> TYPE: PRT
<213> ORGANISM: Artificial Sequence
<220> FEATURE:
<223> OTHER INFORMATION: Synthetic

<400> SEQUENCE: 163

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Gln Gly Leu Glu Trp Met
        35                  40                  45

Gly Trp Ile Asp Pro Glu Asn Gly Asp Thr Glu Ser Ala Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Met Val Thr Val Ser Ser
        115

<210> SEQ ID NO 164
<211> LENGTH: 118
<212> TYPE: PRT
<213> ORGANISM: Artificial Sequence
<220> FEATURE:
<223> OTHER INFORMATION: Synthetic

<400> SEQUENCE: 164

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Asp Tyr
            20                  25                  30

Tyr Leu His Trp Val Arg Gln Ala Pro Gly Gln Gly Leu Glu Trp Met
        35                  40                  45

Gly Trp Ile Asp Pro Glu Asn Gly Asp Thr Glu Ser Ala Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Met Val Thr Val Ser Ser
        115

<210> SEQ ID NO 165
<211> LENGTH: 118
<212> TYPE: PRT
<213> ORGANISM: Artificial Sequence

```
<220> FEATURE:
<223> OTHER INFORMATION: Synthetic

<400> SEQUENCE: 165

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Gln Gly Leu Glu Trp Met
        35                  40                  45

Gly Trp Ile Asp Pro Glu Asn Gly Asp Thr Glu His Ala Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Met Val Thr Val Ser Ser
        115

<210> SEQ ID NO 166
<211> LENGTH: 118
<212> TYPE: PRT
<213> ORGANISM: Artificial Sequence
<220> FEATURE:
<223> OTHER INFORMATION: Synthetic

<400> SEQUENCE: 166

Gln Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Gln Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Gly Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Ala Asn Lys Glu Leu Arg Tyr Phe Asp Val Trp Gly Gln Gly Thr
            100                 105                 110

Met Val Thr Val Ser Ser
        115

<210> SEQ ID NO 167
<211> LENGTH: 118
<212> TYPE: PRT
<213> ORGANISM: Artificial Sequence
<220> FEATURE:
<223> OTHER INFORMATION: Synthetic

<400> SEQUENCE: 167

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Arg Gly Leu Glu Trp Met
```

-continued

```
                    35                  40                  45
Gly Trp Ile Asp Pro Glu Asn Gly Asp Thr Glu Tyr Ala Pro Lys Phe
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Ala Asn Lys Glu Leu Arg Tyr Phe Asp Val Trp Gly Gln Gly Thr
            100                 105                 110

Met Val Thr Val Ser Ser
        115

<210> SEQ ID NO 168
<211> LENGTH: 118
<212> TYPE: PRT
<213> ORGANISM: Artificial Sequence
<220> FEATURE:
<223> OTHER INFORMATION: Synthetic

<400> SEQUENCE: 168

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Asp Tyr
                20                  25                  30

Tyr Leu His Trp Val Arg Gln Ala Pro Gly Gln Gly Leu Glu Trp Met
            35                  40                  45

Gly Trp Ile Asp Pro Glu Asn Gly Asp Thr Glu Tyr Ala Pro Lys Phe
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Ala Asn Lys Glu Leu Arg Tyr Phe Asp Val Trp Gly Gln Gly Thr
            100                 105                 110

Met Val Thr Val Ser Ser
        115

<210> SEQ ID NO 169
<211> LENGTH: 108
<212> TYPE: PRT
<213> ORGANISM: Artificial Sequence
<220> FEATURE:
<223> OTHER INFORMATION: Synthetic

<400> SEQUENCE: 169

Asp Ile Val Leu Thr Gln Ser Pro Ala Thr Leu Ser Val Thr Pro Gly
 1               5                  10                  15

Asp Ser Val Ser Leu Ser Cys Arg Ala Ser Gln Ser Ile Ser Ile Asn
                20                  25                  30

Leu His Trp Tyr Gln Gln Lys Ser His Glu Ser Pro Arg Leu Leu Ile
            35                  40                  45

Lys Phe Ala Ser Gln Ser Ile Ser Gly Ile Pro Ser Arg Phe Ser Gly
 50                  55                  60

Tyr Gly Ser Gly Thr Asp Phe Thr Leu Ser Ile Asn Ser Val Glu Thr
 65                  70                  75                  80

Glu Asp Phe Gly Arg Tyr Phe Cys Gln Gln Ser Asn Ser Phe Pro Leu
                 85                  90                  95

Thr Phe Gly Ala Gly Thr Lys Leu Glu Leu Lys Arg
```

<210> SEQ ID NO 170
<211> LENGTH: 108
<212> TYPE: PRT
<213> ORGANISM: Artificial Sequence
<220> FEATURE:
<223> OTHER INFORMATION: Synthetic

<400> SEQUENCE: 170

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Ile Asn
            20                  25                  30

Leu His Trp Tyr Gln Gln Lys Pro Asp Gln Ser Pro Lys Leu Leu Ile
        35                  40                  45

Lys Phe Ala Ser Gln Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Ser Trp Pro Leu
                85                  90                  95

Thr Phe Gly Gly Gly Thr Lys Val Glu Ile Lys Arg
            100                 105

<210> SEQ ID NO 171
<211> LENGTH: 108
<212> TYPE: PRT
<213> ORGANISM: Artificial Sequence
<220> FEATURE:
<223> OTHER INFORMATION: Synthetic

<400> SEQUENCE: 171

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ile Asn
            20                  25                  30

Leu His Trp Tyr Gln Gln Lys Pro Gly Gln Ala Pro Arg Leu Leu Ile
        35                  40                  45

Tyr Phe Ala Ser Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Asn Ser Trp Pro Leu
                85                  90                  95

Thr Phe Gly Gly Gly Thr Lys Val Glu Ile Lys Arg
            100                 105

<210> SEQ ID NO 172
<211> LENGTH: 108
<212> TYPE: PRT
<213> ORGANISM: Artificial Sequence
<220> FEATURE:
<223> OTHER INFORMATION: Synthetic

<400> SEQUENCE: 172

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ile Asn
            20                  25                  30

```
Leu His Trp Tyr Gln Gln Lys Pro Gly Gln Ala Pro Arg Leu Leu Ile
        35                  40                  45

Tyr Phe Ala Ser Gln Ser Ile Ser Gly Ile Pro Ala Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asn Ser Trp Pro Leu
                85                  90                  95

Thr Phe Gly Gly Gly Thr Lys Val Glu Ile Lys Arg
            100                 105

<210> SEQ ID NO 173
<211> LENGTH: 108
<212> TYPE: PRT
<213> ORGANISM: Artificial Sequence
<220> FEATURE:
<223> OTHER INFORMATION: Synthetic

<400> SEQUENCE: 173

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ile Asn
                20                  25                  30

Leu His Trp Tyr Gln Gln Lys Pro Gly Lys Ala Pro Lys Leu Leu Ile
        35                  40                  45

Tyr Phe Ala Ser Gln Ser Ile Ser Gly Val Pro Ser Arg Phe Ser Gly
 50                  55                  60

Ser Gly Ser Gly Thr Asp Phe Ser Leu Thr Ile Asn Ser Leu Gln Pro
65                  70                  75                  80

Glu Asp Phe Ala Thr Tyr Tyr Cys Gln Gln Ser Asn Ser Phe Pro Leu
                85                  90                  95

Thr Phe Gly Gly Gly Thr Lys Val Glu Ile Lys Arg
            100                 105

<210> SEQ ID NO 174
<211> LENGTH: 108
<212> TYPE: PRT
<213> ORGANISM: Artificial Sequence
<220> FEATURE:
<223> OTHER INFORMATION: Synthetic

<400> SEQUENCE: 174

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ile Asn
                20                  25                  30

Leu His Trp Tyr Gln Gln Lys Pro Gly Lys Ala Pro Lys Leu Leu Ile
        35                  40                  45

Lys Phe Ala Ser Gln Ser Ile Ser Gly Val Pro Ser Arg Phe Ser Gly
 50                  55                  60

Ser Gly Ser Gly Thr Asp Phe Ser Leu Thr Ile Asn Ser Leu Gln Pro
65                  70                  75                  80

Glu Asp Phe Ala Thr Tyr Tyr Cys Gln Gln Ser Asn Ser Phe Pro Leu
                85                  90                  95

Thr Phe Gly Gly Gly Thr Lys Val Glu Ile Lys Arg
            100                 105

<210> SEQ ID NO 175
<211> LENGTH: 108
```

```
<212> TYPE: PRT
<213> ORGANISM: Artificial Sequence
<220> FEATURE:
<223> OTHER INFORMATION: Synthetic

<400> SEQUENCE: 175

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ile Asn
            20                  25                  30

Leu His Trp Tyr Gln Gln Lys Pro Gly Lys Ala Pro Lys Leu Leu Ile
        35                  40                  45

Tyr Phe Ala Ser Gln Ser Ile Ser Gly Val Pro Ser Arg Phe Ser Gly
    50                  55                  60

Tyr Gly Ser Gly Thr Asp Phe Ser Leu Thr Ile Asn Ser Leu Gln Pro
65                  70                  75                  80

Glu Asp Phe Ala Thr Tyr Tyr Cys Gln Gln Ser Asn Ser Phe Pro Leu
                85                  90                  95

Thr Phe Gly Gly Gly Thr Lys Val Glu Ile Lys Arg
            100                 105

<210> SEQ ID NO 176
<211> LENGTH: 108
<212> TYPE: PRT
<213> ORGANISM: Artificial Sequence
<220> FEATURE:
<223> OTHER INFORMATION: Synthetic

<400> SEQUENCE: 176

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ile Asn
            20                  25                  30

Leu His Trp Tyr Gln Gln Lys Pro Gly Lys Ala Pro Lys Leu Leu Ile
        35                  40                  45

Tyr Phe Ala Ser Gln Ser Ile Ser Gly Val Pro Ser Arg Phe Ser Gly
    50                  55                  60

Ser Gly Ser Gly Thr Asp Phe Ser Leu Thr Ile Asn Ser Leu Gln Pro
65                  70                  75                  80

Glu Asp Phe Ala Arg Tyr Tyr Cys Gln Gln Ser Asn Ser Phe Pro Leu
                85                  90                  95

Thr Phe Gly Gly Gly Thr Lys Val Glu Ile Lys Arg
            100                 105

<210> SEQ ID NO 177
<211> LENGTH: 108
<212> TYPE: PRT
<213> ORGANISM: Artificial Sequence
<220> FEATURE:
<223> OTHER INFORMATION: Synthetic

<400> SEQUENCE: 177

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ile Asn
            20                  25                  30

Leu His Trp Tyr Gln Gln Lys Pro Gly Lys Ala Pro Lys Leu Leu Ile
        35                  40                  45

Lys Phe Ala Ser Gln Ser Ile Ser Gly Val Pro Ser Arg Phe Ser Gly
    50                  55                  60
```

Tyr Gly Ser Gly Thr Asp Phe Ser Leu Thr Ile Asn Ser Leu Gln Pro
65                  70                  75                  80

Glu Asp Phe Ala Arg Tyr Tyr Cys Gln Gln Ser Asn Ser Phe Pro Leu
                85                  90                  95

Thr Phe Gly Gly Gly Thr Lys Val Glu Ile Lys Arg
            100                 105

<210> SEQ ID NO 178
<211> LENGTH: 108
<212> TYPE: PRT
<213> ORGANISM: Artificial Sequence
<220> FEATURE:
<223> OTHER INFORMATION: Synthetic

<400> SEQUENCE: 178

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ile Asn
                20                  25                  30

Leu His Trp Tyr Gln Gln Lys Pro Gly Gln Ala Pro Arg Leu Leu Ile
            35                  40                  45

Tyr Phe Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asn Ser Phe Pro Leu
                85                  90                  95

Thr Phe Gly Gly Gly Thr Lys Val Glu Ile Lys Arg
            100                 105

<210> SEQ ID NO 179
<211> LENGTH: 108
<212> TYPE: PRT
<213> ORGANISM: Artificial Sequence
<220> FEATURE:
<223> OTHER INFORMATION: Synthetic

<400> SEQUENCE: 179

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ile Asn
                20                  25                  30

Leu His Trp Tyr Gln Gln Lys Pro Gly Gln Ala Pro Arg Leu Leu Ile
            35                  40                  45

Tyr Phe Ala Ser Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Asn Ser Phe Pro Leu
                85                  90                  95

Thr Phe Gly Gly Gly Thr Lys Val Glu Ile Lys Arg
            100                 105

<210> SEQ ID NO 180
<211> LENGTH: 108
<212> TYPE: PRT
<213> ORGANISM: Artificial Sequence
<220> FEATURE:
<223> OTHER INFORMATION: Synthetic -continued

<400> SEQUENCE: 180

Asp Ile Val Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ile Asn
            20                  25                  30

Leu His Trp Tyr Gln Gln Lys Pro Gly Lys Ala Pro Lys Leu Leu Ile
        35                  40                  45

Tyr Phe Ala Ser Gln Ser Ile Ser Gly Val Pro Ser Arg Phe Ser Gly
    50                  55                  60

Ser Gly Ser Gly Thr Asp Phe Ser Leu Thr Ile Asn Ser Leu Gln Pro
65                  70                  75                  80

Glu Asp Phe Ala Thr Tyr Tyr Cys Gln Gln Ser Asn Ser Phe Pro Leu
                85                  90                  95

Thr Phe Gly Gly Gly Thr Lys Val Glu Ile Lys Arg
            100                 105

<210> SEQ ID NO 181
<211> LENGTH: 108
<212> TYPE: PRT
<213> ORGANISM: Artificial Sequence
<220> FEATURE:
<223> OTHER INFORMATION: Synthetic

<400> SEQUENCE: 181

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Ser Ile Ser Ile Asn
            20                  25                  30

Leu His Trp Tyr Gln Gln Lys Pro Gly Lys Ala Pro Lys Leu Leu Ile
        35                  40                  45

Tyr Phe Ala Ser Gln Ser Ile Ser Gly Val Pro Ser Arg Phe Ser Gly
    50                  55                  60

Ser Gly Ser Gly Thr Asp Phe Ser Leu Thr Ile Asn Ser Leu Gln Pro
65                  70                  75                  80

Glu Asp Phe Ala Thr Tyr Tyr Cys Gln Gln Ser Asn Ser Phe Pro Leu
                85                  90                  95

Thr Phe Gly Gly Gly Thr Lys Val Glu Ile Lys Arg
            100                 105

<210> SEQ ID NO 182
<211> LENGTH: 108
<212> TYPE: PRT
<213> ORGANISM: Artificial Sequence
<220> FEATURE:
<223> OTHER INFORMATION: Synthetic

<400> SEQUENCE: 182

Asp Ile Gln Met Thr Gln Ser Pro Ser Ser Val Ser Ala Thr Val Gly
1               5                   10                  15

Asp Arg Val Thr Ile Thr Cys Arg Ala Ser Gln Ser Ile Ser Ile Asn
            20                  25                  30

Leu His Trp Tyr Gln Gln Lys Pro Gly Lys Ala Pro Lys Leu Leu Ile
        35                  40                  45

Tyr Phe Ala Ser Gln Ser Ile Ser Gly Val Pro Ser Arg Phe Ser Gly
    50                  55                  60

Ser Gly Ser Gly Thr Asp Phe Ser Leu Thr Ile Asn Ser Leu Gln Pro
65                  70                  75                  80

Glu Asp Phe Ala Thr Tyr Tyr Cys Gln Gln Ser Asn Ser Phe Pro Leu

```
                    85                  90                  95

Thr Phe Gly Gly Gly Thr Lys Val Glu Ile Lys Arg
                100                 105

<210> SEQ ID NO 183
<211> LENGTH: 108
<212> TYPE: PRT
<213> ORGANISM: Artificial Sequence
<220> FEATURE:
<223> OTHER INFORMATION: Synthetic

<400> SEQUENCE: 183

Asp Ile Gln Met Thr Gln Ser Pro Ser Ser Val Ser Ala Ser Pro Gly
1               5                   10                  15

Asp Arg Val Thr Ile Thr Cys Arg Ala Ser Gln Ser Ile Ser Ile Asn
            20                  25                  30

Leu His Trp Tyr Gln Gln Lys Pro Gly Lys Ala Pro Lys Leu Leu Ile
        35                  40                  45

Tyr Phe Ala Ser Gln Ser Ile Ser Gly Val Pro Ser Arg Phe Ser Gly
    50                  55                  60

Ser Gly Ser Gly Thr Asp Phe Ser Leu Thr Ile Asn Ser Leu Gln Pro
65                  70                  75                  80

Glu Asp Phe Ala Thr Tyr Tyr Cys Gln Gln Ser Asn Ser Phe Pro Leu
                85                  90                  95

Thr Phe Gly Gly Gly Thr Lys Val Glu Ile Lys Arg
                100                 105

<210> SEQ ID NO 184
<211> LENGTH: 108
<212> TYPE: PRT
<213> ORGANISM: Artificial Sequence
<220> FEATURE:
<223> OTHER INFORMATION: Synthetic

<400> SEQUENCE: 184

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ile Asn
            20                  25                  30

Leu His Trp Tyr Gln Gln Lys Ser Gly Lys Ala Pro Lys Leu Leu Ile
        35                  40                  45

Tyr Phe Ala Ser Gln Ser Ile Ser Gly Val Pro Ser Arg Phe Ser Gly
    50                  55                  60

Ser Gly Ser Gly Thr Asp Phe Ser Leu Thr Ile Asn Ser Leu Gln Pro
65                  70                  75                  80

Glu Asp Phe Ala Thr Tyr Tyr Cys Gln Gln Ser Asn Ser Phe Pro Leu
                85                  90                  95

Thr Phe Gly Gly Gly Thr Lys Val Glu Ile Lys Arg
                100                 105

<210> SEQ ID NO 185
<211> LENGTH: 108
<212> TYPE: PRT
<213> ORGANISM: Artificial Sequence
<220> FEATURE:
<223> OTHER INFORMATION: Synthetic

<400> SEQUENCE: 185

Asp Ile Gln Met Thr Gln Ser Pro Ser Ser Val Ser Ala Ser Val Gly
1               5                   10                  15
```

```
Asp Arg Val Thr Ile Thr Cys Arg Ala Ser Gln Ser Ile Ser Ile Asn
            20                  25                  30

Leu His Trp Tyr Gln Gln Lys Pro His Lys Ala Pro Lys Leu Leu Ile
        35                  40                  45

Tyr Phe Ala Ser Gln Ser Ile Ser Gly Val Pro Ser Arg Phe Ser Gly
    50                  55                  60

Ser Gly Ser Gly Thr Asp Phe Ser Leu Thr Ile Asn Ser Leu Gln Pro
65                  70                  75                  80

Glu Asp Phe Ala Thr Tyr Tyr Cys Gln Gln Ser Asn Ser Phe Pro Leu
                85                  90                  95

Thr Phe Gly Gly Gly Thr Lys Val Glu Ile Lys Arg
            100                 105

<210> SEQ ID NO 186
<211> LENGTH: 108
<212> TYPE: PRT
<213> ORGANISM: Artificial Sequence
<220> FEATURE:
<223> OTHER INFORMATION: Synthetic

<400> SEQUENCE: 186

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ile Asn
            20                  25                  30

Leu His Trp Tyr Gln Gln Lys Pro Gly Glu Ala Pro Lys Leu Leu Ile
        35                  40                  45

Tyr Phe Ala Ser Gln Ser Ile Ser Gly Val Pro Ser Arg Phe Ser Gly
    50                  55                  60

Ser Gly Ser Gly Thr Asp Phe Ser Leu Thr Ile Asn Ser Leu Gln Pro
65                  70                  75                  80

Glu Asp Phe Ala Thr Tyr Tyr Cys Gln Gln Ser Asn Ser Phe Pro Leu
                85                  90                  95

Thr Phe Gly Gly Gly Thr Lys Val Glu Ile Lys Arg
            100                 105

<210> SEQ ID NO 187
<211> LENGTH: 108
<212> TYPE: PRT
<213> ORGANISM: Artificial Sequence
<220> FEATURE:
<223> OTHER INFORMATION: Synthetic

<400> SEQUENCE: 187

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ile Asn
            20                  25                  30

Leu His Trp Tyr Gln Gln Lys Pro Gly Lys Ser Pro Lys Leu Leu Ile
        35                  40                  45

Tyr Phe Ala Ser Gln Ser Ile Ser Gly Val Pro Ser Arg Phe Ser Gly
    50                  55                  60

Ser Gly Ser Gly Thr Asp Phe Ser Leu Thr Ile Asn Ser Leu Gln Pro
65                  70                  75                  80

Glu Asp Phe Ala Thr Tyr Tyr Cys Gln Gln Ser Asn Ser Phe Pro Leu
                85                  90                  95

Thr Phe Gly Gly Gly Thr Lys Val Glu Ile Lys Arg
            100                 105
```

<210> SEQ ID NO 188
<211> LENGTH: 108
<212> TYPE: PRT
<213> ORGANISM: Artificial Sequence
<220> FEATURE:
<223> OTHER INFORMATION: Synthetic

<400> SEQUENCE: 188

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ile Asn
            20                  25                  30

Leu His Trp Tyr Gln Gln Lys Pro Gly Lys Ala Pro Lys Leu Leu Ile
        35                  40                  45

Tyr Phe Ala Ser Gln Ser Ile Ser Gly Ile Pro Ser Arg Phe Ser Gly
    50                  55                  60

Ser Gly Ser Gly Thr Asp Phe Ser Leu Thr Ile Asn Ser Leu Gln Pro
65                  70                  75                  80

Glu Asp Phe Ala Thr Tyr Tyr Cys Gln Gln Ser Asn Ser Phe Pro Leu
                85                  90                  95

Thr Phe Gly Gly Gly Thr Lys Val Glu Ile Lys Arg
            100                 105

<210> SEQ ID NO 189
<211> LENGTH: 108
<212> TYPE: PRT
<213> ORGANISM: Artificial Sequence
<220> FEATURE:
<223> OTHER INFORMATION: Synthetic

<400> SEQUENCE: 189

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ile Asn
            20                  25                  30

Leu His Trp Tyr Gln Gln Lys Pro Gly Lys Ala Pro Lys Leu Leu Ile
        35                  40                  45

Tyr Phe Ala Ser Gln Ser Ile Ser Gly Val Pro Ser Arg Phe Ser Gly
    50                  55                  60

Ser Gly Ser Gly Thr Asp Phe Ser Leu Thr Ile Asn Ser Leu Gln Thr
65                  70                  75                  80

Glu Asp Phe Ala Thr Tyr Tyr Cys Gln Gln Ser Asn Ser Phe Pro Leu
                85                  90                  95

Thr Phe Gly Gly Gly Thr Lys Val Glu Ile Lys Arg
            100                 105

<210> SEQ ID NO 190
<211> LENGTH: 108
<212> TYPE: PRT
<213> ORGANISM: Artificial Sequence
<220> FEATURE:
<223> OTHER INFORMATION: Synthetic

<400> SEQUENCE: 190

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ile Asn
            20                  25                  30

Leu His Trp Tyr Gln Gln Lys Pro Gly Lys Ala Pro Lys Leu Leu Ile
        35                  40                  45

```
Tyr Phe Ala Ser Gln Ser Ile Ser Gly Val Pro Ser Arg Phe Ser Gly
         50                  55                  60

Ser Gly Ser Gly Thr Asp Phe Ser Leu Thr Ile Asn Ser Leu Gln Pro
 65                  70                  75                  80

Glu Asp Phe Ala Thr Tyr Phe Cys Gln Gln Ser Asn Ser Phe Pro Leu
                 85                  90                  95

Thr Phe Gly Gly Gly Thr Lys Val Glu Ile Lys Arg
            100                 105

<210> SEQ ID NO 191
<211> LENGTH: 108
<212> TYPE: PRT
<213> ORGANISM: Artificial Sequence
<220> FEATURE:
<223> OTHER INFORMATION: Synthetic

<400> SEQUENCE: 191

Asp Ile Val Met Thr Gln Ser Pro Ser Ser Val Ser Ala Ser Val Gly
 1               5                  10                  15

Asp Arg Val Thr Ile Thr Cys Arg Ala Ser Gln Ser Ile Ser Ile Asn
             20                  25                  30

Leu His Trp Tyr Gln Gln Lys Pro Gly Lys Ala Pro Lys Leu Leu Ile
         35                  40                  45

Tyr Phe Ala Ser Gln Ser Ile Ser Gly Val Pro Ser Arg Phe Ser Gly
         50                  55                  60

Ser Gly Ser Gly Thr Asp Phe Ser Leu Thr Ile Asn Ser Leu Gln Pro
 65                  70                  75                  80

Glu Asp Phe Ala Arg Tyr Tyr Cys Gln Gln Ser Asn Ser Phe Pro Leu
                 85                  90                  95

Thr Phe Gly Gly Gly Thr Lys Val Glu Ile Lys Arg
            100                 105

<210> SEQ ID NO 192
<211> LENGTH: 108
<212> TYPE: PRT
<213> ORGANISM: Artificial Sequence
<220> FEATURE:
<223> OTHER INFORMATION: Synthetic

<400> SEQUENCE: 192

Asp Ile Gln Leu Thr Gln Ser Pro Ser Ser Val Ser Ala Ser Val Gly
 1               5                  10                  15

Asp Arg Val Thr Ile Thr Cys Arg Ala Ser Gln Ser Ile Ser Ile Asn
             20                  25                  30

Leu His Trp Tyr Gln Gln Lys Pro Gly Lys Ala Pro Lys Leu Leu Ile
         35                  40                  45

Tyr Phe Ala Ser Gln Ser Ile Ser Gly Val Pro Ser Arg Phe Ser Gly
         50                  55                  60

Ser Gly Ser Gly Thr Asp Phe Ser Leu Thr Ile Asn Ser Leu Gln Pro
 65                  70                  75                  80

Glu Asp Phe Ala Arg Tyr Tyr Cys Gln Gln Ser Asn Ser Phe Pro Leu
                 85                  90                  95

Thr Phe Gly Gly Gly Thr Lys Val Glu Ile Lys Arg
            100                 105

<210> SEQ ID NO 193
<211> LENGTH: 108
<212> TYPE: PRT
<213> ORGANISM: Artificial Sequence
```

```
<220> FEATURE:
<223> OTHER INFORMATION: Synthetic

<400> SEQUENCE: 193

Asp Ile Gln Met Thr Gln Ser Pro Ser Ser Val Ser Ala Thr Val Gly
1               5                   10                  15

Asp Arg Val Thr Ile Thr Cys Arg Ala Ser Gln Ser Ile Ser Ile Asn
            20                  25                  30

Leu His Trp Tyr Gln Gln Lys Pro Gly Lys Ala Pro Lys Leu Leu Ile
        35                  40                  45

Tyr Phe Ala Ser Gln Ser Ile Ser Gly Val Pro Ser Arg Phe Ser Gly
    50                  55                  60

Ser Gly Ser Gly Thr Asp Phe Ser Leu Thr Ile Asn Ser Leu Gln Pro
65                  70                  75                  80

Glu Asp Phe Ala Arg Tyr Tyr Cys Gln Gln Ser Asn Ser Phe Pro Leu
                85                  90                  95

Thr Phe Gly Gly Gly Thr Lys Val Glu Ile Lys Arg
            100                 105

<210> SEQ ID NO 194
<211> LENGTH: 108
<212> TYPE: PRT
<213> ORGANISM: Artificial Sequence
<220> FEATURE:
<223> OTHER INFORMATION: Synthetic

<400> SEQUENCE: 194

Asp Ile Gln Met Thr Gln Ser Pro Ser Ser Val Ser Ala Ser Pro Gly
1               5                   10                  15

Asp Arg Val Thr Ile Thr Cys Arg Ala Ser Gln Ser Ile Ser Ile Asn
            20                  25                  30

Leu His Trp Tyr Gln Gln Lys Pro Gly Lys Ala Pro Lys Leu Leu Ile
        35                  40                  45

Tyr Phe Ala Ser Gln Ser Ile Ser Gly Val Pro Ser Arg Phe Ser Gly
    50                  55                  60

Ser Gly Ser Gly Thr Asp Phe Ser Leu Thr Ile Asn Ser Leu Gln Pro
65                  70                  75                  80

Glu Asp Phe Ala Arg Tyr Tyr Cys Gln Gln Ser Asn Ser Phe Pro Leu
                85                  90                  95

Thr Phe Gly Gly Gly Thr Lys Val Glu Ile Lys Arg
            100                 105

<210> SEQ ID NO 195
<211> LENGTH: 108
<212> TYPE: PRT
<213> ORGANISM: Artificial Sequence
<220> FEATURE:
<223> OTHER INFORMATION: Synthetic

<400> SEQUENCE: 195

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ile Asn
            20                  25                  30

Leu His Trp Tyr Gln Gln Lys Ser Gly Lys Ala Pro Lys Leu Leu Ile
        35                  40                  45

Tyr Phe Ala Ser Gln Ser Ile Ser Gly Val Pro Ser Arg Phe Ser Gly
    50                  55                  60

Ser Gly Ser Gly Thr Asp Phe Ser Leu Thr Ile Asn Ser Leu Gln Pro
```

Glu Asp Phe Ala Arg Tyr Tyr Cys Gln Gln Ser Asn Ser Phe Pro Leu
            65                  70                  75                  80

Thr Phe Gly Gly Gly Thr Lys Val Glu Ile Lys Arg
            85                  90                  95

100                 105

<210> SEQ ID NO 196
<211> LENGTH: 108
<212> TYPE: PRT
<213> ORGANISM: Artificial Sequence
<220> FEATURE:
<223> OTHER INFORMATION: Synthetic

<400> SEQUENCE: 196

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ile Asn
            20                  25                  30

Leu His Trp Tyr Gln Gln Lys Pro His Lys Ala Pro Lys Leu Leu Ile
        35                  40                  45

Tyr Phe Ala Ser Gln Ser Ile Ser Gly Val Pro Ser Arg Phe Ser Gly
    50                  55                  60

Ser Gly Ser Gly Thr Asp Phe Ser Leu Thr Ile Asn Ser Leu Gln Pro
65                  70                  75                  80

Glu Asp Phe Ala Arg Tyr Tyr Cys Gln Gln Ser Asn Ser Phe Pro Leu
                85                  90                  95

Thr Phe Gly Gly Gly Thr Lys Val Glu Ile Lys Arg
            100                 105

<210> SEQ ID NO 197
<211> LENGTH: 108
<212> TYPE: PRT
<213> ORGANISM: Artificial Sequence
<220> FEATURE:
<223> OTHER INFORMATION: Synthetic

<400> SEQUENCE: 197

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ile Asn
            20                  25                  30

Leu His Trp Tyr Gln Gln Lys Pro Gly Glu Ala Pro Lys Leu Leu Ile
        35                  40                  45

Tyr Phe Ala Ser Gln Ser Ile Ser Gly Val Pro Ser Arg Phe Ser Gly
    50                  55                  60

Ser Gly Ser Gly Thr Asp Phe Ser Leu Thr Ile Asn Ser Leu Gln Pro
65                  70                  75                  80

Glu Asp Phe Ala Arg Tyr Tyr Cys Gln Gln Ser Asn Ser Phe Pro Leu
                85                  90                  95

Thr Phe Gly Gly Gly Thr Lys Val Glu Ile Lys Arg
            100                 105

<210> SEQ ID NO 198
<211> LENGTH: 108
<212> TYPE: PRT
<213> ORGANISM: Artificial Sequence
<220> FEATURE:
<223> OTHER INFORMATION: Synthetic

<400> SEQUENCE: 198

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ile Asn
            20                  25                  30

Leu His Trp Tyr Gln Gln Lys Pro Gly Lys Ser Pro Lys Leu Leu Ile
        35                  40                  45

Tyr Phe Ala Ser Gln Ser Ile Ser Gly Val Pro Ser Arg Phe Ser Gly
    50                  55                  60

Ser Gly Ser Gly Thr Asp Phe Ser Leu Thr Ile Asn Ser Leu Gln Pro
65                  70                  75                  80

Glu Asp Phe Ala Arg Tyr Tyr Cys Gln Gln Ser Asn Ser Phe Pro Leu
                85                  90                  95

Thr Phe Gly Gly Gly Thr Lys Val Glu Ile Lys Arg
            100                 105

<210> SEQ ID NO 199
<211> LENGTH: 108
<212> TYPE: PRT
<213> ORGANISM: Artificial Sequence
<220> FEATURE:
<223> OTHER INFORMATION: Synthetic

<400> SEQUENCE: 199

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ile Asn
            20                  25                  30

Leu His Trp Tyr Gln Gln Lys Pro Gly Lys Ala Pro Lys Leu Leu Ile
        35                  40                  45

Tyr Phe Ala Ser Gln Ser Ile Ser Gly Ile Pro Ser Arg Phe Ser Gly
    50                  55                  60

Ser Gly Ser Gly Thr Asp Phe Ser Leu Thr Ile Asn Ser Leu Gln Pro
65                  70                  75                  80

Glu Asp Phe Ala Arg Tyr Tyr Cys Gln Gln Ser Asn Ser Phe Pro Leu
                85                  90                  95

Thr Phe Gly Gly Gly Thr Lys Val Glu Ile Lys Arg
            100                 105

<210> SEQ ID NO 200
<211> LENGTH: 108
<212> TYPE: PRT
<213> ORGANISM: Artificial Sequence
<220> FEATURE:
<223> OTHER INFORMATION: Synthetic

<400> SEQUENCE: 200

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ile Asn
            20                  25                  30

Leu His Trp Tyr Gln Gln Lys Pro Gly Lys Ala Pro Lys Leu Leu Ile
        35                  40                  45

Tyr Phe Ala Ser Gln Ser Ile Ser Gly Val Pro Ser Arg Phe Ser Gly
    50                  55                  60

Ser Gly Ser Gly Thr Asp Phe Ser Leu Thr Ile Asn Ser Leu Gln Thr
65                  70                  75                  80

Glu Asp Phe Ala Arg Tyr Tyr Cys Gln Gln Ser Asn Ser Phe Pro Leu
                85                  90                  95

Thr Phe Gly Gly Gly Thr Lys Val Glu Ile Lys Arg
            100                 105

<210> SEQ ID NO 201
<211> LENGTH: 108
<212> TYPE: PRT
<213> ORGANISM: Artificial Sequence
<220> FEATURE:
<223> OTHER INFORMATION: Synthetic

<400> SEQUENCE: 201

Asp Ile Gln Met Thr Gln Ser Pro Ser Val Ser Ala Ser Val Gly
1               5                   10                  15

Asp Arg Val Thr Ile Thr Cys Arg Ala Ser Gln Ser Ile Ser Ile Asn
                20                  25                  30

Leu His Trp Tyr Gln Gln Lys Pro Gly Lys Ala Pro Lys Leu Leu Ile
        35                  40                  45

Tyr Phe Ala Ser Gln Ser Ile Ser Gly Val Pro Ser Arg Phe Ser Gly
    50                  55                  60

Ser Gly Ser Gly Thr Asp Phe Ser Leu Thr Ile Asn Ser Leu Gln Pro
65                  70                  75                  80

Glu Asp Phe Ala Arg Tyr Phe Cys Gln Gln Ser Asn Ser Phe Pro Leu
                85                  90                  95

Thr Phe Gly Gly Gly Thr Lys Val Glu Ile Lys Arg
            100                 105

<210> SEQ ID NO 202
<211> LENGTH: 30
<212> TYPE: PRT
<213> ORGANISM: Artificial Sequence
<220> FEATURE:
<223> OTHER INFORMATION: Synthetic

<400> SEQUENCE: 202

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 203
<211> LENGTH: 14
<212> TYPE: PRT
<213> ORGANISM: Artificial Sequence
<220> FEATURE:
<223> OTHER INFORMATION: Synthetic

<400> SEQUENCE: 203

Trp Val Arg Gln Ala Pro Gly Gln Gly Leu Glu Trp Met Gly
1               5                   10

<210> SEQ ID NO 204
<211> LENGTH: 32
<212> TYPE: PRT
<213> ORGANISM: Artificial Sequence
<220> FEATURE:
<223> OTHER INFORMATION: Synthetic

<400> SEQUENCE: 204

Arg Val Thr Met Thr Thr Asp Thr Ser Thr Ala Tyr Met Glu
1               5                   10                  15

Leu Arg Ser Leu Arg Ser Asp Asp Thr Ala Val Tyr Tyr Cys Asn Ala
            20                  25                  30

```
<210> SEQ ID NO 205
<211> LENGTH: 11
<212> TYPE: PRT
<213> ORGANISM: Artificial Sequence
<220> FEATURE:
<223> OTHER INFORMATION: Synthetic

<400> SEQUENCE: 205

Trp Gly Gln Gly Thr Met Val Thr Val Ser Ser
1               5                   10

<210> SEQ ID NO 206
<211> LENGTH: 30
<212> TYPE: PRT
<213> ORGANISM: Artificial Sequence
<220> FEATURE:
<223> OTHER INFORMATION: Synthetic

<400> SEQUENCE: 206

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser
            20                  25                  30

<210> SEQ ID NO 207
<211> LENGTH: 14
<212> TYPE: PRT
<213> ORGANISM: Artificial Sequence
<220> FEATURE:
<223> OTHER INFORMATION: Synthetic

<400> SEQUENCE: 207

Trp Val Arg Gln Ala Pro Glu Lys Gly Leu Glu Trp Met Gly
1               5                   10

<210> SEQ ID NO 208
<211> LENGTH: 32
<212> TYPE: PRT
<213> ORGANISM: Artificial Sequence
<220> FEATURE:
<223> OTHER INFORMATION: Synthetic

<400> SEQUENCE: 208

Arg Val Thr Ile Thr Ala Asp Thr Ser Thr Asp Thr Gly Tyr Leu Glu
1               5                   10                  15

Leu Ser Ser Leu Arg Ser Glu Asp Thr Ala Val Tyr Tyr Cys Ala Ala
            20                  25                  30

<210> SEQ ID NO 209
<211> LENGTH: 11
<212> TYPE: PRT
<213> ORGANISM: Artificial Sequence
<220> FEATURE:
<223> OTHER INFORMATION: Synthetic

<400> SEQUENCE: 209

Trp Gly Gln Gly Thr Leu Val Thr Val Ser Ser
1               5                   10

<210> SEQ ID NO 210
<211> LENGTH: 23
<212> TYPE: PRT
<213> ORGANISM: Artificial Sequence
<220> FEATURE:
<223> OTHER INFORMATION: Synthetic

<400> SEQUENCE: 210
```

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 211
<211> LENGTH: 15
<212> TYPE: PRT
<213> ORGANISM: Artificial Sequence
<220> FEATURE:
<223> OTHER INFORMATION: Synthetic

<400> SEQUENCE: 211

Trp Tyr Gln Gln Lys Pro Gly Gln Ala Pro Arg Leu Leu Ile Tyr
1               5                   10                  15

<210> SEQ ID NO 212
<211> LENGTH: 32
<212> TYPE: PRT
<213> ORGANISM: Artificial Sequence
<220> FEATURE:
<223> OTHER INFORMATION: Synthetic

<400> SEQUENCE: 212

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 213
<211> LENGTH: 11
<212> TYPE: PRT
<213> ORGANISM: Artificial Sequence
<220> FEATURE:
<223> OTHER INFORMATION: Synthetic

<400> SEQUENCE: 213

Phe Gly Gly Gly Thr Lys Val Glu Ile Lys Arg
1               5                   10

<210> SEQ ID NO 214
<211> LENGTH: 23
<212> TYPE: PRT
<213> ORGANISM: Artificial Sequence
<220> FEATURE:
<223> OTHER INFORMATION: Synthetic

<400> SEQUENCE: 214

Asp Ile Gln Met Thr Gln Ser Pro Ser Ser Val Ser Ala Ser Val Gly
1               5                   10                  15

Asp Arg Val Thr Ile Thr Cys
            20

<210> SEQ ID NO 215
<211> LENGTH: 15
<212> TYPE: PRT
<213> ORGANISM: Artificial Sequence
<220> FEATURE:
<223> OTHER INFORMATION: Synthetic

<400> SEQUENCE: 215

Trp Tyr Gln Gln Lys Pro Gly Lys Ala Pro Lys Leu Leu Ile Tyr
1               5                   10                  15

<210> SEQ ID NO 216
<211> LENGTH: 32

```
<212> TYPE: PRT
<213> ORGANISM: Artificial Sequence
<220> FEATURE:
<223> OTHER INFORMATION: Synthetic

<400> SEQUENCE: 216

Gly Val Pro Ser Arg Phe Ser Gly Ser Gly Ser Gly Thr Asp Phe Ser
1               5                   10                  15

Leu Thr Ile Asn Ser Leu Gln Thr Glu Asp Phe Ala Thr Tyr Tyr Cys
            20                  25                  30

<210> SEQ ID NO 217
<211> LENGTH: 354
<212> TYPE: DNA
<213> ORGANISM: Artificial Sequence
<220> FEATURE:
<223> OTHER INFORMATION: Synthetic

<400> SEQUENCE: 217
caggtgcagc tggtgcagag cggagccgaa gtgaagaaac caggcgcctc cgtgaaggtg      60
tcctgcaagg ccagcggctg caccttcacc gactactatc tgcactgggt ccgccaggca     120
ccagggcagg gactggaatg gatgggctgg atcgaccccg agaacggcga taccgagtac     180
gcccccaagt tccagggcag agtgaccatg accaccgaca ccagcaccag caccgcctac     240
atggaactgc ggagcctgag aagcgacgac accgccgtgt actactgcaa cgccaacaaa     300
gagctgcggt acttcgacgt gtggggccag ggcacaatgg tcaccgtgtc ctct           354

<210> SEQ ID NO 218
<211> LENGTH: 354
<212> TYPE: DNA
<213> ORGANISM: Artificial Sequence
<220> FEATURE:
<223> OTHER INFORMATION: Synthetic

<400> SEQUENCE: 218
caggtgcagc tggtgcagag cggagccgaa gtgaagaaac caggcgcctc cgtgaaggtg      60
tcctgcaagg ccagcggcta caccttcacc gactactatc tgcactgggt ccgccaggca     120
ccagggcagg gactggaatg gatgggctgg atcgaccccg agaacggcga taccgagtac     180
gcccccaagt tccagggcag agtgaccgtg accaccgaca ccagcaccag caccgcctac     240
atggaactgc ggagcctgag aagcgacgac accgccgtgt actactgcaa cgccaacaaa     300
gagctgcggt acttcgacgt gtggggccag ggcacaatgg tcaccgtgtc ctct           354

<210> SEQ ID NO 219
<211> LENGTH: 354
<212> TYPE: DNA
<213> ORGANISM: Artificial Sequence
<220> FEATURE:
<223> OTHER INFORMATION: Synthetic

<400> SEQUENCE: 219
caggtgcagc tggtgcagag cggagcccaa gtgaagaaac caggcgcctc cgtgaaggtg      60
tcctgcaagg ccagcggcta caccttcacc gactactatc tgcactgggt ccgccaggca     120
ccagggcagg gactggaatg gatgggctgg atcgaccccg agaacggcga taccgagtac     180
gcccccaagt tccagggcag agtgaccatg accaccgaca ccagcaccag caccgcctac     240
atggaactgc ggagcctgag aagcgacgac accgccgtgt actactgcaa cgccaacaaa     300
gagctgcggt acttcgacgt gtggggccag ggcacaatgg tcaccgtgtc ctct           354
```

```
<210> SEQ ID NO 220
<211> LENGTH: 354
<212> TYPE: DNA
<213> ORGANISM: Artificial Sequence
<220> FEATURE:
<223> OTHER INFORMATION: Synthetic

<400> SEQUENCE: 220
caggtgcagc tggtgcagag cggagccgaa gtgaagaaac caggcgcctc cgtgaaggtg      60
tcctgcaagg ccagcggcta cccctcacc gactactatc tgcactgggt ccgccaggca     120
ccagggcagg gactggaatg gatgggctgg atcgaccccg agaacggcga taccgagtac    180
gcccccaagt tccagggcag agtgaccatg accaccgaca ccagcaccag caccgcctac    240
atggaactgc ggagcctgag aagcgacgac accgccgtgt actactgcaa cgccaacaaa    300
gagctgcggt acttcgacgt gtggggccag ggcgcaatgg tcaccgtgtc ctct           354

<210> SEQ ID NO 221
<211> LENGTH: 324
<212> TYPE: DNA
<213> ORGANISM: Artificial Sequence
<220> FEATURE:
<223> OTHER INFORMATION: Synthetic

<400> SEQUENCE: 221
gagatcgtga tgacccagag ccctgccacc ctgagcgtgt ctccaggcga gagagccacc     60
ctgtcctgta gagcctccca gagcatcagc atcaatctgc attggtatca gcagaagccc    120
ggccaggccc ccagactgct gatctacttc gccagccagt ccatcagcgg catccccgcc    180 agatttttg gcagcggcag cggcaccgag ttcaccctga ccatcagcag cctgcagagc    240
gaggacttcg ccgtgtatta ttgccagcag agcaacagct ccccctgac cttcggcgga    300 ggcaccaagg tggagatcaa gcgt                                           324

<210> SEQ ID NO 222
<211> LENGTH: 354
<212> TYPE: DNA
<213> ORGANISM: Artificial Sequence
<220> FEATURE:
<223> OTHER INFORMATION: Synthetic

<400> SEQUENCE: 222
caggtgcagc tggtgcagag cggagccgaa gtgaagaaac caggcgcctc cgtgaaggtg      60
tcctgcaagg ccagcggcta caccttcacc gactactatc tgcactgggt ccgccaggca    120
ccagggcagg gactggaatg gatgggctgg atcgaccccg agaacggcga taccgagcac    180
gcccccaagt tccagggcag agtgaccatg accaccgaca ccagcaccag caccgcctac    240
atggaactgc ggagcctgag aagcgacgac accgccgtgt actactgcaa cgccaacaaa    300
gagctgcggt acttcgacgt gtggggccag ggcacaatgg tcaccgtgtc ctct           354

<210> SEQ ID NO 223
<211> LENGTH: 354
<212> TYPE: DNA
<213> ORGANISM: Artificial Sequence
<220> FEATURE:
<223> OTHER INFORMATION: Synthetic

<400> SEQUENCE: 223
caggtgcagc tggtgcagag cggagccgaa gtgaagaaac caggcgcctc cgtgaaggtg      60
tcctgcaagg ccagcggcta caccttcacc gactactatc tgcactgggt ccgccaggca    120
ccagggcagg gactggaatg gatgggctgg atcgaccccg agaacggcga taccgagtcc    180
```

```
gcccccaagt tccagggcag agtgaccatg accaccgaca ccagcaccag caccgcctac    240
atggaactgc ggagcctgag aagcgacgac accgccgtgt actactgcaa cgccaacaaa    300
gagctgcggt acttcgacgt gtggggccag ggcacaatgg tcaccgtgtc ctct          354
```

<210> SEQ ID NO 224
<211> LENGTH: 354
<212> TYPE: DNA
<213> ORGANISM: Artificial Sequence
<220> FEATURE:
<223> OTHER INFORMATION: Synthetic

<400> SEQUENCE: 224

```
caggtgcagc tggtgcagag cggagccgaa gtgaagaaac caggcgcctc cgtgaaggtg    60
tcctgcaagg ccagcggcta caccttcacc gactactatc tgcactgggt ccgccaggca    120
ccagggcagg gactggaatg gatgggctgg atcgaccccg agaacggcga taccgagtac    180
gcccccaagt tccagggcag agtgaccatg accaccgaca ccagcaccag caccgcctac    240
atggaactgc ggagcctgag aagcgaagac accgccgtgt actactgcaa cgccaacaaa    300
gagctgcggt acttcgacgt gtggggccag ggcacaatgg tcaccgtgtc ctct          354
```

<210> SEQ ID NO 225
<211> LENGTH: 354
<212> TYPE: DNA
<213> ORGANISM: Artificial Sequence
<220> FEATURE:
<223> OTHER INFORMATION: Synthetic

<400> SEQUENCE: 225

```
caggtgcagc tggtgcagag cggagccgaa gtgaagaaac caggcgcctc cgtgaaggtg    60
tcctgcaagg ccagcggcta caccttcacc gactactatc tgcactgggt ccgccaggca    120
ccagggcagg gactggaatg gatgggctgg atcgaccccg agaacggcga taccgagtac    180
gcccccaagt tccagggcag agtgaccatg accaccgaca ccagcaccag caccgcctac    240
atggaactgc ggagcctgag aagcgacgac accgccgtgt actactgcaa cgccaacaaa    300
gagctgcggt acttcgacgt gtggggccag ggcacaatgg tcaccgtgcc ctct          354
```

<210> SEQ ID NO 226
<211> LENGTH: 324
<212> TYPE: DNA
<213> ORGANISM: Artificial Sequence
<220> FEATURE:
<223> OTHER INFORMATION: Synthetic

<400> SEQUENCE: 226

```
gagatcgtga tgacccagag ccctgccacc ctgagcgtgt ctccaggcga gagagccacc    60
ctgtcctgta gagcctccca gagcatcagc atcaatctgc attggtatca gcagaagccc    120
ggccaggccc ccagactgct gatctacttc gccagccagt ccatcagcgg catccccgcc    180 agatttctg gcagcggcag cggcaccgag ttcaccctga ccaccagcag cctgcagagc    240
gaggacttcg ccgtgtatta ttgccagcag agcaacagct tcccccctgac cttcggcgga    300 ggcaccaagg tggagatcaa gcgt                                          324
```

<210> SEQ ID NO 227
<211> LENGTH: 354
<212> TYPE: DNA
<213> ORGANISM: Artificial Sequence
<220> FEATURE:
<223> OTHER INFORMATION: Synthetic

<400> SEQUENCE: 227

```
caggtgcagc tggtgcagag cggagccgaa gtgaagaaac caggcgcctc cgtgaaggtg    60
tcctgcaagg ccagcggcta caccctcacc gactactatc tgcactgggt ccgccaggca   120
ccagggcagg gactggaatg gatgggctgg atcgaccccg agaacggcga taccgagtac   180
gcccccaagt tccagggcag agtgaccatg accaccgaca ccagcaccag caccgcctac   240
atggaactgc ggagcctgag aagcgacgac accgccgtgt actactgcaa cgccaacaaa   300
gagctgcggt acttcgacgt gtggggccag ggcacaatgg tcaccgtgtc ctct         354
```

<210> SEQ ID NO 228
<211> LENGTH: 354
<212> TYPE: DNA
<213> ORGANISM: Artificial Sequence
<220> FEATURE:
<223> OTHER INFORMATION: Synthetic

<400> SEQUENCE: 228

```
caggtgcagc tggtgcagag cggagccgaa gtgaagaaac caggcgcctc cgtgaaggtg    60
tcctgcaagg ccagcggcta caccttcacc gactactata tgcactgggt ccgccaggca   120
ccagggcagg gactggaatg gatgggctgg atcgaccccg agaacggcga taccgagtac   180
gcccccaagt tccagggcag agtgaccatg accaccgaca ccagcaccag caccgcctac   240
atggaactgc ggagcctgag aagcgacgac accgccgtgt actactgcaa cgccaacaaa   300
gagctgcggt acttcgacgt gtggggccag ggcacaatgg tcaccgtgtc ctct         354
```

<210> SEQ ID NO 229
<211> LENGTH: 354
<212> TYPE: DNA
<213> ORGANISM: Artificial Sequence
<220> FEATURE:
<223> OTHER INFORMATION: Synthetic

<400> SEQUENCE: 229

```
caggtgcagc tggtgcagag cggagccgaa gtggagaaac caggcgcctc cgtgaaggtg    60
tcctgcaagg ccagcggcta caccttcacc gactactatc tgcactgggt ccgccaggca   120
ccagggcagg gactggaatg gatgggctgg atcgaccccg agaacggcga taccgagtac   180
gcccccaagt tccagggcgg agtgaccatg accaccgaca ccagcaccag caccgcctac   240
atggaactgc ggagcctgag aagcgacgac accgccgtgt actactgcaa cgccaacaaa   300
gagctgcggt acttcgacgt gtggggccag ggcacaatgg tcaccgtgtc ctct         354
```

<210> SEQ ID NO 230
<211> LENGTH: 354
<212> TYPE: DNA
<213> ORGANISM: Artificial Sequence
<220> FEATURE:
<223> OTHER INFORMATION: Synthetic

<400> SEQUENCE: 230

```
caggtgcagc tggtgcagag cggagccgaa gtgaagaaac caggcgcctc cgtgaaggtg    60
tcctgcaagg ccagcggcta caccttcacc gactactatc tgcactgggt ccgccaggca   120
ccagggcggg gactggaatg gatgggctgg atcgaccccg agaacggcga taccgagtac   180
gcccccaagt tccagggcag agtgaccatg accaccgaca ccagcaccag caccgcctac   240
atggaactgc ggagcctgag aagcgacgac accgccgtgt actactgcaa cgccaacaaa   300
gagctgcggt acttcgacgt gtggggccag ggcacaatgg tcaccgtgtc ctct         354
```

<210> SEQ ID NO 231
<211> LENGTH: 324
<212> TYPE: DNA
<213> ORGANISM: Artificial Sequence
<220> FEATURE:
<223> OTHER INFORMATION: Synthetic

<400> SEQUENCE: 231

```
gagatcgtga tgacccagag ccctgccacc ctgagcgtgt ctccaggcga gagagccacc    60
ctgtcctgta gagcctccca gagcatcagc atcaatctgc attggtatca gcagaagccc   120
ggccaggccc ccagactgct gatctacttc gccagccagt ccaccagcgg catccccgcc   180
agattttctg gcagcggcag cggcaccgag ttcaccctga ccatcagcag cctgcagagc   240
gaggacttcg ccgtgtatta ttgccagcag agcaacagct tcccccctga cttcggcgga   300
ggcaccaagg tggagatcaa gcgt                                          324
```

<210> SEQ ID NO 232
<211> LENGTH: 354
<212> TYPE: DNA
<213> ORGANISM: Artificial Sequence
<220> FEATURE:
<223> OTHER INFORMATION: Synthetic

<400> SEQUENCE: 232

```
caggtgcagc tgttgcagag cggagccgaa gtgaagaaac caggcgcctc cgtgaaggtg    60
tcctgcaagg ccagcggcta caccttcacc gactactatc tgcactgggt ccgccaggca   120
ccagggcagg gactggaatg gatgggctgg atcgaccccg agaacggcga taccgagtac   180
gcccccaagt tccagggcag agtgaccatg accaccgaca ccagcaccag caccgcctac   240
atggaactgc ggagcctgag aagcgacgac accgccgtgt actactgcaa cgccaacaaa   300
gagctgcggt acttcgacgt gtggggccag ggcacaatgg tcaccgtgtc ctct         354
```

<210> SEQ ID NO 233
<211> LENGTH: 354
<212> TYPE: DNA
<213> ORGANISM: Artificial Sequence
<220> FEATURE:
<223> OTHER INFORMATION: Synthetic

<400> SEQUENCE: 233

```
caggtgcagc tggtgcagag cggagccgaa gtgaagaaac caggcgcctc cgtgaaggtg    60
tcctgcaagg ccagcggcta cgccttcacc gactactatc tgcactgggt ccgccaggca   120
ccagggcagg gactggaatg gatgggctgg atcgaccccg agaacggcga taccgagtac   180
gcccccaagt tccagggcag agtgaccatg accaccgaca ccagcaccag caccgcctac   240
atggaactgc ggagcctgag aagcgacgac accgccgtgt actactgcaa cgccaacaaa   300
gagctgcggt acttcgacgt gtggggccag ggcacaatgg tcaccgtgtc ctct         354
```

<210> SEQ ID NO 234
<211> LENGTH: 354
<212> TYPE: DNA
<213> ORGANISM: Artificial Sequence
<220> FEATURE:
<223> OTHER INFORMATION: Synthetic

<400> SEQUENCE: 234

```
caggtgcagc tggtgcagag cggagccgaa gtgaagaaac caggcgcctc cgtgaaggtg    60
tcctgcaagg ccagcggcta cgccttcacc gactactatc tgcactgggt ccgccaggca   120
```

```
ccagggcagg gactggaatg gatgggctgg atcgacccg agaacggcga taccgagtac      180
gcccccaagt tccagggcag agtgtccatg accaccgaca ccagcaccag caccgcctac      240
atggaactgc ggagcctgag aagcgacgac accgccgtgt actactgcaa cgccaacaaa      300
gagctgcggt acttcgacgt gtggggccag ggcacaatgg tcaccgtgtc ctct           354
```

<210> SEQ ID NO 235
<211> LENGTH: 324
<212> TYPE: DNA
<213> ORGANISM: Artificial Sequence
<220> FEATURE:
<223> OTHER INFORMATION: Synthetic

<400> SEQUENCE: 235

```
gagatcgtga tgacccagag ccctgccacc ctgagcgtgt ctccaggcga gagagccacc      60
ctgtcctgta gagcctccca gagcatcagc atcaatctgc attggtatca gcagaagccc     120
ggccaggccc ccagactgct gatctacttc gccagccagt ccatcagcgg catccccgcc     180 agatttctg gcagcggcag cggcaccgag ttcaccctga ccatcagcag cctgcagagc     240
gaggacttcg ccgtgcatta ttgccagcag agcaacagct tcccctgac cttcggcgga     300 ggcaccaagg tggagatcaa gcgt                                           324
```

<210> SEQ ID NO 236
<211> LENGTH: 324
<212> TYPE: DNA
<213> ORGANISM: Artificial Sequence
<220> FEATURE:
<223> OTHER INFORMATION: Synthetic

<400> SEQUENCE: 236

```
gagatcgtga tgacccagag ccctgccacc ctgagcgtgt ctccaggcga gagagccacc      60
ctgtcctgta gagcctccca gagcatcagc atcaatctgc attggtatca gcagaagccc     120
ggccaggccc ccagactgct gatctacttc gccagacagt ccatcagcgg catccccgcc     180 agatttctg gcagcggcag cggcaccgag ttcaccctga ccatcagcag cctgcagagc     240
gaggacttcg ccgtgtatta ttgccagcag agcaacagct tcccctgac cttcggcgga     300 ggcaccaagg tggagatcaa gcgt                                           324
```

<210> SEQ ID NO 237
<211> LENGTH: 324
<212> TYPE: DNA
<213> ORGANISM: Artificial Sequence
<220> FEATURE:
<223> OTHER INFORMATION: Synthetic

<400> SEQUENCE: 237

```
gagatcgtga tgacccagag ccctgccacc ctgagcatgt ctccaggcga gagagccacc      60
ctgtcctgta gagcctccca gagcatcagc atcaatctgc attggtatca gcagaagccc     120
ggccaggccc ccagactgct gatctacttc gccagccagt ccatcagcgg catccccgcc     180 agatttctg gcagcggcag cggcaccgag ttcaccctga ccatcagcag cctgcagagc     240
gaggacttcg ccgtgtatta ttgccagcag agcaacagct tcccctgac cttcggcgga     300 ggcaccaagg tggagatcaa gcgt                                           324
```

<210> SEQ ID NO 238
<211> LENGTH: 324
<212> TYPE: DNA
<213> ORGANISM: Artificial Sequence

```
<220> FEATURE:
<223> OTHER INFORMATION: Synthetic

<400> SEQUENCE: 238
gagatcgtga tgacccagag ccctgccacc ctgagcgtgt ctccaggcga gagagccacc    60
ctgtcctgta gagcctccca gagcatcagc atcaatctgc attggtatca gcagaagccc   120
ggccaggccc ccagactgct gatctacttc gccagccagt ccatcagcgg catccccgcc   180
agattttctg gcagcggcag cggcaccgag ttcaccctga ccatcagcag cctgcagagc   240
gagggcttcg ccgtgtatta ttgccagcag agcaacagct tcccccctga cttcggcgga   300
ggcaccaagg tggagatcaa gcgt                                          324

<210> SEQ ID NO 239
<211> LENGTH: 324
<212> TYPE: DNA
<213> ORGANISM: Artificial Sequence
<220> FEATURE:
<223> OTHER INFORMATION: Synthetic

<400> SEQUENCE: 239
gagatcgtga tgacccagag ccctgccacc ctgagcgtgt ctccaggcga gagagccacc    60
ctgtcctgta gagcctccca gagcatcagc atcaatctgc attggtatca gcagaagccc   120
ggccaggccc ccagactgct gatctacttc gccagccagt ccatcagcgg catccccgcc   180
agattttcta gcagcggcag cggcaccgag ttcaccctga ccatcagcag cctgcagagc   240
gaggacttcg ccgtgtatta ttgccagcag agcaacagct tcccccctga cttcggcgga   300
ggcaccaagg tggagatcaa gcgt                                          324

<210> SEQ ID NO 240
<211> LENGTH: 324
<212> TYPE: DNA
<213> ORGANISM: Artificial Sequence
<220> FEATURE:
<223> OTHER INFORMATION: Synthetic

<400> SEQUENCE: 240
gagatcgtga tgacccagag ccctgccacc ctgagcgtgt ctccaggcga gagagccacc    60
ctgtcctgta gagcccccca gagcatcagc atcaatctgc attggtatca gcagaagccc   120
ggccaggccc ccagactgct gatctacttc gccagccagt ccatcagcgg catccccgcc   180
agattttctg gcagcggcag cggcaccgag ttcaccctga ccatcagcag cctgcagagc   240
gaggacttcg ccgtgtatta ttgccagcag agcaacagct tcccccctga cttcggcgga   300
ggcaccaagg tggagatcaa gcgt                                          324

<210> SEQ ID NO 241
<211> LENGTH: 324
<212> TYPE: DNA
<213> ORGANISM: Artificial Sequence
<220> FEATURE:
<223> OTHER INFORMATION: Synthetic

<400> SEQUENCE: 241
gagatcgtga tgacccagag ccctgccacc ctgagcgtgt ctccaggcga gagagccacc    60
ctgtcctgta gagcctcccg gagcatcagc atcaatctgc attggtatca gcagaagccc   120
ggccaggccc ccagactgct gatctacttc gccagccagt ccatcagcgg catccccgcc   180
agattttctg gcagcggcag cggcaccgag ttcaccctga ccatcagcag cctgcagagc   240
gaggacttcg ccgtgtatta ttgccagcag agcaacagct tcccccctga cttcggcgga   300
```

-continued

```
ggcaccaagg tggagatcaa gcgt                                          324
```

<210> SEQ ID NO 242
<211> LENGTH: 354
<212> TYPE: DNA
<213> ORGANISM: Artificial Sequence
<220> FEATURE:
<223> OTHER INFORMATION: Synthetic

<400> SEQUENCE: 242

```
caggtgcagc tggtgcagag cggagccgaa gtgaagaaac caggcgcctc cgtgaaggtg    60
tcctgcaagg ccagcggcta caccttcacc gactactatc tgcactgggt ccgccaggca   120
ccagggcggg gactggaatg gatgggctgg atcgaccccg agaacggcga taccgagcac   180
gcccccaagt tccagggcag agtgaccatg accaccgaca ccagcaccag caccgcctac   240
atggaactgc ggagcctgag aagcgacgac accgccgtgt actactgcaa cgccaacaaa   300
gagctgcggt acttcgacgt gtggggccag ggcacaatgg tcaccgtgtc ctct          354
```

<210> SEQ ID NO 243
<211> LENGTH: 354
<212> TYPE: DNA
<213> ORGANISM: Artificial Sequence
<220> FEATURE:
<223> OTHER INFORMATION: Synthetic

<400> SEQUENCE: 243

```
caggtgcagc tggtgcagag cggagccgaa gtgaagaaac caggcgcctc cgtgaaggtg    60
tcctgcaagg ccagcggcta cgccttcacc gactactatc tgcactgggt ccgccaggca   120
ccagggcagg gactggaatg gatgggctgg atcgaccccg agaacggcga taccgagtcc   180
gcccccaagt tccagggcag agtgaccatg accaccgaca ccagcaccag caccgcctac   240
atggaactgc ggagcctgag aagcgacgac accgccgtgt actactgcaa cgccaacaaa   300
gagctgcggt acttcgacgt gtggggccag ggcacaatgg tcaccgtgtc ctct          354
```

<210> SEQ ID NO 244
<211> LENGTH: 354
<212> TYPE: DNA
<213> ORGANISM: Artificial Sequence
<220> FEATURE:
<223> OTHER INFORMATION: Synthetic

<400> SEQUENCE: 244

```
caggtgcagc tggtgcagag cggagccgaa gtgaagaaac caggcgcctc cgtgaaggtg    60
tcctgcaagg ccagcggcta cgccttcacc gactactatc tgcactgggt ccgccaggca   120
ccagggcagg gactggaatg gatgggctgg atcgaccccg agaacggcga taccgagcac   180
gcccccaagt tccagggcag agtgtccatg accaccgaca ccagcaccag caccgcctac   240
atggaactgc ggagcctgag aagcgacgac accgccgtgt actactgcaa cgccaacaaa   300
gagctgcggt acttcgacgt gtggggccag ggcacaatgg tcaccgtgtc ctct          354
```

<210> SEQ ID NO 245
<211> LENGTH: 354
<212> TYPE: DNA
<213> ORGANISM: Artificial Sequence
<220> FEATURE:
<223> OTHER INFORMATION: Synthetic

<400> SEQUENCE: 245

```
caggtgcagc tggtgcagag cggagccgaa gtgaagaaac caggcgcctc cgtgaaggtg    60
```

```
tcctgcaagg ccagcggcta cccctcacc gactactatc tgcactgggt ccgccaggca    120
ccagggcagg gactggaatg gatgggctgg atcgaccccg agaacggcga taccgagcac    180
gcccccaagt tccagggcag agtgaccatg accaccgaca ccagcaccag caccgcctac    240
atggaactgc ggagcctgag aagcgacgac accgccgtgt actactgcaa cgccaacaaa    300
gagctgcggt acttcgacgt gtggggccag ggcacaatgg tcaccgtgtc ctct          354

<210> SEQ ID NO 246
<211> LENGTH: 354
<212> TYPE: DNA
<213> ORGANISM: Artificial Sequence
<220> FEATURE:
<223> OTHER INFORMATION: Synthetic

<400> SEQUENCE: 246
caggtgcagc tggtgcagag cggagccgaa gtgaagaaac caggcgcctc cgtgaaggtg    60
tcctgcaagg ccagcggcta cccctcacc gactactatc tgcactgggt ccgccaggca    120
ccagggcagg gactggaatg gatgggctgg atcgaccccg agaacggcga taccgagtcc    180
gcccccaagt tccagggcag agtgaccatg accaccgaca ccagcaccag caccgcctac    240
atggaactgc ggagcctgag aagcgacgac accgccgtgt actactgcaa cgccaacaaa    300
gagctgcggt acttcgacgt gtggggccag ggcacaatgg tcaccgtgtc ctct          354

<210> SEQ ID NO 247
<211> LENGTH: 354
<212> TYPE: DNA
<213> ORGANISM: Artificial Sequence
<220> FEATURE:
<223> OTHER INFORMATION: Synthetic

<400> SEQUENCE: 247
caggtgcagc tggtgcagag cggagccgaa gtgaagaaac caggcgcctc cgtgaaggtg    60
tcctgcaagg ccagcggcta caccttcacc gactactatc tgcactgggt ccgccaggca    120
ccagggcggg gactggaatg gatgggctgg atcgaccccg agaacggcga taccgagtcc    180
gcccccaagt tccagggcag agtgaccatg accaccgaca ccagcaccag caccgcctac    240
atggaactgc ggagcctgag aagcgacgac accgccgtgt actactgcaa cgccaacaaa    300
gagctgcggt acttcgacgt gtggggccag ggcacaatgg tcaccgtgtc ctct          354

<210> SEQ ID NO 248
<211> LENGTH: 354
<212> TYPE: DNA
<213> ORGANISM: Artificial Sequence
<220> FEATURE:
<223> OTHER INFORMATION: Synthetic

<400> SEQUENCE: 248
caggtgcagc tggtgcagag cggagccgaa gtgaagaaac caggcgcctc cgtgaaggtg    60
tcctgcaagg ccagcggcta cgccttcacc gactactatc tgcactgggt ccgccaggca    120
ccagggcagg gactggaatg gatgggctgg atcgaccccg agaacggcga taccgagcac    180
gcccccaagt tccagggcag agtgaccatg accaccgaca ccagcaccag caccgcctac    240
atggaactgc ggagcctgag aagcgacgac accgccgtgt actactgcaa cgccaacaaa    300
gagctgcggt acttcgacgt gtggggccag ggcacaatgg tcaccgtgtc ctct          354

<210> SEQ ID NO 249
<211> LENGTH: 354
```

```
<212> TYPE: DNA
<213> ORGANISM: Artificial Sequence
<220> FEATURE:
<223> OTHER INFORMATION: Synthetic

<400> SEQUENCE: 249
caggtgcagc tggtgcagag cggagccgaa gtgaagaaac caggcgcctc cgtgaaggtg      60
tcctgcaagg ccagcggcta cgccttcacc gactactatc tgcactgggt ccgccaggca     120
ccagggcagg gactggaatg gatgggctgg atcgaccccg agaacggcga taccgagtcc     180
gcccccaagt tccagggcag agtgtccatg accaccgaca ccagcaccag caccgcctac     240
atggaactgc ggagcctgag aagcgacgac accgccgtgt actactgcaa cgccaacaaa     300
gagctgcggt acttcgacgt gtggggccag ggcacaatgg tcaccgtgtc ctct           354

<210> SEQ ID NO 250
<211> LENGTH: 354
<212> TYPE: DNA
<213> ORGANISM: Artificial Sequence
<220> FEATURE:
<223> OTHER INFORMATION: Synthetic

<400> SEQUENCE: 250
caggtgcagc tggtgcagag cggagccgaa gtgaagaaac caggcgcctc cgtgaaggtg      60
tcctgcaagg ccagcggcta cgccttcacc gactactatc tgcactgggt ccgccaggca     120
ccagggcggg gactggaatg gatgggctgg atcgaccccg agaacggcga taccgagtac     180
gcccccaagt tccagggcag agtgaccatg accaccgaca ccagcaccag caccgcctac     240
atggaactgc ggagcctgag aagcgacgac accgccgtgt actactgcaa cgccaacaaa     300
gagctgcggt acttcgacgt gtggggccag ggcacaatgg tcaccgtgtc ctct           354

<210> SEQ ID NO 251
<211> LENGTH: 354
<212> TYPE: DNA
<213> ORGANISM: Artificial Sequence
<220> FEATURE:
<223> OTHER INFORMATION: Synthetic

<400> SEQUENCE: 251
caggtgcagc tggtgcagag cggagccgaa gtgaagaaac caggcgcctc cgtgaaggtg      60
tcctgcaagg ccagcggcta caccctcacc gactactatc tgcactgggt ccgccaggca     120
ccagggcggg gactggaatg gatgggctgg atcgaccccg agaacggcga taccgagtac     180
gcccccaagt tccagggcag agtgaccatg accaccgaca ccagcaccag caccgcctac     240
atggaactgc ggagcctgag aagcgacgac accgccgtgt actactgcaa cgccaacaaa     300
gagctgcggt acttcgacgt gtggggccag ggcacaatgg tcaccgtgtc ctct           354

<210> SEQ ID NO 252
<211> LENGTH: 354
<212> TYPE: DNA
<213> ORGANISM: Artificial Sequence
<220> FEATURE:
<223> OTHER INFORMATION: Synthetic

<400> SEQUENCE: 252
gaggtgcagc tgcagcagag cggagccgat ctggtccgca gcggcgccag catcaagctg      60
tcctgcaccg ccagcggctt caacatcaag gactactaca tgcactgggt gaagcagcgg     120
cccgagcagg gcctggaatg gatcggctgg atcgaccccg agaacggcga caccgagtac     180
gcccccaagt tccagggcaa ggccaccatg accgccgaca ccagcagcaa caccgcctac     240
```

```
ctgcagctgt ccagcctgac cagcgaggac accgccgtgt actactgcaa cgcctgcaaa    300
gagctgcggt acttcgacgt gtggggagcc ggcaccaccg tgaccgtgtc cagc           354
```

<210> SEQ ID NO 253
<211> LENGTH: 1017
<212> TYPE: DNA
<213> ORGANISM: Artificial Sequence
<220> FEATURE:
<223> OTHER INFORMATION: Synthetic

<400> SEQUENCE: 253

```
gctagcacca agggcccatc ggtcttcccc ctggcaccct cctccaagag cacctctggg    60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagag agttgagccc    300
aaatcttgtg acaaaactca cacatgccca ccgtgcccag cacctgaact cctggggga    360 ccgtcagtct tcctcttccc cccaaaaccc aaggacaccc tcatgatctc ccggaccct    420 gaggtcacat gcgtggtggt ggacgtgagc cacgaagacc ctgaggtcaa gttcaactgg    480
tacgtggacg gcgtggaggt gcataatgcc aagacaaagc cgcggagga gcagtacaac    540 agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggatgag    720
ctgaccaaga accaggtcag cctgacctgc tggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa taggatcccc cgacctcgac ctctggc      1017
```

<210> SEQ ID NO 254
<211> LENGTH: 354
<212> TYPE: DNA
<213> ORGANISM: Artificial Sequence
<220> FEATURE:
<223> OTHER INFORMATION: Synthetic

<400> SEQUENCE: 254

```
gaggtgcagc tgcagcagag cggagccgat ctggtccgca gcggcgccag catcaagctg    60
tcctgcaccg ccagcggctt caacatcaag gactactacc tgcactgggt gaagcagcgg    120
cccgagcagg gcctggaatg gatcggctgg atcgaccccg agaacggcga caccgagtac    180
gcccccaagt tccagggcaa ggccaccatg accgccgaca ccagcagcaa caccgcctac    240
ctgcagctgt ccagcctgac cagcgaggac accgccgtgt actactgcaa cgcctgcaaa    300
gagctgcggt acttcgacgt gtggggagcc ggcaccaccg tgaccgtgtc cagc          354
```

<210> SEQ ID NO 255
<211> LENGTH: 354
<212> TYPE: DNA
<213> ORGANISM: Artificial Sequence
<220> FEATURE:
<223> OTHER INFORMATION: Synthetic

<400> SEQUENCE: 255

```
gaggtgcagc tgcagcagag cggagccgat ctggtccgca gcggcgccag catcaagctg    60
tcctgcaccg ccagcggctt caacatcaag gactactaca tgcactgggt gaagcagcgg   120
cccgagcagg gcctggaatg gatcggctgg atcgacccg agaacggcga caccgagtac   180
gcccccaagt tccagggcaa ggccaccatg accgccgaca ccagcagcaa caccgcctac   240
ctgcagctgt ccagcctgac cagcgaggac accgccgtgt actactgcaa cgccgccaaa   300
gagctgcggt acttcgacgt gtggggagcc ggcaccaccg tgaccgtgtc cagc         354
```

<210> SEQ ID NO 256
<211> LENGTH: 354
<212> TYPE: DNA
<213> ORGANISM: Artificial Sequence
<220> FEATURE:
<223> OTHER INFORMATION: Synthetic

<400> SEQUENCE: 256

```
gaggtgcagc tgcagcagag cggagccgat ctggtccgca gcggcgccag catcaagctg    60
tcctgcaccg ccagcggctt caacatcaag gactactaca tgcactgggt gaagcagcgg   120
cccgagcagg gcctggaatg gatcggctgg atcgacccg agaacggcga caccgagtac   180
gcccccaagt tccagggcaa ggccaccatg accgccgaca ccagcagcaa caccgcctac   240
ctgcagctgt ccagcctgac cagcgaggac accgccgtgt actactgcaa cgcccggaaa   300
gagctgcggt acttcgacgt gtggggagcc ggcaccaccg tgaccgtgtc cagc         354
```

<210> SEQ ID NO 257
<211> LENGTH: 354
<212> TYPE: DNA
<213> ORGANISM: Artificial Sequence
<220> FEATURE:
<223> OTHER INFORMATION: Synthetic

<400> SEQUENCE: 257

```
gaggtgcagc tgcagcagag cggagccgat ctggtccgca gcggcgccag catcaagctg    60
tcctgcaccg ccagcggctt caacatcaag gactactaca tgcactgggt gaagcagcgg   120
cccgagcagg gcctggaatg gatcggctgg atcgacccg agaacggcga caccgagtac   180
gcccccaagt tccagggcaa ggccaccatg accgccgaca ccagcagcaa caccgcctac   240
ctgcagctgt ccagcctgac cagcgaggac accgccgtgt actactgcaa cgccaacaaa   300
gagctgcggt acttcgacgt gtggggagcc ggcaccaccg tgaccgtgtc cagc         354
```

<210> SEQ ID NO 258
<211> LENGTH: 354
<212> TYPE: DNA
<213> ORGANISM: Artificial Sequence
<220> FEATURE:
<223> OTHER INFORMATION: Synthetic

<400> SEQUENCE: 258

```
gaggtgcagc tgcagcagag cggagccgat ctggtccgca gcggcgccag catcaagctg    60
tcctgcaccg ccagcggctt caacatcaag gactactaca tgcactgggt gaagcagcgg   120
cccgagcagg gcctggaatg gatcggctgg atcgacccg agaacggcga caccgagtac   180
gcccccaagt tccagggcaa ggccaccatg accgccgaca ccagcagcaa caccgcctac   240
ctgcagctgt ccagcctgac cagcgaggac accgccgtgt actactgcaa cgccgacaaa   300
gagctgcggt acttcgacgt gtggggagcc ggcaccaccg tgaccgtgtc cagc         354
```

<210> SEQ ID NO 259
<211> LENGTH: 354
<212> TYPE: DNA
<213> ORGANISM: Artificial Sequence
<220> FEATURE:
<223> OTHER INFORMATION: Synthetic

<400> SEQUENCE: 259

```
gaggtgcagc tgcagcagag cggagccgat ctggtccgca gcggcgccag catcaagctg    60
tcctgcaccg ccagcggctt caacatcaag gactactaca tgcactgggt gaagcagcgg   120
cccgagcagg gcctggaatg gatcggctgg atcgaccccg agaacggcga caccgagtac   180
gcccccaagt tccagggcaa ggccaccatg accgccgaca ccagcagcaa caccgcctac   240
ctgcagctgt ccagcctgac cagcgaggac accgccgtgt actactgcaa cgccgagaaa   300
gagctgcggt acttcgacgt gtggggagcc ggcaccaccg tgaccgtgtc cagc         354
```

<210> SEQ ID NO 260
<211> LENGTH: 354
<212> TYPE: DNA
<213> ORGANISM: Artificial Sequence
<220> FEATURE:
<223> OTHER INFORMATION: Synthetic

<400> SEQUENCE: 260

```
gaggtgcagc tgcagcagag cggagccgat ctggtccgca gcggcgccag catcaagctg    60
tcctgcaccg ccagcggctt caacatcaag gactactaca tgcactgggt gaagcagcgg   120
cccgagcagg gcctggaatg gatcggctgg atcgaccccg agaacggcga caccgagtac   180
gcccccaagt tccagggcaa ggccaccatg accgccgaca ccagcagcaa caccgcctac   240
ctgcagctgt ccagcctgac cagcgaggac accgccgtgt actactgcaa cgcccagaaa   300
gagctgcggt acttcgacgt gtggggagcc ggcaccaccg tgaccgtgtc cagc         354
```

<210> SEQ ID NO 261
<211> LENGTH: 354
<212> TYPE: DNA
<213> ORGANISM: Artificial Sequence
<220> FEATURE:
<223> OTHER INFORMATION: Synthetic

<400> SEQUENCE: 261

```
gaggtgcagc tgcagcagag cggagccgat ctggtccgca gcggcgccag catcaagctg    60
tcctgcaccg ccagcggctt caacatcaag gactactaca tgcactgggt gaagcagcgg   120
cccgagcagg gcctggaatg gatcggctgg atcgaccccg agaacggcga caccgagtac   180
gcccccaagt tccagggcaa ggccaccatg accgccgaca ccagcagcaa caccgcctac   240
ctgcagctgt ccagcctgac cagcgaggac accgccgtgt actactgcaa cgccggcaaa   300
gagctgcggt acttcgacgt gtggggagcc ggcaccaccg tgaccgtgtc cagc         354
```

<210> SEQ ID NO 262
<211> LENGTH: 354
<212> TYPE: DNA
<213> ORGANISM: Artificial Sequence
<220> FEATURE:
<223> OTHER INFORMATION: Synthetic

<400> SEQUENCE: 262

```
gaggtgcagc tgcagcagag cggagccgat ctggtccgca gcggcgccag catcaagctg    60
tcctgcaccg ccagcggctt caacatcaag gactactaca tgcactgggt gaagcagcgg   120
cccgagcagg gcctggaatg gatcggctgg atcgaccccg agaacggcga caccgagtac   180
```

```
gcccccaagt tccagggcaa ggccaccatg accgccgaca ccagcagcaa caccgcctac    240
ctgcagctgt ccagcctgac cagcgaggac accgccgtgt actactgcaa cgcccacaaa    300
gagctgcggt acttcgacgt gtggggagcc ggcaccaccg tgaccgtgtc cagc          354

<210> SEQ ID NO 263
<211> LENGTH: 354
<212> TYPE: DNA
<213> ORGANISM: Artificial Sequence
<220> FEATURE:
<223> OTHER INFORMATION: Synthetic

<400> SEQUENCE: 263
gaggtgcagc tgcagcagag cggagccgat ctggtccgca gcggcgccag catcaagctg    60
tcctgcaccg ccagcggctt caacatcaag gactactaca tgcactgggt gaagcagcgg    120
cccgagcagg gcctggaatg gatcggctgg atcgaccccg agaacggcga caccgagtac    180
gcccccaagt tccagggcaa ggccaccatg accgccgaca ccagcagcaa caccgcctac    240
ctgcagctgt ccagcctgac cagcgaggac accgccgtgt actactgcaa cgccatcaaa    300
gagctgcggt acttcgacgt gtggggagcc ggcaccaccg tgaccgtgtc cagc          354

<210> SEQ ID NO 264
<211> LENGTH: 354
<212> TYPE: DNA
<213> ORGANISM: Artificial Sequence
<220> FEATURE:
<223> OTHER INFORMATION: Synthetic

<400> SEQUENCE: 264
gaggtgcagc tgcagcagag cggagccgat ctggtccgca gcggcgccag catcaagctg    60
tcctgcaccg ccagcggctt caacatcaag gactactaca tgcactgggt gaagcagcgg    120
cccgagcagg gcctggaatg gatcggctgg atcgaccccg agaacggcga caccgagtac    180
gcccccaagt tccagggcaa ggccaccatg accgccgaca ccagcagcaa caccgcctac    240
ctgcagctgt ccagcctgac cagcgaggac accgccgtgt actactgcaa cgccctgaaa    300
gagctgcggt acttcgacgt gtggggagcc ggcaccaccg tgaccgtgtc cagc          354

<210> SEQ ID NO 265
<211> LENGTH: 354
<212> TYPE: DNA
<213> ORGANISM: Artificial Sequence
<220> FEATURE:
<223> OTHER INFORMATION: Synthetic

<400> SEQUENCE: 265
gaggtgcagc tgcagcagag cggagccgat ctggtccgca gcggcgccag catcaagctg    60
tcctgcaccg ccagcggctt caacatcaag gactactaca tgcactgggt gaagcagcgg    120
cccgagcagg gcctggaatg gatcggctgg atcgaccccg agaacggcga caccgagtac    180
gcccccaagt tccagggcaa ggccaccatg accgccgaca ccagcagcaa caccgcctac    240
ctgcagctgt ccagcctgac cagcgaggac accgccgtgt actactgcaa cgccaagaaa    300
gagctgcggt acttcgacgt gtggggagcc ggcaccaccg tgaccgtgtc cagc          354

<210> SEQ ID NO 266
<211> LENGTH: 354
<212> TYPE: DNA
<213> ORGANISM: Artificial Sequence
<220> FEATURE:
<223> OTHER INFORMATION: Synthetic
```

<400> SEQUENCE: 266

```
gaggtgcagc tgcagcagag cggagccgat ctggtccgca gcggcgccag catcaagctg      60
tcctgcaccg ccagcggctt caacatcaag gactactaca tgcactgggt gaagcagcgg     120
cccgagcagg gcctggaatg gatcggctgg atcgacccg  agaacggcga caccgagtac     180
gcccccaagt tccagggcaa ggccaccatg accgccgaca ccagcagcaa caccgcctac     240
ctgcagctgt ccagcctgac cagcgaggac accgccgtgt actactgcaa cgccatgaaa     300
gagctgcggt acttcgacgt gtggggagcc ggcaccaccg tgaccgtgtc cagc           354
```

<210> SEQ ID NO 267
<211> LENGTH: 354
<212> TYPE: DNA
<213> ORGANISM: Artificial Sequence
<220> FEATURE:
<223> OTHER INFORMATION: Synthetic

<400> SEQUENCE: 267

```
gaggtgcagc tgcagcagag cggagccgat ctggtccgca gcggcgccag catcaagctg      60
tcctgcaccg ccagcggctt caacatcaag gactactaca tgcactgggt gaagcagcgg     120
cccgagcagg gcctggaatg gatcggctgg atcgacccg  agaacggcga caccgagtac     180
gcccccaagt tccagggcaa ggccaccatg accgccgaca ccagcagcaa caccgcctac     240
ctgcagctgt ccagcctgac cagcgaggac accgccgtgt actactgcaa cgccttcaaa     300
gagctgcggt acttcgacgt gtggggagcc ggcaccaccg tgaccgtgtc cagc           354
```

<210> SEQ ID NO 268
<211> LENGTH: 354
<212> TYPE: DNA
<213> ORGANISM: Artificial Sequence
<220> FEATURE:
<223> OTHER INFORMATION: Synthetic

<400> SEQUENCE: 268

```
gaggtgcagc tgcagcagag cggagccgat ctggtccgca gcggcgccag catcaagctg      60
tcctgcaccg ccagcggctt caacatcaag gactactaca tgcactgggt gaagcagcgg     120
cccgagcagg gcctggaatg gatcggctgg atcgacccg  agaacggcga caccgagtac     180
gcccccaagt tccagggcaa ggccaccatg accgccgaca ccagcagcaa caccgcctac     240
ctgcagctgt ccagcctgac cagcgaggac accgccgtgt actactgcaa cgcccccaaa     300
gagctgcggt acttcgacgt gtggggagcc ggcaccaccg tgaccgtgtc cagc           354
```

<210> SEQ ID NO 269
<211> LENGTH: 354
<212> TYPE: DNA
<213> ORGANISM: Artificial Sequence
<220> FEATURE:
<223> OTHER INFORMATION: Synthetic

<400> SEQUENCE: 269

```
gaggtgcagc tgcagcagag cggagccgat ctggtccgca gcggcgccag catcaagctg      60
tcctgcaccg ccagcggctt caacatcaag gactactaca tgcactgggt gaagcagcgg     120
cccgagcagg gcctggaatg gatcggctgg atcgacccg  agaacggcga caccgagtac     180
gcccccaagt tccagggcaa ggccaccatg accgccgaca ccagcagcaa caccgcctac     240
ctgcagctgt ccagcctgac cagcgaggac accgccgtgt actactgcaa cgccagcaaa     300
gagctgcggt acttcgacgt gtggggagcc ggcaccaccg tgaccgtgtc cagc           354
```

<210> SEQ ID NO 270
<211> LENGTH: 354
<212> TYPE: DNA
<213> ORGANISM: Artificial Sequence
<220> FEATURE:
<223> OTHER INFORMATION: Synthetic

<400> SEQUENCE: 270
gaggtgcagc tgcagcagag cggagccgat ctggtccgca gcggcgccag catcaagctg      60
tcctgcaccg ccagcggctt caacatcaag gactactaca tgcactgggt gaagcagcgg     120
cccgagcagg gcctggaatg gatcggctgg atcgaccccg agaacggcga caccgagtac     180
gcccccaagt tccagggcaa ggccaccatg accgccgaca ccagcagcaa caccgcctac     240
ctgcagctgt ccagcctgac cagcgaggac accgccgtgt actactgcaa cgccaccaaa     300
gagctgcggt acttcgacgt gtggggagcc ggcaccaccg tgaccgtgtc cagc           354

<210> SEQ ID NO 271
<211> LENGTH: 354
<212> TYPE: DNA
<213> ORGANISM: Artificial Sequence
<220> FEATURE:
<223> OTHER INFORMATION: Synthetic

<400> SEQUENCE: 271
gaggtgcagc tgcagcagag cggagccgat ctggtccgca gcggcgccag catcaagctg      60
tcctgcaccg ccagcggctt caacatcaag gactactaca tgcactgggt gaagcagcgg     120
cccgagcagg gcctggaatg gatcggctgg atcgaccccg agaacggcga caccgagtac     180
gcccccaagt tccagggcaa ggccaccatg accgccgaca ccagcagcaa caccgcctac     240
ctgcagctgt ccagcctgac cagcgaggac accgccgtgt actactgcaa cgcctacaaa     300
gagctgcggt acttcgacgt gtggggagcc ggcaccaccg tgaccgtgtc cagc           354

<210> SEQ ID NO 272
<211> LENGTH: 354
<212> TYPE: DNA
<213> ORGANISM: Artificial Sequence
<220> FEATURE:
<223> OTHER INFORMATION: Synthetic

<400> SEQUENCE: 272
gaggtgcagc tgcagcagag cggagccgat ctggtccgca gcggcgccag catcaagctg      60
tcctgcaccg ccagcggctt caacatcaag gactactaca tgcactgggt gaagcagcgg     120
cccgagcagg gcctggaatg gatcggctgg atcgaccccg agaacggcga caccgagtac     180
gcccccaagt tccagggcaa ggccaccatg accgccgaca ccagcagcaa caccgcctac     240
ctgcagctgt ccagcctgac cagcgaggac accgccgtgt actactgcaa cgccgtgaaa     300
gagctgcggt acttcgacgt gtggggagcc ggcaccaccg tgaccgtgtc cagc           354

<210> SEQ ID NO 273
<211> LENGTH: 354
<212> TYPE: DNA
<213> ORGANISM: Artificial Sequence
<220> FEATURE:
<223> OTHER INFORMATION: Synthetic

<400> SEQUENCE: 273
gaggtgcagc tggtgcagag cggagccgaa gtgaagaagc caggcgccac cgtcaagatc      60
agctgcaagg tgtccggcta caccttcacc gactactaca tgcactgggt gcagcaggct     120

```
ccaggcaagg gactggaatg gatgggctgg atcgaccccg agaacggcga caccgagtac      180
gcccccaagt tccagggcag agtgaccatc accgccgaca ccagcaccga caccgcctac      240
atggaactga gcagcctgcg gagcgaggac accgccgtgt actactgcaa cgcctgcaaa      300
gagctgcggt acttcgacgt gtggggccag ggcaccatgg tgaccgtgtc tagc            354
```

<210> SEQ ID NO 274
<211> LENGTH: 354
<212> TYPE: DNA
<213> ORGANISM: Artificial Sequence
<220> FEATURE:
<223> OTHER INFORMATION: Synthetic

<400> SEQUENCE: 274

```
caggtgcagc tggtgcagag cggagccgaa gtgaagaagc ctggcgccag cgtcaaggtg       60
tcctgcaagg tgtccggcta caccctgacc gactactaca tgcactgggt gcgccaggct      120
ccaggcaagg gactggaatg gatgggctgg atcgaccccg agaacggcga caccgagtac      180
gcccccaagt tccagggcag agtgaccatg accgaggaca ccagcaccga caccgcctac      240
atggaactga gcagcctgcg gagcgaggac accgccgtgt actactgcaa cgcctgcaaa      300
gagctgcggt acttcgacgt gtggggccag ggcaccatgg tgaccgtgtc cagc            354
```

<210> SEQ ID NO 275
<211> LENGTH: 354
<212> TYPE: DNA
<213> ORGANISM: Artificial Sequence
<220> FEATURE:
<223> OTHER INFORMATION: Synthetic

<400> SEQUENCE: 275

```
caggtgcagc tggtgcagag cggagccgaa gtgaagaagc ctggcgccag cgtcaaggtg       60
tcctgcaagg cctccggcta caccttcacc gactactaca tgcactgggt gcgccaggct      120
ccaggccagg gactggaatg gatgggctgg atcgaccccg agaacggcga caccgagtac      180
gcccccaagt tccagggcag agtgaccatg accaccgaca ccagcaccag caccgcctac      240
atggaactgc ggagcctgcg gagcgacgac accgccgtgt actactgcaa cgcctgcaaa      300
gagctgcggt acttcgacgt gtggggccag ggcaccatgg tgaccgtgtc cagc            354
```

<210> SEQ ID NO 276
<211> LENGTH: 354
<212> TYPE: DNA
<213> ORGANISM: Artificial Sequence
<220> FEATURE:
<223> OTHER INFORMATION: Synthetic

<400> SEQUENCE: 276

```
gaggtgcagc tggtgcagag cggagccgaa gtgaagaagc aggcgccac cgtcaagatc       60 agctgcaagg tgtccggcta caccttcacc gactactaca tgcactgggt gcagcaggct      120
ccaggcaagg gactggaatg gatgggctgg atcgaccccg agaacggcga caccgagtac      180
gcccccaagt tccagggcag agtgaccatc accgccgaca ccagcaccga caccgcctac      240
atggaactga gcagcctgcg gagcgaggac accgccgtgt actactgcgc cacctgcaaa      300
gagctgcggt acttcgacgt gtggggccag ggcaccatgg tgaccgtgtc tagc            354
```

<210> SEQ ID NO 277
<211> LENGTH: 354
<212> TYPE: DNA
<213> ORGANISM: Artificial Sequence
<220> FEATURE:
<223> OTHER INFORMATION: Synthetic

<400> SEQUENCE: 277

| caggtgcagc tggtgcagag cggagccgaa gtgaagaagc ctggcgccag cgtcaaggtg | 60 |
| tcctgcaagg tgtccggcta caccctgacc gactactaca tgcactgggt gcgccaggct | 120 |
| ccaggcaagg gactggaatg gatgggctgg atcgaccccg agaacggcga caccgagtac | 180 |
| gcccccaagt tccagggcag agtgaccatg accgaggaca ccagcaccga caccgcctac | 240 |
| atggaactga gcagcctgcg gagcgaggac accgccgtgt actactgcgc cacctgcaaa | 300 |
| gagctgcggt acttcgacgt gtggggccag ggcaccatgg tgaccgtgtc cagc | 354 |

<210> SEQ ID NO 278
<211> LENGTH: 354
<212> TYPE: DNA
<213> ORGANISM: Artificial Sequence
<220> FEATURE:
<223> OTHER INFORMATION: Synthetic

<400> SEQUENCE: 278

| caggtgcagc tggtgcagag cggagccgaa gtgaagaagc ctggcgccag cgtcaaggtg | 60 |
| tcctgcaagg cctccggcta caccttcacc gactactaca tgcactgggt gcgccaggct | 120 |
| ccaggccagg gactggaatg gatgggctgg atcgaccccg agaacggcga caccgagtac | 180 |
| gcccccaagt tccagggcag agtgaccatg accaccgaca ccagcaccag caccgcctac | 240 |
| atggaactgc ggagcctgcg gagcgacgac accgccgtgt actactgcgc cggtgcaaa | 300 |
| gagctgcggt acttcgacgt gtggggccag ggcaccatgg tgaccgtgtc cagc | 354 |

<210> SEQ ID NO 279
<211> LENGTH: 354
<212> TYPE: DNA
<213> ORGANISM: Artificial Sequence
<220> FEATURE:
<223> OTHER INFORMATION: Synthetic

<400> SEQUENCE: 279

| gaggtgcagc tgcagcagag cggagccgat ctggtccgca gcggcgccag catcaagctg | 60 |
| tcctgcaccg ccagcggctt caacatcaag gactactacc tgcactgggt gaagcagcgg | 120 |
| cccgagcagg gcctggaatg gatcggctgg atcgaccccg agaacggcga caccgagtac | 180 |
| gcccccaagt tccagggcaa ggccaccatg accgccgaca ccagcagcaa caccgcctac | 240 |
| ctgcagctgt ccagcctgac cagcgaggac accgccgtgt actactgcaa cgccaacaaa | 300 |
| gagctgcggt acttcgacgt gtggggagcc ggcaccaccg tgaccgtgtc cagc | 354 |

<210> SEQ ID NO 280
<211> LENGTH: 354
<212> TYPE: DNA
<213> ORGANISM: Artificial Sequence
<220> FEATURE:
<223> OTHER INFORMATION: Synthetic

<400> SEQUENCE: 280

| gaggtgcagc tggtgcagag cggagccgaa gtgaagaagc ctggcgccac cgtcaagatc | 60 |
| agctgcaagg ccagcggcta caccttcagc gactactacc tgcactgggt gcgccaggct | 120 |
| ccaggcaagg gactggaatg gatgggctgg atcgaccccg agaacggcga caccgagtac | 180 |
| gcccccaagt tccagggcag agtgaccatc accgccgaca ccagcaccga caccggctac | 240 |
| ctggaactga gcagcctgcg gagcgaggac accgccgtgt actactgcgc cgccaacaaa | 300 |

```
gagctgcggt acttcgacgt gtggggccag ggcaccctgg tgaccgtgtc cagc    354
```

<210> SEQ ID NO 281
<211> LENGTH: 354
<212> TYPE: DNA
<213> ORGANISM: Artificial Sequence
<220> FEATURE:
<223> OTHER INFORMATION: Synthetic

<400> SEQUENCE: 281

```
gaggtgcagc tggtgcagag cggagccgaa gtgaagaagc ctggcgccac cgtcaagatc    60
agctgcaagg ccagcggcta caccttcagc gactactacc tgcactgggt gcgccagcgg    120
ccaggcaagg gactggaatg gatgggctgg atcgaccccg agaacggcga caccgagtac    180
gcccccaagt tccagggcag agtgaccatc accgccgaca ccagcaccga caccggctac    240
ctggaactga gcagcctgcg gagcgaggac accgccgtgt actactgcgc cgccaacaaa    300
gagctgcggt acttcgacgt gtggggccag ggcaccctgg tgaccgtgtc cagc    354
```

<210> SEQ ID NO 282
<211> LENGTH: 354
<212> TYPE: DNA
<213> ORGANISM: Artificial Sequence
<220> FEATURE:
<223> OTHER INFORMATION: Synthetic

<400> SEQUENCE: 282

```
gaggtgcagc tggtgcagag cggagccgaa gtgaagaagc ctggcgccac cgtcaagatc    60
agctgcaagg ccagcggcta caccttcagc gactactacc tgcactgggt gcgccaggct    120
ccagagaagg gactggaatg gatgggctgg atcgaccccg agaacggcga caccgagtac    180
gcccccaagt tccagggcag agtgaccatc accgccgaca ccagcaccga caccggctac    240
ctggaactga gcagcctgcg gagcgaggac accgccgtgt actactgcgc cgccaacaaa    300
gagctgcggt acttcgacgt gtggggccag ggcaccctgg tgaccgtgtc cagc    354
```

<210> SEQ ID NO 283
<211> LENGTH: 354
<212> TYPE: DNA
<213> ORGANISM: Artificial Sequence
<220> FEATURE:
<223> OTHER INFORMATION: Synthetic

<400> SEQUENCE: 283

```
gaggtgcagc tggtgcagag cggagccgaa gtgaagaagc ctggcgccac cgtcaagatc    60
agctgcaagg ccagcggcta caccttcagc gactactacc tgcactgggt gcgccaggct    120
ccaggcaagg gactggaatg gatgggctgg atcgaccccg agaacggcga caccgagtac    180
gcccccaagt tccagggcaa ggtgaccatc accgccgaca ccagcaccga caccggctac    240
ctggaactga gcagcctgcg gagcgaggac accgccgtgt actactgcgc cgccaacaaa    300
gagctgcggt acttcgacgt gtggggccag ggcaccctgg tgaccgtgtc cagc    354
```

<210> SEQ ID NO 284
<211> LENGTH: 354
<212> TYPE: DNA
<213> ORGANISM: Artificial Sequence
<220> FEATURE:
<223> OTHER INFORMATION: Synthetic

<400> SEQUENCE: 284

```
gaggtgcagc tggtgcagag cggagccgaa gtgaagaagc ctggcgccac cgtcaagatc    60
```

```
agctgcaagg ccagcggcta caccttcagc gactactacc tgcactgggt gcgccagcgg      120
ccagagaagg gactggaatg gatgggctgg atcgaccccg agaacggcga caccgagtac      180
gcccccaagt tccagggcaa ggtgaccatc accgccgaca ccagcaccga caccggctac      240
ctggaactga gcagcctgcg gagcgaggac accgccgtgt actactgcgc cgccaacaaa      300
gagctgcggt acttcgacgt gtggggccag ggcaccctgg tgaccgtgtc cagc            354
```

<210> SEQ ID NO 285
<211> LENGTH: 354
<212> TYPE: DNA
<213> ORGANISM: Artificial Sequence
<220> FEATURE:
<223> OTHER INFORMATION: Synthetic

<400> SEQUENCE: 285

```
gaggtgcagc tggtgcagag cggagccgaa gtgaagaagc caggcgccac cgtcaagatc      60
agctgcaagg tgtccggcta caccttcacc gactactacc tgcactgggt gcagcaggct     120
ccaggcaagg gactggaatg gatgggctgg atcgaccccg agaacggcga caccgagtac     180
gcccccaagt tccagggcag agtgaccatc accgccgaca ccagcaccga caccgcctac     240
atggaactga gcagcctgcg gagcgaggac accgccgtgt actactgcaa cgccaacaaa     300
gagctgcggt acttcgacgt gtggggccag ggcaccatgg tgaccgtgtc tagc           354
```

<210> SEQ ID NO 286
<211> LENGTH: 354
<212> TYPE: DNA
<213> ORGANISM: Artificial Sequence
<220> FEATURE:
<223> OTHER INFORMATION: Synthetic

<400> SEQUENCE: 286

```
caggtgcagc tggtgcagag cggagccgaa gtgaagaagc ctggcgccag cgtcaaggtg      60
tcctgcaagg cctccggcta caccttcacc gactactacc tgcactgggt gcgccaggct     120
ccaggccagg gactggaatg gatgggctgg atcgaccccg agaacggcga caccgagtac     180
gcccccaagt tccagggcag agtgaccatg accaccgaca ccagcaccag caccgcctac     240
atggaactgc ggagcctgcg gagcgacgac accgccgtgt actactgcaa cgccaacaaa     300
gagctgcggt acttcgacgt gtggggccag ggcaccatgg tgaccgtgtc cagc           354
```

<210> SEQ ID NO 287
<211> LENGTH: 354
<212> TYPE: DNA
<213> ORGANISM: Artificial Sequence
<220> FEATURE:
<223> OTHER INFORMATION: Synthetic

<400> SEQUENCE: 287

```
caggtgcagc tggtgcagag cggagccgaa gtgaagaagc ctggcgccag cgtcaaggtg      60
tcctgcaagg tgtccggcta caccctgacc gactactacc tgcactgggt gcgccaggct     120
ccaggcaagg gactggaatg gatgggctgg atcgaccccg agaacggcga caccgagtac     180
gcccccaagt tccagggcag agtgaccatg accgaggaca ccagcaccga caccgcctac     240
atggaactga gcagcctgcg gagcgaggac accgccgtgt actactgcgc caccaacaaa     300
gagctgcggt acttcgacgt gtggggccag ggcaccatgg tgaccgtgtc cagc           354
```

<210> SEQ ID NO 288
<211> LENGTH: 354

```
<212> TYPE: DNA
<213> ORGANISM: Artificial Sequence
<220> FEATURE:
<223> OTHER INFORMATION: Synthetic

<400> SEQUENCE: 288
gaggtgcagc tggtgcagag cggagccgaa gtgaagaaac ctggagccac cgtgaagatc     60
agctgcaagg ccagcggcta caccttcagc gactactatc tgcactgggt gcgccaggcc    120
cctgagaagg gcctggaatg gatgggctgg atcgaccccg agaacggcga taccgagtac    180
gcccccaagt tccagggcag agtgaccatc accgccgaca ccagcaccga caccggctac    240
ctggaactga gcagcctgag aagcgaggac accgccgtgt actactgcgc ccggaacaaa    300
gagctgcggt acttcgacgt gtggggccag ggcaccctgg tgacagtgtc ctca           354

<210> SEQ ID NO 289
<211> LENGTH: 354
<212> TYPE: DNA
<213> ORGANISM: Artificial Sequence
<220> FEATURE:
<223> OTHER INFORMATION: Synthetic

<400> SEQUENCE: 289
gaggtgcagc tggtgcagag cggagccgaa gtgaagaaac ctggagccac cgtgaagatc     60
agctgcaagg ccagcggcta caccttcagc gactactatc tgcactgggt gcgccaggcc    120
cctgagaagg gcctggaatg gatgggctgg atcgaccccg agaacggcga taccgagtac    180
gcccccaagt tccagggcag agtgaccatc accgccgaca ccagcaccga caccggctac    240
ctggaactga gcagcctgag aagcgaggac accgccgtgt actactgcaa cgccaacaaa    300
gagctgcggt acttcgacgt gtggggccag ggcaccctgg tgacagtgtc ctca           354

<210> SEQ ID NO 290
<211> LENGTH: 354
<212> TYPE: DNA
<213> ORGANISM: Artificial Sequence
<220> FEATURE:
<223> OTHER INFORMATION: Synthetic

<400> SEQUENCE: 290
gaggtgcagc tggtgcagag cggagccgaa gtgaagaaac ctggagccac cgtgaagatc     60
agctgcaagg ccagcggcta caccttcagc gactactatc tgcactgggt gcgccaggcc    120
cctgagaagg gcctggaatg gatgggctgg atcgaccccg agaacggcga taccgagtac    180
gcccccaagt tccagggcag agtgaccatc accgccgaca ccagcaccga caccggctac    240
ctggaactga gcagcctgag aagcgaggac accgccgtgt actactgcaa ccggaacaaa    300
gagctgcggt acttcgacgt gtggggccag ggcaccctgg tgacagtgtc ctca           354

<210> SEQ ID NO 291
<211> LENGTH: 354
<212> TYPE: DNA
<213> ORGANISM: Artificial Sequence
<220> FEATURE:
<223> OTHER INFORMATION: Synthetic

<400> SEQUENCE: 291
caggtgcagc tggtgcagag cggagccgaa gtgaagaaac ctggagccac cgtgaagatc     60
agctgcaagg ccagcggcta caccttcagc gactactatc tgcactgggt gcgccaggcc    120
cctgagaagg gcctggaatg gatgggctgg atcgaccccg agaacggcga taccgagtac    180
gcccccaagt tccagggcag agtgaccatc accgccgaca ccagcaccga caccggctac    240
```

```
ctggaactga gcagcctgag aagcgaggac accgccgtgt actactgcgc cgccaacaaa    300
gagctgcggt acttcgacgt gtggggccag ggcaccctgg tgacagtgtc ctca          354
```

<210> SEQ ID NO 292
<211> LENGTH: 354
<212> TYPE: DNA
<213> ORGANISM: Artificial Sequence
<220> FEATURE:
<223> OTHER INFORMATION: Synthetic

<400> SEQUENCE: 292

```
gaggtgcagc tgcagcagag cggagccgaa gtgaagaaac tggagccac cgtgaagatc     60 agctgcaagg ccagcggcta caccttcagc gactactatc tgcactgggt gcgccaggcc   120
cctgagaagg gcctggaatg gatgggctgg atcgaccccg agaacggcga taccgagtac   180
gcccccaagt tccagggcag agtgaccatc accgccgaca ccagcaccga caccggctac   240
ctggaactga gcagcctgag aagcgaggac accgccgtgt actactgcgc cgccaacaaa   300
gagctgcggt acttcgacgt gtggggccag ggcaccctgg tgacagtgtc ctca         354
```

<210> SEQ ID NO 293
<211> LENGTH: 354
<212> TYPE: DNA
<213> ORGANISM: Artificial Sequence
<220> FEATURE:
<223> OTHER INFORMATION: Synthetic

<400> SEQUENCE: 293

```
gaggtgcagc tggtgcagag cggagccgac gtgaagaaac tggagccac cgtgaagatc     60 agctgcaagg ccagcggcta caccttcagc gactactatc tgcactgggt gcgccaggcc   120
cctgagaagg gcctggaatg gatgggctgg atcgaccccg agaacggcga taccgagtac   180
gcccccaagt tccagggcag agtgaccatc accgccgaca ccagcaccga caccggctac   240
ctggaactga gcagcctgag aagcgaggac accgccgtgt actactgcgc cgccaacaaa   300
gagctgcggt acttcgacgt gtggggccag ggcaccctgg tgacagtgtc ctca         354
```

<210> SEQ ID NO 294
<211> LENGTH: 354
<212> TYPE: DNA
<213> ORGANISM: Artificial Sequence
<220> FEATURE:
<223> OTHER INFORMATION: Synthetic

<400> SEQUENCE: 294

```
gaggtgcagc tggtgcagag cggagccgaa ctgaagaaac tggagccac cgtgaagatc     60 agctgcaagg ccagcggcta caccttcagc gactactatc tgcactgggt gcgccaggcc   120
cctgagaagg gcctggaatg gatgggctgg atcgaccccg agaacggcga taccgagtac   180
gcccccaagt tccagggcag agtgaccatc accgccgaca ccagcaccga caccggctac   240
ctggaactga gcagcctgag aagcgaggac accgccgtgt actactgcgc cgccaacaaa   300
gagctgcggt acttcgacgt gtggggccag ggcaccctgg tgacagtgtc ctca         354
```

<210> SEQ ID NO 295
<211> LENGTH: 354
<212> TYPE: DNA
<213> ORGANISM: Artificial Sequence
<220> FEATURE:
<223> OTHER INFORMATION: Synthetic

<400> SEQUENCE: 295

```
gaggtgcagc tggtgcagag cggagccgaa gtggtgaaac ctggagccac cgtgaagatc    60
agctgcaagg ccagcggcta caccttcagc gactactatc tgcactgggt gcgccaggcc   120
cctgagaagg gcctggaatg gatgggctgg atcgaccccg agaacggcga taccgagtac   180
gcccccaagt tccagggcag agtgaccatc accgccgaca ccagcaccga caccggctac   240
ctggaactga gcagcctgag aagcgaggac accgccgtgt actactgcgc cgccaacaaa   300
gagctgcggt acttcgacgt gtggggccag ggcaccctgg tgacagtgtc ctca          354

<210> SEQ ID NO 296
<211> LENGTH: 354
<212> TYPE: DNA
<213> ORGANISM: Artificial Sequence
<220> FEATURE:
<223> OTHER INFORMATION: Synthetic

<400> SEQUENCE: 296
gaggtgcagc tggtgcagag cggagccgaa gtgaagcggc tggagccac cgtgaagatc     60 agctgcaagg ccagcggcta caccttcagc gactactatc tgcactgggt gcgccaggcc   120
cctgagaagg gcctggaatg gatgggctgg atcgaccccg agaacggcga taccgagtac   180
gcccccaagt tccagggcag agtgaccatc accgccgaca ccagcaccga caccggctac   240
ctggaactga gcagcctgag aagcgaggac accgccgtgt actactgcgc cgccaacaaa   300
gagctgcggt acttcgacgt gtggggccag ggcaccctgg tgacagtgtc ctca          354

<210> SEQ ID NO 297
<211> LENGTH: 354
<212> TYPE: DNA
<213> ORGANISM: Artificial Sequence
<220> FEATURE:
<223> OTHER INFORMATION: Synthetic

<400> SEQUENCE: 297
gaggtgcagc tggtgcagag cggagccgaa gtgaagaaaa gcggagccac cgtgaagatc    60
agctgcaagg ccagcggcta caccttcagc gactactatc tgcactgggt gcgccaggcc   120
cctgagaagg gcctggaatg gatgggctgg atcgaccccg agaacggcga taccgagtac   180
gcccccaagt tccagggcag agtgaccatc accgccgaca ccagcaccga caccggctac   240
ctggaactga gcagcctgag aagcgaggac accgccgtgt actactgcgc cgccaacaaa   300
gagctgcggt acttcgacgt gtggggccag ggcaccctgg tgacagtgtc ctca          354

<210> SEQ ID NO 298
<211> LENGTH: 354
<212> TYPE: DNA
<213> ORGANISM: Artificial Sequence
<220> FEATURE:
<223> OTHER INFORMATION: Synthetic

<400> SEQUENCE: 298
gaggtgcagc tggtgcagag cggagccgaa gtgaagaaac tggagccag cgtgaagatc     60 agctgcaagg ccagcggcta caccttcagc gactactatc tgcactgggt gcgccaggcc   120
cctgagaagg gcctggaatg gatgggctgg atcgaccccg agaacggcga taccgagtac   180
gcccccaagt tccagggcag agtgaccatc accgccgaca ccagcaccga caccggctac   240
ctggaactga gcagcctgag aagcgaggac accgccgtgt actactgcgc cgccaacaaa   300
gagctgcggt acttcgacgt gtggggccag ggcaccctgg tgacagtgtc ctca          354
```

```
<210> SEQ ID NO 299
<211> LENGTH: 354
<212> TYPE: DNA
<213> ORGANISM: Artificial Sequence
<220> FEATURE:
<223> OTHER INFORMATION: Synthetic

<400> SEQUENCE: 299
gaggtgcagc tggtgcagag cggagccgaa gtgaagaaac ctggagccac catcaagatc      60
agctgcaagg ccagcggcta caccttcagc gactactatc tgcactgggt gcgccaggcc     120
cctgagaagg gcctggaatg gatgggctgg atcgaccccg agaacggcga taccgagtac     180
gcccccaagt tccagggcag agtgaccatc accgccgaca ccagcaccga caccggctac     240
ctggaactga gcagcctgag aagcgaggac accgccgtgt actactgcgc cgccaacaaa     300
gagctgcggt acttcgacgt gtggggccag ggcaccctgg tgacagtgtc ctca           354

<210> SEQ ID NO 300
<211> LENGTH: 354
<212> TYPE: DNA
<213> ORGANISM: Artificial Sequence
<220> FEATURE:
<223> OTHER INFORMATION: Synthetic

<400> SEQUENCE: 300
gaggtgcagc tggtgcagag cggagccgaa gtgaagaaac ctggagccac cgtgaagctg      60
agctgcaagg ccagcggcta caccttcagc gactactatc tgcactgggt gcgccaggcc     120
cctgagaagg gcctggaatg gatgggctgg atcgaccccg agaacggcga taccgagtac     180
gcccccaagt tccagggcag agtgaccatc accgccgaca ccagcaccga caccggctac     240
ctggaactga gcagcctgag aagcgaggac accgccgtgt actactgcgc cgccaacaaa     300
gagctgcggt acttcgacgt gtggggccag ggcaccctgg tgacagtgtc ctca           354

<210> SEQ ID NO 301
<211> LENGTH: 354
<212> TYPE: DNA
<213> ORGANISM: Artificial Sequence
<220> FEATURE:
<223> OTHER INFORMATION: Synthetic

<400> SEQUENCE: 301
gaggtgcagc tggtgcagag cggagccgaa gtgaagaaac ctggagccac cgtgaagatc      60
agctgcacag ccagcggcta caccttcagc gactactatc tgcactgggt gcgccaggcc     120
cctgagaagg gcctggaatg gatgggctgg atcgaccccg agaacggcga taccgagtac     180
gcccccaagt tccagggcag agtgaccatc accgccgaca ccagcaccga caccggctac     240
ctggaactga gcagcctgag aagcgaggac accgccgtgt actactgcgc cgccaacaaa     300
gagctgcggt acttcgacgt gtggggccag ggcaccctgg tgacagtgtc ctca           354

<210> SEQ ID NO 302
<211> LENGTH: 354
<212> TYPE: DNA
<213> ORGANISM: Artificial Sequence
<220> FEATURE:
<223> OTHER INFORMATION: Synthetic

<400> SEQUENCE: 302
gaggtgcagc tggtgcagag cggagccgaa gtgaagaaac ctggagccac cgtgaagatc      60
agctgcaagg ccagcggctt caccttcagc gactactatc tgcactgggt gcgccaggcc     120
cctgagaagg gcctggaatg gatgggctgg atcgaccccg agaacggcga taccgagtac     180
```

```
gcccccaagt tccagggcag agtgaccatc accgccgaca ccagcaccga caccggctac    240
ctggaactga gcagcctgag aagcgaggac accgccgtgt actactgcgc cgccaacaaa    300
gagctgcggt acttcgacgt gtggggccag ggcaccctgg tgacagtgtc ctca          354
```

<210> SEQ ID NO 303
<211> LENGTH: 354
<212> TYPE: DNA
<213> ORGANISM: Artificial Sequence
<220> FEATURE:
<223> OTHER INFORMATION: Synthetic

<400> SEQUENCE: 303

```
gaggtgcagc tggtgcagag cggagccgaa gtgaagaaac tggagccac cgtgaagatc      60 agctgcaagg ccagcggcta caacttcagc gactactatc tgcactgggt gcgccaggcc    120
cctgagaagg gcctggaatg gatgggctgg atcgaccccg agaacggcga taccgagtac    180
gcccccaagt tccagggcag agtgaccatc accgccgaca ccagcaccga caccggctac    240
ctggaactga gcagcctgag aagcgaggac accgccgtgt actactgcgc cgccaacaaa    300
gagctgcggt acttcgacgt gtggggccag ggcaccctgg tgacagtgtc ctca          354
```

<210> SEQ ID NO 304
<211> LENGTH: 354
<212> TYPE: DNA
<213> ORGANISM: Artificial Sequence
<220> FEATURE:
<223> OTHER INFORMATION: Synthetic

<400> SEQUENCE: 304

```
gaggtgcagc tggtgcagag cggagccgaa gtgaagaaac tggagccac cgtgaagatc      60 agctgcaagg ccagcggcta caccatcagc gactactatc tgcactgggt gcgccaggcc    120
cctgagaagg gcctggaatg gatgggctgg atcgaccccg agaacggcga taccgagtac    180
gcccccaagt tccagggcag agtgaccatc accgccgaca ccagcaccga caccggctac    240
ctggaactga gcagcctgag aagcgaggac accgccgtgt actactgcgc cgccaacaaa    300
gagctgcggt acttcgacgt gtggggccag ggcaccctgg tgacagtgtc ctca          354
```

<210> SEQ ID NO 305
<211> LENGTH: 354
<212> TYPE: DNA
<213> ORGANISM: Artificial Sequence
<220> FEATURE:
<223> OTHER INFORMATION: Synthetic

<400> SEQUENCE: 305

```
gaggtgcagc tggtgcagag cggagccgaa gtgaagaaac tggagccac cgtgaagatc      60 agctgcaagg ccagcggcta caccttcaag gactactatc tgcactgggt gcgccaggcc    120
cctgagaagg gcctggaatg gatgggctgg atcgaccccg agaacggcga taccgagtac    180
gcccccaagt tccagggcag agtgaccatc accgccgaca ccagcaccga caccggctac    240
ctggaactga gcagcctgag aagcgaggac accgccgtgt actactgcgc cgccaacaaa    300
gagctgcggt acttcgacgt gtggggccag ggcaccctgg tgacagtgtc ctca          354
```

<210> SEQ ID NO 306
<211> LENGTH: 354
<212> TYPE: DNA
<213> ORGANISM: Artificial Sequence
<220> FEATURE:
<223> OTHER INFORMATION: Synthetic

<400> SEQUENCE: 306
gaggtgcagc tggtgcagag cggagccgaa gtgaagaaac ctggagccac cgtgaagatc    60
agctgcaagg ccagcggcta caccttcagc gactactatc tgcactgggt gaagcaggcc   120
cctgagaagg gcctggaatg gatgggctgg atcgaccccg agaacggcga taccgagtac   180
gcccccaagt tccagggcag agtgaccatc accgccgaca ccagcaccga caccggctac   240
ctggaactga gcagcctgag aagcgaggac accgccgtgt actactgcgc cgccaacaaa   300
gagctgcggt acttcgacgt gtggggccag ggcaccctgg tgacagtgtc ctca         354

<210> SEQ ID NO 307
<211> LENGTH: 354
<212> TYPE: DNA
<213> ORGANISM: Artificial Sequence
<220> FEATURE:
<223> OTHER INFORMATION: Synthetic

<400> SEQUENCE: 307
gaggtgcagc tggtgcagag cggagccgaa gtgaagaaac ctggagccac cgtgaagatc    60
agctgcaagg ccagcggcta caccttcagc gactactatc tgcactgggt gcgccaggcc   120
ccaggcaagg gcctggaatg gatgggctgg atcgaccccg agaacggcga taccgagtac   180
gcccccaagt tccagggcag agtgaccatc accgccgaca ccagcaccga caccggctac   240
ctggaactga gcagcctgag aagcgaggac accgccgtgt actactgcgc cgccaacaaa   300
gagctgcggt acttcgacgt gtggggccag ggcaccctgg tgacagtgtc ctca         354

<210> SEQ ID NO 308
<211> LENGTH: 354
<212> TYPE: DNA
<213> ORGANISM: Artificial Sequence
<220> FEATURE:
<223> OTHER INFORMATION: Synthetic

<400> SEQUENCE: 308
gaggtgcagc tggtgcagag cggagccgaa gtgaagaaac ctggagccac cgtgaagatc    60
agctgcaagg ccagcggcta caccttcagc gactactatc tgcactgggt gcgccaggcc   120
cctgagaagg gcctggaatg gatgggctgg atcgaccccg agaacggcga taccgagtac   180
gcccccaagt tccagggcag agccaccatc accgccgaca ccagcaccga caccggctac   240
ctggaactga gcagcctgag aagcgaggac accgccgtgt actactgcgc cgccaacaaa   300
gagctgcggt acttcgacgt gtggggccag ggcaccctgg tgacagtgtc ctca         354

<210> SEQ ID NO 309
<211> LENGTH: 354
<212> TYPE: DNA
<213> ORGANISM: Artificial Sequence
<220> FEATURE:
<223> OTHER INFORMATION: Synthetic

<400> SEQUENCE: 309
gaggtgcagc tggtgcagag cggagccgaa gtgaagaaac ctggagccac cgtgaagatc    60
agctgcaagg ccagcggcta caccttcagc gactactatc tgcactgggt gcgccaggcc   120
cctgagaagg gcctggaatg gatgggctgg atcgaccccg agaacggcga taccgagtac   180
gcccccaagt tccagggcag agtgaccatg accgccgaca ccagcaccga caccggctac   240
ctggaactga gcagcctgag aagcgaggac accgccgtgt actactgcgc cgccaacaaa   300
gagctgcggt acttcgacgt gtggggccag ggcaccctgg tgacagtgtc ctca         354

<210> SEQ ID NO 310
<211> LENGTH: 354
<212> TYPE: DNA
<213> ORGANISM: Artificial Sequence
<220> FEATURE:
<223> OTHER INFORMATION: Synthetic

<400> SEQUENCE: 310
gaggtgcagc tggtgcagag cggagccgaa gtgaagaaac ctggagccac cgtgaagatc      60
agctgcaagg ccagcggcta caccttcagc gactactatc tgcactgggt gcgccaggcc     120
cctgagaagg gcctggaatg gatgggctgg atcgaccccg agaacggcga taccgagtac     180
gcccccaagt tccagggcag agtgaccatc accaccgaca ccagcaccga caccggctac     240
ctggaactga gcagcctgag aagcgaggac accgccgtgt actactgcgc cgccaacaaa     300
gagctgcggt acttcgacgt gtggggccag ggcaccctgg tgacagtgtc ctca           354

<210> SEQ ID NO 311
<211> LENGTH: 354
<212> TYPE: DNA
<213> ORGANISM: Artificial Sequence
<220> FEATURE:
<223> OTHER INFORMATION: Synthetic

<400> SEQUENCE: 311
gaggtgcagc tggtgcagag cggagccgaa gtgaagaaac ctggagccac cgtgaagatc      60
agctgcaagg ccagcggcta caccttcagc gactactatc tgcactgggt gcgccaggcc     120
cctgagaagg gcctggaatg gatgggctgg atcgaccccg agaacggcga taccgagtac     180
gcccccaagt tccagggcag agtgaccatc accgccgaca ccagcagcga caccggctac     240
ctggaactga gcagcctgag aagcgaggac accgccgtgt actactgcgc cgccaacaaa     300
gagctgcggt acttcgacgt gtggggccag ggcaccctgg tgacagtgtc ctca           354

<210> SEQ ID NO 312
<211> LENGTH: 354
<212> TYPE: DNA
<213> ORGANISM: Artificial Sequence
<220> FEATURE:
<223> OTHER INFORMATION: Synthetic

<400> SEQUENCE: 312
gaggtgcagc tggtgcagag cggagccgaa gtgaagaaac ctggagccac cgtgaagatc      60
agctgcaagg ccagcggcta caccttcagc gactactatc tgcactgggt gcgccaggcc     120
cctgagaagg gcctggaatg gatgggctgg atcgaccccg agaacggcga taccgagtac     180
gcccccaagt tccagggcag agtgaccatc accgccgaca ccagcaccaa caccggctac     240
ctggaactga gcagcctgag aagcgaggac accgccgtgt actactgcgc cgccaacaaa     300
gagctgcggt acttcgacgt gtggggccag ggcaccctgg tgacagtgtc ctca           354

<210> SEQ ID NO 313
<211> LENGTH: 354
<212> TYPE: DNA
<213> ORGANISM: Artificial Sequence
<220> FEATURE:
<223> OTHER INFORMATION: Synthetic

<400> SEQUENCE: 313
gaggtgcagc tggtgcagag cggagccgaa gtgaagaaac ctggagccac cgtgaagatc      60
agctgcaagg ccagcggcta caccttcagc gactactatc tgcactgggt gcgccaggcc     120

```
cctgagaagg gcctggaatg gatgggctgg atcgaccccg agaacggcga taccgagtac      180
gcccccaagt tccagggcag agtgaccatc accgccgaca ccagcaccga caccgcctac      240
ctggaactga gcagcctgag aagcgaggac accgccgtgt actactgcgc cgccaacaaa      300
gagctgcggt acttcgacgt gtggggccag ggcaccctgg tgacagtgtc ctca            354
```

<210> SEQ ID NO 314
<211> LENGTH: 354
<212> TYPE: DNA
<213> ORGANISM: Artificial Sequence
<220> FEATURE:
<223> OTHER INFORMATION: Synthetic

<400> SEQUENCE: 314

```
gaggtgcagc tggtgcagag cggagccgaa gtgaagaaac tggagccac cgtgaagatc       60 agctgcaagg ccagcggcta caccttcagc gactactatc tgcactgggt gcgccaggcc     120
cctgagaagg gcctggaatg gatgggctgg atcgaccccg agaacggcga taccgagtac     180
gcccccaagt tccagggcag agtgaccatc accgccgaca ccagcaccga caccggctac     240
atggaactga gcagcctgag aagcgaggac accgccgtgt actactgcgc cgccaacaaa     300
gagctgcggt acttcgacgt gtggggccag ggcaccctgg tgacagtgtc ctca           354
```

<210> SEQ ID NO 315
<211> LENGTH: 354
<212> TYPE: DNA
<213> ORGANISM: Artificial Sequence
<220> FEATURE:
<223> OTHER INFORMATION: Synthetic

<400> SEQUENCE: 315

```
gaggtgcagc tggtgcagag cggagccgaa gtgaagaaac tggagccac cgtgaagatc       60 agctgcaagg ccagcggcta caccttcagc gactactatc tgcactgggt gcgccaggcc     120
cctgagaagg gcctggaatg gatgggctgg atcgaccccg agaacggcga taccgagtac     180
gcccccaagt tccagggcag agtgaccatc accgccgaca ccagcaccga caccggctac     240
ctgcagctga gcagcctgag aagcgaggac accgccgtgt actactgcgc cgccaacaaa     300
gagctgcggt acttcgacgt gtggggccag ggcaccctgg tgacagtgtc ctca           354
```

<210> SEQ ID NO 316
<211> LENGTH: 354
<212> TYPE: DNA
<213> ORGANISM: Artificial Sequence
<220> FEATURE:
<223> OTHER INFORMATION: Synthetic

<400> SEQUENCE: 316

```
gaggtgcagc tggtgcagag cggagccgaa gtgaagaaac tggagccac cgtgaagatc       60 agctgcaagg ccagcggcta caccttcagc gactactatc tgcactgggt gcgccaggcc     120
cctgagaagg gcctggaatg gatgggctgg atcgaccccg agaacggcga taccgagtac     180
gcccccaagt tccagggcag agtgaccatc accgccgaca ccagcaccga caccggctac     240
ctggaactgc ggagcctgag aagcgaggac accgccgtgt actactgcgc cgccaacaaa     300
gagctgcggt acttcgacgt gtggggccag ggcaccctgg tgacagtgtc ctca           354
```

<210> SEQ ID NO 317
<211> LENGTH: 354
<212> TYPE: DNA
<213> ORGANISM: Artificial Sequence

```
<220> FEATURE:
<223> OTHER INFORMATION: Synthetic

<400> SEQUENCE: 317
gaggtgcagc tggtgcagag cggagccgaa gtgaagaaac ctggagccac cgtgaagatc      60
agctgcaagg ccagcggcta caccttcagc gactactatc tgcactgggt gcgccaggcc     120
cctgagaagg gcctggaatg gatgggctgg atcgaccccg agaacggcga taccgagtac     180 gccccccaagt tccagggcag agtgaccatc accgccgaca ccagcaccga caccggctac    240
ctggaactga gcagcctgac cagcgaggac accgccgtgt actactgcgc cgccaacaaa    300
gagctgcggt acttcgacgt gtggggccag ggcacccctgg tgacagtgtc ctca          354

<210> SEQ ID NO 318
<211> LENGTH: 354
<212> TYPE: DNA
<213> ORGANISM: Artificial Sequence
<220> FEATURE:
<223> OTHER INFORMATION: Synthetic

<400> SEQUENCE: 318
gaggtgcagc tggtgcagag cggagccgaa gtgaagaaac ctggagccac cgtgaagatc      60
agctgcaagg ccagcggcta caccttcagc gactactatc tgcactgggt gcgccaggcc     120
cctgagaagg gcctggaatg gatgggctgg atcgaccccg agaacggcga taccgagtac     180 gccccccaagt tccagggcag agtgaccatc accgccgaca ccagcaccga caccggctac    240
ctggaactga gcagcctgag aagcgacgac accgccgtgt actactgcgc cgccaacaaa    300
gagctgcggt acttcgacgt gtggggccag ggcacccctgg tgacagtgtc ctca          354

<210> SEQ ID NO 319
<211> LENGTH: 354
<212> TYPE: DNA
<213> ORGANISM: Artificial Sequence
<220> FEATURE:
<223> OTHER INFORMATION: Synthetic

<400> SEQUENCE: 319
gaggtgcagc tggtgcagag cggagccgaa gtgaagaaac ctggagccac cgtgaagatc      60
agctgcaagg ccagcggcta caccttcagc gactactatc tgcactgggt gcgccaggcc     120
cctgagaagg gcctggaatg gatgggctgg atcgaccccg agaacggcga taccgagtac     180 gccccccaagt tccagggcag agtgaccatc accgccgaca ccagcaccga caccggctac    240
ctggaactga gcagcctgag aagcgaggac accgccgtgt actactgcgc cgccaacaaa    300
gagctgcggt acttcgacgt gtggggagcc ggcacccctgg tgacagtgtc ctca          354

<210> SEQ ID NO 320
<211> LENGTH: 354
<212> TYPE: DNA
<213> ORGANISM: Artificial Sequence
<220> FEATURE:
<223> OTHER INFORMATION: Synthetic

<400> SEQUENCE: 320
gaagtgcagc tggtgcagag cggagccgaa gtgaagaaac ctggcgccac cgtgaagatc      60
agctgcaagg ccagcggcta cgccttcagc gactactacc tgcactgggt gcgccaggcc     120
cctgagaagg gcctcgaatg gatgggctgg atcgaccccg agaacggcga taccgagtac    180 gccccccaagt tccagggcag agtgaccatc accgccgaca ccagcaccga caccggctac    240
ctggaactga gcagcctgag aagcgaggac accgccgtgt actactgcgc cgccaacaaa    300
```

```
gagctgcggt acttcgacgt gtggggccag ggcacactgg tgaccgtgtc ctca        354

<210> SEQ ID NO 321
<211> LENGTH: 354
<212> TYPE: DNA
<213> ORGANISM: Artificial Sequence
<220> FEATURE:
<223> OTHER INFORMATION: Synthetic

<400> SEQUENCE: 321
gaagtgcagc tggtgcagag cggagccgaa gtgaagaaac ctggcgccac cgtgaagatc    60
agctgcaagg ccagcggcta caccctgagc gactactacc tgcactgggt gcgccaggcc   120
cctgagaagg gcctcgaatg gatgggctgg atcgaccccg agaacggcga taccgagtac   180
gcccccaagt tccagggcag agtgaccatc accgccgaca ccagcaccga caccggctac   240
ctggaactga gcagcctgag aagcgaggac accgccgtgt actactgcgc cgccaacaaa   300
gagctgcggt acttcgacgt gtggggccag ggcacactgg tgaccgtgtc ctca        354

<210> SEQ ID NO 322
<211> LENGTH: 354
<212> TYPE: DNA
<213> ORGANISM: Artificial Sequence
<220> FEATURE:
<223> OTHER INFORMATION: Synthetic

<400> SEQUENCE: 322
gaagtgcagc tggtgcagag cggagccgaa gtgaagaaac ctggcgccac cgtgaagatc    60
agctgcaagg ccagcggcta caccttcagc gactactacc tgcactgggt gcgccaggcc   120
cctgagaagg gcctcgaatg gatgggctgg atcgaccccg agaacggcga taccgagagc   180
gcccccaagt tccagggcag agtgaccatc accgccgaca ccagcaccga caccggctac   240
ctggaactga gcagcctgag aagcgaggac accgccgtgt actactgcgc cgccaacaaa   300
gagctgcggt acttcgacgt gtggggccag ggcacactgg tgaccgtgtc ctca        354

<210> SEQ ID NO 323
<211> LENGTH: 354
<212> TYPE: DNA
<213> ORGANISM: Artificial Sequence
<220> FEATURE:
<223> OTHER INFORMATION: Synthetic

<400> SEQUENCE: 323
gaagtgcagc tggtgcagag cggagccgaa gtgaagaaac ctggcgccac cgtgaagatc    60
agctgcaagg ccagcggcta cgccctgagc gactactacc tgcactgggt gcgccaggcc   120
cctgagaagg gcctcgaatg gatgggctgg atcgaccccg agaacggcga taccgagtac   180
gcccccaagt tccagggcag agtgaccatc accgccgaca ccagcaccga caccggctac   240
ctggaactga gcagcctgag aagcgaggac accgccgtgt actactgcgc cgccaacaaa   300
gagctgcggt acttcgacgt gtggggccag ggcacactgg tgaccgtgtc ctca        354

<210> SEQ ID NO 324
<211> LENGTH: 354
<212> TYPE: DNA
<213> ORGANISM: Artificial Sequence
<220> FEATURE:
<223> OTHER INFORMATION: Synthetic

<400> SEQUENCE: 324
gaagtgcagc tggtgcagag cggagcccag gtgaagaaac ctggcgccac cgtgaagatc    60
```

```
agctgcaagg ccagcggcta cccctgagc gactactacc tgcactgggt gcgccaggcc    120
cctgagaagg gcctcgaatg gatgggctgg atcgaccccg agaacggcga taccgagtac    180
gcccccaagt tccagggcag agtgaccatc accgccgaca ccagcaccga caccggctac    240
ctggaactga gcagcctgag aagcgaggac accgccgtgt actactgcgc cgccaacaaa    300
gagctgcggt acttcgacgt gtggggccag ggcacactgg tgaccgtgtc ctca           354
```

<210> SEQ ID NO 325
<211> LENGTH: 354
<212> TYPE: DNA
<213> ORGANISM: Artificial Sequence
<220> FEATURE:
<223> OTHER INFORMATION: Synthetic

<400> SEQUENCE: 325

```
gaagtgcagc tggtgcagag cggagccgaa gtgaagaaac ctggcgccac cgtgaagatc     60
agctgcaagg ccagcggcta cccctgagc gactactacc tgcactgggt gcgccaggcc    120
cctgagaagg gcctcgaatg gatgggctgg atcgaccccg agaacggcga taccgagagc    180
gcccccaagt tccagggcag agtgaccatc accgccgaca ccagcaccga caccggctac    240
ctggaactga gcagcctgag aagcgaggac accgccgtgt actactgcgc cgccaacaaa    300
gagctgcggt acttcgacgt gtggggccag ggcacactgg tgaccgtgtc ctca           354
```

<210> SEQ ID NO 326
<211> LENGTH: 354
<212> TYPE: DNA
<213> ORGANISM: Artificial Sequence
<220> FEATURE:
<223> OTHER INFORMATION: Synthetic

<400> SEQUENCE: 326

```
gaagtgcagc tggtgcagag cggagccgaa gtgaagaaac ctggcgccac cgtgaagatc     60
agctgcaagg ccagcggcta caccttcagc gactactacc tgcactgggt gcgccaggcc    120
cctgagaagg gcctcgaatg gatgggctgg atcgaccccg agaacggcga taccgagcac    180
gcccccaagt tccagggcag agtgaccatc accgccgaca ccagcaccga caccggctac    240
ctggaactga gcagcctgag aagcgaggac accgccgtgt actactgcgc cgccaacaaa    300
gagctgcggt acttcgacgt gtggggccag ggcacactgg tgaccgtgtc ctca           354
```

<210> SEQ ID NO 327
<211> LENGTH: 354
<212> TYPE: DNA
<213> ORGANISM: Artificial Sequence
<220> FEATURE:
<223> OTHER INFORMATION: Synthetic

<400> SEQUENCE: 327

```
gaagtgcagc tggtgcagag cggagccgaa gtgaagaaac ctggcgccac cgtgaagatc     60
agctgcaagg ccagcggcta cccctgagc gactactacc tgcactgggt gcgccaggcc    120
cctgagaagg gcctcgaatg gatgggctgg atcgaccccg agaacggcga taccgagcac    180
gcccccaagt tccagggcag agtgaccatc accgccgaca ccagcaccga caccggctac    240
ctggaactga gcagcctgag aagcgaggac accgccgtgt actactgcgc cgccaacaaa    300
gagctgcggt acttcgacgt gtggggccag ggcacactgg tgaccgtgtc ctca           354
```

<210> SEQ ID NO 328
<211> LENGTH: 354

```
<212> TYPE: DNA
<213> ORGANISM: Artificial Sequence
<220> FEATURE:
<223> OTHER INFORMATION: Synthetic

<400> SEQUENCE: 328
caggtccagc tcgtgcagag cggagccgaa gtgaagaagc ctggcgcttc cgtcaaggtg      60
tcctgcaagg ccagcggcta caccttcacc gactactacc tgcactgggt ccgccaggct     120
ccaggccagg gactggaatg gatgggctgg atcgaccccg agaacggcga caccgagtac     180
gcccccaagt tccagggcag agtgaccatg accaccgaca ccagcaccag caccgcctac     240
atggaactgc ggagcctgag atctgacgat accgccgtgt actactgcgc cgccaacaaa     300
gagctgcggt acttcgacgt gtggggacag ggcacaatgg tcacagtgtc ctca           354

<210> SEQ ID NO 329
<211> LENGTH: 354
<212> TYPE: DNA
<213> ORGANISM: Artificial Sequence
<220> FEATURE:
<223> OTHER INFORMATION: Synthetic

<400> SEQUENCE: 329
caggtccagc tcgtgcagag cggagccgaa gtgaagaagc ctggcgcttc cgtcaaggtg      60
tcctgcaagg ccagcggcta caccctgacc gactactacc tgcactgggt ccgccaggct     120
ccaggccagg gactggaatg gatgggctgg atcgaccccg agaacggcga caccgagtac     180
gcccccaagt tccagggcag agtgaccatg accaccgaca ccagcaccag caccgcctac     240
atggaactgc ggagcctgag atctgacgat accgccgtgt actactgcgc cgccaacaaa     300
gagctgcggt acttcgacgt gtggggacag ggcacaatgg tcacagtgtc ctca           354

<210> SEQ ID NO 330
<211> LENGTH: 354
<212> TYPE: DNA
<213> ORGANISM: Artificial Sequence
<220> FEATURE:
<223> OTHER INFORMATION: Synthetic

<400> SEQUENCE: 330
caggtccagc tcgtgcagag cggagccgaa gtgaagaagc ctggcgcttc cgtcaaggtg      60
tcctgcaagg ccagcggcta caccttcacc gactactacc tgcactgggt ccgccaggct     120
ccaggccagg gactggaatg gatgggctgg atcgaccccg agaacggcga caccgagagc     180
gcccccaagt tccagggcag agtgaccatg accaccgaca ccagcaccag caccgcctac     240
atggaactgc ggagcctgag atctgacgat accgccgtgt actactgcgc cgccaacaaa     300
gagctgcggt acttcgacgt gtggggacag ggcacaatgg tcacagtgtc ctca           354

<210> SEQ ID NO 331
<211> LENGTH: 354
<212> TYPE: DNA
<213> ORGANISM: Artificial Sequence
<220> FEATURE:
<223> OTHER INFORMATION: Synthetic

<400> SEQUENCE: 331
caggtccagc tcgtgcagag cggagccgaa gtgaagaagc ctggcgcttc cgtcaaggtg      60
tcctgcaagg ccagcggcta caccctgacc gactactacc tgcactgggt ccgccaggct     120
ccaggccagg gactggaatg gatgggctgg atcgaccccg agaacggcga caccgagagc     180
gcccccaagt tccagggcag agtgaccatg accaccgaca ccagcaccag caccgcctac     240
```

```
atggaactgc ggagcctgag atctgacgat accgccgtgt actactgcgc cgccaacaaa    300
gagctgcggt acttcgacgt gtggggacag ggcacaatgg tcacagtgtc ctca          354
```

<210> SEQ ID NO 332
<211> LENGTH: 354
<212> TYPE: DNA
<213> ORGANISM: Artificial Sequence
<220> FEATURE:
<223> OTHER INFORMATION: Synthetic

<400> SEQUENCE: 332

```
caggtccagc tcgtgcagag cggagccgaa gtgaagaagc ctggcgcttc cgtcaaggtg     60
tcctgcaagg ccagcggcta caccttcacc gactactacc tgcactgggt ccgccaggct    120
ccaggccagg gactggaatg gatgggctgg atcgaccccg agaacggcga caccgagcac    180 gccccccaagt tccagggcag agtgaccatg accaccgaca ccagcaccag caccgcctac   240
atggaactgc ggagcctgag atctgacgat accgccgtgt actactgcgc cgccaacaaa   300
gagctgcggt acttcgacgt gtggggacag ggcacaatgg tcacagtgtc ctca         354
```

<210> SEQ ID NO 333
<211> LENGTH: 354
<212> TYPE: DNA
<213> ORGANISM: Artificial Sequence
<220> FEATURE:
<223> OTHER INFORMATION: Synthetic

<400> SEQUENCE: 333

```
caggtccagc tcgtgcagag cggagccgaa gtggagaagc ctggcgcttc cgtcaaggtg     60
tcctgcaagg ccagcggcta caccttcacc gactactacc tgcactgggt ccgccaggct    120
ccaggccagg gactggaatg gatgggctgg atcgaccccg agaacggcga caccgagtac    180 gccccccaagt tccagggcgg cgtgaccatg accaccgaca ccagcaccag caccgcctac   240
atggaactgc ggagcctgag atctgacgat accgccgtgt actactgcgc cgccaacaaa   300
gagctgcggt acttcgacgt gtggggacag ggcacaatgg tcacagtgtc ctca         354
```

<210> SEQ ID NO 334
<211> LENGTH: 355
<212> TYPE: DNA
<213> ORGANISM: Artificial Sequence
<220> FEATURE:
<223> OTHER INFORMATION: Synthetic

<400> SEQUENCE: 334

```
caggtccagc tcgtgcagag cggagccgaa gtgaagaagc ctggcgcttc cgtcaaggtg     60
tcctgcaagg ccagcggcta caccttcacc gactactacc tgcactgggt ccgccaggct    120
ccaggccggg gactggaatg gatgggctgg atcgaccccg agaacggcga caccgagtac    180 gccccccaagt tccagggcag agtgaccatg accaccgaca ccagcaccag caccgcctac   240
atggaactgc ggagcctgag atctgacgat accgccgtgt actactgcgc cgccaacaaa   300
gagctgcggt acttcgacgt gtggggacag ggcacaatgg tcacagtgtc ctcac        355
```

<210> SEQ ID NO 335
<211> LENGTH: 355
<212> TYPE: DNA
<213> ORGANISM: Artificial Sequence
<220> FEATURE:
<223> OTHER INFORMATION: Synthetic

<400> SEQUENCE: 335

```
caggtccagc tcgtgcagag cggagccgaa gtgaagaagc ctggcgcttc cgtcaaggtg      60
tcctgcaagg ccagcggcta cgccttcacc gactactacc tgcactgggt ccgccaggct     120
ccaggccagg gactggaatg gatgggctgg atcgaccccg agaacggcga caccgagtac     180
gcccccaagt tccagggcag agtgaccatg accaccgaca ccagcaccag caccgcctac     240
atggaactgc ggagcctgag atctgacgat accgccgtgt actactgcgc cgccaacaaa     300
gagctgcggt acttcgacgt gtggggacag ggcacaatgg tcacagtgtc ctcac          355

<210> SEQ ID NO 336
<211> LENGTH: 324
<212> TYPE: DNA
<213> ORGANISM: Artificial Sequence
<220> FEATURE:
<223> OTHER INFORMATION: Synthetic

<400> SEQUENCE: 336
gacatcgtgc tgacccagag ccccgccacc ctgagcgtga cccctggcga cagcgtgagc      60
ctgagctgcc gggcctccca gagcatcagc atcaacctgc actggtatca gcagaagagc     120
cacgagagcc ccaggctgct gatcaagttc gccagccagt ccatcagcgg catccccagc     180
cggttcagcg gctacggcag cggcaccgac ttcaccctga gcatcaacag cgtggagaca     240
gaggacttcg gccggtactt ctgccagcag agcaacagct ggcccctgac cttcggagcc     300
ggcaccaagc tggaactgaa gcgt                                            324

<210> SEQ ID NO 337
<211> LENGTH: 318
<212> TYPE: DNA
<213> ORGANISM: Artificial Sequence
<220> FEATURE:
<223> OTHER INFORMATION: Synthetic

<400> SEQUENCE: 337
acggtggccg ctcccagcgt gttcatcttc ccccccagcg acgagcagct gaagagcggc      60
accgccagcg tggtctgcct gctgaacaac ttctaccccc gggaggccaa ggtgcagtgg     120
aaggtggaca acgccctgca gtctggcaac agccaggaaa gcgtcaccga gcaggacagc     180
aaggatagca cctacagcct gagcagcacc ctgaccctga gcaaggccga ctacgagaag     240
cacaaggtgt acgcctgcga ggtcacccac cagggcctgt ctagccccgt caccaagagc     300
ttcaaccggg gcgagtgc                                                   318

<210> SEQ ID NO 338
<211> LENGTH: 324
<212> TYPE: DNA
<213> ORGANISM: Artificial Sequence
<220> FEATURE:
<223> OTHER INFORMATION: Synthetic

<400> SEQUENCE: 338
gacatcgtgc tgacccagag ccccgccacc ctgagcgtga cccctggcga cagcgtgagc      60
ctgagctgcc gggcctccca gagcatcagc atcaacctgc actggtatca gcagaagagc     120
cacgagagcc ccaggctgct gatcaagttc gccagccagt ccatcagcgg catccccagc     180
cggttcagcg gctacggcag cggcaccgac ttcaccctga gcatcaacag cgtggagaca     240
gaggacttcg gccggtactt ctgccagcag agcaacagct cccccctgac cttcggagcc     300
ggcaccaagc tggaactgaa gcgt                                            324
```

<210> SEQ ID NO 339
<211> LENGTH: 324
<212> TYPE: DNA
<213> ORGANISM: Artificial Sequence
<220> FEATURE:
<223> OTHER INFORMATION: Synthetic

<400> SEQUENCE: 339

```
gagatcgtgc tgacccagag ccccgacttc cagagcgtga cccccaaaga aaaagtgacc        60
atcacctgcc gggcttccca gagcatcagc atcaacctgc actggtatca gcagaagccc       120
gaccagtccc ccaagctgct gatcaagttc gccagccagt ccatcagcgg cgtgcccagc       180
cggtttagcg gcagcggctc cggcaccgac ttcaccctga ccatcaacag cctggaagcc       240
gaggacgccg ccacctacta ctgccagcag agcaacagct ggcccctgac ctttggcggc       300
ggaacaaagg tggaaatcaa gcgt                                              324
```

<210> SEQ ID NO 340
<211> LENGTH: 324
<212> TYPE: DNA
<213> ORGANISM: Artificial Sequence
<220> FEATURE:
<223> OTHER INFORMATION: Synthetic

<400> SEQUENCE: 340

```
gagatcgtga tgacccagag ccccgccacc ctgtccgtga gccctggcga gcgggccacc        60
ctgagctgcc gggcctccca gagcatcagc atcaacctgc actggtatca gcagaagccc       120
ggccaggccc ccagactgct gatctacttc gccagccagt ccatcagcgg catccccgcc       180
aggttcagcg gcagcggctc cggcaccgag ttcaccctga ccatcagcag cctgcagagc       240
gaggacttcg ccgtgtacta ctgccagcag agcaacagct ggcccctgac ctttggcggc       300
ggaacaaagg tggagatcaa gcgt                                              324
```

<210> SEQ ID NO 341
<211> LENGTH: 324
<212> TYPE: DNA
<213> ORGANISM: Artificial Sequence
<220> FEATURE:
<223> OTHER INFORMATION: Synthetic

<400> SEQUENCE: 341

```
gagatcgtgc tgacccagag ccccgccacc ctgtccctca gccctggcga gcgggccacc        60
ctgagctgcc gggcctccca gagcatcagc atcaacctgc actggtatca gcagaagccc       120
ggccaggccc ccagactgct gatctacttc gccagccagt ccatcagcgg catccccgcc       180
aggttcagcg gcagcggctc cggcaccgac ttcaccctga ccatcagcag cctggagccc       240
gaggacttcg ccgtgtacta ctgccagcag agcaacagct ggcccctgac ctttggcggc       300
ggaacaaagg tggagatcaa gcgt                                              324
```

<210> SEQ ID NO 342
<211> LENGTH: 324
<212> TYPE: DNA
<213> ORGANISM: Artificial Sequence
<220> FEATURE:
<223> OTHER INFORMATION: Synthetic

<400> SEQUENCE: 342

```
gacatccaga tgacccagag ccccagcagc gtgtccgcca gcgtgggcga cagagtgacc        60
atcacctgcc gggccagcca gagcatcagc atcaacctgc actggtatca gcagaagccc       120
ggcaaggccc ccaagctgct gatctacttc gccagccagt ccatcagcgg cgtgcccagc       180
```

```
cggtttagcg gcagcggctc cggcaccgac ttcagcctga ccatcaacag cctgcagccc    240
gaggacttcg ccacctacta ctgccagcag agcaacagct tccccctgac ctttggcggc    300
ggaacaaagg tggagatcaa gcgt                                          324
```

<210> SEQ ID NO 343
<211> LENGTH: 324
<212> TYPE: DNA
<213> ORGANISM: Artificial Sequence
<220> FEATURE:
<223> OTHER INFORMATION: Synthetic

<400> SEQUENCE: 343

```
gacatccaga tgacccagag ccccagcagc gtgtccgcca gcgtgggcga cagagtgacc     60
atcacctgcc gggccagcca gagcatcagc atcaacctgc actggtatca gcagaagccc    120
ggcaaggccc ccaagctgct gatcaagttc gccagccagt ccatcagcgg cgtgcccagc    180
cggtttagcg gcagcggctc cggcaccgac ttcagcctga ccatcaacag cctgcagccc    240
gaggacttcg ccacctacta ctgccagcag agcaacagct tccccctgac ctttggcggc    300
ggaacaaagg tggagatcaa gcgt                                          324
```

<210> SEQ ID NO 344
<211> LENGTH: 324
<212> TYPE: DNA
<213> ORGANISM: Artificial Sequence
<220> FEATURE:
<223> OTHER INFORMATION: Synthetic

<400> SEQUENCE: 344

```
gacatccaga tgacccagag ccccagcagc gtgtccgcca gcgtgggcga cagagtgacc     60
atcacctgcc gggccagcca gagcatcagc atcaacctgc actggtatca gcagaagccc    120
ggcaaggccc ccaagctgct gatctacttc gccagccagt ccatcagcgg cgtgcccagc    180
cggtttagcg gctacggctc cggcaccgac ttcagcctga ccatcaacag cctgcagccc    240
gaggacttcg ccacctacta ctgccagcag agcaacagct tccccctgac ctttggcggc    300
ggaacaaagg tggagatcaa gcgt                                          324
```

<210> SEQ ID NO 345
<211> LENGTH: 324
<212> TYPE: DNA
<213> ORGANISM: Artificial Sequence
<220> FEATURE:
<223> OTHER INFORMATION: Synthetic

<400> SEQUENCE: 345

```
gacatccaga tgacccagag ccccagcagc gtgtccgcca gcgtgggcga cagagtgacc     60
atcacctgcc gggccagcca gagcatcagc atcaacctgc actggtatca gcagaagccc    120
ggcaaggccc ccaagctgct gatctacttc gccagccagt ccatcagcgg cgtgcccagc    180
cggtttagcg gcagcggctc cggcaccgac ttcagcctga ccatcaacag cctgcagccc    240
gaggacttcg cccggtacta ctgccagcag agcaacagct tccccctgac ctttggcggc    300
ggaacaaagg tggagatcaa gcgt                                          324
```

<210> SEQ ID NO 346
<211> LENGTH: 324
<212> TYPE: DNA
<213> ORGANISM: Artificial Sequence
<220> FEATURE:
<223> OTHER INFORMATION: Synthetic

<400> SEQUENCE: 346

```
gacatccaga tgacccagag ccccagcagc gtgtccgcca gcgtgggcga cagagtgacc      60
atcacctgcc gggccagcca gagcatcagc atcaacctgc actggtatca gcagaagccc     120
ggcaaggccc ccaagctgct gatcaagttc gccagccagt ccatcagcgg cgtgcccagc     180
cggtttagcg gctacggctc cggcaccgac ttcagcctga ccatcaacag cctgcagccc     240
gaggacttcg cccggtacta ctgccagcag agcaacagct tcccctgac ctttggcggc      300
ggaacaaagg tggagatcaa gcgt                                            324
```

<210> SEQ ID NO 347
<211> LENGTH: 324
<212> TYPE: DNA
<213> ORGANISM: Artificial Sequence
<220> FEATURE:
<223> OTHER INFORMATION: Synthetic

<400> SEQUENCE: 347

```
gagatcgtgc tgacccagag ccccgccacc ctgtccctca gccctggcga gcgggccacc      60
ctgagctgcc gggcctccca gagcatcagc atcaacctgc actggtatca gcagaagccc     120
ggccaggccc ccagactgct gatctacttc gccagccagt ccatcagcgg catccccgcc     180
aggttcagcg gcagcggctc cggcaccgac ttcaccctga ccatcagcag cctggagccc     240
gaggacttcg ccgtgtacta ctgccagcag agcaacagct tcccctgac ctttggcggc      300
ggaacaaagg tggagatcaa gcgt                                            324
```

<210> SEQ ID NO 348
<211> LENGTH: 324
<212> TYPE: DNA
<213> ORGANISM: Artificial Sequence
<220> FEATURE:
<223> OTHER INFORMATION: Synthetic

<400> SEQUENCE: 348

```
gagatcgtga tgacccagag ccccgccacc ctgtccgtga gccctggcga gcgggccacc      60
ctgagctgcc gggcctccca gagcatcagc atcaacctgc actggtatca gcagaagccc     120
ggccaggccc ccagactgct gatctacttc gccagccagt ccatcagcgg catccccgcc     180
aggttcagcg gcagcggctc cggcaccgag ttcaccctga ccatcagcag cctgcagagc     240
gaggacttcg ccgtgtacta ctgccagcag agcaacagct tcccctgac ctttggcggc      300
ggaacaaagg tggagatcaa gcgt                                            324
```

<210> SEQ ID NO 349
<211> LENGTH: 324
<212> TYPE: DNA
<213> ORGANISM: Artificial Sequence
<220> FEATURE:
<223> OTHER INFORMATION: Synthetic

<400> SEQUENCE: 349

```
gacatcgtga tgacccagag ccctagcagc gtgtctgcca gcgtgggcga cagagtgacc      60
atcacctgtc gggccagcca gagcatcagc atcaatctgc actggtatca gcagaagccc     120
ggcaaggccc ccaagctgct gatctacttc gccagccagt ccatcagcgg cgtgcccagc     180
agattttctg gcagcggcag cggcaccgac ttcagcctga ccatcaacag cctgcagccc     240
gaggacttcg ccacctacta ctgccagcag agcaacagct tcccctgac cttcggcgga      300
ggcaccaagg tggagatcaa gcgt                                            324
```

<210> SEQ ID NO 350
<211> LENGTH: 324
<212> TYPE: DNA
<213> ORGANISM: Artificial Sequence
<220> FEATURE:
<223> OTHER INFORMATION: Synthetic

<400> SEQUENCE: 350

| | | | | | |
|---|---|---|---|---|---|
| gacatccagc tgacccagag | ccctagcagc | gtgtctgcca | gcgtgggcga | cagagtgacc | 60 |
| atcacctgtc gggccagcca | gagcatcagc | atcaatctgc | actggtatca | gcagaagccc | 120 |
| ggcaaggccc ccaagctgct | gatctacttc | gccagccagt | ccatcagcgg | cgtgcccagc | 180 |
| agattttctg gcagcggcag | cggcaccgac | ttcagcctga | ccatcaacag | cctgcagccc | 240 |
| gaggacttcg ccacctacta | ctgccagcag | agcaacagct | tccccctgac | cttcggcgga | 300 |
| ggcaccaagg tggagatcaa gcgt | | | | | 324 |

<210> SEQ ID NO 351
<211> LENGTH: 324
<212> TYPE: DNA
<213> ORGANISM: Artificial Sequence
<220> FEATURE:
<223> OTHER INFORMATION: Synthetic

<400> SEQUENCE: 351

| | | | | | |
|---|---|---|---|---|---|
| gacatccaga tgacccagag | ccctagcagc | gtgtctgcca | ccgtgggcga | cagagtgacc | 60 |
| atcacctgtc gggccagcca | gagcatcagc | atcaatctgc | actggtatca | gcagaagccc | 120 |
| ggcaaggccc ccaagctgct | gatctacttc | gccagccagt | ccatcagcgg | cgtgcccagc | 180 |
| agattttctg gcagcggcag | cggcaccgac | ttcagcctga | ccatcaacag | cctgcagccc | 240 |
| gaggacttcg ccacctacta | ctgccagcag | agcaacagct | tccccctgac | cttcggcgga | 300 |
| ggcaccaagg tggagatcaa gcgt | | | | | 324 |

<210> SEQ ID NO 352
<211> LENGTH: 324
<212> TYPE: DNA
<213> ORGANISM: Artificial Sequence
<220> FEATURE:
<223> OTHER INFORMATION: Synthetic

<400> SEQUENCE: 352

| | | | | | |
|---|---|---|---|---|---|
| gacatccaga tgacccagag | ccctagcagc | gtgtctgcca | gccctggcga | cagagtgacc | 60 |
| atcacctgtc gggccagcca | gagcatcagc | atcaatctgc | actggtatca | gcagaagccc | 120 |
| ggcaaggccc ccaagctgct | gatctacttc | gccagccagt | ccatcagcgg | cgtgcccagc | 180 |
| agattttctg gcagcggcag | cggcaccgac | ttcagcctga | ccatcaacag | cctgcagccc | 240 |
| gaggacttcg ccacctacta | ctgccagcag | agcaacagct | tccccctgac | cttcggcgga | 300 |
| ggcaccaagg tggagatcaa gcgt | | | | | 324 |

<210> SEQ ID NO 353
<211> LENGTH: 324
<212> TYPE: DNA
<213> ORGANISM: Artificial Sequence
<220> FEATURE:
<223> OTHER INFORMATION: Synthetic

<400> SEQUENCE: 353

| | | | | | |
|---|---|---|---|---|---|
| gacatccaga tgacccagag | ccctagcagc | gtgtctgcca | gcgtgggcga | cagagtgacc | 60 |
| atcacctgtc gggccagcca | gagcatcagc | atcaatctgc | actggtatca | gcagaagagc | 120 |

```
ggcaaggccc ccaagctgct gatctacttc gccagccagt ccatcagcgg cgtgcccagc    180
agattttctg gcagcggcag cggcaccgac ttcagcctga ccatcaacag cctgcagccc    240
gaggacttcg ccacctacta ctgccagcag agcaacagct cccccctgac cttcggcgga    300
ggcaccaagg tggagatcaa gcgt                                           324
```

<210> SEQ ID NO 354
<211> LENGTH: 324
<212> TYPE: DNA
<213> ORGANISM: Artificial Sequence
<220> FEATURE:
<223> OTHER INFORMATION: Synthetic

<400> SEQUENCE: 354

```
gacatccaga tgacccagag ccctagcagc gtgtctgcca gcgtgggcga cagagtgacc     60
atcacctgtc gggccagcca gagcatcagc atcaatctgc actggtatca gcagaagccc    120
cacaaggccc ccaagctgct gatctacttc gccagccagt ccatcagcgg cgtgcccagc    180
agattttctg gcagcggcag cggcaccgac ttcagcctga ccatcaacag cctgcagccc    240
gaggacttcg ccacctacta ctgccagcag agcaacagct cccccctgac cttcggcgga    300
ggcaccaagg tggagatcaa gcgt                                           324
```

<210> SEQ ID NO 355
<211> LENGTH: 324
<212> TYPE: DNA
<213> ORGANISM: Artificial Sequence
<220> FEATURE:
<223> OTHER INFORMATION: Synthetic

<400> SEQUENCE: 355

```
gacatccaga tgacccagag ccctagcagc gtgtctgcca gcgtgggcga cagagtgacc     60
atcacctgtc gggccagcca gagcatcagc atcaatctgc actggtatca gcagaagccc    120
ggcgaggccc ccaagctgct gatctacttc gccagccagt ccatcagcgg cgtgcccagc    180
agattttctg gcagcggcag cggcaccgac ttcagcctga ccatcaacag cctgcagccc    240
gaggacttcg ccacctacta ctgccagcag agcaacagct cccccctgac cttcggcgga    300
ggcaccaagg tggagatcaa gcgt                                           324
```

<210> SEQ ID NO 356
<211> LENGTH: 324
<212> TYPE: DNA
<213> ORGANISM: Artificial Sequence
<220> FEATURE:
<223> OTHER INFORMATION: Synthetic

<400> SEQUENCE: 356

```
gacatccaga tgacccagag ccctagcagc gtgtctgcca gcgtgggcga cagagtgacc     60
atcacctgtc gggccagcca gagcatcagc atcaatctgc actggtatca gcagaagccc    120
ggcaagagcc ccaagctgct gatctacttc gccagccagt ccatcagcgg cgtgcccagc    180
agattttctg gcagcggcag cggcaccgac ttcagcctga ccatcaacag cctgcagccc    240
gaggacttcg ccacctacta ctgccagcag agcaacagct cccccctgac cttcggcgga    300
ggcaccaagg tggagatcaa gcgt                                           324
```

<210> SEQ ID NO 357
<211> LENGTH: 324
<212> TYPE: DNA
<213> ORGANISM: Artificial Sequence

```
<220> FEATURE:
<223> OTHER INFORMATION: Synthetic

<400> SEQUENCE: 357
gacatccaga tgacccagag ccctagcagc gtgtctgcca gcgtgggcga cagagtgacc      60
atcacctgtc gggccagcca gagcatcagc atcaatctgc actggtatca gcagaagccc     120
ggcaaggccc ccaagctgct gatctacttc gccagccagt ccatcagcgg catccccagc     180
agattttctg gcagcggcag cggcaccgac ttcagcctga ccatcaacag cctgcagccc     240
gaggacttcg ccacctacta ctgccagcag agcaacagct tccccctgac cttcggcgga     300
ggcaccaagg tggagatcaa gcgt                                            324

<210> SEQ ID NO 358
<211> LENGTH: 324
<212> TYPE: DNA
<213> ORGANISM: Artificial Sequence
<220> FEATURE:
<223> OTHER INFORMATION: Synthetic

<400> SEQUENCE: 358
gacatccaga tgacccagag ccctagcagc gtgtctgcca gcgtgggcga cagagtgacc      60
atcacctgtc gggccagcca gagcatcagc atcaatctgc actggtatca gcagaagccc     120
ggcaaggccc ccaagctgct gatctacttc gccagccagt ccatcagcgg cgtgcccagc     180
agattttctg gcagcggcag cggcaccgac ttcagcctga ccatcaacag cctgcagacc     240
gaggacttcg ccacctacta ctgccagcag agcaacagct tccccctgac cttcggcgga     300
ggcaccaagg tggagatcaa gcgt                                            324

<210> SEQ ID NO 359
<211> LENGTH: 324
<212> TYPE: DNA
<213> ORGANISM: Artificial Sequence
<220> FEATURE:
<223> OTHER INFORMATION: Synthetic

<400> SEQUENCE: 359
gacatccaga tgacccagag ccctagcagc gtgtctgcca gcgtgggcga cagagtgacc      60
atcacctgtc gggccagcca gagcatcagc atcaatctgc actggtatca gcagaagccc     120
ggcaaggccc ccaagctgct gatctacttc gccagccagt ccatcagcgg cgtgcccagc     180
agattttctg gcagcggcag cggcaccgac ttcagcctga ccatcaacag cctgcagccc     240
gaggacttcg ccacctactt ttgccagcag agcaacagct tccccctgac cttcggcgga     300
ggcaccaagg tggagatcaa gcgt                                            324

<210> SEQ ID NO 360
<211> LENGTH: 324
<212> TYPE: DNA
<213> ORGANISM: Artificial Sequence
<220> FEATURE:
<223> OTHER INFORMATION: Synthetic

<400> SEQUENCE: 360
gacatcgtga tgacccagag ccctagcagc gtgtctgcca gcgtgggcga cagagtgacc      60
atcacctgtc gggccagcca gagcatcagc atcaatctgc actggtatca gcagaagccc     120
ggcaaggccc ccaagctgct gatctacttc gccagccagt ccatcagcgg cgtgcccagc     180
agattttctg gcagcggcag cggcaccgac ttcagcctga ccatcaacag cctgcagccc     240
```

```
gaggacttcg cccggtacta ctgccagcag agcaacagct tccccctgac cttcggcgga    300
ggcaccaagg tggagatcaa gcgt                                           324
```

<210> SEQ ID NO 361
<211> LENGTH: 324
<212> TYPE: DNA
<213> ORGANISM: Artificial Sequence
<220> FEATURE:
<223> OTHER INFORMATION: Synthetic

<400> SEQUENCE: 361

```
gacatccagc tgacccagag ccctagcagc gtgtctgcca gcgtgggcga cagagtgacc     60
atcacctgtc gggccagcca gagcatcagc atcaatctgc actggtatca gcagaagccc    120
ggcaaggccc ccaagctgct gatctacttc gccagccagt ccatcagcgg cgtgcccagc    180
agattttctg gcagcggcag cggcaccgac ttcagcctga ccatcaacag cctgcagccc    240
gaggacttcg cccggtacta ctgccagcag agcaacagct tccccctgac cttcggcgga    300
ggcaccaagg tggagatcaa gcgt                                           324
```

<210> SEQ ID NO 362
<211> LENGTH: 324
<212> TYPE: DNA
<213> ORGANISM: Artificial Sequence
<220> FEATURE:
<223> OTHER INFORMATION: Synthetic

<400> SEQUENCE: 362

```
gacatccaga tgacccagag ccctagcagc gtgtctgcca ccgtgggcga cagagtgacc     60
atcacctgtc gggccagcca gagcatcagc atcaatctgc actggtatca gcagaagccc    120
ggcaaggccc ccaagctgct gatctacttc gccagccagt ccatcagcgg cgtgcccagc    180
agattttctg gcagcggcag cggcaccgac ttcagcctga ccatcaacag cctgcagccc    240
gaggacttcg cccggtacta ctgccagcag agcaacagct tccccctgac cttcggcgga    300
ggcaccaagg tggagatcaa gcgt                                           324
```

<210> SEQ ID NO 363
<211> LENGTH: 324
<212> TYPE: DNA
<213> ORGANISM: Artificial Sequence
<220> FEATURE:
<223> OTHER INFORMATION: Synthetic

<400> SEQUENCE: 363

```
gacatccaga tgacccagag ccctagcagc gtgtctgcca gccctggcga cagagtgacc     60
atcacctgtc gggccagcca gagcatcagc atcaatctgc actggtatca gcagaagccc    120
ggcaaggccc ccaagctgct gatctacttc gccagccagt ccatcagcgg cgtgcccagc    180
agattttctg gcagcggcag cggcaccgac ttcagcctga ccatcaacag cctgcagccc    240
gaggacttcg cccggtacta ctgccagcag agcaacagct tccccctgac cttcggcgga    300
ggcaccaagg tggagatcaa gcgt                                           324
```

<210> SEQ ID NO 364
<211> LENGTH: 324
<212> TYPE: DNA
<213> ORGANISM: Artificial Sequence
<220> FEATURE:
<223> OTHER INFORMATION: Synthetic -continued

<400> SEQUENCE: 364
gacatccaga tgacccagag ccctagcagc gtgtctgcca gcgtgggcga cagagtgacc    60
atcacctgtc gggccagcca gagcatcagc atcaatctgc actggtatca gcagaagagc   120
ggcaaggccc ccaagctgct gatctacttc gccagccagt ccatcagcgg cgtgcccagc   180
agattttctg gcagcggcag cggcaccgac ttcagcctga ccatcaacag cctgcagccc   240
gaggacttcg cccggtacta ctgccagcag agcaacagct cccccctgac cttcggcgga   300
ggcaccaagg tggagatcaa gcgt                                          324

<210> SEQ ID NO 365
<211> LENGTH: 324
<212> TYPE: DNA
<213> ORGANISM: Artificial Sequence
<220> FEATURE:
<223> OTHER INFORMATION: Synthetic

<400> SEQUENCE: 365
gacatccaga tgacccagag ccctagcagc gtgtctgcca gcgtgggcga cagagtgacc    60
atcacctgtc gggccagcca gagcatcagc atcaatctgc actggtatca gcagaagccc   120
cacaaggccc ccaagctgct gatctacttc gccagccagt ccatcagcgg cgtgcccagc   180
agattttctg gcagcggcag cggcaccgac ttcagcctga ccatcaacag cctgcagccc   240
gaggacttcg cccggtacta ctgccagcag agcaacagct cccccctgac cttcggcgga   300
ggcaccaagg tggagatcaa gcgt                                          324

<210> SEQ ID NO 366
<211> LENGTH: 324
<212> TYPE: DNA
<213> ORGANISM: Artificial Sequence
<220> FEATURE:
<223> OTHER INFORMATION: Synthetic

<400> SEQUENCE: 366
gacatccaga tgacccagag ccctagcagc gtgtctgcca gcgtgggcga cagagtgacc    60
atcacctgtc gggccagcca gagcatcagc atcaatctgc actggtatca gcagaagccc   120
ggcgaggccc ccaagctgct gatctacttc gccagccagt ccatcagcgg cgtgcccagc   180
agattttctg gcagcggcag cggcaccgac ttcagcctga ccatcaacag cctgcagccc   240
gaggacttcg cccggtacta ctgccagcag agcaacagct cccccctgac cttcggcgga   300
ggcaccaagg tggagatcaa gcgt                                          324

<210> SEQ ID NO 367
<211> LENGTH: 324
<212> TYPE: DNA
<213> ORGANISM: Artificial Sequence
<220> FEATURE:
<223> OTHER INFORMATION: Synthetic

<400> SEQUENCE: 367
gacatccaga tgacccagag ccctagcagc gtgtctgcca gcgtgggcga cagagtgacc    60
atcacctgtc gggccagcca gagcatcagc atcaatctgc actggtatca gcagaagccc   120
ggcaagagcc ccaagctgct gatctacttc gccagccagt ccatcagcgg cgtgcccagc   180
agattttctg gcagcggcag cggcaccgac ttcagcctga ccatcaacag cctgcagccc   240
gaggacttcg cccggtacta ctgccagcag agcaacagct cccccctgac cttcggcgga   300
ggcaccaagg tggagatcaa gcgt                                          324

<210> SEQ ID NO 368
<211> LENGTH: 324
<212> TYPE: DNA
<213> ORGANISM: Artificial Sequence
<220> FEATURE:
<223> OTHER INFORMATION: Synthetic

<400> SEQUENCE: 368

```
gacatccaga tgacccagag ccctagcagc gtgtctgcca gcgtgggcga cagagtgacc      60
atcacctgtc gggccagcca gagcatcagc atcaatctgc actggtatca gcagaagccc     120
ggcaaggccc ccaagctgct gatctacttc gccagccagt ccatcagcgg catccccagc     180
agattttctg gcagcggcag cggcaccgac ttcagcctga ccatcaacag cctgcagccc     240
gaggacttcg cccggtacta ctgccagcag agcaacagct tccccctgac cttcggcgga     300
ggcaccaagg tggagatcaa gcgt                                            324
```

<210> SEQ ID NO 369
<211> LENGTH: 324
<212> TYPE: DNA
<213> ORGANISM: Artificial Sequence
<220> FEATURE:
<223> OTHER INFORMATION: Synthetic

<400> SEQUENCE: 369

```
gacatccaga tgacccagag ccctagcagc gtgtctgcca gcgtgggcga cagagtgacc      60
atcacctgtc gggccagcca gagcatcagc atcaatctgc actggtatca gcagaagccc     120
ggcaaggccc ccaagctgct gatctacttc gccagccagt ccatcagcgg cgtgcccagc     180
agattttctg gcagcggcag cggcaccgac ttcagcctga ccatcaacag cctgcagacc     240
gaggacttcg cccggtacta ctgccagcag agcaacagct tccccctgac cttcggcgga     300
ggcaccaagg tggagatcaa gcgt                                            324
```

<210> SEQ ID NO 370
<211> LENGTH: 324
<212> TYPE: DNA
<213> ORGANISM: Artificial Sequence
<220> FEATURE:
<223> OTHER INFORMATION: Synthetic

<400> SEQUENCE: 370

```
gacatccaga tgacccagag ccctagcagc gtgtctgcca gcgtgggcga cagagtgacc      60
atcacctgtc gggccagcca gagcatcagc atcaatctgc actggtatca gcagaagccc     120
ggcaaggccc ccaagctgct gatctacttc gccagccagt ccatcagcgg cgtgcccagc     180
agattttctg gcagcggcag cggcaccgac ttcagcctga ccatcaacag cctgcagccc     240
gaggacttcg cccggtactt ttgccagcag agcaacagct tccccctgac cttcggcgga     300
ggcaccaagg tggagatcaa gcgt                                            324
```

<210> SEQ ID NO 371
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is Met or Leu

```
<400> SEQUENCE: 371

Asp Tyr Tyr Xaa His
1               5

<210> SEQ ID NO 372
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: Xaa is Tyr, His, or Ser

<400> SEQUENCE: 372

Trp Ile Asp Pro Glu Asn Gly Asp Thr Glu Xaa Ala Pro Lys Phe Gln
1               5                   10                  15

Gly

<210> SEQ ID NO 373
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is Cys, Ala, Asn, Asp, Glu, Gln, Gly, His,
      Ile, Leu, Pro or Val

<400> SEQUENCE: 373

Xaa Lys Glu Leu Arg Tyr Phe Asp Val
1               5

<210> SEQ ID NO 374
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is Ser or Pro
<220> FEATURE:
<221> NAME/KEY: misc_feature
<222> LOCATION: (4)..(4)
<223> OTHER INFORMATION: Xaa is Gln or Arg

<400> SEQUENCE: 374

Arg Ala Xaa Xaa Ser Ile Ser Ile Asn Leu His
1               5                   10

<210> SEQ ID NO 375
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is Ser or Arg
<220> FEATURE:
<221> NAME/KEY: misc_feature
<222> LOCATION: (6)..(6)
<223> OTHER INFORMATION: Xaa is Ile or Thr
```

```
<400> SEQUENCE: 375

Phe Ala Xaa Gln Ser Xaa Ser
1               5

<210> SEQ ID NO 376
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa is Trp or Phe

<400> SEQUENCE: 376

Gln Gln Ser Asn Ser Xaa Pro Leu Thr
1               5

<210> SEQ ID NO 377
<211> LENGTH: 105
<212> TYPE: PRT
<213> ORGANISM: Homo sapiens

<400> SEQUENCE: 377

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 378
<211> LENGTH: 29
<212> TYPE: PRT
<213> ORGANISM: Mus musculus

<400> SEQUENCE: 378

Arg Ile Arg Lys Glu Lys Met Glu Thr Glu Gly Cys Asn Gln Gly
1               5                   10                  15

Ala Phe Leu Val Glu Thr Glu Gln Gly Gly Asn Val Cys
            20                  25

<210> SEQ ID NO 379
<211> LENGTH: 15
<212> TYPE: PRT
<213> ORGANISM: Artificial Sequence
<220> FEATURE:
<223> OTHER INFORMATION: Synthetic

<400> SEQUENCE: 379

Gly Gly Gly Gly Ser Gly Gly Gly Ser Gly Gly Gly Gly Ser
1               5                   10                  15
```

```
<210> SEQ ID NO 380
<211> LENGTH: 20
<212> TYPE: DNA
<213> ORGANISM: Artificial Sequence
<220> FEATURE:
<223> OTHER INFORMATION: Synthetic

<400> SEQUENCE: 380
ccatggccca ggtgcagctg                                              20

<210> SEQ ID NO 381
<211> LENGTH: 18
<212> TYPE: DNA
<213> ORGANISM: Artificial Sequence
<220> FEATURE:
<223> OTHER INFORMATION: Synthetic

<400> SEQUENCE: 381
gcggccgctg tcgtacgc                                                18

<210> SEQ ID NO 382
<211> LENGTH: 27
<212> TYPE: DNA
<213> ORGANISM: Artificial Sequence
<220> FEATURE:
<223> OTHER INFORMATION: Synthetic

<400> SEQUENCE: 382
gaacggcgat accgagtccg cccccaa                                      27

<210> SEQ ID NO 383
<211> LENGTH: 27
<212> TYPE: DNA
<213> ORGANISM: Artificial Sequence
<220> FEATURE:
<223> OTHER INFORMATION: Synthetic

<400> SEQUENCE: 383
ttgggggcgg actcggtatc gccgttc                                      27

<210> SEQ ID NO 384
<211> LENGTH: 27
<212> TYPE: DNA
<213> ORGANISM: Artificial Sequence
<220> FEATURE:
<223> OTHER INFORMATION: Synthetic

<400> SEQUENCE: 384
cggcgatacc gagcacgccc ccaagtt                                      27

<210> SEQ ID NO 385
<211> LENGTH: 27
<212> TYPE: DNA
<213> ORGANISM: Artificial Sequence
<220> FEATURE:
<223> OTHER INFORMATION: Synthetic

<400> SEQUENCE: 385
aacttggggg cgtgctcggt atcgccg                                      27

<210> SEQ ID NO 386
<211> LENGTH: 27
<212> TYPE: DNA
<213> ORGANISM: Artificial Sequence
<220> FEATURE:
<223> OTHER INFORMATION: Synthetic
```

<400> SEQUENCE: 386
ggccagcggc tacgccttca ccgacta                27

<210> SEQ ID NO 387
<211> LENGTH: 27
<212> TYPE: DNA
<213> ORGANISM: Artificial Sequence
<220> FEATURE:
<223> OTHER INFORMATION: Synthetic

<400> SEQUENCE: 387
tagtcggtga aggcgtagcc gctggcc                27

<210> SEQ ID NO 388
<211> LENGTH: 31
<212> TYPE: DNA
<213> ORGANISM: Artificial Sequence
<220> FEATURE:
<223> OTHER INFORMATION: Synthetic

<400> SEQUENCE: 388
gccagcggct acaccctcac cgactactat c            31

<210> SEQ ID NO 389
<211> LENGTH: 31
<212> TYPE: DNA
<213> ORGANISM: Artificial Sequence
<220> FEATURE:
<223> OTHER INFORMATION: Synthetic

<400> SEQUENCE: 389
gatagtagtc ggtgagggtg tagccgctgg c            31

<210> SEQ ID NO 390
<211> LENGTH: 29
<212> TYPE: DNA
<213> ORGANISM: Artificial Sequence
<220> FEATURE:
<223> OTHER INFORMATION: Synthetic

<400> SEQUENCE: 390
tgtcctgtag agcccccag agcatcagc               29

<210> SEQ ID NO 391
<211> LENGTH: 29
<212> TYPE: DNA
<213> ORGANISM: Artificial Sequence
<220> FEATURE:
<223> OTHER INFORMATION: Synthetic

<400> SEQUENCE: 391
gctgatgctc tggggggctc tacaggaca              29

<210> SEQ ID NO 392
<211> LENGTH: 31
<212> TYPE: DNA
<213> ORGANISM: Artificial Sequence
<220> FEATURE:
<223> OTHER INFORMATION: Synthetic

<400> SEQUENCE: 392
gatctacttc gccagacagt ccatcagcgg c            31

```
<210> SEQ ID NO 393
<211> LENGTH: 31
<212> TYPE: DNA
<213> ORGANISM: Artificial Sequence
<220> FEATURE:
<223> OTHER INFORMATION: Synthetic

<400> SEQUENCE: 393
gccgctgatg gactgtctgg cgaagtagat c                              31

<210> SEQ ID NO 394
<211> LENGTH: 31
<212> TYPE: DNA
<213> ORGANISM: Artificial Sequence
<220> FEATURE:
<223> OTHER INFORMATION: Synthetic

<400> SEQUENCE: 394
cctgtagagc ctcccggagc atcagcatca a                              31

<210> SEQ ID NO 395
<211> LENGTH: 31
<212> TYPE: DNA
<213> ORGANISM: Artificial Sequence
<220> FEATURE:
<223> OTHER INFORMATION: Synthetic

<400> SEQUENCE: 395
ttgatgctga tgctccggga ggctctacag g                              31
```

ANTI-IL-12/IL-23 ANTIBODIES

CROSS-REFERENCE TO RELATED APPLICATIONS

This application is the National Stage of International Application No. PCT/AU2009/001047, filed Aug. 14, 2009, which claims the benefit of Australian Application No. 2008904178, filed Aug. 14, 2008, and U.S. Provisional Application No. 61/089,028, filed Aug. 14, 2008, the disclosures of which are incorporated herein by reference in their entireties for all purposes.

FIELD

The present invention relates to antibodies which bind to human IL-12 and IL-23.

BACKGROUND

Bibliographic details of the publications referred to by author in this specification are collected alphabetically at the end of the description.

Reference to any prior art in this specification is not, and should not be taken as, an acknowledgment or any form of suggestion that this prior art forms part of the common general knowledge in any country.

Interleukin-12 (also known as cytotoxic lymphocyte maturation factor or natural killer cell stimulatory factor) is a 75-kDa heterodimeric protein. It consists of a p35 subunit which is comprised of a bundle of four alpha helicies that resembles the class I cytokines. The 11 amino acids C-terminal to C63 in p35 are termed the disulphide bond loop, as this region contains numerous residues that contact p40, the other subunit of IL-12, including an interchain disulphide bond with C177 in p40. The p40 subunit folds like the extracellular domain of other class I receptors, such as growth hormone receptor (GHR).

The p40 subunit has three domains labelled D1, D2 and D3. Each domain is a β-sheet structure with the D2 domain containing the C177 interchain disulphide bond. There is also an N-linked glycosylation site (GlcNAc-GlcNAc-mannose, where GlcNAc is N-acetylglucosamine) on D2 (Yoon et al. 2000 Embo J 19 3530-41).

Interleukin-23 was discovered more recently (2000) by searching sequence databases with a computationally derived profile of members of the interleukin-6 helical cytokine family. This search led to the discovery of a novel cytokine subunit which was named IL-23p19 (p19). This subunit was co-expressed with IL-12p40 leading to secretion of a heterodimeric protein called Interleukin-23 (IL-23). IL-23p19 is thought to resemble IL-12p35 in that it contains a four helix bundle (Oppmann et al. 2000 Immunity 13 715-25).

The specific effects of IL-12 on its target cell types are mediated by the IL-12R complex, which consists of IL-12Rβ1 (Chua et al. 1994 J Immunol 153 128-36) and IL-12Rβ2 (Presky et al. 1996 Proc Natl Acad Sci USA 93 14002-7). The specific effects of IL-23 on its target cell types are meditated by the IL-23R complex, which consists of IL-12Rβ1 and IL-23R (Parham et al. 2002 J Immunol 168 5699-708).

IL-12Rβ1 binding to IL-12 and IL-23 is mediated via the common p40 subunit. This was demonstrated using competition experiments in which a homodimer of the p40 subunit (p80) competed with IL-12 for binding to IL-12Rβ1. However p80 had no effect on the binding of IL-12 to IL-12Rβ2 (Presky et al. 1996 Ann NY Acad Sci 795 390-3).

It follows that the p35 subunit or the heterodimeric interface of IL-12 is responsible for binding to IL-12Rβ2 thereby conferring IL-12 selectivity on the IL-12R complex (Trinchieri et al. 2003 Immunity 19 641-4). Likewise p19 or the heterodimeric interface of IL-23 is responsible for binding to IL-23R thereby conferring IL-23 selectivity on the IL-23R complex.

The signalling of the IL-12R and IL-23R complex has been elucidated. The IL-12R activates the Janus kinase (JAK)—signal transducer and activator of transcription (STAT) pathway of signal transduction. The actual cellular effects of IL-12 are due mainly to STAT4 activation (Kaplan et al. 1996 Nature 382 174-7). There is a STAT4 binding site on IL-12Rβ2 indicating that this receptor is vital for signalling (Yao et al. 1999 Arch Biochem Biophys 368 147-55). This is also demonstrated in the correlation of the expression of IL-12Rβ2 to the responsiveness of $T_H1$ cells to IL-12 (Rogge et al. 1997 J Exp Med 185 825-31). The IL-23R activates similar complexes to IL-12R such as the JAK-STAT pathways. STAT3 is more prominently induced than STAT4 by binding of IL-23 to the IL-23R and the other resulting DNA-binding STAT transcription factor complexes are different (Parham, Chirica et al. 2002 J Immunol 168 5699-708).

The biological effects of both IL-12 and IL-23 are distinct from each other. IL-12 is secreted by activated inflammatory cells (monocytes, macrophages, neutrophils, microglia, dendritic cells). IL-12 has mainly been studied for its effects on lymphocytes, although it affects other types of cells also. During the inflammatory response, IL-12 induces NK cells and T cells to produce interferon-γ (IFN-γ). Then IL-12, possibly in combination with IFN-γ, induces T cells to differentiate into $T_H1$ cells. This response stimulates the cellular immune system and maximises the killing effect of macrophages on pathogens and the proliferation of CD8+ T cells (Trinchieri 2003 Nat Rev Immunol 3 133-46). Overproduction of IL-12 has been correlated with heightened proinflammatory activities and tissue damage typical of autoimmunity (Leonard et al. 1997 Crit. Rev Immunol 17 545-53). Dysregulated IL-12 production has been implicated in the following diseases: psoriasis (Yawalkar et al. 1998 J Invest Dermatol 111 1053-7; de Rie 1999 Dermatology 199 101; Shaker et al. 2006 Clin Biochem 39 119-25), Crohn's Disease (Neurath et al. 1995 J Exp Med 182 1281-90; Simpson et al. 1998 J Exp Med 187 1225-34; Camoglio et al. 2002 Eur J Immunol 32 261-9), Multiple Sclerosis (Fassbender et al. 1998 Neurology 51 753-8; Laman et al. 1998 J Neuroimmunol 86 30-45), rheumatoid arthritis (Kim et al. 2000 Clin Exp Immunol 119 175-81; Leung et al. 2000 J Immunol 164 6495-502) among other autoimmune diseases. The role of IL-12 in these diseases is not clear however it is thought that the overpolarisation of the $T_H1$ response may be involved (Gordon et al. 2005 Curr Opin Gastroenterol 21 431-7).

IL-23 is secreted by activated human macrophages as well as dendritic cells (Verreck et al. 2004 Proc Natl Acad Sci USA 101 4560-5). IL-23 predominantly acts on memory T-cells and has been postulated to promote autoimmune disease through the regulation of IL-17A and IL-17F as demonstrated in the ability of murine splenocytes to secrete IL-17 in response to IL-23. In humans the IL-23/IL-17 pathway is present, and IL-23 has been shown to be an equally good inducer of IL-21, IL-22, IFN-γ, TNF-α along with IL-17, all pro-inflammatory cytokines. In vitro IL-6 and TGF-β1 promote naïve T-cells down a newly discovered T-cell pathway ($T_H17$) (Zhou et al. 2007 Nat Immunol 8 967-74). These cell are further driven in a autocrine manner via secretion of IL-21. Lastly, IL-23 and/or IL-1β are thought to maintain cells in this $T_H17$ response (For a review see Dong 2008 Nat Rev Immunol 8 337-48). Also of interest is the transcription factor RORγt which has been shown to be upregulated in the $T_H17$ response (Chen et al. 2007 Arthritis Rheum 56 2936-46).

Since both IL-12 and IL-23 contain a common subunit, it has been difficult to attribute disease states solely to overproduction of one interleukin or the other. However research indicates that IL-23 dysregulation has been implicated in the following diseases: psoriasis (Lee et al. 2004 J Exp Med 199 125-30; Torti et al. 2007 J Am Acad Dermatol 57 1059-68), Crohn's disease (Neurath 2007 Nat Med 13 26-8) and Multiple Sclerosis (Cua et al. 2003 Nature 421 744-8) among other autoimmune diseases.

IL-12p40 can be secreted as a monomer (IL-12p40) or as a homodimer (IL-12p80) which is two p40 subunits held together by a disulphide bond (Gillessen et al. 1995 Eur J Immunol 25 200-6). These p40 species are secreted at 50-fold excess compared with IL-12 in a murine shock model (Gillessen, Carvajal et al. 1995 Eur J Immunol 25 200-6) and 10-20 fold excess in human peripheral blood mononuclear cells (PBMCs) (D'Andrea et al. 1992 J Exp Med 176 1387-98). IL-12p80 can antagonise IL-12 activity in vitro 20-fold greater than that of IL-12p40 (Gillessen, Carvajal et al. 1995 Eur J Immunol 25 200-6). Recombinant IL-12p80 has been shown to bind to IL-12β1 (Wang et al. 1999 Eur J Immunol 29 2007-13).

IL-12p40/p80 is considered an antagonist of the IL-12/23 receptor complex because recombinant murine IL-12p80 (rmIL-12p80) has been shown to compete with IL-12/23 binding to IL-12Rβ1 in vivo and in vitro (Mattner et al. 1993 Eur J Immunol 23 2202-8; Gillessen, Carvajal et al. 1995 Eur J Immunol 25 200-6; Gately et al. 1996 Ann NY Acad Sci 795 1-12). The homodimer has also been shown to prevent IL-12 mediated shock in the murine model (Mattner et al. 1997 Infect Immun 65 4734-7). In an investigation of IL-23 mediated immunological functions IL-12p40 impaired IL-23 induced cytokine production by competitive binding to the IL-12Rβ1 (Shimozato et al. 2006 Immunology 117 22-8). More recently IL-12p40 or IL-12p80 has been implicated in other biological roles. One of the earliest established activities of IL-12p80 is as a chemoattractant for macrophages. IL-12Rβ1 deficient macrophages but not IL-12Rβ2 or IL-12p35 deficient macrophages, have reduced chemoattractive responses to rmIL-12p80, indicating that IL-12Rβ1 can mediate responses to IL-12p80 in the absence of IL-12Rβ2 and that IL-12p80 activity is independent of IL-12 (Russell et al. 2003 J Immunol 171 6866-74). IL-12p80 can also act as an inducer of dendritic cell (DC) migration. IL-12p40-deficient DCs are unable to migrate from the lungs to the lymph nodes in response to mycobacteria. The fact that the loss of both IL-12p35 and IL-23p19 did not impact on the ability of mycobacterially activated DCs both to migrate in response to chemokines and to drive T-cell expansion highlights this unique role for IL-12p40 (Khader et al. 2006 J Exp Med 203 1805-15). IL-12p40 and IL-12p80 have also been shown to mediate inflammatory responses in the lung and has been shown to induce IFN-γ production by CD8$^+$ T cells (Cooper et al. 2007 Trends Immunol 28 33-8).

Since IL-12 and IL-23 have been implicated in a variety of disorders several therapeutic strategies have been designed to inhibit IL-12 and/or IL-23 activity. Some of the earliest described antibodies were murine monoclonal antibodies that were secreted by hybridomas of mice immunised with IL-12 (Strober et al. PCT Publication No. WO 97/15327; Gately et al. WO99/37682 A2, Neurath, Fuss et al. 1995 J Exp Med 182 1281-90). The use of these murine antibodies for treating humans is limited due to issues arising from administration of a mouse immunoglobulin to humans. Such issues include the raising of auto-antibodies against the mouse immunoglobulin thereby removing its presence in the serum and negating any therapeutic effect. This effect known as the human antimouse antibody (HAMA) was overcome in part with the advent of chimeric antibodies which limited the murine sequence to only the variable regions of the antibody (Junghans et al. 1990 Cancer Res 50 1495-502; Brown et al. 1991 Proc Natl Acad Sci USA 88 2663-7). Chimeric antibodies have been described that bind to IL-12 (Perritt et al. PCT publication No. WO 02/097048A2). Even more human-like antibodies are 'humanised' antibodies' which contain the complementarity determining regions of a donor murine antibody but have variable framework regions derived from a human acceptor antibody (Jones et al. 1986 Nature 321 522-5, Winter U.S. Pat. No. 5,225,539, Queen et al. U.S. Pat. No. 5,693,761). Such 'humanised' antibodies against IL-12 and IL-23 are described by Lacy et al. in WO 07/005,608. Recently, fully human antibodies derived from display libraries derived from human sources (Winter et al. U.S. Pat. No. 7,306,907; MacCafferty et al. U.S. Pat. No. 5,969,108) or from mice with human immunoglobulin transgenes have been described (Tomizuka et al. U.S. Pat. No. 7,041,870; Kucherlapati et al. U.S. Pat. No. 5,939,598). Salfeld et al. (U.S. Pat. No. 6,9141,28) describe fully human antibodies against IL-12.

Five broad classes of antibodies might be anticipated on the basis of interactions with IL-12, IL-23, IL-12p40 and IL-12p80 (FIG. 1). The first class of antibodies are those that specifically interact with IL-12p40 present in IL-12 and IL-23, along with the IL-12p40 monomer and the IL-12p80 homodimer (FIG. 1.1). The second class of antibodies are those that specifically interact with IL-12p35 (as exemplified by antibody G161-566 in Devergne et al. 2001 Am J Pathol 159 1763-76; FIG. 1.2). The third class of antibodies are those that specifically interact with IL-12 but not with IL-23, IL-12p35, and IL-12p40 (as exemplified by antibody 20C2 in D'Andrea, Rengaraju et al. 1992 J Exp Med 176 1387-98; FIG. 1.3). The fourth class of antibodies are those that specifically interact with IL-23p19 (as exemplified by Presta et al. WO 2007/027714; FIG. 1.4). The fifth class of antibodies are those that specifically interact with IL-23p40 but not with IL-12p40, exploiting sequence on the IL-12p40 subunit that is exposed on IL-23 but masked by the IL-12p35 subunit in IL-12 (as exemplified by Benson et al. U.S. Pat. No. 7,247,711; FIG. 1.5). This current invention describes novel forms of the first class of antibodies that specifically interact with IL-12p40, IL-12p80, IL-12 and IL-23 (FIG. 1.1).

Some information is known about the method by which this first class of antibodies inhibit the IL-12/23 receptor-ligand complex and thereby exert their antagonistic effect. Giles-Komar et al (WO 2006/069036) describe an anti-IL-12p40 antibody that is specific for amino acid residues 1-88 of IL-12p40. This antibody was further characterised as specifically inhibiting the interaction of IL-12 and IL-23 with IL-12Rβ1 (Papp et al. 2008 Lancet 371 1675-84). Likewise another antibody has been described in the literature as inhibiting the IL-12/23 interaction with IL-12Rβ1 (Ding et al. 2008 Curr Opin Investig Drugs 9 515-22). The present invention describes antibodies that inhibit the IL-12/23 receptor-ligand complex via a novel mechanism of action (FIG. 2.3). These novel mechanism of action involves the selective neutralisation of the IL-12/IL-12Rβ2 interaction and the IL-23/IL-23R interaction. They differ from antibodies described previously (see above) in that they do not neutralise the binding of IL-12/23 to IL-12Rβ1. These antibodies are also novel in that they do not inhibit IL-12p40/p80 binding to IL-12Rβ1 and thus do not inhibit the role IL-12p40/80 plays in host defense, thereby potentially increasing the safety profile of these antibodies relative to other IL-12/23 antibodies. Such antibodies with novel mechanisms of actions could lead to improvement in the treatment of diseases associated with IL-12/23 but with reduced safety concerns. Additionally, these antibodies could have improved efficacy since they do not inhibit the natural antagonists of IL-12 and IL-23, IL-12p40 or IL-12p80. This would allow both the antibody and IL-12p40 or IL-12p80 to function as antagonists thereby increasing the level of inhibition above that of administering the antibody alone.

SUMMARY OF THE INVENTION

The present invention provides an antibody comprising an antigen binding domain which binds to human IL-12 and human IL-23, wherein the antibody binds human IL-12p40 existing as a monomer (human IL-12p40) and as a homodimer (human IL-12p80) and wherein the antibody inhibits the binding of human IL-12 to human IL-12Rβ2 and human IL-23 to human IL-23R but does not inhibit the binding of human IL-12 or human IL-23 or human IL-12p40 or human IL-12p80 to human IL-12Rβ1.

The present invention further provides a method for treating or reducing the symptoms of at least one IL-12 and/or IL-23 disease in a cell, tissue, organ, animal or patient comprising the use of the antibody of the present invention or a specified portion or variant thereof.

The antibody of the present invention may also be used in detecting or measuring the presence of IL-12, IL-23, IL-12p40 or IL-12p80 in a sample. The method involves addition of the antibody to the sample and measuring the binding of the antibody to IL-12, IL-23, IL-12p40 or IL-12p80 present in the sample.

In order that the nature of the present invention may be more fully understood various forms thereof will now be described with reference to the following FIGURES and EXAMPLES.

BRIEF DESCRIPTION OF THE FIGURES

FIG. 1.1) An antibody that binds to the p40 subunit of IL-12, IL-23, IL-12p40 and IL-12p80; FIG. 1.2) An antibody that binds to p35 subunit of IL-12; FIG. 1.3) An antibody that binds to the p35 and p40 subunit of IL-12 as a heterodimer; FIG. 1.4) An antibody that binds to the p19 subunit of IL-23; FIG. 1.5) An antibody that binds to p40 present in IL-23, IL-12p40 and IL-12p80 but not IL-12.

FIG. 2.1) Subunits of IL-12 and IL-23. FIG. 2.2) An antibody that inhibits IL-12 binding to IL-12Rβ2. FIG. 2.3) An antibody that inhibits IL-12 binding to IL-12Rβ2 and IL-23 binding to IL-23R.

Figure 28:
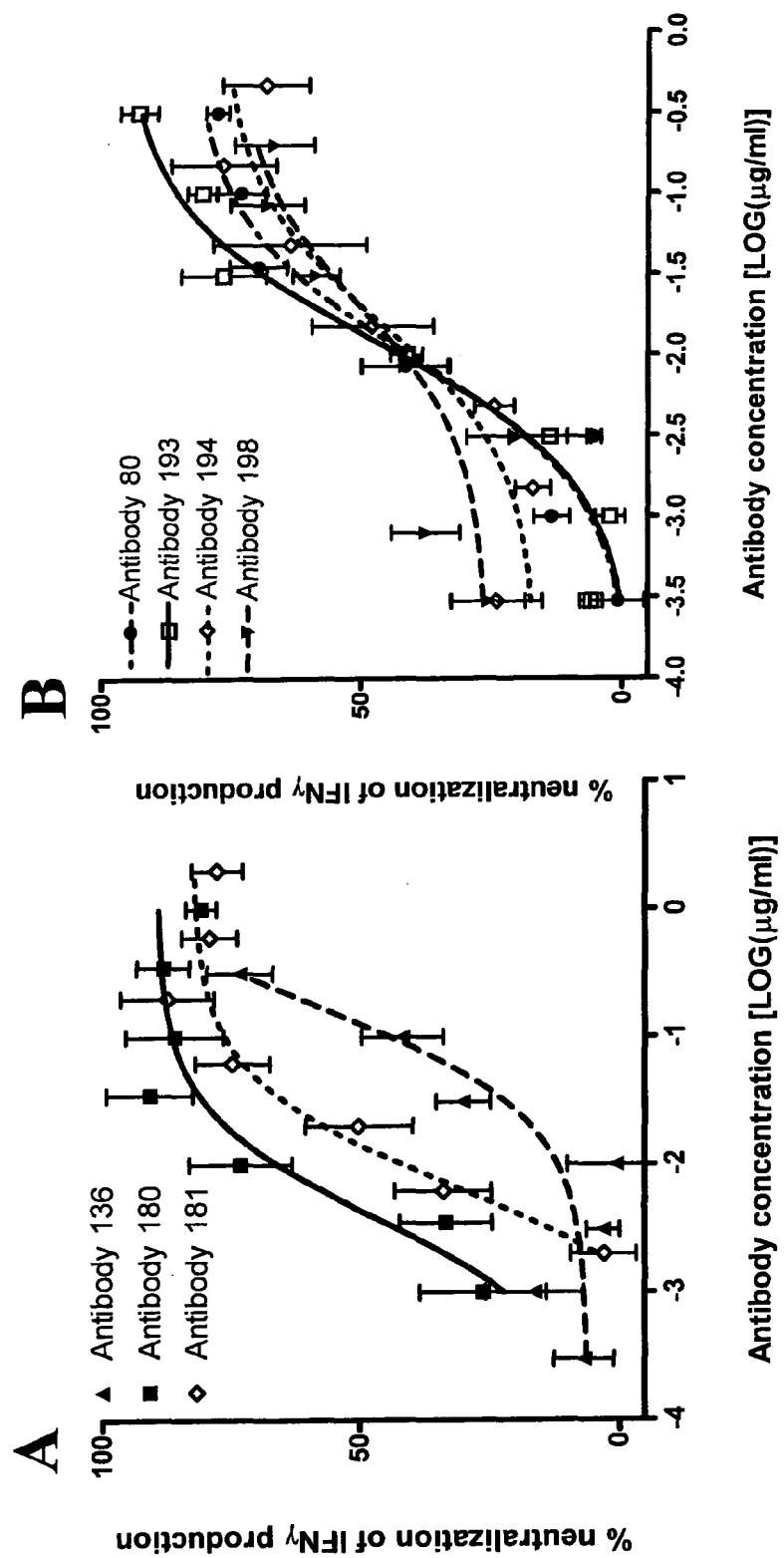

FIG. 28: Various humanized and affinity matured antibodies inhibited chimeric IL-12 induced IFN-γ release from murine splenocytes. Shown are two groups of affinity matured humanized lead antibodies, those based on Antibody 80 (A) and those based on Antibody 136 (B).

Figure 29:
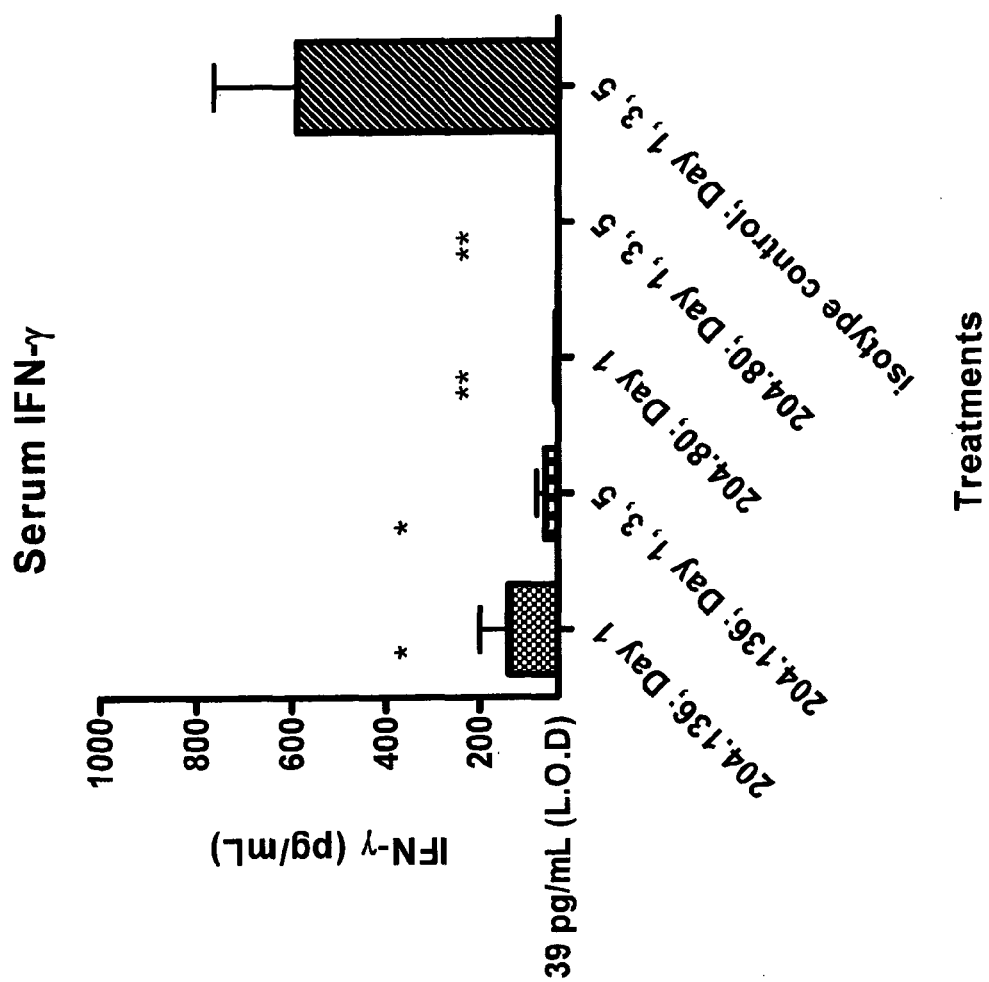

FIG. 29: Mice given repeated injections of chimeric IL-12 have elevated serum levels of IFN-γ. When treated with Antibody 80 or Antibody 136 the levels of serum IFN-γ decreased relative to treatment with an isotype control antibody.

Figure 30:
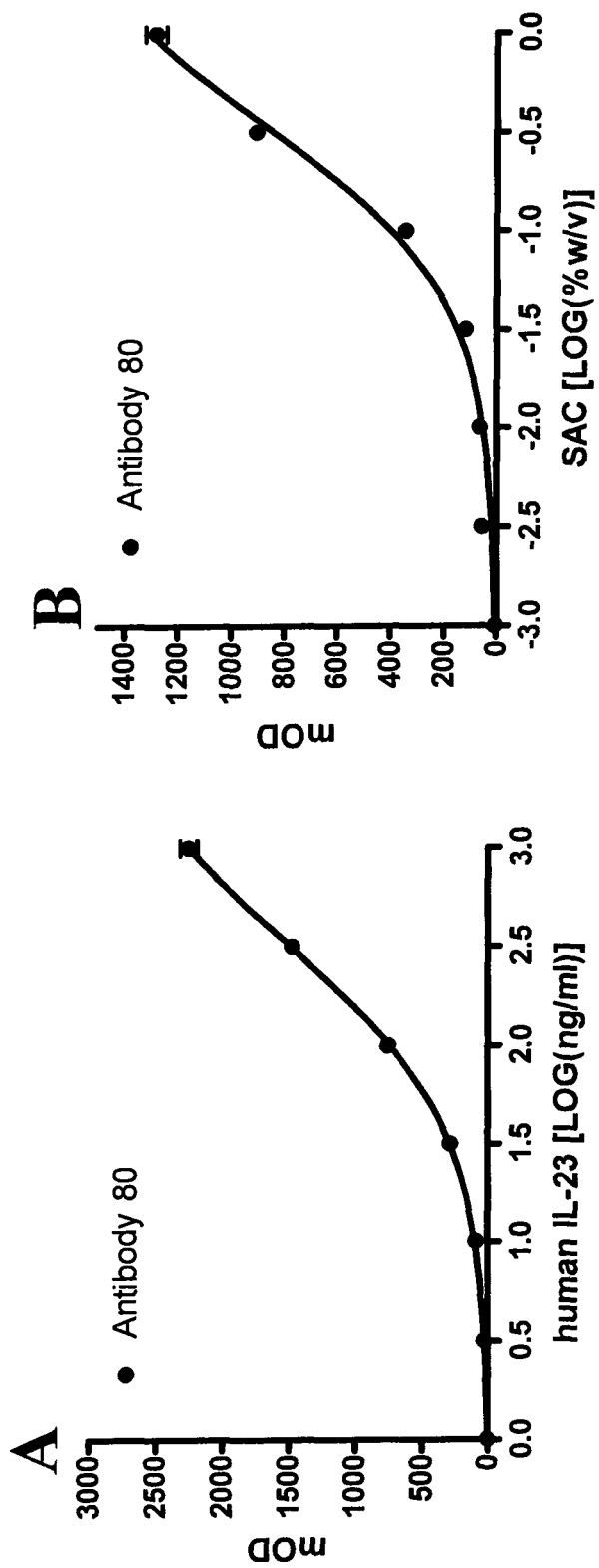

FIG. 30: (A) Antibody 80 is capable of detecting recombinant IL-23 in a sandwich ELISA. (B) Antibody 80 is capable of detecting native produced IL-23 produced by SAC stimulated PBMCs, in a sandwich ELISA.

Figure 31:
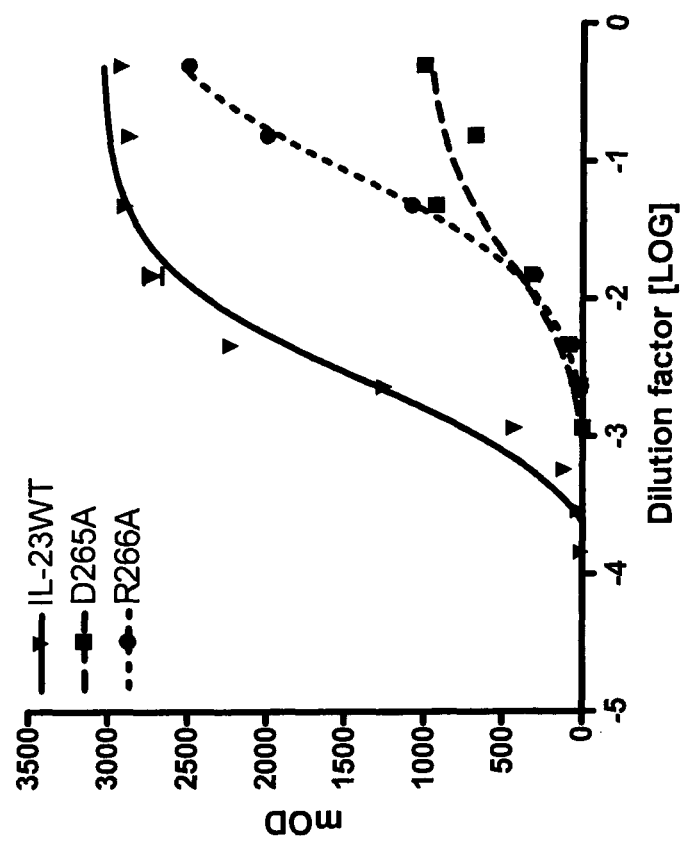

FIG. 31: Antibody 80 bound strongly to IL-23WT protein but had reduced binding to IL-23 mutants D265A and R266A by ELISA.

DETAILED DESCRIPTION

The present inventors raised a panel of antibodies against IL-12. In screening these antibodies it was surprisingly found that a particular subset of antibodies bound human IL-12 and IL-23 and inhibited the binding of IL-12 to IL-12Rβ2 and IL-23 to IL-23R but did not inhibit the binding of IL-12 or IL-23 or IL-12p40 or IL-12p80 to IL-12Rβ1. The activity of IL-12 and IL-23 was therefore able to be modified in a manner which had not been previously achievable.

Accordingly the present invention provides an antibody comprising an antigen binding domain which binds to human IL-12 and human IL-23, wherein the antibody binds human IL-12p40 existing as a monomer (human IL-12p40) and as a homodimer (human IL-12p80) and wherein the antibody inhibits the binding of human IL-12 to human IL-12Rβ2 and human IL-23 to human IL-23R but does not inhibit the binding of human IL-12 or human IL-23 or human IL-12p40 or human IL-12p80 to human IL-12Rβ1.

In a preferred embodiment the antibody competes for binding to human IL-12 and/or human IL-23 with an antibody comprising a heavy chain variable region having the sequence of PMA204 (SEQ ID NO. 6) and/or an antibody comprising a light chain variable region having the sequence of PMA204 (SEQ ID NO. 7).

As used herein "competes" means that the test antibody when used at the same concentration as PMA204 reduces the binding of PMA204 to IL-12, IL-23 or IL-12p40 by at least 10% as tested by ELISA.

The present invention provides an antibody or variant thereof which binds IL-12p40 present in IL-12 and IL-23 having a sequence listed as SEQ ID No 1 and given below:

IWELKKDVYVVELDWYPDAPGEMVVLTCDTPEEDGITWTLDQSSEVL

GSGKTLTIQVKEFGDAGQYTCHKGGEVLSHSLLLLHKKEDGIWSTDI

LKDQKEPKNKTFLRCEAKNYSGRFTCWWLTTISTDLTFSVKSSRGSS

DPQGVTCGAATLSAERVRGDNKEYEYSVECQEDSACPAAEESLPIEV

MVDAVHKLKYENYTSSFFIRDIIKPDPPKNLQLKPLKNSRQVEVSWE

YPDTWSTPHSYFSLTFCVQVQGKSKREKKDRVFTDKTSATVICRKNA

SISVRAQDRYYSSSWSEWASVPCS

In a preferred embodiment the epitope bound by the antibody is within the sequence sequence VQVQGK-SKREKKDRVFTDKTSATVICRKNASISV (SEQ ID NO: 65). In particular the antibody binds to human IL-12p40 (SEQ ID No. 1) at Asp 265.

In another aspect the present invention provides an antibody comprising an antigen binding domain which binds to human IL-23 (SEQ ID NO: 66), wherein the level of binding of the antibody to human IL-23 (SEQ ID NO: 66) is greater than the level of binding of the antibody to mutant IL-23 D265A (SEQ ID NO: 75).

This antibody can also bind human IL-12p40 existing as a monomer (human IL-12p40) and as a homodimer (human IL-12p80) and inhibits the binding of human IL-12 to human IL-12Rβ2 and human IL-23 to human IL-23R but does not inhibit the binding of human IL-12 or human IL-23 or human IL-12p40 or human IL-12p80 to human IL-12Rβ1.

The present invention provides antibodies that could be used to treat at least one IL-12 and/or one IL-23 related condition by selectively neutralising IL-12 binding to IL-12Rβ2 and IL-23 binding to IL-23R.

The present invention provides an antibody which comprises 3 heavy chain CDR sequences selected from:

```
                                        (SEQ ID NO: 371)
CDRHC1 DYYX₁H, wherein;
    X₁ = M or L;

(SEQ ID NO: 372)
CDRHC2 WIDPENGDTEX₂APKFQG, wherein;
    X₂ = Y, H, or S;

(SEQ ID NO: 373)
CDRHC3 X₃KELRYFDV, wherein;
    X₃ = C, A, N, D, E, Q, G, H, I, L, P or V.
```

The present invention provides an antibody which comprises 3 light chain CDR sequences selected from:

```
                                        (SEQ ID NO: 374)
    CDRLC1 RAX₄X₅SISINLH, wherein;
        X₄ = S or P;
        X₅ = Q or R;

(SEQ ID NO: 375)
    CDRLC2 FAX₆QSX₇S, wherein;
        X₆ = S or R;
        X₇ = I or T;

(SEQ ID NO: 376)
    CDRLC3 QQSNSX₈PLT, wherein;
        X₈ = W or F
```

The present invention provides an antibody which comprises 3 heavy chain CDR sequences selected from:

```
                                        (SEQ ID NO: 371)
CDRHC1 DYYX₁H, wherein;
    X₁ = M or L;

(SEQ ID NO: 372)
CDRHC2 WIDPENGDTEX₂APKFQG, wherein;
    X₂ = Y, H, or S;

(SEQ ID NO: 373)
CDRHC3 X₃KELRYFDV, wherein;
    X₃ = C, A, N, D, E, Q, G, H, I, L, P or V.
``` and 3 light chain CDR sequences selected from:

```
                                        (SEQ ID NO: 374)
    CDRLC1 RAX₄X₅SISINLH, wherein;
        X₄ = S or P;
        X₅ = Q or R;
```

-continued

CDRLC2 FAX$_6$QSX$_7$S, wherein; (SEQ ID NO: 375)
    X$_6$ = S or R;
    X$_7$ = I or T;

CDRLC3 QQSNSX$_8$PLT, wherein; (SEQ ID NO: 376)
    X$_8$ = W or F

The present invention provides an antibody which comprises of an immunoglobulin heavy variable region consisting of one of the following sequences:
SEQ ID NO: 6, SEQ ID NO: 62, SEQ ID NO: 114, SEQ ID NO: 142, SEQ ID NO: 28, SEQ ID NO: 87, SEQ ID NO: 115, SEQ ID NO: 143, SEQ ID NO: 29, SEQ ID NO: 88, SEQ ID NO: 116, SEQ ID NO: 144, SEQ ID NO: 30, SEQ ID NO: 90, SEQ ID NO: 117, SEQ ID NO: 145, SEQ ID NO: 31, SEQ ID NO: 91, SEQ ID NO: 118, SEQ ID NO: 146, SEQ ID NO: 33, SEQ ID NO: 92, SEQ ID NO: 119, SEQ ID NO: 147, SEQ ID NO: 34, SEQ ID NO: 93, SEQ ID NO: 120, SEQ ID NO: 148, SEQ ID NO: 35, SEQ ID NO: 94, SEQ ID NO: 122, SEQ ID NO: 149, SEQ ID NO: 36, SEQ ID NO: 95, SEQ ID NO: 124, SEQ ID NO: 150, SEQ ID NO: 38, SEQ ID NO: 96, SEQ ID NO: 125, SEQ ID NO: 151, SEQ ID NO: 39, SEQ ID NO: 97, SEQ ID NO: 126, SEQ ID NO: 152, SEQ ID NO: 40, SEQ ID NO: 99, SEQ ID NO: 127, SEQ ID NO: 153, SEQ ID NO: 41, SEQ ID NO: 100, SEQ ID NO: 128, SEQ ID NO: 154, SEQ ID NO: 42, SEQ ID NO: 101, SEQ ID NO: 129, SEQ ID NO: 155, SEQ ID NO: 43, SEQ ID NO: 102, SEQ ID NO: 130, SEQ ID NO: 156, SEQ ID NO: 44, SEQ ID NO: 103, SEQ ID NO: 131, SEQ ID NO: 157, SEQ ID NO: 45, SEQ ID NO: 104, SEQ ID NO: 132, SEQ ID NO: 158, SEQ ID NO: 53, SEQ ID NO: 105, SEQ ID NO: 133, SEQ ID NO: 159, SEQ ID NO: 54, SEQ ID NO: 106, SEQ ID NO: 134, SEQ ID NO: 160, SEQ ID NO: 55, SEQ ID NO: 107, SEQ ID NO: 135, SEQ ID NO: 161, SEQ ID NO: 56, SEQ ID NO: 108, SEQ ID NO: 136, SEQ ID NO: 162, SEQ ID NO: 57, SEQ ID NO: 109, SEQ ID NO: 137, SEQ ID NO: 163, SEQ ID NO: 58, SEQ ID NO: 110, SEQ ID NO: 138, SEQ ID NO: 164, SEQ ID NO: 59, SEQ ID NO: 111, SEQ ID NO: 139, SEQ ID NO: 165, SEQ ID NO: 60, SEQ ID NO: 112, SEQ ID NO: 140, SEQ ID NO: 166, SEQ ID NO: 61, SEQ ID NO: 113, SEQ ID NO: 141 and SEQ ID NO: 167.

The present invention provides an antibody which comprises of an immunoglobulin light variable region consisting of one of the following sequences: SEQ ID NO: 7, SEQ ID NO: 169, SEQ ID NO: 181, SEQ ID NO: 193, SEQ ID NO: 32, SEQ ID NO: 170, SEQ ID NO: 182, SEQ ID NO: 194, SEQ ID NO: 37, SEQ ID NO: 171, SEQ ID NO: 183, SEQ ID NO: 195, SEQ ID NO: 42, SEQ ID NO: 172, SEQ ID NO: 184, SEQ ID NO: 196, SEQ ID NO: 46, SEQ ID NO: 173, SEQ ID NO: 185, SEQ ID NO: 197, SEQ ID NO: 47, SEQ ID NO: 174, SEQ ID NO: 186, SEQ ID NO: 198, SEQ ID NO: 48, SEQ ID NO: 175, SEQ ID NO: 187, SEQ ID NO: 199, SEQ ID NO: 49, SEQ ID NO: 176, SEQ ID NO: 188, SEQ ID NO: 200, SEQ ID NO: 50, SEQ ID NO: 177, SEQ ID NO: 189, SEQ ID NO: 201, SEQ ID NO: 51, SEQ ID NO: 178, SEQ ID NO: 190, SEQ ID NO: 52, SEQ ID NO: 179 and SEQ ID NO: 192

The present invention provides an antibody which further comprises human heavy chain acceptor framework. Particularly an antibody wherein said acceptor framework comprises an amino acid sequence selected from the group consisting of SEQ ID NO: 202, SEQ ID NO: 205, SEQ ID NO: 208, SEQ ID NO: 203, SEQ ID NO: 206, SEQ ID NO: 209, SEQ ID NO: 204 and SEQ ID NO: 207.

The present invention provides an antibody which further comprises human light chain acceptor framework. Particularly an antibody wherein said acceptor framework comprises an amino acid sequence selected from the group consisting of SEQ ID NO: 210, SEQ ID NO: 213, SEQ ID NO: 216, SEQ ID NO: 211, SEQ ID NO: 214, SEQ ID NO: 212 and SEQ ID NO: 215.

The present invention provides an antibody which comprises two immunoglobulin variable regions, wherein the said two immunoglobulin variable regions are selected from a group consisting of:

SEQ ID NO: 6 & SEQ ID NO: 7
SEQ ID NO: 6 & SEQ ID NO: 169
SEQ ID NO: 28 & SEQ ID NO: 179
SEQ ID NO: 29 & SEQ ID NO: 179
SEQ ID NO: 30 & SEQ ID NO: 179
SEQ ID NO: 31 & SEQ ID NO: 32
SEQ ID NO: 33 & SEQ ID NO: 179
SEQ ID NO: 34 & SEQ ID NO: 51
SEQ ID NO: 34 & SEQ ID NO: 47
SEQ ID NO: 35 & SEQ ID NO: 179
SEQ ID NO: 36 & SEQ ID NO: 37
SEQ ID NO: 38 & SEQ ID NO: 179
SEQ ID NO: 38 & SEQ ID NO: 51
SEQ ID NO: 38 & SEQ ID NO: 32
SEQ ID NO: 38 & SEQ ID NO: 47
SEQ ID NO: 38 & SEQ ID NO: 52
SEQ ID NO: 39 & SEQ ID NO: 179
SEQ ID NO: 40 & SEQ ID NO: 179
SEQ ID NO: 41 & SEQ ID NO: 42
SEQ ID NO: 43 & SEQ ID NO: 179
SEQ ID NO: 44 & SEQ ID NO: 179
SEQ ID NO: 44 & SEQ ID NO: 51
SEQ ID NO: 44 & SEQ ID NO: 32
SEQ ID NO: 44 & SEQ ID NO: 47
SEQ ID NO: 44 & SEQ ID NO: 52
SEQ ID NO: 45 & SEQ ID NO: 179
SEQ ID NO: 45 & SEQ ID NO: 179
SEQ ID NO: 53 & SEQ ID NO: 41
SEQ ID NO: 54 & SEQ ID NO: 179
SEQ ID NO: 55 & SEQ ID NO: 179
SEQ ID NO: 56 & SEQ ID NO: 179
SEQ ID NO: 57 & SEQ ID NO: 179
SEQ ID NO: 58 & SEQ ID NO: 42
SEQ ID NO: 59 & SEQ ID NO: 179
SEQ ID NO: 60 & SEQ ID NO: 179
SEQ ID NO: 61 & SEQ ID NO: 42
SEQ ID NO: 62 & SEQ ID NO: 42
SEQ ID NO: 87 & SEQ ID NO: 7
SEQ ID NO: 88 & SEQ ID NO: 7
SEQ ID NO: 90 & SEQ ID NO: 7
SEQ ID NO: 91 & SEQ ID NO: 7
SEQ ID NO: 92 & SEQ ID NO: 7
SEQ ID NO: 93 & SEQ ID NO: 7
SEQ ID NO: 94 & SEQ ID NO: 7
SEQ ID NO: 95 & SEQ ID NO: 7
SEQ ID NO: 96 & SEQ ID NO: 7
SEQ ID NO: 97 & SEQ ID NO: 7
SEQ ID NO: 99 & SEQ ID NO: 7
SEQ ID NO: 100 & SEQ ID NO: 7
SEQ ID NO: 101 & SEQ ID NO: 7
SEQ ID NO: 102 & SEQ ID NO: 7
SEQ ID NO: 103 & SEQ ID NO: 7
SEQ ID NO: 104 & SEQ ID NO: 7
SEQ ID NO: 105 & SEQ ID NO: 7
SEQ ID NO: 106 & SEQ ID NO: 171
SEQ ID NO: 106 & SEQ ID NO: 172
SEQ ID NO: 107 & SEQ ID NO: 171
SEQ ID NO: 107 & SEQ ID NO: 172
SEQ ID NO: 108 & SEQ ID NO: 171
SEQ ID NO: 108 & SEQ ID NO: 172
SEQ ID NO: 109 & SEQ ID NO: 170
SEQ ID NO: 110 & SEQ ID NO: 171
SEQ ID NO: 111 & SEQ ID NO: 172
SEQ ID NO: 112 & SEQ ID NO: 169
SEQ ID NO: 113 & SEQ ID NO: 173

-continued

SEQ ID NO: 113 & SEQ ID NO: 174
SEQ ID NO: 113 & SEQ ID NO: 175
SEQ ID NO: 113 & SEQ ID NO: 176
SEQ ID NO: 113 & SEQ ID NO: 177
SEQ ID NO: 113 & SEQ ID NO: 176
SEQ ID NO: 114 & SEQ ID NO: 173
SEQ ID NO: 114 & SEQ ID NO: 174
SEQ ID NO: 114 & SEQ ID NO: 175
SEQ ID NO: 114 & SEQ ID NO: 176
SEQ ID NO: 114 & SEQ ID NO: 177
SEQ ID NO: 115 & SEQ ID NO: 173
SEQ ID NO: 115 & SEQ ID NO: 174
SEQ ID NO: 115 & SEQ ID NO: 175
SEQ ID NO: 115 & SEQ ID NO: 176
SEQ ID NO: 115 & SEQ ID NO: 177
SEQ ID NO: 115 & SEQ ID NO: 181
SEQ ID NO: 115 & SEQ ID NO: 182
SEQ ID NO: 115 & SEQ ID NO: 183
SEQ ID NO: 115 & SEQ ID NO: 184
SEQ ID NO: 115 & SEQ ID NO: 185
SEQ ID NO: 115 & SEQ ID NO: 186
SEQ ID NO: 115 & SEQ ID NO: 187
SEQ ID NO: 115 & SEQ ID NO: 188
SEQ ID NO: 115 & SEQ ID NO: 189
SEQ ID NO: 115 & SEQ ID NO: 190
SEQ ID NO: 115 & SEQ ID NO: 192
SEQ ID NO: 115 & SEQ ID NO: 193
SEQ ID NO: 115 & SEQ ID NO: 194
SEQ ID NO: 115 & SEQ ID NO: 195
SEQ ID NO: 115 & SEQ ID NO: 196
SEQ ID NO: 115 & SEQ ID NO: 197
SEQ ID NO: 115 & SEQ ID NO: 198
SEQ ID NO: 115 & SEQ ID NO: 199
SEQ ID NO: 115 & SEQ ID NO: 200
SEQ ID NO: 115 & SEQ ID NO: 201
SEQ ID NO: 116 & SEQ ID NO: 173
SEQ ID NO: 116 & SEQ ID NO: 174
SEQ ID NO: 116 & SEQ ID NO: 175
SEQ ID NO: 116 & SEQ ID NO: 176
SEQ ID NO: 116 & SEQ ID NO: 177
SEQ ID NO: 117 & SEQ ID NO: 173
SEQ ID NO: 117 & SEQ ID NO: 174
SEQ ID NO: 117 & SEQ ID NO: 175
SEQ ID NO: 117 & SEQ ID NO: 176
SEQ ID NO: 117 & SEQ ID NO: 177
SEQ ID NO: 118 & SEQ ID NO: 178
SEQ ID NO: 118 & SEQ ID NO: 179
SEQ ID NO: 119 & SEQ ID NO: 178
SEQ ID NO: 119 & SEQ ID NO: 179
SEQ ID NO: 119 & SEQ ID NO: 51
SEQ ID NO: 119 & SEQ ID NO: 189
SEQ ID NO: 119 & SEQ ID NO: 46
SEQ ID NO: 119 & SEQ ID NO: 47
SEQ ID NO: 119 & SEQ ID NO: 48
SEQ ID NO: 119 & SEQ ID NO: 49
SEQ ID NO: 119 & SEQ ID NO: 50
SEQ ID NO: 119 & SEQ ID NO: 51
SEQ ID NO: 119 & SEQ ID NO: 52
SEQ ID NO: 120 & SEQ ID NO: 178
SEQ ID NO: 120 & SEQ ID NO: 179
SEQ ID NO: 122 & SEQ ID NO: 176
SEQ ID NO: 124 & SEQ ID NO: 176
SEQ ID NO: 125 & SEQ ID NO: 176
SEQ ID NO: 126 & SEQ ID NO: 176
SEQ ID NO: 127 & SEQ ID NO: 176
SEQ ID NO: 128 & SEQ ID NO: 176
SEQ ID NO: 129 & SEQ ID NO: 176
SEQ ID NO: 130 & SEQ ID NO: 176
SEQ ID NO: 131 & SEQ ID NO: 176
SEQ ID NO: 132 & SEQ ID NO: 176
SEQ ID NO: 133 & SEQ ID NO: 176
SEQ ID NO: 134 & SEQ ID NO: 176
SEQ ID NO: 135 & SEQ ID NO: 176
SEQ ID NO: 136 & SEQ ID NO: 176
SEQ ID NO: 137 & SEQ ID NO: 176
SEQ ID NO: 138 & SEQ ID NO: 176
SEQ ID NO: 139 & SEQ ID NO: 176
SEQ ID NO: 140 & SEQ ID NO: 176
SEQ ID NO: 141 & SEQ ID NO: 176
SEQ ID NO: 142 & SEQ ID NO: 176

-continued

SEQ ID NO: 143 & SEQ ID NO: 176
SEQ ID NO: 144 & SEQ ID NO: 176
SEQ ID NO: 145 & SEQ ID NO: 176
SEQ ID NO: 146 & SEQ ID NO: 176
SEQ ID NO: 147 & SEQ ID NO: 176
SEQ ID NO: 148 & SEQ ID NO: 176
SEQ ID NO: 149 & SEQ ID NO: 176
SEQ ID NO: 150 & SEQ ID NO: 176
SEQ ID NO: 151 & SEQ ID NO: 176
SEQ ID NO: 152 & SEQ ID NO: 176
SEQ ID NO: 153 & SEQ ID NO: 189
SEQ ID NO: 154 & SEQ ID NO: 189
SEQ ID NO: 155 & SEQ ID NO: 189
SEQ ID NO: 156 & SEQ ID NO: 189
SEQ ID NO: 157 & SEQ ID NO: 189
SEQ ID NO: 158 & SEQ ID NO: 189
SEQ ID NO: 159 & SEQ ID NO: 189
SEQ ID NO: 160 & SEQ ID NO: 189
SEQ ID NO: 161 & SEQ ID NO: 189
SEQ ID NO: 161 & SEQ ID NO: 179
SEQ ID NO: 162 & SEQ ID NO: 189
SEQ ID NO: 162 & SEQ ID NO: 179
SEQ ID NO: 163 & SEQ ID NO: 189
SEQ ID NO: 163 & SEQ ID NO: 179
SEQ ID NO: 164 & SEQ ID NO: 189
SEQ ID NO: 164 & SEQ ID NO: 179
SEQ ID NO: 165 & SEQ ID NO: 189
SEQ ID NO: 165 & SEQ ID NO: 179
SEQ ID NO: 166 & SEQ ID NO: 189
SEQ ID NO: 166 & SEQ ID NO: 179
SEQ ID NO: 167 & SEQ ID NO: 189
SEQ ID NO: 167 & SEQ ID NO: 179
SEQ ID NO: 168 & SEQ ID NO: 189

The present invention provides an antibody wherein said human acceptor framework comprises at least one Framework Region amino acid substitution at a key residue, said key residue selected from the group consisting of a residue adjacent to a CDR, a glycosylation site residue, a rare residue, a residue capable of interacting with a p40 subunit of human IL-12, a residue capable of interacting with a CDR, a canonical residue, a contact residue between heavy chain variable region and light chain variable region; a residue within a Vernier zone and a residue in a region that overlaps between a Chothia-defined VH domain CDR1 and a Kabat-defined first heavy chain framework. In a further aspect the said human acceptor framework comprises at least one Framework Region amino acid substitution, wherein the amino acid sequence of the framework is at least 65% identical to the sequence of said human acceptor framework and comprises at least 70 amino acid residues identical to said human acceptor framework.

The present invention provides an antibody that is a consensus human VH domain. Additionally, the present invention provides for an antibody that is a consensus human VL domain.

The present invention provides an antibody wherein said human acceptor framework comprises at least one Framework Region amino acid substitution, wherein the amino acid sequence of the framework is at least 65% identical to the sequence of said human acceptor framework and comprises at least 70 amino acid residues identical to said human acceptor framework.

The present invention describes an antibody in which the antibody contains a human or non-human primate heavy chain immunoglobulin constant region selected from a group consisting of IgG1, IgG2, IgG3, IgG4, IgM, IgE and IgA.

The present invention describes an antibody in which the antibody contains a human or non-human primate light chain immunoglobulin constant region selected from a group consisting of kappa or lambda.

The present invention also provides a method of producing the antibody of the present invention the method comprising
  (i) immunising an animal with human IL-12p40 or a fragment of human IL-12p40 to obtain a first panel of antibodies;
  (ii) selecting from the first panel antibodies which bind to human IL-12 and human IL-23 to form a second panel of antibodies; and
  (iii) selecting from the second panel antibodies which bind p40 existing as a monomer (human IL-12p40) and as a homodimer (human IL-12p80) and which inhibit the binding of human IL-12 to human IL-12Rβ2 and human IL-23 to human IL-23R but do not inhibit the binding of human IL-12 or human IL-23 or human IL-12p40 or human IL-12p80 to human IL-12Rβ1.

This method may also comprise at step (ii) selecting antibodies which also bind a peptide having the sequence VQVQGKSKREKKDRVFTDKTSATVICRKNASISV (SEQ ID NO. 65).

The present invention also provides another method of producing the antibody of the present invention the method comprising
  (i) immunising an animal with a peptide having the sequence VQVQGKSKREKKDRVFTDKTSATVI-CRKNASISV (SEQ ID NO. 65) to obtain a first panel of antibodies;
  (ii) selecting from the first panel antibodies which bind to human IL-12 and human IL-23 to form a second panel of antibodies; and
  (iii) selecting from the second panel antibodies which bind p40 existing as a monomer (human IL-12p40) and as a homodimer (human IL-12p80) and which inhibit the binding of human IL-12 to human IL-12Rβ2 and human IL-23 to human IL-23R but do not inhibit the binding of human IL-12 or human IL-23 or human IL-12p40 or human IL-12p80 to human IL-12Rβ1.

The present invention also provides a further method of producing the antibody of the present invention the method comprising
  (i) obtaining a human antibody display library to form a first panel of antibodies;
  (ii) selecting from the first panel antibodies which bind to human IL-12 and human IL-23 to form a second panel of antibodies; and
  (iii) selecting from the second panel antibodies which bind p40 existing as a monomer (human IL-12p40) and/or as a homodimer (human IL-12p80) and which inhibit the binding of human IL-12 to human IL-12Rβ2 and human IL-23 to human IL-23R but do not inhibit the binding of human IL-12 or human IL-23 or human IL-12p40 or human IL-12p80 to human IL-12Rβ1.

The present invention provides a nucleic acid molecule which encodes a VH domain of the present invention. It is preferred that the nucleic acid molecule has a sequence selected from:

| | | |
|---|---|---|
| SEQ ID NO: 217 | SEQ ID NO: 264 | SEQ ID NO: 302 |
| SEQ ID NO: 218 | SEQ ID NO: 266 | SEQ ID NO: 303 |
| SEQ ID NO: 219 | SEQ ID NO: 267 | SEQ ID NO: 304 |
| SEQ ID NO: 220 | SEQ ID NO: 268 | SEQ ID NO: 305 |
| SEQ ID NO: 222 | SEQ ID NO: 269 | SEQ ID NO: 306 |
| SEQ ID NO: 223 | SEQ ID NO: 270 | SEQ ID NO: 307 |
| SEQ ID NO: 224 | SEQ ID NO: 271 | SEQ ID NO: 308 |
| SEQ ID NO: 225 | SEQ ID NO: 272 | SEQ ID NO: 309 |
| SEQ ID NO: 227 | SEQ ID NO: 273 | SEQ ID NO: 310 |
| SEQ ID NO: 228 | SEQ ID NO: 274 | SEQ ID NO: 311 |
| SEQ ID NO: 229 | SEQ ID NO: 275 | SEQ ID NO: 312 |
| SEQ ID NO: 230 | SEQ ID NO: 276 | SEQ ID NO: 313 |
| SEQ ID NO: 232 | SEQ ID NO: 277 | SEQ ID NO: 314 |
| SEQ ID NO: 233 | SEQ ID NO: 278 | SEQ ID NO: 315 |
| SEQ ID NO: 234 | SEQ ID NO: 279 | SEQ ID NO: 316 |
| SEQ ID NO: 242 | SEQ ID NO: 280 | SEQ ID NO: 317 |
| SEQ ID NO: 243 | SEQ ID NO: 281 | SEQ ID NO: 318 |
| SEQ ID NO: 244 | SEQ ID NO: 282 | SEQ ID NO: 319 |
| SEQ ID NO: 245 | SEQ ID NO: 283 | SEQ ID NO: 320 |
| SEQ ID NO: 246 | SEQ ID NO: 284 | SEQ ID NO: 321 |
| SEQ ID NO: 247 | SEQ ID NO: 285 | SEQ ID NO: 322 |
| SEQ ID NO: 248 | SEQ ID NO: 286 | SEQ ID NO: 323 |
| SEQ ID NO: 249 | SEQ ID NO: 287 | SEQ ID NO: 324 |
| SEQ ID NO: 250 | SEQ ID NO: 289 | SEQ ID NO: 325 |
| SEQ ID NO: 251 | SEQ ID NO: 291 | SEQ ID NO: 326 |
| SEQ ID NO: 252 | SEQ ID NO: 292 | SEQ ID NO: 327 |
| SEQ ID NO: 254 | SEQ ID NO: 293 | SEQ ID NO: 328 |
| SEQ ID NO: 255 | SEQ ID NO: 294 | SEQ ID NO: 329 |
| SEQ ID NO: 257 | SEQ ID NO: 295 | SEQ ID NO: 330 |
| SEQ ID NO: 258 | SEQ ID NO: 296 | SEQ ID NO: 331 |
| SEQ ID NO: 259 | SEQ ID NO: 297 | SEQ ID NO: 332 |
| SEQ ID NO: 260 | SEQ ID NO: 298 | SEQ ID NO: 333 |
| SEQ ID NO: 261 | SEQ ID NO: 299 | SEQ ID NO: 334 |
| SEQ ID NO: 262 | SEQ ID NO: 300 | SEQ ID NO: 335 |
| SEQ ID NO: 263 | SEQ ID NO: 301 | |

The present invention provides a nucleic acid molecule which encodes a VL domain of the present invention. It is preferred that the nucleic acid molecule has a sequence selected from:

| | | |
|---|---|---|
| SEQ ID NO: 221 | SEQ ID NO: 341 | SEQ ID NO: 356 |
| SEQ ID NO: 226 | SEQ ID NO: 342 | SEQ ID NO: 357 |
| SEQ ID NO: 231 | SEQ ID NO: 343 | SEQ ID NO: 358 |
| SEQ ID NO: 235 | SEQ ID NO: 344 | SEQ ID NO: 359 |
| SEQ ID NO: 236 | SEQ ID NO: 345 | SEQ ID NO: 361 |
| SEQ ID NO: 237 | SEQ ID NO: 346 | SEQ ID NO: 362 |
| SEQ ID NO: 238 | SEQ ID NO: 347 | SEQ ID NO: 363 |
| SEQ ID NO: 239 | SEQ ID NO: 348 | SEQ ID NO: 364 |
| SEQ ID NO: 240 | SEQ ID NO: 350 | SEQ ID NO: 365 |
| SEQ ID NO: 241 | SEQ ID NO: 351 | SEQ ID NO: 366 |
| SEQ ID NO: 336 | SEQ ID NO: 352 | SEQ ID NO: 367 |
| SEQ ID NO: 338 | SEQ ID NO: 353 | SEQ ID NO: 368 |
| SEQ ID NO: 339 | SEQ ID NO: 354 | SEQ ID NO: 369 |
| SEQ ID NO: 340 | SEQ ID NO: 355 | SEQ ID NO: 370 |

The present invention also provides a method of treating a disease in a subject comprising administering to the subject an antibody of the present invention wherein the disease is selected from the group consisting of rheumatoid arthritis, osteoarthritis, reactive arthritis, psoriatic arthritis, bone loss, airways hypersensitivity, chronic obstructive pulmonary disease, a demyelinating disorder, psoriasis, multiple sclerosis, dermal hypersensitivity, acute and chronic transplant rejection, allograft rejection, graft-versus host disease, systemic sclerosis, systemic lupus erythematosus, an autoimmune inflammatory bowel disease, a urological inflammatory disorder, a cardiovascular disease, a vasculitis, a periodic fever, a glucose metabolism disorder, a pulmonary disease, a cancer, peridontitis, hepatic stromal keratitis, an allergy, inflammatory pain, a spondyloarthropathy, septicaemia, septic or endotoxic shock, meningitis, surgical trauma, an autoimmune haematological disorder, Alzheimer's disease, sarcoidosis, cirrhosis, hepatitis (including autoimmune hepatitis), primary biliary cirrhosis, uveitis, thyroiditis, atherosclerosis, alopecia, Wilson's disease, glomerulonephritis and dislipidemia.

The present invention further provides at least one antibody, specified portion or variant thereof in a method or composition, when administered in a therapeutically effective amount, for modulation, for treating or reducing the symptoms of at least one IL-12 and/or IL-23 disease in a cell, tissue, organ, animal or patient and/or, as needed in many different conditions, such as but not limited to, prior to, subsequent to, or during a related disease or treatment condition, as known in the art and/or as described herein.

The present invention further provides at least one antibody, specified portion or variant thereof in a method or composition, when administered in a therapeutically effective amount, for modulation, for treating or reducing the symptoms of immune, neurological and related disorders, such as, but not limited to, arthritis, osteoarthritis, rheumatoid arthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type IC, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, yersinia and salmonella associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasculitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjorgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), $T_H 2$ Type and $T_H 1$ Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma), Abetalipoprotemia, Acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti cd3 therapy, antiphospholipid syndrome, anti-receptor hypersensitivity reactions, aordic and peripheral aneuryisms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, Burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chromic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetes, diabetes mellitus, diabetic ateriosclerotic disease, Diffuse Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, epstein-barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallerrorden-Spatz disease, Hashimoto's thyroiditis, hay fever, heart transplant rejection, hemachromatosis, hemodialysis, hemolytic uremic syndrome/thrombolytic thrombocytopenic purpura, hemorrhage, hepatitis (A), His bundle arrythmias, EQV infection/HIV neuropathy, Hodgkin's disease, hyperkinetic movement disorders, hypersensitity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza A, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, legionella, leishmaniasis, leprosy, lesions of the corticospinal system, lipedema, liver transplant rejection, lymphedema, malaria, malignant lymphoma, malignant histiocytosis, malignant melanoma, meningitis, meningococcemia, metabolic/idiopathic, migraine headache, mitochondrial multiple system disorder, mixed connective tissue disease, monoclonal gammopathy, multiple myeloma, multiple systems degenerations (Mencel Dejerine-Thomas Shi-Drager and Machado-Joseph), myasthenia gravis, *mycobacterium avium* intracellulare, *mycobacterium tuberculosis*, myelodyplastic syndrome, myocardial infarction, myocardial ischemic disorders, nasopharyngeal carcinoma, neonatal chronic lung disease, nephritis, nephrosis, neurodegenerative diseases, neurogenic I muscular atrophies, neutropenic fever, non-hodgkins lymphoma, occlusion of the abdominal aorta and its branches, occulsive arterial disorders, okt3 therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherlosclerotic disease, peripheral vascular disorders, peritonitis, pernicious anemia, *Pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, Progressive supranucleo Palsy, primary pulmonary hypertension, radiation therapy, Raynaud's phenomenon and disease, Raynoud's disease, Refsum's disease, regular narrow QRS tachycardia, renovascular hypertension, reperfusion injury, restrictive cardiomyopathy, sarcomas, scleroderma, senile chorea, Senile Dementia of Lewy body type, seronegative arthropathies, shock, sickle cell anemia, skin allograft rejection, skin changes syndrome, small bowel transplant rejection, solid tumors, specific arrythmias, spinal ataxia, spinocerebellar degenerations, streptococcal myositis, structural lesions of the cerebellum, Subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, Telangiectasia, thromboangitis obliterans, thrombocytopenia, toxicity, transplants, trauma/hemorrhage, type M hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue.

Included with the scope of the invention is an anti-IL-12/IL-23 antibody which has been affinity matured.

Numerous methods for affinity maturation of antibodies are known in the art. Many of these are based on the general strategy of generating panels or libraries of variant proteins by mutagenesis followed by selection and/or screening for improved affinity. Mutagenesis is often performed at the DNA level, for example by error prone PCR (Thie 2009), by gene shuffling (Kolkman 2001), by use of mutagenic chemicals or irradiation, by use of 'mutator' strains with error prone replication machinery (Greener 1996) or by somatic hypermutation approaches that harness natural affinity maturation machinery (Peled 2008). Mutagenesis can also be performed at the RNA level, for example by use of Qβ replicase (Kopsidas 2006). Library-based methods allowing screening for improved variant proteins can be based on various display technologies such as phage, yeast, ribosome, bacterial or mammalian cells, and are well known in the art (Benhar 2007). Affinity maturation can be achieved by more directed/predictive methods for example by site-directed mutagenesis or gene synthesis guided by findings from 3D protein modeling (see for example Queen 1989; or U.S. Pat. Nos 6,180,370; or 5,225,539).

Accordingly the present invention provides a method for producing an antigen binding domain that binds human IL-12p40, the method comprising a. providing, by way of addition, deletion, substitution or insertion of one or more amino acids in the amino acid sequence of a parent VH domain comprising HCDR1, HCDR2 and HCDR3, wherein the parent VH domain HCDR1, HCDR2 and HCDR3 are a set of CDRs defined above, a VH domain which is an amino acid sequence variant of the parent VH domain, and optionally combining the VH domain thus provided with one or more VL domains to provide one or more VH/VL combinations; and b. testing said VH domain which is an amino acid sequence variant of the parent VH domain or the VH/VL combination or combinations to identify an antibody antigen binding domain for human IL-12p40.

It is preferred that the parent VH domain has the VH domain amino acid sequence shown in SEQ ID NO: 6, SEQ ID NO: 62, SEQ ID NO: 114, SEQ ID NO: 142, SEQ ID NO: 28, SEQ ID NO: 87, SEQ ID NO: 115, SEQ ID NO: 143, SEQ ID NO: 29, SEQ ID NO: 88, SEQ ID NO: 116, SEQ ID NO: 144, SEQ ID NO: 30, SEQ ID NO: 90, SEQ ID NO: 117, SEQ ID NO: 145, SEQ ID NO: 31, SEQ ID NO: 91, SEQ ID NO: 118, SEQ ID NO: 146, SEQ ID NO: 33, SEQ ID NO: 92, SEQ ID NO: 119, SEQ ID NO: 147, SEQ ID NO: 34, SEQ ID NO: 93, SEQ ID NO: 120, SEQ ID NO: 148, SEQ ID NO: 35, SEQ ID NO: 94, SEQ ID NO: 122, SEQ ID NO: 149, SEQ ID NO: 36, SEQ ID NO: 95, SEQ ID NO: 124, SEQ ID NO: 150, SEQ ID NO: 38, SEQ ID NO: 96, SEQ ID NO: 125, SEQ ID NO: 151, SEQ ID NO: 39, SEQ ID NO: 97, SEQ ID NO: 126, SEQ ID NO: 152, SEQ ID NO: 40, SEQ ID NO: 99, SEQ ID NO: 127, SEQ ID NO: 153, SEQ ID NO: 41, SEQ ID NO: 100, SEQ ID NO: 128, SEQ ID NO: 154, SEQ ID NO: 42, SEQ ID NO: 101, SEQ ID NO: 129, SEQ ID NO: 155, SEQ ID NO: 43, SEQ ID NO: 102, SEQ ID NO: 130, SEQ ID NO: 156, SEQ ID NO: 44, SEQ ID NO: 103, SEQ ID NO: 131, SEQ ID NO: 157, SEQ ID NO: 45, SEQ ID NO: 104, SEQ ID NO: 132, SEQ ID NO: 158, SEQ ID NO: 53, SEQ ID NO: 105, SEQ ID NO: 133, SEQ ID NO: 159, SEQ ID NO: 54, SEQ ID NO: 106, SEQ ID NO: 134, SEQ ID NO: 160, SEQ ID NO: 55, SEQ ID NO: 107, SEQ ID NO: 135, SEQ ID NO: 161, SEQ ID NO: 56, SEQ ID NO: 108, SEQ ID NO: 136, SEQ ID NO: 162, SEQ ID NO: 57, SEQ ID NO: 109, SEQ ID NO: 137, SEQ ID NO: 163, SEQ ID NO: 58, SEQ ID NO: 110, SEQ ID NO: 138, SEQ ID NO: 164, SEQ ID NO: 59, SEQ ID NO: 111, SEQ ID NO: 139, SEQ ID NO: 165, SEQ ID NO: 60, SEQ ID NO: 112, SEQ ID NO: 140, SEQ ID NO: 166, SEQ ID NO: 61, SEQ ID NO: 113, SEQ ID NO: 141 or SEQ ID NO: 167.

The VH domain which is an amino acid sequence variant of the parent VH domain may be provided by CDR mutagenesis.

In this method the one or more VL domains are provided by way of addition, deletion, substitution or insertion of one or more amino acids in the amino acid sequence of a parent VL domain comprising LCDR1, LCDR2 and LCDR3, wherein the parent VL domain LCDR1, LCDR2 and LCDR3 are a VL set of CDRs as defined above, producing one or more VL domains each of which is an amino acid sequence variant of the parent VL domain.

It is preferred that the parent VL domain has the VL domain amino acid sequence shown in SEQ ID NO: 7, SEQ ID NO: 169, SEQ ID NO: 181, SEQ ID NO: 193, SEQ ID NO: 32, SEQ ID NO: 170, SEQ ID NO: 182, SEQ ID NO: 194, SEQ ID NO: 37, SEQ ID NO: 171, SEQ ID NO: 183, SEQ ID NO: 195, SEQ ID NO: 42, SEQ ID NO: 172, SEQ ID NO: 184, SEQ ID NO: 196, SEQ ID NO: 46, SEQ ID NO: 173, SEQ ID NO: 185, SEQ ID NO: 197, SEQ ID NO: 47, SEQ ID NO: 174, SEQ ID NO: 186, SEQ ID NO: 198, SEQ ID NO: 48, SEQ ID NO: 175, SEQ ID NO: 187, SEQ ID NO: 199, SEQ ID NO: 49, SEQ ID NO: 176, SEQ ID NO: 188, SEQ ID NO: 200, SEQ ID NO: 50, SEQ ID NO: 177, SEQ ID NO: 189, SEQ ID NO: 201, SEQ ID NO: 51, SEQ ID NO: 178, SEQ ID NO: 190, SEQ ID NO: 52, SEQ ID NO: 179 or SEQ ID NO: 192.

The VL domain which is an amino acid sequence variant of the parent VL domain may be provided by CDR mutagenesis.

The antibody antigen-binding domain may be provided as a component of an IgG, scFv or Fab antibody molecule.

The present invention also provides a method for producing an antigen binding domain that binds human IL-12p40 which method comprises:

a. providing starting nucleic acid encoding a VH domain or a starting repertoire of nucleic acids each encoding a VH domain, wherein the VH domain is selected from the group consisting of SEQ ID NO: 6, SEQ ID NO: 62, SEQ ID NO: 114, SEQ ID NO: 142, SEQ ID NO: 28, SEQ ID NO: 87, SEQ ID NO: 115, SEQ ID NO: 143, SEQ ID NO: 29, SEQ ID NO: 88, SEQ ID NO: 116, SEQ ID NO: 144, SEQ ID NO: 30, SEQ ID NO: 90, SEQ ID NO: 117, SEQ ID NO: 145, SEQ ID NO: 31, SEQ ID NO: 91, SEQ ID NO: 118, SEQ ID NO: 146, SEQ ID NO: 33, SEQ ID NO: 92, SEQ ID NO: 119, SEQ ID NO: 147, SEQ ID NO: 34, SEQ ID NO: 93, SEQ ID NO: 120, SEQ ID NO: 148, SEQ ID NO: 35, SEQ ID NO: 94, SEQ ID NO: 122, SEQ ID NO: 149, SEQ ID NO: 36, SEQ ID NO: 95, SEQ ID NO: 124, SEQ ID NO: 150, SEQ ID NO: 38, SEQ ID NO: 96, SEQ ID NO: 125, SEQ ID NO: 151, SEQ ID NO: 39, SEQ ID NO: 97, SEQ ID NO: 126, SEQ ID NO: 152, SEQ ID NO: 40, SEQ ID NO: 99, SEQ ID NO: 127, SEQ ID NO: 153, SEQ ID NO: 41, SEQ ID NO: 100, SEQ ID NO: 128, SEQ ID NO: 154, SEQ ID NO: 42, SEQ ID NO: 101, SEQ ID NO: 129, SEQ ID NO: 155, SEQ ID NO: 43, SEQ ID NO: 102, SEQ ID NO: 130, SEQ ID NO: 156, SEQ ID NO: 44, SEQ ID NO: 103, SEQ ID NO: 131, SEQ ID NO: 157, SEQ ID NO: 45, SEQ ID NO: 104, SEQ ID NO: 132, SEQ ID NO: 158, SEQ ID NO: 53, SEQ ID NO: 105, SEQ ID NO: 133, SEQ ID NO: 159, SEQ ID NO: 54, SEQ ID NO: 106, SEQ ID NO: 134, SEQ ID NO: 160, SEQ ID NO: 55, SEQ ID NO: 107, SEQ ID NO: 135, SEQ ID NO: 161, SEQ ID NO: 56, SEQ ID NO: 108, SEQ ID NO: 136, SEQ ID NO: 162, SEQ ID NO: 57, SEQ ID NO: 109, SEQ ID NO: 137, SEQ ID NO: 163, SEQ ID NO: 58, SEQ ID NO: 110, SEQ ID NO: 138, SEQ ID NO: 164, SEQ ID NO: 59, SEQ ID NO: 111, SEQ ID NO: 139, SEQ ID NO: 165, SEQ ID NO: 60, SEQ ID NO: 112, SEQ ID NO: 140, SEQ ID NO: 166, SEQ ID NO: 61, SEQ ID NO: 113, SEQ ID NO: 141 and SEQ ID NO: 167;

b. combining said starting nucleic acid or starting repertoire with donor nucleic acid or donor nucleic acids encoding or produced by mutation of the amino acid sequence, such that said donor nucleic acid is or donor nucleic acids are inserted into the VH domain in the starting nucleic acid or starting repertoire, so as to provide a product repertoire of nucleic acids encoding VH domains; expressing the nucleic acids of said product repertoire to produce product VH domains;

c. optionally combining said product VH domains with one or more VL domains;

d. selecting a antigen binding domain for human IL-12p40, e. recovering said antigen binding domain or nucleic acid encoding it, wherein, the antigen binding domain comprises a product VH domain and optionally a VL domain The present invention also provides a method for producing an antigen binding domain that binds human IL-12p40 which method comprises:

a. providing starting nucleic acid encoding a VL domain or a starting repertoire of nucleic acids each encoding a VL domain, wherein the VL domain is selected from the group consisting of SEQ ID NO: 7, SEQ ID NO: 169, SEQ ID NO: 181, SEQ ID NO: 193, SEQ ID NO: 32, SEQ ID NO: 170, SEQ ID NO: 182, SEQ ID NO: 194, SEQ ID NO: 37, SEQ ID NO: 171, SEQ ID NO: 183, SEQ ID NO: 195, SEQ ID NO: 42, SEQ ID NO: 172, SEQ ID NO: 184, SEQ ID NO: 196, SEQ ID NO: 46, SEQ ID NO: 173, SEQ ID NO: 185, SEQ ID NO: 197, SEQ ID NO: 47, SEQ ID NO: 174, SEQ ID NO: 186, SEQ ID NO: 198, SEQ ID NO: 48, SEQ ID NO: 175, SEQ ID NO: 187, SEQ ID NO: 199, SEQ ID NO: 49, SEQ ID NO: 176, SEQ ID NO: 188, SEQ ID NO: 200, SEQ ID NO: 50, SEQ ID NO: 177, SEQ ID NO: 189, SEQ ID NO: 201, SEQ ID NO: 51, SEQ ID NO: 178, SEQ ID NO: 190, SEQ ID NO: 52, SEQ ID NO: 179 and SEQ ID NO: 192 b. combining said starting nucleic acid or starting repertoire with donor nucleic acid or donor nucleic acids encoding or produced by mutation of the amino acid sequence, such that said donor nucleic acid is or donor nucleic acids are inserted into the VL domain in the starting nucleic acid or starting repertoire, so as to provide a product repertoire of nucleic acids encoding VL domains; expressing the nucleic acids of said product repertoire to produce product VL domains;

c. optionally combining said product VL domains with one or more VH domains;

d. selecting a antigen binding domain for human IL-12p40, e. recovering said antigen binding domain or nucleic acid encoding it, wherein the antigen binding domain comprises a product VH domain and optionally a VL domain.

In these methods the donor nucleic acids may be produced by mutation of said HCDR1 and/or HCDR2 and/or HCDR3. The donor nucleic acid may also be provided by random mutation of nucleic acid.

The antibody of the present invention may be selected from a wide range of antibody molecules well known in the art. In certain embodiments the antibody is selected from a group consisting of an immunoglobulin molecule, a monoclonal antibody (mAb), a chimeric antibody, a CDR-grafted antibody, a humanised antibody, a synhumanised antibody, a primatised antibody, a domain antibody, a camelid derived antibody fragment, a Fab, a Fab', a F(ab')$_2$, a Fv, a scFv, a disulphide linked Fv, a diabody, a multivalent antibody, a dual specific antibody, a bispecific antibody, an immunoglobulin constant region binding domain and a protein scaffold into which antigen binding domains have been grafted (as exemplified in Qiu et al. 2007 Nat Biotechnol 25 921-9) and variants thereof. The present invention also extends to antibody compositions, nucleic acids encoding the antibody and complementary nucleic acids, vectors, host cells, compositions, formulations, devices, transgenic animals, transgenic plants and methods of making and using thereof, as described and enabled herein, in combination with what is known in the art.

The present invention provides isolated nucleic acid molecules comprising, complementary or hybridising to a polynucleotide encoding specific antibodies or variants thereof, comprising at least one specified sequence, domain, portion or variant thereof. The present invention provides recombinant vectors comprising said antibody derived nucleic acid molecules, host cells containing such nucleic acids and/or recombinant vectors, as well as methods of making and/or using such antibody nucleic acids, vectors and/or host cells.

The present invention also provides at least one composition comprising (a) an isolated antibody, specified portion or variant thereof encoding nucleic acid and/or antibody as described herein; and (b) a suitable carrier or diluent. The carrier or diluent can optionally be pharmaceutically acceptable, according to known methods. The composition can optionally further comprise at least one other compound, protein or composition.

The present invention also provides at least one method for expressing the antibodies or variants thereof in a host cell, comprising culturing a host cell as described herein and/or as known in the art under conditions in which the antibody or variant thereof is expressed in recoverable amounts.

The present invention provides at least one antibody encoding nucleic acid, comprising a nucleic acid that hybridises under stringent conditions, or has at least 95% identity, to a nucleic acid encoding an antibody. The invention further provides an isolated antibody encoded by such nucleic acid. The invention further provides an antibody vector, comprising such a nucleic acid, wherein the vector optionally further comprises at least one promoter selected from the group consisting of a late or early SV40 promoter, a CMV promoter, an HSV tk promoter, a pgk promoter, a human immunoglobulin promoter, and an EF-1α promoter. Such a vector can optionally further comprise at least one selection gene or portion thereof selected from at least one of methotrexate (MTX), dihydrofolate reductase (DHFR), green fluorescent protein (GFP), neomycin (G418), or glutamine synthetase (GS). The invention further comprises a mammalian host cell comprising such an isolated nucleic acid, optionally, wherein said host is at least one selected from COS-1, COS-7, HEK293, BHK21, CHO, BSC-1, HwpG2, PerCP, 653, SP2/0, 293, HeLa, myeloma, or lymphoma cells, or any derivative, immortalised or transformed cell thereof.

The invention also provides at least one method for producing at least one antibody composition, comprising at least one antibody and a carrier or diluent, optionally, further wherein said carrier or diluent is pharmaceutically acceptable, and/or further comprising at least one compound or protein selected from a TNF antagonist, an antirheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an IL-23 agent, an IL-12 agent, a mineral, a nutritional, a thyroid agent, a vitamin, a calcium related hormone, an antidiarrheal, an antitussive, an antiemetic, an antiulcer, a laxative, an anticoagulant, an erythropoietin, a filgrastim, a sargramostim, an immunising agent, an immunoglobulin, an immunosuppressive, a growth hormone, a hormone replacement drug, an estrogen receptor modulator, a mydriatic, a cycloplegic, an alkylating agent, an antimetabolite, a mitotic inhibitor, a radiopharmaceutical, an antidepressant, an antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha, a cytokine, and a cytokine antagonist.

The present invention also provides at least one method for treating an IL-12/23 condition in a cell, tissue, organ or animal, comprising contacting or administering a immune related- or infectious related-condition modulating effective amount of at least one antibody with, or to, said cell, tissue, organ or animal, optionally, wherein said animal is a primate, optionally a monkey or a human. The method can further optionally include wherein said effective amount is about 0.001-100 mg/kilogram of said cells, tissue, organ or animal. Such a method can further include wherein said contacting or said administrating is by at least one mode selected from intravenous, intramuscular, bolus, intraperitoneal, subcutaneous, respiratory, inhalation, topical, nasal, vaginal, rectal, buccal, sublingual, intranasal, subdermal, and transdermal. Such a method can further comprise administering, prior, concurrently or after said contacting or administering, at least one composition comprising a therapeutically effective amount of at least one compound or protein selected from at least one of a TNF antagonist, an antirheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an IL-23 agent, and IL-12 agent, a mineral, a nutritional, a thyroid agent, a vitamin, a calcium related hormone, an antidiarrheal, an antitussive, an antiemetic, an antiulcer, a laxative, an anticoagulant, an erythropoietin, a filgrastim, a sargramostim, an immunising agent, an immunoglobulin, an immunosuppressive, a growth hormone, a hormone replacement drug, an estrogen receptor modulator, a mydriatic, a cycloplegic, an alkylating agent, an antimetabolite, a mitotic inhibitor, a radiopharmaceutical, an antidepressant, an antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha, a cytokine, and a cytokine antagonist.

The invention also includes at least one formulation comprising at least one antibody, and at least one formulating agent selected from sterile water, sterile buffered water, or at least one preservative selected from the group consisting of phenol, m-cresol, p-cresol, o-cresol, chlorocresol, benzyl alcohol, alkylparaben, benzalkonium chloride, benzethonium chloride, sodium dehydroacetate and thimerosal, or mixtures thereof in an aqueous diluent, optionally, wherein the concentration of protein is about 0.1 mg/ml to about 100 mg/ml, further comprising at least one isotonicity agent or at least one physiologically acceptable buffer.

The invention also provides at least one article of manufacture for human pharmaceutical use, comprising packaging material and a container comprising a solution or a lyophilised form of at least one antibody of the invention, optionally, further wherein said container is a glass or plastic container having a stopper for multi-use administration, optionally, further wherein said container is a blister pack, capable of being punctured and used in intravenous, intramuscular, bolus, intraperitoneal, subcutaneous, topical, respiratory, inhalation, nasal, vaginal, rectal, buccal, sublingual, intranasal, subdermal, or transdermal administration; said container is a component of an intravenous, intramuscular, bolus, intraperitoneal, subcutaneous, respiratory, inhalation, nasal, vaginal, topical, rectal, buccal, sublingual, intranasal, subdermal, or transdermal delivery device or system; said container is a component of an injector or pen-injector device or system for intravenous, intramuscular, bolus, intraperitoneal, subcutaneous, respiratory, inhalation, topical, nasal, vaginal, rectal, buccal, sublingual, intranasal, subdermal, or transdermal delivery.

The invention also provides at least one method for producing at least one antibody of the invention, comprising providing a host cell, transgenic animal, transgenic plant or plant cell capable of expressing in recoverable amounts said human antibody, optionally, further wherein said host cell is a mammalian cell, a plant cell or a yeast cell; said transgenic animal is a mammal; said transgenic mammal is selected from a goat, a cow, a sheep, a horse, and a non-human primate.

The invention further provides at least one method for treating at least one IL-12/23 mediated disorder, comprising at least one of (a) administering an effective amount of a composition or pharmaceutical composition comprising at least one binding protein to a cell, tissue, organ, animal or patient in need of such modulation, treatment or therapy; and (b) further administering, before, concurrently, and/or after said administering in (a) above, at least one selected from an immune related therapeutic, a TNF antagonist, an antirheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, a neurological agent, a mineral, a nutritional, a thyroid agent, a vitamin, a calcium related hormone, an antidiarrheal, an antitussive, an antiemetic, an antiulcer, a laxative, an anticoagulant, an erythropoietin, a filgrastim, a sargramostim, an immunising agent, an immunoglobulin, an immunosuppressive, a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, adonepezil, a tacrine, an asthma medication, a beta agonist, an inhaled steroid, a leukotriene inhibitor, a methylxanthine, a cromolyn, an epinephrine or analog, a dornase alpha, a cytokine, and a cytokine antagonist.

IL-12p40 is present in the proteins IL-12 and IL-23 and exists as an IL-12p40 monomer and an IL-12p80 homodimer. The present invention describes an antibody that binds to IL-12, IL-23, IL-12p40, IL-12p80, and will likely bind to any newly discovered proteins which contain the IL-12p40 subunit. The antibody specifically binds to IL-12p40 but not IL-12p35 or IL-23p19. The present invention further provides compositions, formulations, methods, devices and uses of such antibodies, including therapeutic uses.

In one embodiment the antibody is able to neutralise IL-12 to IL-12Rβ2 which this thought to bind to IL-12 at the p40/p35 interface. In another embodiment the antibody is able to inhibit the binding of IL-23 to IL-23R which is likely thought to be mediated through interactions at the p19/p40 interface. In a further embodiment the antibody is able to inhibit the binding of IL-12 to IL-12Rβ2 and IL-23 binding to IL-23R. By binding to IL-12p40 in a location close to the interface with p35 or p19 the antibody is inhibiting the binding of the relevant receptors to IL-12 and/or IL-23.

This invention describes antibodies that bind to both IL-12p40/80, but not neutralise the binding of IL-12p40 or IL-12p80 to IL-12Rβ1. Regulation of IL-12 or IL-23 systems can still be accomplished via the IL-12p40/80 subunit in the presence of the antibody, since these proteins are still free to bind to IL-12Rβ1. The advantage of the following method of action is that it will allow the natural regulators of the IL-12 and IL-23 system (IL-12p40/p80) to continue to compete along with the antibody which also acts as an antagonist of IL-12 and IL-23. Hence a dual antagonist system could be established via this method of action leading to greater efficacy of the antibody when used as a therapeutic. There are also potential safety profile improvements in using antibodies that do not inhibit the IL-12p40/80 biological function. IL-12p40/80 has recently been shown to have divergent roles in addition to serving as an antagonist and regulating the IL-12/IL-23 pathways. The antibody will not prevent IL-12p40/80 acting as a chemoattractant for macrophages and as an inducer of DC migration in response to a pathogen challenge. This could lead to improvements in the safety profile of the antibody when administered as a therapeutic agent.

All scientific citations, patents, patent applications and manufacturer's technical specifications referred to hereinafter are incorporated herein by reference in their entirety.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

It is to be understood that unless otherwise indicated, the present invention is not limited to specific formulation components, manufacturing methods, dosage regimens, or the like, as such may vary.

It must be noted that, as used in the subject specification, the singular forms "a", "an" and "the" include plural aspects unless the context clearly dictates otherwise. Thus, for example, reference to "a" includes a single as well as two or more; reference to "an" includes a single as well as two or more; reference to "the" includes a single as well as two or more and so forth.

The term "polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogues of a protein sequence. A polypeptide may be monomeric or polymeric.

The term "isolated protein" or "isolated polypeptide" is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesised or synthesised in a cellular system different from the cell from which it naturally originates will be "isolated" from its naturally associated components. A protein may also be rendered substantially free of naturally associated components by isolation, using protein purification techniques well known in the art. The term "recovering" as used herein, refers to the process of rendering a chemical species, such as a polypeptide, substantially free of naturally associated components by isolation, e.g., using protein purification techniques well known in the art.

The term "human IL-12" (abbreviated herein as hIL-12, or IL-12), as used herein, includes a human cytokine that is secreted primarily by antigen presenting cells such as monocytes, macrophages and dendritic cells. The term includes a heterodimeric protein comprising a 35 kD subunit (p35) and a 40 kD subunit (p40) which are both linked together with a disulfide bridge. The heterodimeric protein is referred to as a "p70 protein". The term human IL-12 is intended to include recombinant human IL-12 (rhIL-12), which can be prepared by standard recombinant expression methods. IL-12 belongs to a family of interleukins the newest member being IL-35, which shares the IL-12p35 subunit (Niedbala et al. 2007 Eur J Immunol 37 3021-9). The recent discovery of IL-35 indicates that there are likely to be more forms of both the IL-12p40 and IL-12p35 that are yet to be discovered. It is logical to assume that antibodies described in the present invention would bind to all newly discovered proteins that contain forms of IL-12p40.

The term "human IL-23" (abbreviated herein as hIL-23, or IL-23), as used herein, includes a heterodimeric human cytokine belonging to a family of five such heterodimeric cytokines including IL-12 and IL-27 (Trinchieri et al. 2003 Immunity 19 641-4). The term includes a heterodimeric protein comprising of the subunits p19 and p40 which are both linked together with a disulfide bridge. The term human IL-23 is intended to include recombinant human IL-23 (rh IL-23), which can be prepared by standard recombinant expression methods.

The term "IL-12/23" as used herein, refers to human IL-12 and IL-23 collectively.

The term "IL-12p40", identicial to "IL-23p40", and also referred to simply as "p40" and "p40 subunit", as used herein, includes the 40 kD subunit of the human cytokine IL-12 (p40) and the 40 kD subunit of the human cytokine IL-23.

The term "IL-12p80", and also referred to simply as "p80", as used herein, includes 2 monomeric 40 kD subunits of the human cytokine IL-12 (p40) linked together by a disulphide bond to form a dimeric protein.

The term "IL-12p35", also referred to simply as "p35", as used herein, includes the kD subunit of the human cytokines, IL-12 (p70) and IL-35.

The term "IL-23p19", also referred to simply as "p19", as used herein, includes the 19 kD subunit of the human cytokine IL-23.

The IL-12R complex is composed of two subunits, named IL-12 receptor beta 1, used herein as IL-12Rβ1, and IL-12 receptor beta 2, used herein as IL-12Rβ2, both of which are required for high affinity binding of IL-12 and signalling. This IL-12R was initially characterised on PHA-activated lymphoblasts and IL-2 activated NK cells (Chizzonite et al. 1992 J Immunol 148 3117-24; Chua et al. 1994 J Immunol 153 128-36). It was shown that IL-12R132 is responsible for signalling via the Tyk2/JAK2 and STAT4 pathway leading cells down a $T_H1$ pathway (IFN-γ secreting) (Presky et al. 1996 Proc Natl Acad Sci USA 93 14002-7; Watford et al. 2004 Immunol Rev 202 139-56). IL-12Rβ1 has since been shown to be involved in signalling by phosphorylating Tyk2 and STAT3 (Zou et al. 1997 J Biol Chem 272 6073-7).

The IL-23R complex is composed of two subunits, IL-12Rβ1 which is present in the IL-12R complex, and the IL-23 receptor, used herein as IL-23R. The engagement of IL-23R by IL-23 results in JAK2 autophosphorylation and phosphorylation of IL-23R. This results in the localisation and phosphorylation of STAT3, as well as STAT1, STAT4 and STAT5 (Parham et al. 2002 J Immunol 168 5699-708).

"Biological activity" as used herein, refers to all inherent biological properties of the cytokine. Biological properties of IL-12 include but are not limited to binding IL-12Rβ1 and/or IL-12Rβ2; induction of IFN-γ secretion and regulation of balance between antigen-specific T helper type 1 ($T_H1$) and type 2 ($T_H2$) lymphocytes. Biological properties of IL-23 include but are not limited to binding IL-12Rβ1 and/or IL-23R, inducing IFN-γ production, inducing IL-17 production, inducing IL-21 production, inducing IL-22 production, $T_H17$ cell differentiation and activating the antigen-presenting functions of dendritic cells, and selectively inducing proliferation of memory T cells.

The terms "specific binding" or "specifically binding", as used herein, in reference to the interaction of an antibody, a protein, or a peptide with a second chemical species, mean that the interaction is dependent upon the presence of a particular structure (e.g., an antigenic determinant or epitope) on the chemical species; for example, an antibody recognises and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Non-limiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The term "antigen binding domain" or "antigen binding portion" of an antibody, as used herein, refers to one or more fragments of an antibody or protein that retain the ability to specifically bind to an antigen (e.g., IL-12). It has been shown that the antigen-binding function of an antibody can be performed by fragments of a full-length antibody. Such antibody embodiments may also be bispecific, dual specific, or multispecific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. 1989 Nature 341 544-6, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); (see e.g., Bird et al. 1988 Science 242 423-6; Huston et al. 1988 Proc Natl Acad Sci USA 85 5879-83). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., 1993, Proc. Natl. Acad. Sci. USA 90:6444-6448; Poljak, R. J., et al., 1994, Structure 2:1121-1123). Such antibody binding portions are known in the art (Kontermann and Dubel eds., Antibody Engineering 2001 Springer-Verlag. New York. 790 pp., ISBN 3-540-41354-5).

The term "antibody construct" as used herein refers to a polypeptide comprising one or more antigen binding portions of the invention linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g. Holliger et al. 1993 Proc Natl Acad Sci USA 90 6444-8).

An immunoglobulin constant domain refers to a heavy or light chain constant domain. Human IgG heavy chain and light chain constant domain amino acid sequences are known in the art and examples are represented below.

Human heavy chain IgG$_1$ constant domain (or derivatives thereof like NCBI Accession No: P01857) (SEQ ID NO: 8)

ASTKNPDVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

Human light chain kappa constant domain (like NCBI Accession No: P01834) (SEQ ID NO: 9)

TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC

Human light chain lambda constant domain (like NCBI Accession No: P01842) (SEQ ID NO: 377)

QPKAAPSVTLFPPSSEELQANKATLVCLISDFYPGAVTVAWKADSSPVKA

GVETTTPSKQSNNKYAASSYLSLTPEQWKSHRSYSCQVTHEGSTVEKTVA

PTECS

Still further, an antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov et al. 1995 Hum Antibodies Hybridomas 6 93-101) and use of a cysteine residue, a marker peptide and a C-terminal polyhistidine tag to make bivalent and biotinylated scFv (Kipriyanov et al. 1994 Mol Immunol 31 1047-58). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds hIL-12 is substantially free of antibodies that specifically bind antigens other than hIL-12). An isolated antibody that specifically binds hIL-12 may, however, have cross-reactivity to other antigens, such as IL-12 molecules from other species. Moreover, an isolated antibody may be substantially free of other cellular material and/or chemicals.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library (Hoogenboom 1997 Trends Biotechnol 15 62-70; Azzazy et al. 2002 Clin Biochem 35 425-45; Gavilondo et al. 2000 Biotechniques 29 128-32, 134-6, 138 passim Hoogenboom et al. 2000 Immunol Today 21 371-8), antibodies isolated from an animal (e.g., a mouse) that is transgenic for human immunoglobulin genes (see e.g., Taylor et al. 1992 Nucleic Acids Res 20 6287-95, Little et al. 2000 Immunol Today 21 364-70) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "chimeric antibody" refers to antibodies which comprise heavy and light chain variable region sequences from one species and constant region sequences from another species, such as antibodies having murine heavy and light chain variable regions linked to human constant regions.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "humanised antibody" refers to antibodies which comprise heavy and light chain variable region sequences from a non-human species (e.g., a mouse) but in which at least a portion of the VH and/or VL sequence has been altered to be more "human-like", ie, more similar to human germline variable sequences. One type of humanised antibody is a CDR-grafted antibody, in which human CDR sequences are introduced into non-human VH and VL sequences to replace the corresponding non-human CDR sequences.

The terms "Kabat numbering", "Kabat definitions" and "Kabat labeling" are used interchangeably herein. These terms, which are recognised in the art, refer to a system of numbering amino acid residues which are more variable (ie. hypervariable) than other amino acid residues in the heavy and light chain variable regions of an antibody, or an antigen binding portion thereof (Kabat et al. 1971 Ann NY Acad Sci 190 382-93 and Kabat, E. A., et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the terms "acceptor" and "acceptor antibody" refer to the antibody or nucleic acid sequence providing or encoding at least 80%, at least 85%, at least 90%, at least 95%, at least 98% or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, preferably, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available). As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest, National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia et al. 1987 J Mol Biol 196 901-17 and Chothia et al. 1989 Nature 342 877-83) found that certain sub-portions within Kabat CDRs adopt nearly identical peptide backbone conformations, despite having great diversity at the level of amino acid sequence. These sub-portions were designated L1, L2 and L3 or H1, H2 and H3 where the "L" and the "H" designate the light chain and the heavy chains regions, respectively. These regions may be referred to as Chothia CDRs, which have boundaries that overlap with Kabat CDRs. Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilise CDRs defined according to any of these systems, although preferred embodiments use Kabat or Chothia defined CDRs.

As used herein, the term "canonical" residue refers to a residue in a CDR or framework that defines a particular canonical CDR structure as defined by Chothia et al (Chothia and Lesk 1987 J Mol Biol 196 901-17; Chothia et al. 1992 J Mol Biol 227 799-817) and are incorporated herein by reference. According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In a preferred embodiment, the donor antibody is an antibody from a species different from the antibody from which the framework regions are obtained or derived. In the context of a humanised antibody, the term "donor antibody" refers to a non-human antibody providing one or more CDRs. As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region.

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. (See, e.g., Shapiro et al. 2002 Crit. Rev Immunol 22 183-200; Marchalonis et al. 2001 Adv Exp Med Biol 484 13-30). One of the advantages provided by various embodiments of the present invention stems from the recognition that germline antibody genes are more likely than mature antibody genes to conserve essential amino acid sequence structures characteristic of individuals in the species, hence less likely to be recognised as from a foreign source when used therapeutically in that species.

As used herein, the term "key" residues refer to certain residues within the variable region that have more impact on the binding specificity and/or affinity of an antibody, in particular a humanised antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a VH domain CDR1 and the Kabat definition of the first heavy chain framework.

As used herein, the term "humanised antibody" is an antibody or a variant, derivative, analog or fragment thereof which immunospecifically binds to an antigen of interest and which comprises a framework (FR) region having substantially the amino acid sequence of a human antibody and a complementarity determining region (CDR) having substantially the amino acid sequence of a non-human antibody. As used herein, the term "substantially" in the context of a CDR refers to a CDR having an amino acid sequence at least 80%, preferably at least 85%, at least 90%, at least 95%, at least 98% or at least 99% identical to the amino acid sequence of a non-human antibody CDR. A humanised antibody comprises substantally all of at least one, and typically two, variable domains (Fab, Fab', F(ab')2, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanised antibody also comprises at least a portion of an immunoglobulin constant region (Fc), typically that of a human immunoglobulin. In some embodiments, a humanised antibody contains both the light chain as well as at least the variable domain of a heavy chain. The antibody also may include the $C_H1$, hinge, $C_H2$, $C_H3$, and $C_H4$ regions of the heavy chain. In some embodiments, a humanised antibody only contains a humanised light chain. In some embodiments, a humanised antibody only contains a humanised heavy chain. In specific embodiments, a humanised antibody only contains a humanised variable domain of a light chain and/or humanised heavy chain.

The humanised antibody can be selected from any class of immunoglobulins, including IgM, IgG, IgD, IgA and IgE, and any isotype, including without limitation IgG1, IgG2, IgG3 and IgG4. The humanised antibody may comprise sequences from more than one class or isotype, and particular constant domains may be selected to optimise desired effector functions using techniques well-known in the art.

The framework and CDR regions of a humanised antibody need not correspond precisely to the parental sequences, e.g., the donor antibody CDR or the consensus framework may be mutagenised by substitution, insertion and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanised antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones, Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence. As used herein, "Vernier" zone refers to a subset of framework residues that may adjust CDR structure and fine-tune the fit to antigen as described by Foote et al. 1992 J Mol Biol 224 487-99. Vernier zone residues form a layer underlying the CDRs and may impact on the structure of CDRs and the affinity of the antibody.

As used herein, the term "neutralising" refers to neutralisation of biological activity of a cytokine when an antibody specifically binds the cytokine. Preferably a neutralising antibody is a neutralising antibody whose binding to IL-12 and/or IL-23 results in inhibition of a biological activity of IL-12 and/or IL-23. Preferably the neutralising antibody binds IL-12 and/or IL-23 and reduces a biologically activity of IL-12 and/or IL-23 by at least about 50%, 60%, 80%, 85% or more. As used herein, the term "inhibition" refers to the reduction of a biological activity of a cytokine when an antibody specifically binds the cytokine. Inhibition of a biological activity of IL-12 and/or IL-23 by a neutralising antibody can be assessed by measuring one or more indicators of IL-12 and/or IL-23 biological activity well known in the art. For example inhibition of human phytohemagglutinin blast proliferation in a in-vitro IL-12 PHA assay or inhibition of receptor binding in a human IL-12 receptor binding assay (See Example).

The term "activity" includes activities such as the binding specificity/affinity of an antibody for an antigen, for example, an anti-IL-12 antibody that binds to an IL-12 antigen and/or the neutralising potency of an antibody, for example, an anti-IL-12 antibody whose binding to IL-12 inhibits the biological activity of hIL-12, e.g. inhibition of PHA blast proliferation or inhibition of receptor binding in a human IL-12 receptor binding assay, or an in vitro IL-12 PHA assay.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognises its target antigen in a complex mixture of proteins and/or macromolecules.

The present invention also provides an antibody that inhibits IL-12/23 activity in antigen presenting cells (APCs), such as but not limited to, macrophages, microglia, mesangial phagocytes, synovial A cells, stem cell precursors, Langerhans cells, Kupffer cells, dendritic cells, B cells, and the like. Such APCs can be present in different tissues, e.g., but not limited to, skin, epidermis, liver, spleen, brain, spinal cord, thymus, bone marrow, joint synovial fluid, kidneys, blood, and the like. Such APCs can also be limited to outside or inside the blood brain barrier.

The present invention provides isolated, recombinant and/or synthetic antibodies, specified portions or variants thereof, as well as compositions and encoding nucleic acid molecules comprising at least one polynucleotide encoding at least one antibody. Such antibodies, specified portions or variants thereof of the present invention comprise specific full length antibody sequences, domains, fragments and specified variants thereof, and methods of making and using said nucleic acids and antibodies, specified portions or variants thereof, including therapeutic compositions, methods and devices.

The antibodies that can be used in the invention are optionally characterised by their ability to treat patients for extended periods with good to excellent alleviation of symptoms and low toxicity. Low immunogenicity and/or high affinity, as well as other suitable properties, may contribute to the therapeutic results achieved. "Low immunogenicity" is defined herein as raising significant HAHA, HACA or HAMA responses in less than about 75%, or preferably less than about 50% of the patients treated and/or raising low titres in the patient treated (less than about 300, preferably, less than about 100 measured with a double antigen enzyme immunoassay; Elliott et al. 1994 Lancet 344 1125-7).

The isolated nucleic acids of the present invention can be used for production of at least one antibody, fragment or specified variant thereof, which can be used in a cell, tissue, organ or animal (including mammals and humans), to modulate, treat, alleviate, help prevent the incidence of, or reduce the symptoms of, at least one IL-12 and/or IL-23 condition.

Such a method can comprise administering an effective amount of a composition or a pharmaceutical composition comprising at least one antibody or specified portion or variant to a cell, tissue, organ, animal or patient in need of such modulation, treatment, alleviation, prevention, or reduction in symptoms, effects or mechanisms. The effective amount can comprise an amount of about 0.001 to 500 mg/kg per single or multiple administration, or to achieve a serum concentration of 0.01-5000 µg/ml serum concentration per single or multiple administration, or any effective range or value therein, as done and determined using known methods, as described herein or known in the relevant arts.

Antibodies that are specific for the IL-12p40 subunit can be raised against an appropriate immunogenic antigen, such as isolated IL-12p40, IL-12 or IL-23 protein or a portion thereof (including synthetic molecules, such as synthetic peptides). Preparation of immunogenic antigens and monoclonal antibody production can be performed using any suitable technique. A variety of methods have been described (see e.g., Kohler et al. 1975 Nature 256 495-7 and Kohler et al. 1976 Eur J Immunol 6 511-9; Galfre et al. 1977 Nature 266 550-2; Koprowski et al., U.S. Pat. No. 4,172,124; Harlow, E. and D. Lane, 1988, Using Antibodies: A Laboratory Manual, Cold Spring Harbor Laboratory: Cold Spring Harbor, N.Y.; Current Protocols In Molecular Biology, Vol. 2 (e.g., Supplement 27, Summer '94), Ausubel, F. M. et al., Eds., John Wiley & Sons: New York, N.Y., Chapter 11, (1991-2003)), each of which is entirely incorporated herein by reference. Generally, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMAIWA, NEURO 2A, or the like, or heteromyelomas, fusion products thereof, or any cell or fusion cell derived therefrom, or any other suitable cell line as known in the art, see, e.g., www.atcc.org, www.lifetech.com., and the like, each of which is entirely incorporated herein by reference) with antibody producing cells, such as, but not limited to, isolated or cloned spleen cells, or any other cells expressing heavy or light chain constant, variable, framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridised, and the like or any combination thereof. See, e.g., Ausubel, supra, and Colligan, Immunology, supra, chapter 2, each entirely incorporated herein by reference.

Antibody producing cells can be obtained from the peripheral blood or, preferably, the spleen or lymph nodes, of humans or other suitable animals that have been immunised with the antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from Cambridge Antibody Technologies, Cambridgeshire, UK; MorphoSys, Martinsreid/Planegg, DE; Biovation, Aberdeen, Scotland, UK; Bioinvent, Lund, Sweden; Dyax Corp., Enzon, Affymax/Biosite; Xoma, Berkeley, Calif.; Ixsys. See, e.g., EP 368,684, PCT/GB91/01134; PCT/GB92/01755; PCT/GB92/002240; PCT/GB92/00883; PCT/GB93/00605; U.S. Ser. No. 08/350, 260 (May 12, 1994); PCT/GB94/01422; PCT/GB94/02662; PCT/GB97/01835; (CAT/MRC); WO90/14443; WO90/14424; WO90/14430; PCT/U5594/1234; WO92/18619; WO96/07754; (Scripps); WO96/13583, WO97/08320 (MorphoSys); WO95/16027 (BioInvent); WO88/06630; WO90/3809 (Dyax); U.S. Pat. No. 4,704,692 (Enzon); PCT/US91/02989 (Affymax); WO89/06283; EP 371 998; EP 550 400; (Xoma); EP 229 046; PCT/US91/07149 (Ixsys); or stochastically generated peptides or proteins U.S. Pat. Nos. 5,723,323, 5,763,192, 5,814,476, 5,817,483, 5,824,514, 5,976,862, WO 86/05803, EP 590 689 (Ixsys, now Applied Molecular Evolution (AME), each entirely incorporated herein by reference) or that rely upon immunisation of transgenic animals (e.g., SCID mice, Nguyen et al. 1997 Microbiol Immunol 41 901-7; Sandhu et al. 1996 Crit. Rev Biotechnol 16 95-118; each entirely incorporated by reference as well as related patents and applications) that are capable of producing a repertoire of human antibodies, as known in the art and/or as described herein. Such techniques, include, but are not limited to, ribosome display (Hanes et al. 1997 Proc Natl Acad Sci USA 94 4937-42; Hanes et al. 1998 Proc Natl Acad Sci USA 95 14130-5); single cell antibody producing technologies (e.g., selected lymphocyte antibody method ("SLAM") U.S. Pat. No. 5,627,052, Wen et al. 1987 Eur J Immunol 17 887-92; Babcook et al. 1996 Proc Natl Acad Sci USA 93 7843-8); gel microdroplet and flow cytometry (Powell et al. 1990 Biotechnology (NY) 8 333-7); One Cell Systems, Cambridge, Mass.; (Gray et al. 1995 J Immunol Methods 182 155-63; Kenney et al. 1995 Biotechnology (NY) 13 787-90); B-cell selection (Steenbakkers et al. 1994 Mol Biol Rep 19 125-34; Jonak et al., Progress Biotech, Vol. 5, In Vitro Immunization in Hybridoma Technology, Borrebaeck, ed., Elsevier Science Publishers B.V., Amsterdam, Netherlands (1988), each of which is entirely incorporated herein by reference).

For in vivo use of antibodies in humans, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison (1985); Oi (1986); Gillies (1989); U.S. Pat. Nos. 5,807,715; 4,816,567; and 4,816,397.

Included within the scope of the invention, and useful in practicing the methods of the invention, are de-immunized antibodies that have sequence variations produced using methods described in, for example, Patent Publication Nos. EP 0983303A1, WO 2000/34317, and WO 98/52976.

Another approach included within the scope of the invention in order to minimize the immunogenic and allergic responses intrinsic to mouse or other non-human monoclonal antibodies and thus to increase the efficacy and safety of the administered antibodies, is "veneering". The term "veneered antibody" refers to the selective replacement of framework region residues from, for example, a mouse heavy or light chain variable region with human framework region residues in order to provide a xenogeneic molecule comprising an antigen-binding site which retains substantially all of the native framework region folding structure. Veneering techniques are based on the understanding that the ligand-binding characteristics of an antigen-binding site are determined primarily by the structure and relative disposition of the heavy and light chain CDR sets within the antigen-binding surface (Davies (1990)). Thus, antigen-binding specificity can be preserved in a humanized antibody only wherein the CDR structures, their interaction with each other, and their interaction with the rest of the V region domains are carefully maintained. By using veneering techniques, exterior (e.g. solvent accessible) framework region residues, which are readily encountered by the immune system, are selectively replaced with human residues to provide a hybrid molecule that comprises either a weakly immunogenic, or substantially non-immunogenic, veneered surface.

The scope of the present invention also extends to humanized anti-IL-12/IL-23 antibodies. By "humanized" is intended forms of anti-IL-12/IL-23 antibodies that contain minimal sequence derived from non-human immunoglobulin sequences. For the most part, humanized antibodies are human immunoglobulins (recipient antibody) in which residues from a hypervariable region (also known as complementarity determining region or CDR) of the recipient are replaced by residues from a hypervariable region of a non-human species (donor antibody) such as mouse, rat, rabbit, or nonhuman primate having the desired specificity, affinity, and capacity.

Humanized antibodies within the scope, and suitable for use in the methods, of the present invention may, for example, have binding characteristics similar to those exhibited by non-humanized antibodies, such as, for example the PMA204 monoclonal antibody described herein.

Humanization can be essentially performed following the method of Winter and co-workers (Jones (1986); Riechmann (1988); Verhoeyen (1988)), by substituting rodent or mutant rodent CDRs or CDR sequences for the corresponding sequences of a human antibody. See also U.S. Pat. Nos. 5,225, 539; 5,585,089; 5,693,761; 5,693,762; and 5,859,205.

Antibodies can be humanized using a variety of techniques known in the art including, for example, CDR-grafting (EP 239400; PCT publication WO 91/09967; U.S. Pat. Nos. 5,225,539; 5,530,101; and 5,585,089), veneering or resurfacing (EP 592106; EP 519596; Padlan (1991); Studnicka (1994); Roguska (1994)), and chain shuffling (U.S. Pat. No. 5,565,332).

In some instances, residues within the framework regions of one or more variable regions of the human immunoglobulin are replaced by corresponding non-human residues (see, for example, Queen et al. U.S. Pat. No. 5,585,089; U.S. Pat. Nos. 5,693,761; 5,693,762; and 6,180,370; see also, e.g., Riechmann (1988)).

"Superhumanization" is a humanization approach where the CDRs conferring antigen specificity ('donor') are grafted to human germline framework sequences ('acceptor') that are known to be expressed with human CDRs that are structurally identical or similar to the 'donor' CDRs (Tan 2002, see also International Publication No. WO 2004/006955). By using frameworks encoded by human genomic V gene sequences, rather than sequences that can include somatic mutations, this approach has enhanced potential for reduced immunogenicity. By emphasizing the structural homologies between donor and acceptor CDRs, this approach also has enhanced potential for affinity retention.

Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence.

The humanized antibody optionally also will comprise at least a portion of an immunoglobulin constant region (Fc), typically that of a human immunoglobulin. For further details see Jones (1986); Riechmann (1988); and Presta (1992). Accordingly, such "humanized" antibodies may include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585, 089; 5,693,761; 5,693,762; 5,859,205. See also U.S. Pat. No. 6,180,370, and International Publication No. WO 2001/27160 where humanized antibodies and techniques for producing humanized antibodies having improved affinity for a predetermined antigen are disclosed.

Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope (Jespers (1988)).

Human antibodies can also be produced using transgenic animals which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes.

For an overview of this technology for producing human antibodies, see Lonberg and Huszar (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0598877; U.S. Pat. Nos. 5,413,923; 5,625,126; 5,633,425; 5,569,825; 5,661,016; 5,545,806; 5,814,318; 5,885,793; 5,916,771; 5,939,598; 6,075,181; and 6,114,598.

The choice of human variable domains, both light and heavy, to be used in making the humanised antibodies can be used to reduce antigenicity. According to the so-called "best-fit" method, the sequence of the variable domain of a rodent antibody is screened against the entire library of known human variable-domain sequences. The human sequence that is closest to that of the rodent is then accepted as the human framework (FR) for the humanised antibody (Chothia and Lesk 1987 J Mol Biol 196 901-17; Sims et al. 1993 J Immunol 151 2296-308, each of which is entirely incorporated herein by reference). Another method uses a particular framework derived from the consensus sequence of all human antibodies of a particular subgroup of light or heavy chains. The same framework can be used for several different humanised antibodies (Carter et al. 1992 Proc Natl Acad Sci USA 89 4285-9; Presta et al. 1993 J Immunol 151 2623-32, each of which is entirely incorporated herein by reference).

Antibodies can also optionally be humanised with retention of high affinity for the antigen and other favorable biological properties. To achieve this goal, according to a preferred method, humanised antibodies are prepared by a process of analysis of the parental sequences and various conceptual humanised products using three-dimensional models of the parental and humanised sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

Human antibodies, particulary human monoclonal antibodies, can be made by the hybridoma method. Human myeloma and mouse-human heteromyeloma cell lines for the production of human monoclonal antibodies have been described, for example, by Kozbor, J. Immunol. 133:3001 (1984); Brodeur et al., Monoclonal Antibody Production Techniques and Applications, pp. 51-63 (Marcel Dekker, Inc., New York, 1987); and Boerner et al., J. Immunol. 147:86 (1991), each of which is entirely incorporated herein by reference.

Alternatively, phage display technology, in addition to that presented above, can be used to produce human antibodies and antibody fragments in vitro, from immunoglobulin variable (V) domain gene repertoires from unimmunised donors. According to one non-limiting example of this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, Johnson 1993 Current Opinions in Structural Biology 3 564-571, each of which is entirely incorporated herein by reference.

Several sources of V-gene segments can be used for phage display. Clackson et al. (Clackson et al. 1991 Nature 352 624-8) isolated a diverse array of anti-oxazolone antibodies from a small random combinatorial library of V genes derived from the spleens of immunised mice. A repertoire of V genes from unimmunised human donors can be constructed and antibodies to a diverse array of antigens (including self-antigens) can be isolated essentially following the techniques described by Marks et al. 1991 J Mol Biol 222 581-97, or Griffiths et al. 1993 Embo J 12 725-34, each of which is entirely incorporated herein by reference.

In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al. 1992 Biotechnology (NY) 10 779-83). In this method, the affinity of "primary" human antibodies obtained by phage display can be improved by sequentially replacing the heavy and light chain V region genes with repertoires of naturally occurring variants (repertoires) of V domain genes obtained from unimmunised donors. This technique allows the production of antibodies and antibody fragments with affinities in the nM range.

A strategy for making very large phage antibody repertoires has been described by Waterhouse et al (Waterhouse et al. 1993 Nucleic Acids Res 21 2265-6). Gene shuffling can also be used to derive human antibodies from rodent antibodies, where the human antibody has similar affinities and specificities to the starting rodent antibody. According to this method, which is also referred to as "epitope imprinting," the heavy or light chain V domain gene of rodent antibodies obtained by phage display technique is replaced with a repertoire of human V domain genes, creating rodent-human chimeras. Selection with antigen results in isolation of human variable domains capable of restoring a functional antigen-binding site, i.e. the epitope governs (imprints) the choice of partner. When the process is repeated in order to replace the remaining rodent V domain, a human antibody is obtained (see PCT WO 93/06213). Unlike traditional humanisation of rodent antibodies by CDR grafting, this technique provides completely human antibodies, which have no framework or CDR residues of rodent origin.

Bispecific antibodies can also be used that are monoclonal, preferably human or humanised, antibodies that have binding specificities for at least two different antigens. In the present case, one of the binding specificities is for at least one IL-12 and/or IL-23 protein; the other one is for any other antigen. For example, bispecific antibodies specifically binding an IL-12/23 protein and at least one neurotrophic factor, or two different types of IL-12/23 polypeptides are within the scope of the present invention.

Methods for making bispecific antibodies are known in the art. Traditionally, the recombinant production of bispecific antibodies is based on the co-expression of two immunoglobulin heavy chain-light chain pairs, where the two heavy chains have different specificities (Milstein et al. 1983 Nature 305 537-40). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829, and in Traunecker et al. 1991 Embo J 10 3655-9 entirely incorporated herein by reference.

According to a different and more preferred approach, antibody-variable domains with the desired binding specificities (antibody-antigen combining sites) are fused to immunoglobulin constant-domain sequences. The fusion preferably is with an immunoglobulin heavy-chain constant domain, comprising at least part of the hinge, the second heavy chain constant region ($C_H2$), and the third heavy chain constant region ($C_H3$). It is preferred to have the first heavy-chain constant region ($C_H1$), containing the site necessary for light-chain binding, present in at least one of the fusions. DNA encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the production of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation. For further details of generating bispecific antibodies, see, for example Suresh et al. 1986 Methods Enzymol 121 210-28.

Antibodies are bifunctional molecules, the N-terminal variable segments from the heavy and light chains associate together in a specific manner to generate a three-dimensional structure with affinity for a particular epitope on the surface of an antigen. The constant region segments are responsible for prolonged serum half-life and the effector functions of the antibody and relate to complement binding, stimulation of phagocytosis, antibody-dependent cellular cytotoxicity (ADCC) and triggering of granulocyte granule release. It could be envisioned that an anti-IL-12/23 antibody would be capable of performing effector functions like ADCC or CDC (complement direted cytotoxicity). This is due to the discovery that IL-12 could exist as a membrane bound form (Quinones et al. 2000 J Exp Med 192 507-16) to which an antibody could bind and recruit effector cells. Alternatively, the present antibody could bind to IL-12 or IL-23 bound to the surface of cells and thus form a complex capable of recruiting effector cells to the target cell surface (Vogel et al. 1996 Int Immunol 8 1955-62).

It thus follows that the therapeutic utility of antibodies can be enhanced by modulating their functional characteristics, such as antibody-dependent cellular cytotoxicity, complement-dependent cytotoxicity, serum half-life, biodistribution and binding to Fc receptors. This modulation can be achieved by protein engineering, glycoengineering or chemical methods. Depending on the therapeutic application and the desired level of effector activity required, it could be advantageous to either increase or decrease any of these activities. For a review of the current methods of Fc enhancement see Carter 2006 Nat Rev Immunol 6 343-57; Presta 2006 Adv Drug Deliv Rev 58 640-56. Such enhancements could include mutation of the Fc portion of an antibody to determine mutants with increased affinity for Fc receptors (Shields et al. 2001 J Biol Chem 276 6591-604; Lazar et al. 2006 Proc Natl Acad Sci USA 103 4005-10) and tailoring of the glycan structure through expression of antibodies in cells with engineered glycosylation profiles (Yamane-Ohnuki et al. 2004 Biotechnol Bioeng 87 614-22; Li et al. 2006 Nat Biotechnol 24 210-5; Schuster et al. 2007 Biotechnol J 2 700-8).

A number of methods for modulating antibody serum half-life and biodistribution are based on modifying the interaction between antibody and the neonatal Fc receptor (FcRn), a receptor with a key role in protecting IgG from catabolism, and maintaining high serum antibody concentration. Dall'Acqua et al (2002) describe substitutions in the Fc region of IgG1 that enhance binding affinity to FcRn, thereby increasing serum half-life, and further demonstrate enhanced bioavailability and modulation of ADCC activity with triple substitution of M252Y/S254T/T256E (Dall' Acqua 2006). See also U.S. Pat. Nos 6,277,375; 6,821,505; and 7,083,784. Hinton et al (2004, 2005) have described constant domain amino acid substitutions at positions 250 and 428 that confer increased in vivo half-life. See also U.S. Pat. No 7,217,797. Petkova et al (2006) have described constant domain amino acid substitutions at positions 307, 380 and 434 that confer increased in vivo half-life. See also Shields et al (2001) and WO 2000/42072. Other examples of constant domain amino acid substitutions which modulate binding to Fc receptors and subsequent function mediated by these receptors, including FcRn binding and serum half-life, are described in U.S. Pat. Application Nos 20090142340; 20090068175; and 20090092599.

The glycans linked to antibody molecules are known to influence interactions of antibody with Fc receptors and glycan receptors and thereby influence antibody activity, including serum half-life (Kaneko Y et al, 2006; Jones A J et al, 2007; Kanda Y et al, 2007). Hence, certain glycoforms that modulate desired antibody activities can confer therapeutic advantage. Methods for generating engineered glycoforms are known in the art and include but are not limited to those described in U.S. Pat. Nos. 6,602,684; 7,326,681; 7,388,081; and WO 2008/006554.

Extension of half-life by addition of polyethylene glycol (PEG) has been widely used to extend the serum half-life of proteins, as reviewed, for example, by Fishburn (2008).

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/00373; and EP 03089). Heteroconjugate antibodies can be made using any convenient cross-linking methods. Suitable cross-linking agents are well known in the art, and are disclosed in U.S. Pat. No. 4,676,980, along with a number of cross-linking techniques.

In a preferred embodiment, at least one antibody or specified portion or variant of the present invention is produced by a cell line, a mixed cell line, an immortalised cell or clonal population of immortalised cells. Immortalised binding producing cells can be produced using suitable methods, for example, fusion of a human antibody-producing cell and a heteromyeloma or immortalisation of an activated human B cell via infection with Epstein Barr virus (Gustafsson et al. 1991 Hum Antibodies Hybridomas 2 26-32; Zanella et al. 1992 J Immunol Methods 156 205-15; Niedbala et al. 1998 Hybridoma 17 299-304). Preferably, the human anti-human IL-12/23 proteins, fragments, specified portions or variants are generated by immunisation of a transgenic animal (e.g., mouse, rat, hamster, non-human primate, and the like) capable of producing a repertoire of human antibodies, as described herein and/or as known in the art. Cells that produce a human antibody can be isolated from such animals and immortalised using suitable methods, such as the methods described herein.

Transgenic mice that can produce a repertoire of human antibodies that bind to human antigens can be produced by known methods (e.g., but not limited to, U.S. Pat. Nos. 5,770, 428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Taylor, Carmack et al. 1992 Nucleic Acids Res 20 6287-95; Tuaillon et al. 1993 Proc Natl Acad Sci USA 90 3720-4; Green et al. 1994 Nat Genet. 7 13-21; Lonberg et al. 1994 Nature 368 856-9; Taylor et al. 1994 Int Immunol 6 579-91; Lonberg et al. 1995 Int Rev Immunol 13 65-93; Fishwild et al. 1996 Nat Biotechnol 14 845-51; Mendez et al. 1997 Nat Genet. 15 146-56, which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

The term "functionally rearranged," as used herein refers to a segment of DNA from an immunoglobulin locus that has undergone V(D)J recombination, thereby producing an immunoglobulin gene that encodes an immunoglobulin chain (e.g., heavy chain, light chain), or any portion thereof. A functionally rearranged immunoglobulin gene can be directly or indirectly identified using suitable methods, such as, for example, nucleotide sequencing, hybridization (e.g., Southern blotting, Northern blotting) using probes that can anneal to coding joints between gene segments or enzymatic amplification of immunoglobulin genes (e.g., polymerase chain reaction) with primers that can anneal to coding joints between gene segments. Whether a cell produces an antibody comprising a particular variable region or a variable region comprising a particular sequence (e.g., at least one CDR sequence) can also be determined using suitable methods. In one example, mRNA can be isolated from an antibody-producing cell (e.g., a hybridoma or recombinant cell or other suitable source) and used to produce cDNA encoding the antibody or specified portion or variant thereof. The cDNA can be cloned and sequenced or can be amplified (e.g., by polymerase chain reaction or other known and suitable methods) using a first primer that anneals specifically to a portion of the variable region of interest (e.g., CDR, coding joint) and a second primer that anneals specifically to non-variable region sequences (e.g., $C_H1$, $V_H$).

Screening antibodies, specified portions or variants thereof for specific binding to similar proteins or fragments can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. WO 91/17271, WO 91/18980, WO 91/19818, and WO 93/08278. Other systems for generating libraries of peptides have aspects of both in vitro chemical synthesis and recombinant methods. See, PCT Patent Publication Nos. WO 92/05258, WO 92/14843, and WO 96/19256. See also, U.S. Pat. Nos. 5,658,754; and 5,643,768. Peptide display libraries, vector, and screening kits are commercially available from such suppliers as Invitrogen (Carlsbad, Calif.), and Cambridge Antibody Technologies (Cambridgeshire, UK). See, e.g., U.S. Pat. Nos. 4,704,692, 4,939,666, 4,946,778, 5,260, 203, 5,455,030, 5,518,889, 5,534,621, 5,656,730, 5,763,733, 5,767,260, 5,856,456, assigned to Enzon; U.S. Pat. Nos. 5,223,409, 5,403,484, 5,571,698, 5,837,500, assigned to Dyax, U.S. Pat. Nos. 5,427,908, 5,580,717, assigned to Affymax; U.S. Pat. No. 5,885,793, assigned to Cambridge Anitibody Technologies; U.S. Pat. No. 5,750,373, assigned to Genentech, U.S. Pat. Nos. 5,618,920, 5,595,898, 5,576,195, 5,698,435, 5,693,493, 5,698,417, assigned to Xoma, Colligan, supra; Ausubel, supra; or Sambrook, supra, each of the above patents and publications entirely incorporated herein by reference.

Antibodies, specified portions and variants thereof of the present invention can also be prepared by providing at least one antibody, specified portion or variant thereof encoding nucleic acid to transgenic animals or mammals, such as goats, cows, horses, sheep, and the like, that produce such antibodies, specified portions or variants thereof in their milk. Such animals can be provided using known methods. See, e.g., but not limited to, U.S. Pat. Nos. 5,827,690; 5,849,992; 4,873, 316; 5,849,992; 5,994,616; 5,565,362; 5,304,489, each of which is entirely incorporated herein by reference.

Antibodies, specified portions and variants thereof of the present invention can additionally be prepared using at least one antibody or specified portion or variant encoding nucleic acid to provide transgenic plants and cultured plant cells (e.g., but not limited to, tobacco, maize and bryophytes) that produce such antibodies, specified portions or variants thereof in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al. 1999 Curr Top Microbiol Immunol 240 95-118 and references cited therein. Also, transgenic maize have been used to express mammalian proteins at commercial production levels, with biological activities equivalent to those produced in other recombinant systems or purified from natural sources. See, e.g Hood et al. 1999 Adv Exp Med Biol 464 127-47 and references cited therein. Antibodies have also been produced in large amounts from transgenic plant seeds including tobacco seeds and potato tubers. See, e.g., Conrad et al. 1998 Plant Mol Biol 38 101-9 and references cited therein. Antibodies, have also been transiently expressed and secreted by such genetically modified moss protoplasts and show an unaltered antigen-binding affinity and, in extensive tests, revealed up to 40-fold enhanced ADCC (Schuster, Jost et al. 2007 Biotechnol J 2 700-8). Thus, antibodies, specified portions and variants thereof of the present invention can also be produced using transgenic plants, according to known methods. See also, e.g., Whitelam et al. 1994 Biochem Soc Trans 22 940-4; Ma et al. 1995 Trends Biotechnol 13 522-7; Ma et al. 1995 Plant Physiol 109 341-6 and references cited therein. Each of the above references is entirely incorporated herein by reference. The antibodies of the invention can bind human IL-12/23 with a wide range of affinities ($K_D$). In a preferred embodiment, at least one antibody of the present invention can optionally bind human IL-12/23 with high affinity. For example, an antibody can bind human IL-12/23 proteins with a $K_D$ equal to or less than about $10^{-9}M$ or, more preferably, with a $K_D$ equal to or less than about 0.1-9.9 (or any range or value therein) X $10^{-10}$ M, $10^{-11}$, $10^{-12}$, $10^{-13}$ or any range or value therein. The affinity or avidity of an antibody for an antigen can be determined experimentally using any suitable method. (See, for example, Berzofsky, et al., "Antibody-Antigen Interactions", In Fundamental Immunology, Paul, W. E., Ed., Raven Press: New York, N.Y. (1984); Kuby, Janis Immunology, W.H. Freeman and Company: New York, N.Y. (1992); and methods described herein). The measured affinity of a particular antibody with its binding partner can vary if measured under different conditions (e.g., salt concentration, pH). Thus, measurements of affinity and other antigen-binding parameters (e.g., $K_D$, $K_a$, $K_d$) are preferably made with standardised solutions of antibody and binding partner, and a standardised buffer, such as the buffer described herein.

Isolated nucleic acid molecules of the present invention can include nucleic acid molecules comprising an open reading frame (ORF), optionally with one or more introns, e.g., but not limited to, at least one specified portion of at least one CDR, as CDR1, CDR2 and/or CDR3 of at least one heavy chain or light chain, respectively; nucleic acid molecules comprising the coding sequence for an antibody, specified portion or variant thereof; and nucleic acid molecules which comprise a nucleotide sequence substantially different from those described above but which, due to the degeneracy of the genetic code, still encode at least one antibody as described herein and/or as known in the art. Of course, the genetic code is well known in the art. Thus, it would be routine for one skilled in the art to generate such degenerate nucleic acid variants that code for specific antibody, specified portion or variants thereof of the present invention. See, e.g., Ausubel, et al., supra, and such nucleic acid variants are included in the present invention.

As indicated herein, nucleic acid molecules of the present invention which comprise a nucleic acid encoding an antibody or specified portion or variant can include, but are not limited to, those encoding the amino acid sequence of an antibody fragment, by itself; the coding sequence for the entire antibody or a portion thereof; the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an antibody or specified portion or variant can be fused to a marker sequence, such as a sequence encoding a peptide that facilitates purification of the fused antibody or specified portion or variant comprising an antibody fragment or portion.

The present invention provides isolated nucleic acids that hybridise under selective hybridisation conditions to a polynucleotide encoding an antibody of the present invention. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably at least 85% or 90% full-length sequences, and more preferably at least 95% full-length sequences. The cDNA libraries can be normalised to increase the representation of rare sequences. Low or moderate stringency hybridisation conditions are typically, but not exclusively, employed with sequences having a reduced sequence identity relative to complementary sequences. Moderate and high stringency conditions can optionally be employed for sequences of greater identity. Low stringency conditions allow selective hybridisation of sequences having about 70% sequence identity and can be employed to identify orthologous or paralogous sequences.

Optionally, polynucleotides of this invention will encode at least a portion of an antibody or specified portion or variant encoded by the polynucleotides described herein. The polynucleotides of this invention embrace nucleic acid sequences that can be employed for selective hybridisation to a polynucleotide encoding an antibody or specified portion or variant of the present invention. See, e.g., Ausubel, supra; Colligan, supra, each entirely incorporated herein by reference.

The isolated nucleic acids of the present invention can be made using (a) recombinant methods, (b) synthetic techniques, and (c) purification techniques, or combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention, excluding the coding sequence, is optionally a vector, adapter, or linker for cloning and/or expression of a polynucleotide of the present invention.

Additional sequences can be added to such cloning and/or expression sequences to optimise their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra)

The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridise, under stringent conditions, to the polynucleotides of the present invention are used to identify the desired sequence in a cDNA or genomic DNA library. The isolation of RNA, and construction of cDNA and genomic libraries, is well known to those of ordinary skill in the art. (See, e.g., Ausubel, supra; or Sambrook, supra)

A cDNA or genomic library can be screened using a probe based upon the sequence of a polynucleotide of the present invention, such as those disclosed herein. Probes can be used to hybridise with genomic DNA or cDNA sequences to isolate homologous genes in the same or different organisms. Those of skill in the art will appreciate that various degrees of stringency of hybridisation can be employed in the assay; and either the hybridisation or the wash medium can be stringent. As the conditions for hybridisation become more stringent, there must be a greater degree of complementarity between the probe and the target for duplex formation to occur. The degree of stringency can be controlled by one or more of temperature, ionic strength, pH and the presence of a partially denaturing solvent, such as formamide. For example, the stringency of hybridisation is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridisation medium and/or wash medium. The degree of complementarity will optimally be 100%, or 90-100%, or any range or value therein. However, it should be understood that minor sequence variations in the probes and primers can be compensated for by reducing the stringency of the hybridisation and/or wash medium.

Methods of amplification of RNA or DNA are well known in the art and can be used according to the present invention without undue experimentation, based on the teaching and guidance presented herein. Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; U.S. Pat. Nos. 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, PCR technology can be used to amplify the sequences of polynucleotides of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage®-GC Genomic PCR Kit (Clontech). The T4 gene 32 protein (Boehringer Mannheim) can be used to improve yield of long PCR products.

The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridisation with a complementary sequence, or by polymerisation with a DNA polymerase using the single strand as a template. One of skill in the art will recognise that while chemical synthesis of DNA can be limited to sequences of about 100 or more bases, longer sequences can be obtained by the ligation of shorter sequences.

The present invention further provides recombinant expression cassettes comprising a nucleic acid of the present invention. A nucleic acid sequence of the present invention, for example, a cDNA or a genomic sequence encoding an antibody or specified portion or variant of the present invention, can be used to construct a recombinant expression cassette that can be introduced into at least one desired host cell. A recombinant expression cassette will typically comprise a polynucleotide of the present invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the present invention.

In some embodiments, isolated nucleic acids that serve as promoter, enhancer, or other elements can be introduced in the appropriate position (upstream, downstream or in intron) of a non-heterologous form of a polynucleotide of the present invention so as to up or down regulate expression of a polynucleotide of the present invention. For example, endogenous promoters can be altered in vivo or in vitro by mutation, deletion and/or substitution.

The present invention also relates to vectors that include isolated nucleic acid molecules of the present invention, host cells that are genetically engineered with the recombinant vectors, and the production of at least one antibody or specified portion or variant by recombinant techniques, as is well known in the art. See, e.g., Sambrook, et al., supra; Ausubel, et al., supra, each entirely incorporated herein by reference. The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but not limited to, methotrexate (MTX), dihydrofolate reductase (DHFR, U.S. Pat. Nos. 4,399,216; 4,634,665; 4,656,134; 4,956,288; 5,149,636; and 5,179,017), ampicillin, neomycin (G418), mycophenolic acid, or glutamine synthetase (GS, U.S. Pat. Nos. 5,122,464; 5,770,359; and 5,827,739) resistance for eukaryotic cell culture, and tetracycline or ampicillin resistance genes for culturing in E. coli and other bacteria or prokaryotics (the above patents are entirely incorporated herein by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one antibody, specified portion or variant of the present invention can be expressed in a modified form, such as a fusion protein, and can include not only secretion signals, but also additional heterologous functional regions. For instance, a region of additional amino acids, particularly charged amino acids, can be added to the N-terminus of an antibody, specified portion or variant to improve stability and persistence in the host cell, during purification, or during subsequent handling and storage. Also, peptide moieties can be added to an antibody, specified portion or variant of the present invention to facilitate purification. Such regions can be removed prior to final preparation of an antibody or at least one fragment thereof. Such methods are described in many standard laboratory manuals, such as Sambrook, supra, Chapters 17.29-17.42 and 18.1-18.74; Ausubel, supra, Chapters 16, 17 and 18. Those of ordinary skill in the art are knowledgeable in the numerous expression systems available for expression of a nucleic acid encoding a protein of the present invention.

Alternatively, nucleic acids of the present invention can be expressed in a host cell by turning on (by manipulation) in a host cell that contains endogenous DNA encoding an antibody, specified portion or variant of the present invention. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, COS-7 cells, CHO cells, hep G2 cells, P3X63Ag8.653, SP2/0-Ag14, 293 cells, HeLa cells and the like, which are readily available from, for example, American Type Culture Collection, Manassas, Va. Preferred host cells include cells of lymphoid origin, such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or a SP2/0-Ag14 cell. Expression vectors for these cells can include one or more of the following expression control sequences, such as, but not limited to, an origin of replication; a promoter (e.g., late or early SV40 promoters, the CMV promoter; U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague et al. 1983 J Virol 45 773-81). Additionally, gene sequences to control replication in the host cell can be incorporated into the vector, as known in the art.

An antibody, specified portion or variant can be recovered and purified from recombinant cell cultures by well-known methods, including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See e.g., Colligan, Current Protocols in Immunology, or Current Protocols in Protein Science, John Wiley & Sons, NY, N.Y., (1997-2003), e.g., Chapters 1, 4, 6, 8, 9, 10, each entirely incorporated herein by reference.

Antibodies, specified portions or variants thereof of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody, specified portion or variant of the present invention can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

The isolated antibodies of the present invention comprise an antibody or specified portion or variant encoded by any one of the polynucleotides of the present invention as discussed more fully herein, or any isolated or prepared antibody, specified portion or variant thereof.

Preferably, the antibody or antigen-binding fragment binds human IL-12/23 proteins and, thereby substantially neutralises the biological activity of the proteins. An antibody, specified portion or variant thereof, that partially or preferably substantially neutralises at least one biological activity of at least one IL-12/23 protein and thereby inhibit activities mediated through the binding of IL-12 to at least one IL-12 receptor, or IL-23 to at least one IL-23 receptor or through other IL-12 or IL-23-dependent or mediated mechanisms. As used herein, the term "neutralising antibody" refers to an antibody that can inhibit human IL-12p40 protein or fragment related-dependent activity by about 20-120%, preferably by at least about 60, 70, 80, 90, 91, 92, 93, 94, 95, 96, 97, 98, 99, 100% or more depending on the assay. The capacity of the antibody or specified portion or variant to inhibit human IL-12/23 related-dependent activity is preferably assessed by at least one suitable antibody or protein assay, as described herein and/or as known in the art. An antibody, specified portion or variant of the invention can be of any class (IgG, IgA, IgM, IgE, IgD, etc.) or isotype and can comprise a kappa or lambda light chain. In one embodiment, the antibody or specified portion or variant comprises an IgG heavy chain or defined fragment, for example, at least one of isotypes, IgG1, IgG2, IgG3 or IgG4. Antibodies of this type can be prepared by employing a transgenic mouse or other trangenic non-human mammal comprising at least one human light chain (e.g., IgG, IgA and IgM; e.g., γ1, γ2, γ3, γ4) transgene as described herein and/or as known in the art. In another embodiment, the antibody, specified portion or variant thereof comprises an IgG1 heavy chain and an IgG1 light chain.

At least one antibody, specified portion or variant of the invention binds at least one specified epitope specific to IL-12p40 protein, fragment, portion or any combination thereof. As non-limiting examples, an antibody, specified portion or variant specifically binds at least one epitope comprising at least 1-3 amino acids of the entire amino acid sequence of IL-12p40 subunit. The at least one specified epitope can comprise any combination of at least one amino acid of IL-12p40 such as, but not limited to, 1, 2, 3, 4, 5, 6, 7, 8, 9, 10, 11, 12, 13 or 14 amino acids of at least one of, 1-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-210, 210-220, 220-230, 230-240, 240-250, 250-260, 260-270, 280-290, 290-300, 300-306, 1-7, 14-21, 29-52, 56-73, 83-93, 96-105, 156-175, 194-204, 208-246, 254-273, 279-281, or 289-300 of SEQ ID NO:1 (human IL-12p40 subunit, 306 amino acids). These predicted epitopes are available on IL-12, IL-23, IL-12p40 monomer and IL-12p80 homodimer.

The antibody can comprise at least one of a heavy or light chain variable region having a defined amino acid sequence. For example, in a preferred embodiment, the antibody comprises at least one of at least one heavy chain variable region and/or at least one light chain variable region. Human antibodies that bind to human IL-12/23 proteins and/or fragments and that comprise a defined heavy or light chain variable region can be prepared using suitable methods, such as phage display (Katsube et al. 1998 Int J Mol Med 1 863-8) or methods that employ transgenic animals, as known in the art and/or as described herein. For example, a transgenic mouse, comprising a functionally rearranged human immunoglobulin heavy chain transgene and a transgene comprising DNA from a human immunoglobulin light chain locus that can undergo functional rearrangement, can be immunised with human IL-12 and/or IL-23 proteins, receptors, and/or fragments thereof to elicit the production of antibodies. If desired, the antibody producing cells can be isolated and hybridomas or other immortalised antibody-producing cells can be prepared as described herein and/or as known in the art. Alternatively, the antibody, specified portion or variant can be expressed using the encoding nucleic acid or portion thereof in a suitable host cell.

The invention also relates to antibodies, antigen-binding fragments, immunoglobulin chains and CDRs comprising amino acids in a sequence that is substantially the same as an amino acid sequence described herein. Preferably, such antibodies or antigen-binding fragments and antibodies comprising such chains or CDRs can bind human IL-12/23 proteins, and/or fragments with high affinity (e.g., $K_D$ less than or equal to about $10^{-9}$M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

An antibody or specified portion or variant of the present invention can include one or more amino acid substitutions, deletions or additions, either from natural mutations or human manipulation, as specified herein. Of course, the number of amino acid substitutions a skilled artisan would make depends on many factors, including those described above. Generally speaking, the number of amino acid substitutions, insertions or deletions for any given binding polypeptide will not be more than 40, 30, 20, 19, 18, 17, 16, 15, 14, 13, 12, 11, 10, 9, 8, 7, 6, 5, 4, 3, 2, 1, such as 1-30 or any range or value therein, as specified herein.

Amino acids in antibody, specified portion or variant of the present invention that are essential for function can be identified by methods known in the art, such as site-directed mutagenesis or alanine-scanning mutagenesis (e.g., Ausubel, supra, Chapters 8, 15; Cunningham et al. 1989 Science 244 1081-5). The latter procedure introduces single alanine mutations at every residue in the molecule. The resulting mutant molecules are then tested for biological activity, such as, but not limited to, at least one IL-12/23 neutralising activity. Sites that are critical for an antibody, specified portion or variant binding can also be identified by structural analysis such as crystallisation, nuclear magnetic resonance or photoaffinity labeling (de Vos et al. 1992 Science 255 306-12; Smith et al. 1992 J Mol Biol 224 899-904).

In another aspect, the invention relates to antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments of the invention can comprise one or more organic moieties that are covalently bonded, directly or indirectly, to the antibody, specified portion or variant. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example, $PEG_{5000}$ and $PEG_{20,000}$, wherein the subscript is the average molecular weight of the polymer in Daltons, can be used.

The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-49-octadecanoate ($C_{18}$, oleate), all cis-$\Delta$5,8,11,14-eicosatetraenoate ($C_{20}$, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The modified antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups, such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., Bioconjugate Techniques, Academic Press: San Diego, Calif. (1996)). An activating group can be bonded directly to the organic group (e.g., hydrophilic polymer, fatty acid, fatty acid ester), or through a linker moiety, for example, a divalent $C_1$-$C_{12}$ group wherein one or more carbon atoms can be replaced by a heteroatom, such as oxygen, nitrogen or sulfur. Suitable linker moieties include, for example, tetraethylene glycol, —$(CH_2)_3$—, —NH—$(CH_2)_6$—NH—, —$(CH_2)_2$—NH— and —$CH_2$—O—$CH_2$—$CH_2$—O—$CH_2$—$CH_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclised to produce an activated maleimido derivative of the fatty acid. (see, for example, Thompson, et al., WO 92/16221, the entire teachings of which are incorporated herein by reference.)

The modified antibodies of the invention can be produced by reacting an antibody or antigen-binding fragment with a modifying agent. For example, the organic moieties can be bonded to the antibody in a non-site specific manner by employing an amine-reactive modifying agent, for example, an NHS ester of PEG. Modified antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified antibodies and antigen-binding fragments comprising an organic moiety that is bonded to specific sites of an antibody, specified portion or variant of the present invention can be prepared using suitable methods, such as reverse proteolysis (Fisch et al. 1992 Bioconjug Chem 3 147-53; Werlen et al. 1994 Bioconjug Chem 5 411-7; Capellas et al. 1997 Biotechnol Bioeng 56 456-63; Kumaran et al. 1997 Protein Sci 6 2233-41 and the methods described in Hermanson, G. T., Bioconjugate Techniques, Academic Press: San Diego, Calif. (1996)).

The antibody compositions of the invention can optionally further comprise an effective amount of at least one compound or protein selected from at least one of an anti-infective drug, a cardiovascular (CV) system drug, a central nervous system (CNS) drug, an autonomic nervous system (ANS) drug, a respiratory tract drug, a gastrointestinal (G1) tract drug, a hormonal drug, a drug for fluid or electrolyte balance, a hematologic drug, an antineoplastic, an immunomodulation drug, an ophthalmic, otic or nasal drug, a topical drug, a nutritional drug or the like. Such drugs are well known in the art, including formulations, indications, dosing and administration for each presented herein (see, e.g., Nursing 2001

Handbook of Drugs, 21$^{st}$ edition, Springhouse Corp., Springhouse, Pa., 2001; Health Professional's Drug Guide 2001, ed., Shannon, Wilson, Stang, Prentice-Hall, Inc, Upper Saddle River, N.J.; Pharmcotherapy Handbook, Wells et al., ed., Appleton & Lange, Stamford, Conn., each entirely incorporated herein by reference).

Antibody, specified portion or variant compositions of the present invention can further comprise at least one of any suitable auxiliary, such as, but not limited to, diluent, binder, stabiliser, buffers, salts, lipophilic solvents, preservative, adjuvant or the like. Pharmaceutically acceptable auxiliaries are preferred. Non-limiting examples of, and methods of preparing such sterile solutions are well known in the art, such as, but not limited to, Gennaro, Ed., *Remington's Pharmaceutical Sciences*, 18$^{th}$ Edition, Mack Publishing Co. (Easton, Pa.) 1990. Pharmaceutically acceptable carriers can be routinely selected that are suitable for the mode of administration, solubility and/or stability of the antibody composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatised sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin, such as human serum albumin (HSA), recombinant human albumin (rHA), gelatin, casein, and the like. Representative amino acids which can also function in a buffering capacity include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Antibody compositions can also include a buffer or a pH adjusting agent; typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts, such as citrate.

Additionally, the antibody, specified portion or variant compositions of the invention can include polymeric excipients/additives, such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates such as "TWEEN® 20" and "TWEEN® 80"), lipids (e.g., phospholipids, fatty acids), steroids (e.g., cholesterol), and chelating agents (e.g., EDTA).

These and additional known pharmaceutical excipients and/or additives suitable for use in the antibody compositions according to the invention are known in the art, e.g., as listed in "Remington: The Science & Practice of Pharmacy", 19$^{th}$ ed., Williams & Williams, (1995), and in the "Physician's Desk Reference", 52$^{nd}$ ed., Medical Economics, Montvale, N.J. (1998), the disclosures of which are entirely incorporated herein by reference. Preferred carrier or excipient materials are carbohydrates (e.g., saccharides and alditols) and buffers (e.g., citrate) or polymeric agents.

The invention provides for stable formulations, which comprise preferably a phosphate buffer with saline or a chosen salt, as well as preserved solutions and formulations containing a preservative, as well as multi-use preserved formulations suitable for pharmaceutical or veterinary use, comprising at least one antibody, specified portion or variant in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3, 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

Any method of the present invention can comprise administering an effective amount of a composition or pharmaceutical composition comprising at least one antibody, specified portion or variant to a cell, tissue, organ, animal or patient in need of such modulation, treatment or therapy. Such a method can optionally further comprise co-administration or combination therapy for treating such immune diseases, wherein the administering of said at least one antibody, specified portion or variant thereof further comprises administering, before, concurrently, and/or after, at least one selected from at least one multiple sclerosis therapeutic (including but not limited to, beta-interferon 1a and beta-interferon 1b (e.g., Avonex™, Rebif™, Betaseon™), glutiramer acetate (e.g., Copaxone), cyclophasphamide, azathioprine, glucocorticosteroids, methotrexate, Paclitaxel, 2-chlorodeoxyadenosine, mitoxantrone, IL-10, TGBb, CD4, CD52, antegren, CD11, CD18, TNFalpha, IL-1, IL-2, and/or CD4 antibody or antibody receptor fusion, interferon alpha, immunoglobulin, Lismide (Requinimax™), insulin-like growth factor-1 (IGF-1), elprodil, pirfenidone, oral myelin, or compounds that act on one or more of at least one of: autoimmune suppression of myelin destruction, immune regulation, activation, proliferation, migration and/or suppressor cell function of T-cells, inhibition of T cell receptor/peptide/MHC-II interaction, induction of T cell aenergy, deletion of autoreactive T cells, reduction of trafficking across blood brain baffler, alteration of balance of pro-inflammatory ($T_H1$) and immunomodulatory ($T_H2$) cytokines, inhibition of matrix metalloprotease inhibitors, neuroprotection, reduction of gliosis, promotion of re-myelination), TNF antagonist (e.g., but not limited to a TNF antibody or fragment, a soluble TNF receptor or fragment, fusion proteins thereof or a small molecule TNF antagonist), an antirheumatic, a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifintgal, an antiparasitic, an antiviral, a carbapenem, cephalosporin, a fluororquinolone, a macrolide, a penicillin, a sulfonamide, a tetracycline, another antimicrobial), an antipsoriatic, a corticosteriod, an anabolic steroid, an IL-12/23 agent, a mineral, a nutritional, a thyroid agent, a vitamin, a calcium related honnone, an antidiarrheal, an antitussive, an antiemetic, an antiulcer, a laxative, an anticoagulant, an erythropieitin (e.g., epoetin alpha), a filgrastim (e.g., G-CSF, Neupogen®), a sargramostim (GM-CSF, Leukine), an immunising agent, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a syinpathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme®), a cytokine or a cytokine antagonist. Suitable dosages are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

TNF antagonists suitable for compositions, combination therapy, co-administration, devices and/or methods of the present invention (further comprising at least one antibody, specified portion and variant thereof, of the present invention), include, but are not limited to, anti-TNF antibodies, antigen-binding fragments thereof, and receptor molecules which bind specifically to TNF; compounds which prevent and/or inhibit TNF synthesis, TNF release or its action on target cells, such as thalidomide, tenidap, phosphodiesterase inhibitors (e.g., pentoxifylline and rolipram), A2b adenosine receptor agonists and A2b adenosine receptor enhancers; compounds which prevent and/or inhibit TNF receptor signalling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

As used herein, a "tumor necrosis factor antibody," "TNF antibody," "TNFα antibody," or fragment and the like decreases, blocks, inhibits, abrogates or interferes with TNFα activity in vitro, in situ and/or preferably in vivo. For example, a suitable TNF human antibody of the present invention can bind TNFα and includes anti-TNF antibodies, antigen-binding fragments thereof, and specified mutants or domains thereof that bind specifically to TNFα. A suitable TNF antibody or fragment can also decrease block, abrogate, interfere, prevent and/or inhibit TNF RNA, DNA or protein synthesis, TNF release, TNF receptor signaling, membrane TNF cleavage, TNF activity, TNF production and/or synthesis.

Preferred TNF receptor molecules useful in the present invention are those that bind TNFα with high affinity (see, e.g., Feldmann et al., International Publication No. WO 92/07076; Loetscher et al. 1990 Cell 61 351-9; Schall et al. 1990 Cell 61 361-70, which references are entirely incorporated herein by reference) and optionally possess low immunogenicity. In particular, the 55 kDa (p55 TNF-R) and the 75 kDa (p75 TNF-R) TNF cell surface receptors are useful in the present invention. Truncated forms of these receptors, comprising the extracellular domains (ECD) of the receptors or functional portions thereof (see, e.g., Corcoran et al. 1994 Eur J Biochem 223 831-40), are also useful in the present invention. Truncated forms of the TNF receptors, comprising the ECD, have been detected in urine and serum as 30 kDa and 40 kDa TNFα inhibitory antibodies (Engelmann et al. 1990 J Biol Chem 265 1531-6). TNF receptor multimeric molecules and TNF immunoreceptor fusion molecules, and derivatives and fragments or portions thereof, are additional examples of TNF receptor molecules which are useful in the methods and compositions of the present invention. The TNF receptor molecules which can be used in the invention are characterised by their ability to treat patients for extended periods with good to excellent alleviation of symptoms and low toxicity. Low immunogenicity and/or high affinity, as well as other undefined properties, may contribute to the therapeutic results achieved.

Typically, treatment of pathologic conditions is effected by administering an effective amount or dosage of at least one antibody composition that total, on average, a range from at least about 0.01 to 500 milligrams of at least one antibody, specified portion or variant/kilogram of patient per dose, and, preferably, from at least about 0.1 to 100 milligrams of an antibody, specified portion or variant/kilogram of patient per single or multiple administration, depending upon the specific activity of antibody, specified portion or variant contained in the composition. Alternatively, the effective serum concentration can comprise 0.1-5000 µg/ml serum concentration per single or multiple administration. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved. Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually, a dosage of active ingredient can be about 0.1 to 100 milligrams per kilogram of body weight. Ordinarily, 0.1 to 50, and, preferably, 0.1 to 10 milligrams per kilogram per administration or in sustained release form is effective to obtain desired results.

As a non-limiting example, treatment of humans or animals can be provided as a one-time or periodic dosage of at least one antibody, specified portion or variant of the present invention, 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or, alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or, alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.1 milligram to about 500 milligrams of active ingredient per unit or container. In these pharmaceutical compositions, the active ingredient will ordinarily be present in an amount of about 0.5-99.999% by weight based on the total weight of the composition.

For parenteral administration, the antibody, specified portion or variant can be formulated as a solution, suspension, emulsion or lyophilised powder in association, or separately provided, with a pharmaceutically acceptable parenteral vehicle. Examples of such vehicles are water, saline, Ringer's solution, dextrose solution, and 1-10% human serum albumin. Liposomes and nonaqueous vehicles, such as fixed oils, may also be used. The vehicle or lyophilised powder may contain additives that maintain isotonicity (e.g., sodium chloride, mannitol) and chemical stability (e.g., buffers and preservatives). The formulation is sterilised by known or suitable techniques.

Suitable pharmaceutical carriers are described in the most recent edition of Remington's Pharmaceutical Sciences, A. Osol, a standard reference text in this field.

It can be sometimes desirable to deliver the antibodies of the present invention to the subject over prolonged periods of time, for example, for periods of one week to one year from a single administration. Various slow release, depot or implant dosage forms can be utilised. For example, a dosage form can contain a pharmaceutically acceptable non-toxic salt of the compounds that has a low degree of solubility in body fluids, for example, (a) an acid addition salt with a polybasic acid, such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation, such as zinc, calcium, bismuth, barium, magnesium, aluminium, copper, cobalt, nickel, cadmium and the like, or with an organic cation formed from e.g., N,N'-dibenzyl-ethylenediamine or ethylenediamine; or (c) combinations of (a) and (b) e.g., a zinc tannate salt. Additionally, the compounds of the present invention or, preferably, a relatively insoluble salt, such as those just described, can be formulated in a gel, for example, an aluminium monostearate gel with, e.g. sesame oil, suitable for injection. Particularly preferred salts are zinc salts, zinc tannate salts, pamoate salts, and the like. Another type of slow release depot formulation for injection would contain the compound or salt dispersed for encapsulation in a slow degrading, non-toxic, non-antigenic polymer, such as a polylactic acid/polyglycolic acid polymer, for example, as described in U.S. Pat. No. 3,773,919. The compounds or, preferably, relatively insoluble salts, such as those described above, can also be formulated in cholesterol matrix silastic pellets, particularly for use in animals. Additional slow release, depot or implant formulations, e.g., gas or liquid liposomes, are known in the literature (U.S. Pat. No. 5,770, 222 and "Sustained and Controlled Release Drug Delivery Systems", J. R. Robinson ed., Marcel Dekker, Inc., N.Y., 1978).

Having generally described the invention, the same will be more readily understood by reference to the following examples, which are provided by way of illustration and are not intended as limiting.

EXAMPLES OF THE INVENTION

All references to IL-12, IL-23, IL-12p40, IL-12p80, IL-12Rβ1, IL-12Rβ2 and IL-23 in these examples refer to human forms of the protein unless otherwise stated.

Refer to TABLE 10 for the corresponding protein and DNA sequences for each antibody listed in these examples.

Example 1

1.1 Isolation of Hybridoma and Generation of Chimeric Antibodies

Using standard murine hybridoma generation techniques and recombinant IL-12 as an immunogen, two hybridoma cell lines were obtained, PMA202 and PMA204. These cell lines secreted antibody that bound to IL-12p40 (SEQ ID NO: 1), IL-12 (SEQ ID NO: 1 and SEQ ID NO: 2) and IL-23 (SEQ ID NO: 1 and SEQ ID NO: 3) as tested in an ELISA (PMA204—FIG. 3). The antibodies were isotyped as murine IgG$_1$kappa.

After extracting RNA from the cell lines, PMA202 and PMA204, and using PCR techniques, the sequences of the murine heavy chain and light chain variable regions were obtained. These sequences are as follows, with the CDRs underlined and defined according to Kabat (Kabat et al. 1971 Ann N Y Acad Sci 190 382-93 and Kabat, E. A., et al. (1991) Sequences of Proteins of Immunological Interest, Fifth Edition, U.S. Department of Health and Human Services, NIH Publication No. 91-3242). Note all subsequent protein sequences encoding variable regions of antibodies are numbered according to the Kabat numbering system.

PMA202 Murine Heavy Chain variable region
(SEQ ID NO: 4)
QIQLVQSGPELKKPGETVKISCKASGYTFT<u>NYGMN</u>WVKQAPGKGLKWM GW<u>INTYTGEPTYADDFKG</u>RFAFSLETSASTAYLQINNFKNEDTATYFC AR<u>SLSTMITTTFAY</u>WGQGTLVTVSS PMA202 Murine Light Chain variable region
(SEQ ID NO: 5)
SIVMTQTPKFLLVSAGDRVTITC<u>KASQSVSNDVA</u>WYQQKPGQSPKLLI YY<u>ASNRYT</u>GVPDRFTGSGYGTDFTFTISTVQAEDLAVYFC<u>QQDYSSPY</u>

<u>T</u>FGGGTKLEIKR

PMA204 Murine Heavy Chain variable region
(SEQ ID NO: 6)
EVQLQQSGADLVRSGASIKLSCTASGFNIK<u>DYYMH</u>WVKQRPEQGLEWI GW<u>IDPENGDTEYAPKFQG</u>KATMTADTSSNTAYLQLSSLTSEDTAVYYC NA<u>CKELRYFDV</u>WGAGTTVTVSS PMA204 Murine Light Chain variable region
(SEQ ID NO: 7)
DIVLTQSPATLSVTPGDSVSLSCRASQSISINLHWYQQKSHESPRLLI

KFASQSISGIPSRFSGYGSGTDFTLSINSVETEDFGRYFCQQSNSWPL

TFGAGTKLELKR

Using the PMA202 protein sequences as a template, a new optimized nucleotide sequence was produced in which the murine heavy chain variable region was grafted onto a human IgG$_1$ domain (CH1, CH2 and CH3) (SEQ ID NO: 8), and the light chain variable region was grafted onto a human kappa constant domain (SEQ ID NO: 9) as seen below. This chimeric antibody was named Antibody 202.1:

Antibody 202.1 heavy chain
(SEQ ID NO: 10)
QIQLVQSGPELKKPGETVKISCKASGYTFTNYGMNWVKQAPGKGLKW

MGWINTYTGEPTYADDFKGRFAFSLETSASTAYLQINNFKNEDTATY

FCARSLSTMITTTFAYWGQGTLVTVSSASTKNPDVFPLAPSSKSTSG

GTAALGCLVKDYFPEPVTVSWNSGALTSGVHTFPAVLQSSGLYSLSS

VVTVPSSSLGTQTYICNVNHKPSNTKVDKKVEPKSCDKTHTCPPCPA

PELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSN

KALPAPIEKTISKAKGQPREPQVYTLPPSRDELTKNQVSLTCLVKGF

YPSDIAVEWESNGQPENNYKTTPPVLDSDGSFFLYSKLTVDKSRWQQ

GNVFSCSVMHEALHNHYTQKSLSLSPGK

Antibody 202.1 light chain
(SEQ ID NO: 11)
SIVMTQTPKFLLVSAGDRVTITCKASQSVSNDVAWYQQKPGQSPKLL

IYYASNRYTGVPDRFTGSGYGTDFTFTISTVQAEDLAVYFCQQDYSS

PYTFGGGTKLEIKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC

Using the PMA204 protein sequence as a template, a new optimized nucleotide sequence was produced in which the murine heavy chain variable region was grafted onto a human IgG1 domain (CH1, CH2 and CH3) (SEQ ID NO: 8), and the light chain variable region was grafted onto a human kappa constant domain (SEQ ID NO: 9) as seen below. This chimeric antibody was named Antibody 1.

Antibody 1 heavy chain
(SEQ ID NO: 12)
EVQLQQSGADLVRSGASIKLSCTASGFNIKDYYMHWVKQRPEQGLEWI

GWIDPENGDTEYAPKFQGKATMTADTSSNTAYLQLSSLTSEDTAVYYC

NACKELRYFDVWGAGTTVTVSSASTKNPDVFPLAPSSKSTSGGTAALG

CLVKDYFPEPVTVSWNSGALTSGVHTFPAVLQSSGLYSLSSVVTVPSS

SLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNA

KTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEA

LHNHYTQKSLSLSPGK

Antibody 1 light chain
(SEQ ID NO: 13)
DIVLTQSPATLSVTPGDSVSLSCRASQSISINLHWYQQKSHESPRLLI

KFASQSISGIPSRFSGYGSGTDFTLSINSVETEDFGRYFCQQSNSWPL

TFGAGTKLELKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC

Figure 1:
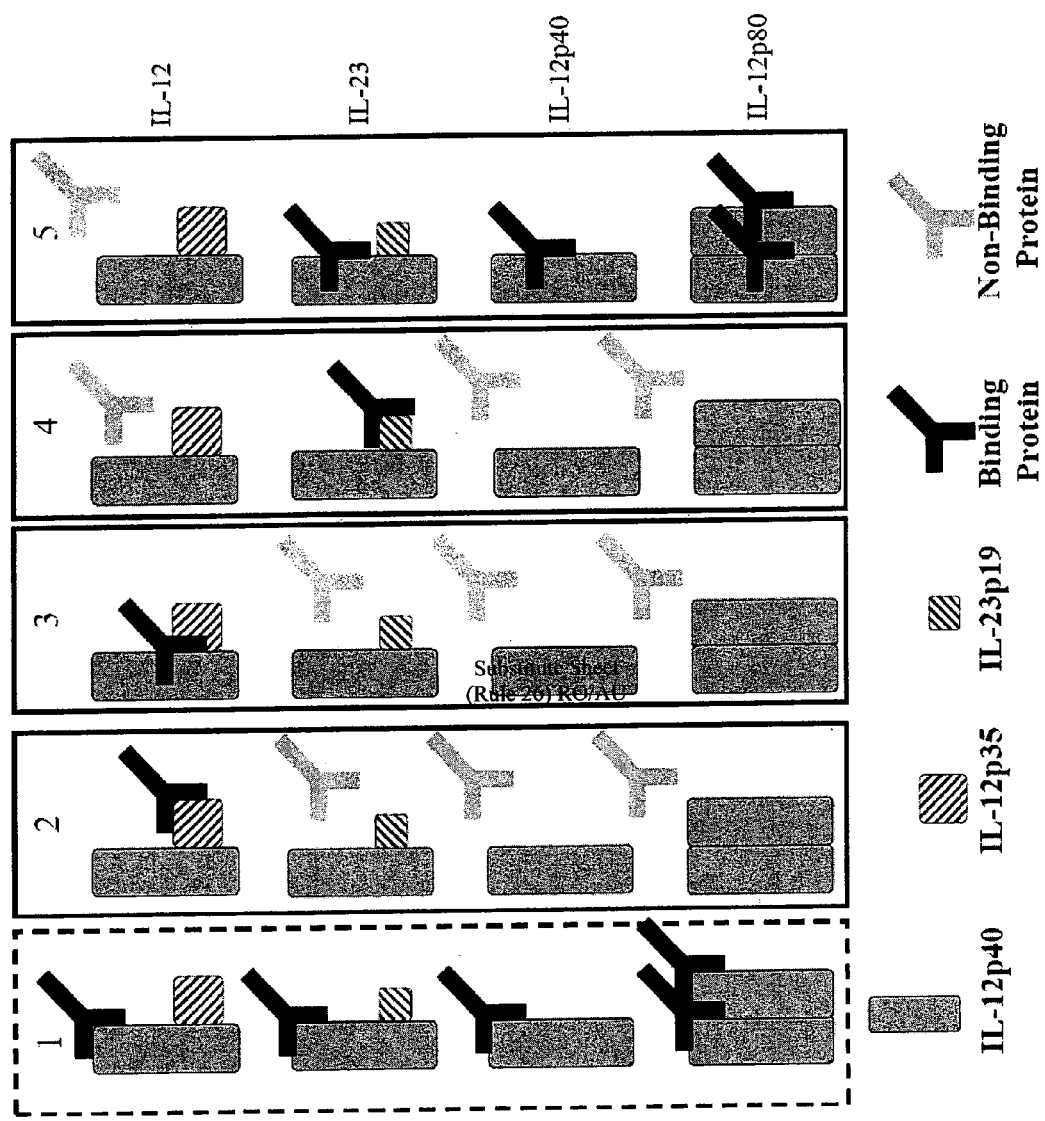
FIG. 1: The different classes of Anti-IL-12/23 antibodies.
Figure 2:
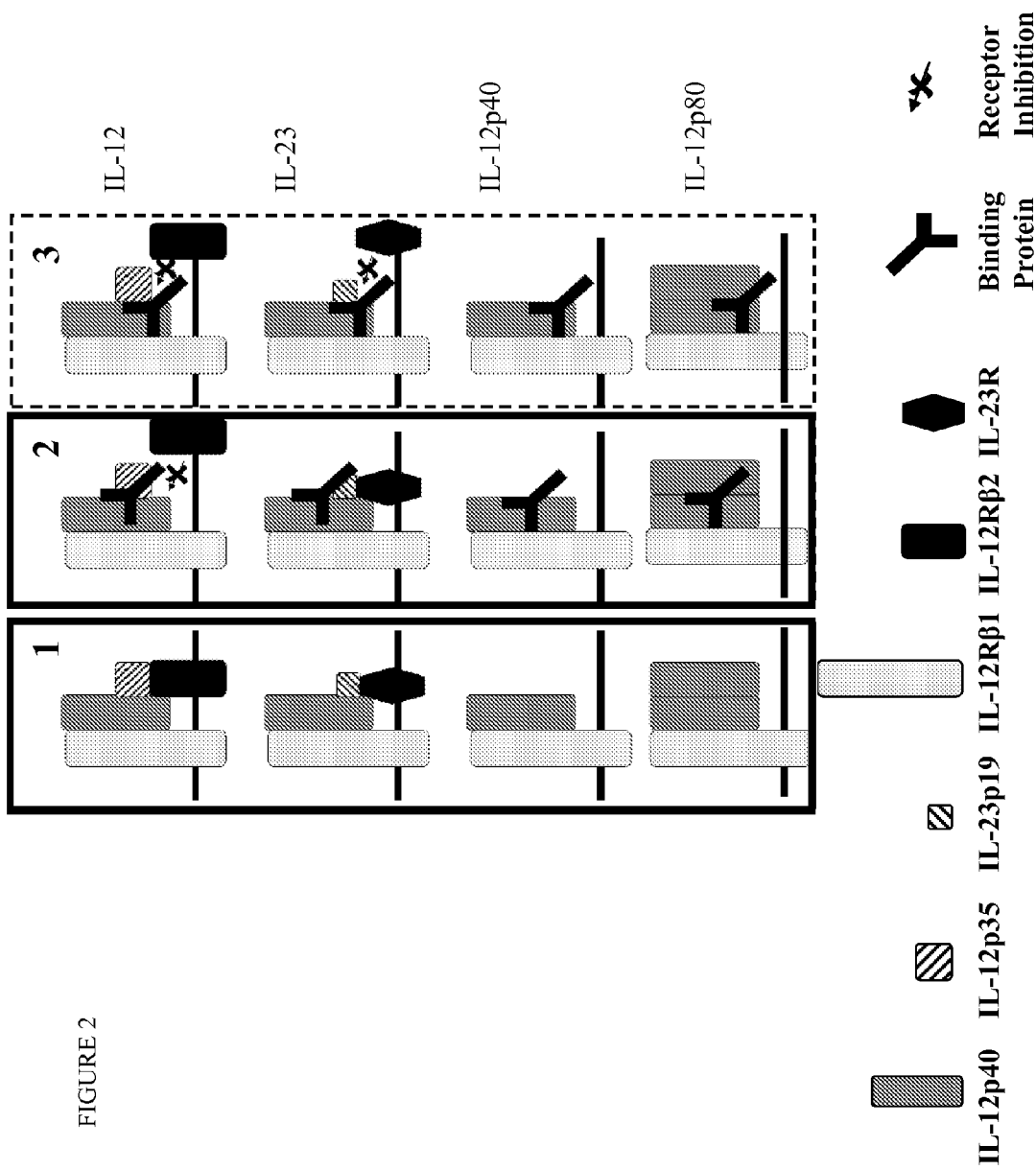
FIG. 2: IL-12/23 receptor interactions. IL-12 binds to IL-12Rβ1 and IL-12Rβ2. IL-23 binds to IL-12Rβ1 and IL-23R. IL-12p40 binds to IL-12Rβ1. IL-12p80 binds to IL-12Rβ1.
Figure 3:
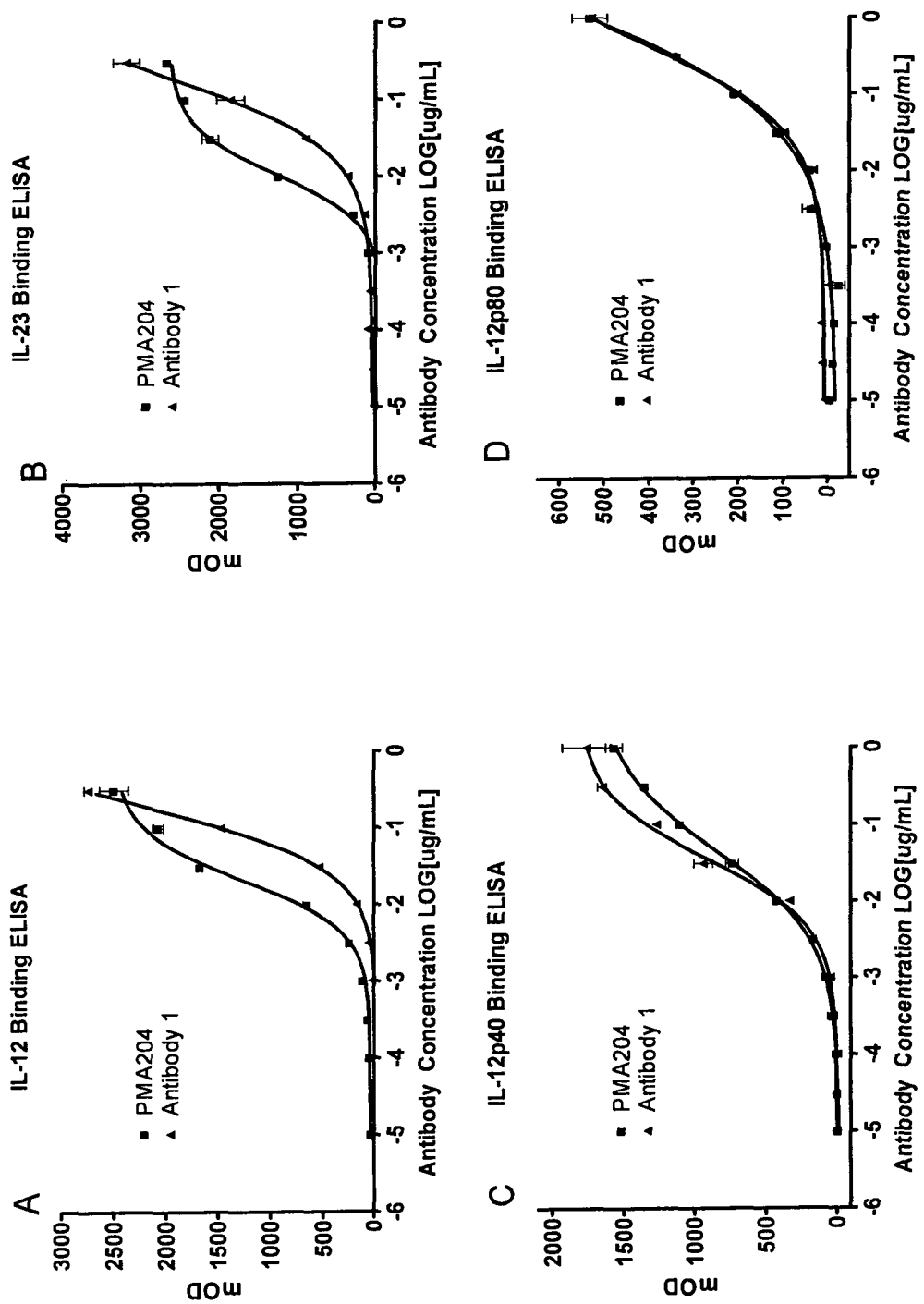
FIG. 3: PMA204 and Antibody 1 bind to IL-12 (A), IL-23 (B), IL-12p40 (C) and IL-12p80 (D) in a dose dependent manner as measured by ELISA.

Both antibodies were produced transiently in a HEK cell line and purified using Protein A chromatography. Antibody 1 was tested in ELISA (FIG. 3) and Surface Plasmon Resonance (SPR) (TABLE 1) assays against IL-12, IL-23, IL-12p40 and shown to be specific for the p40 subunit of IL-12/23. The binding profile was similar to that of the original mouse antibody PMA204 (FIG. 3).

TABLE 1

SPR data for Antibody 1

| Analyte | $k_a$ (1/Ms) | $k_d$ (1/s) | $K_D$ (pM) |
|---|---|---|---|
| IL-12 | $1.36 \times 10^6$ | $6.45 \times 10^{-5}$ | 47.7 |
| IL-23 | $2.55 \times 10^6$ | $1.14 \times 10^{-4}$ | 44.6 |
| IL-12p40 | $1.07 \times 10^6$ | $7.12 \times 10^{-5}$ | 66.3 |

Example 2

2.1 Specificity of PMA204 and Antibody 1

PMA204 and Antibody 1 bound equally well to human IL-12, IL-23, IL-12p40 and IL-12p80 in a dose dependent manner as determined using ELISA (FIG. 3). Using SPR, kinetic data for Antibody 1 including the $k_a$ (on-rate), $k_d$ (the off-rate) and the equilibrium dissociation constant ($K_D$) were calculated and are listed in TABLE 1. Antibody 1 bound to human IL-12, IL-23, IL-12p40 with similar $K_D$ values of between 40-70 pM (TABLE 1).

Figure 4:
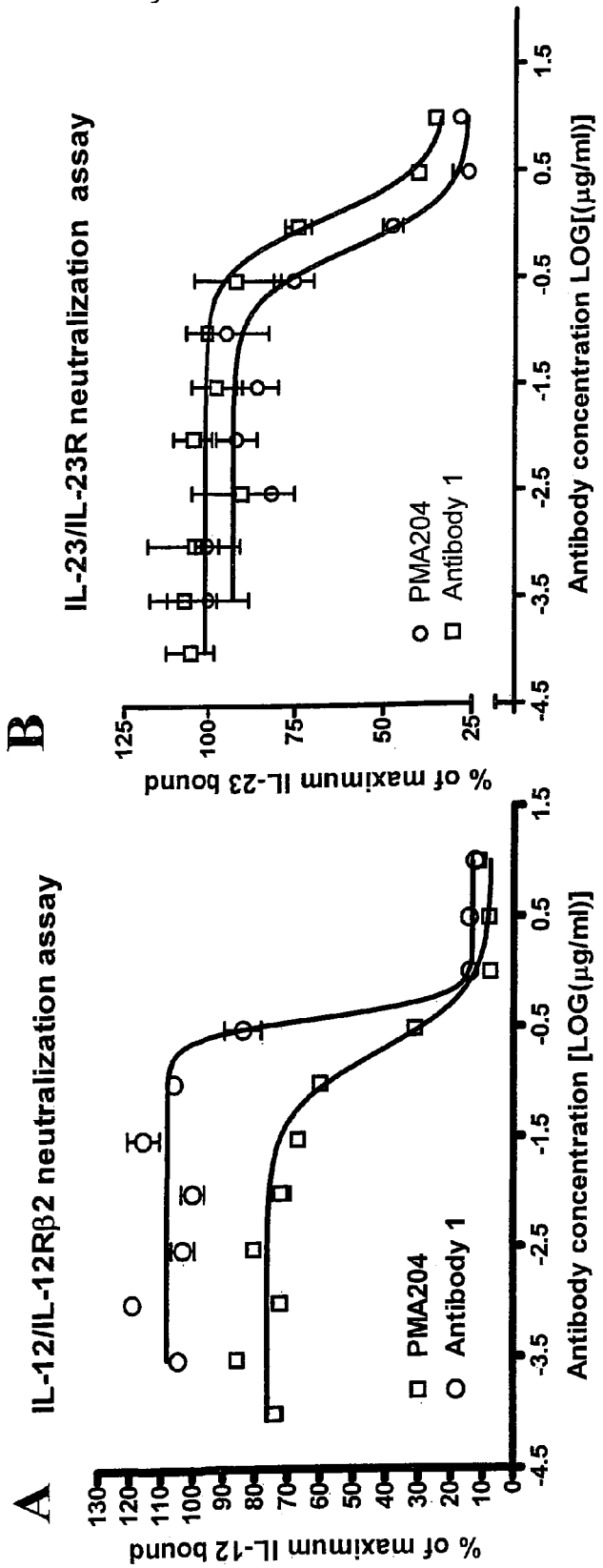
FIG. 4: PMA204 and Antibody 1 neutralize the binding of IL-12 to IL-12Rβ2 (A) and IL-23 to IL-23R (B).

2.2 PMA204 and Antibody 1 Neutralize IL-12 Binding to IL-12Rβ2 and IL-23 Binding to IL-23R Using receptor neutralization assays it was demonstrated that PMA204 and Antibody 1 neutralized the binding of IL-12 to the extracellular domain of IL-12Rβ2 (SEQ ID NO: 15) (FIG. 4A) and the binding of IL-23 to the extracellular domain of IL-23R (SEQ ID NO: 16) (FIG. 4B).

2.3 PMA204 and Antibody 1 do not Neutralize IL-12, IL-12p40, IL-12p80 or IL-23 Binding to IL-12Rβ1

Figure 5:
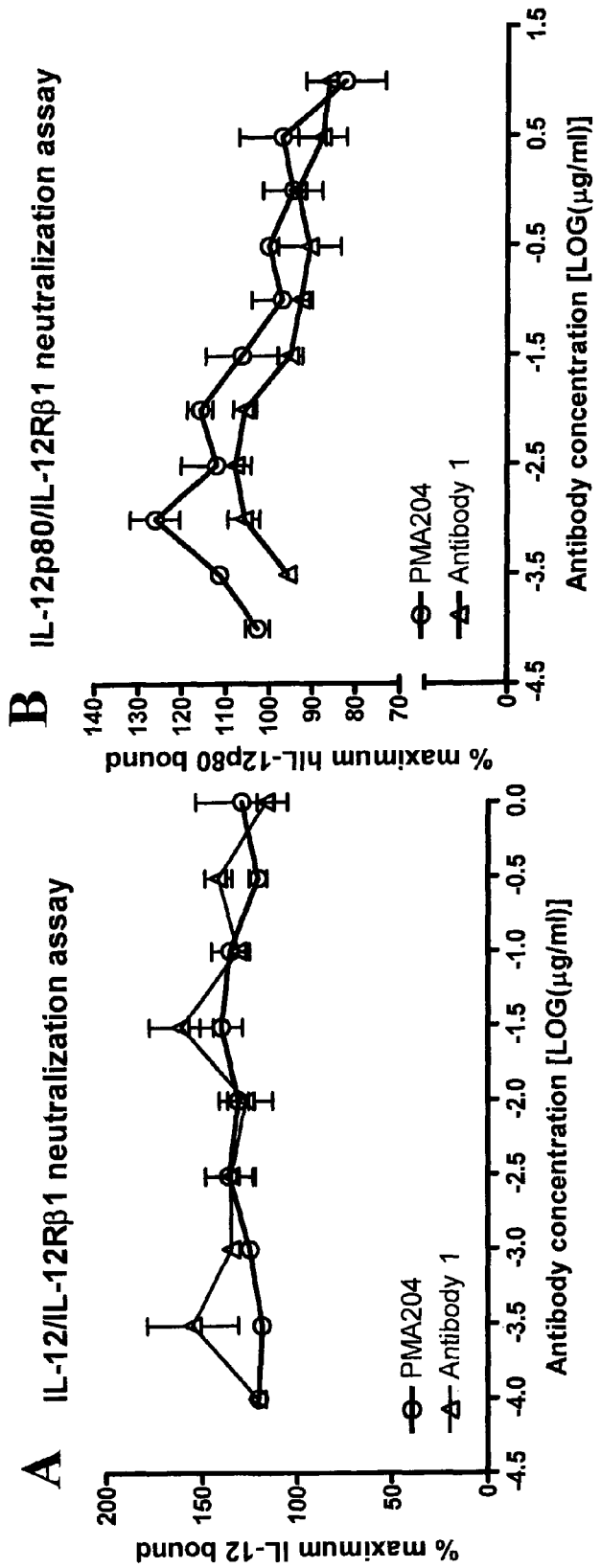
FIG. 5: PMA204 and Antibody 1 do not inhibit the binding of IL-12 to IL-12Rβ1 (A) and IL-12p80 to IL-12Rβ1 (B).
Figure 6:
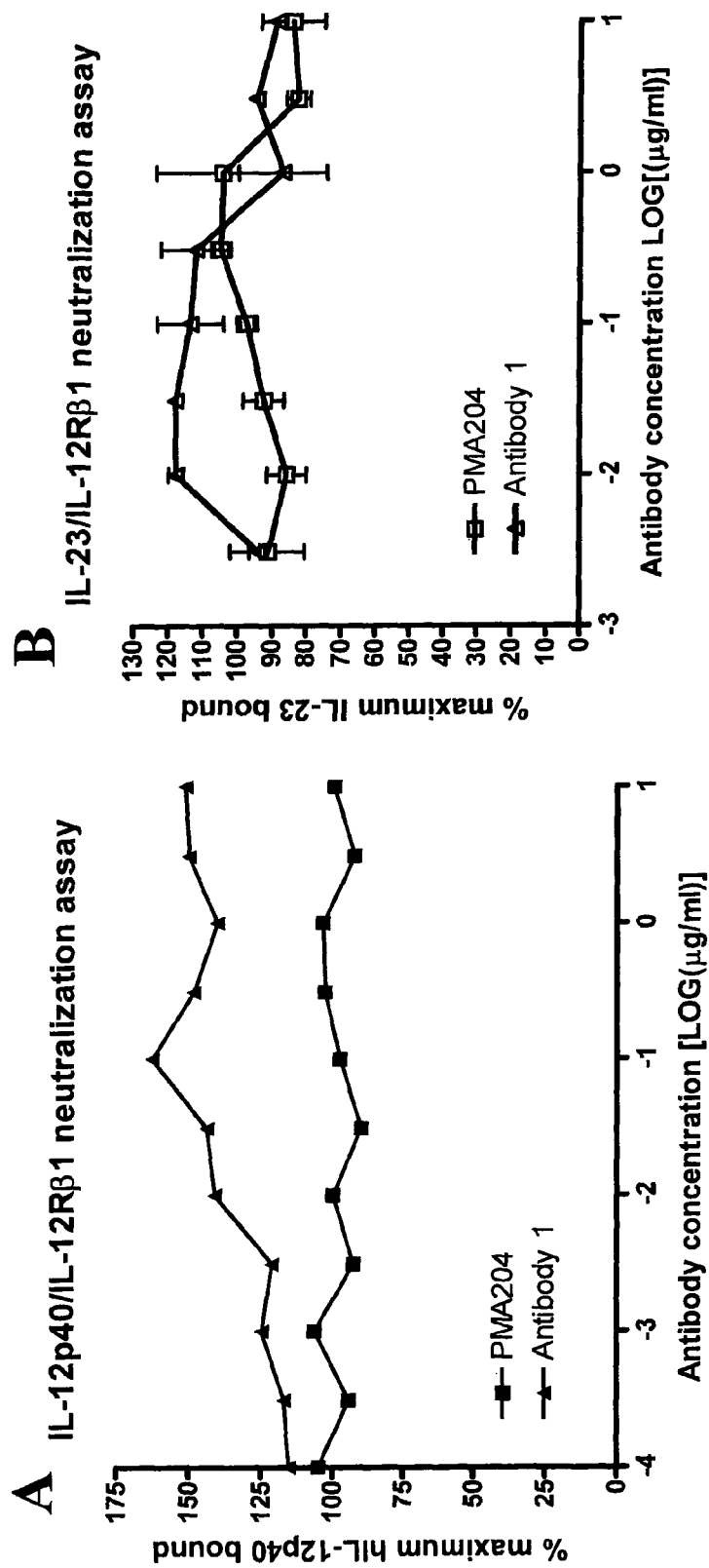
FIG. 6: PMA204 and Antibody 1 do not inhibit the binding of IL-12p40 to IL-12Rβ1 (A) and IL-23 to IL-12Rβ1 (B).

PMA204 and Antibody 1 do not neutralize the binding of IL-12 and IL-12p80 to IL-12Rβ1 (SEQ ID NO: 14) (FIG. 5). IL-12p40 and IL-23 binding to IL-12Rβ1 was not inhibited by PMA204 or Antibody 1 (FIG. 6).

Figure 7:
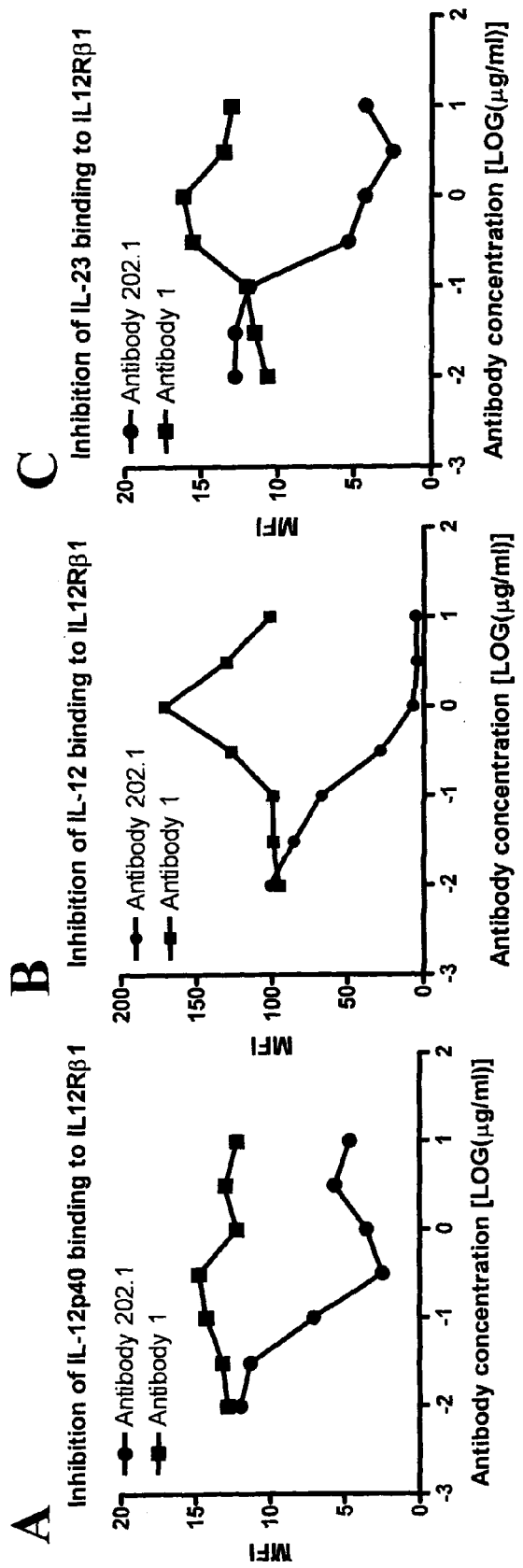
FIG. 7: Antibody 1 does not inhibit the binding of IL-12p40 (A), IL-12 (B), IL-23 (C) to an IL-12Rβ1 stably transfected Jurkat cell line. The positive control Antibody 202.1 inhibits the binding of IL-12p40, IL-12 and IL-23 to this cell line in a dose dependant manner.

2.4 Antibody 1 does not Inhibit the Binding of IL-12/23 to IL-12Rβ1 Transfected Cell Lines A stably transfected Jurkat cell line overexpressing IL-12Rβ1 was generated. This cell line was negative for IL-12Rβ2 and IL-23R as determined by flow cytometry. Binding of IL-12p40, IL-12 and IL-23 to the cell line was confirmed using flow cytometry. In an experiment in which Antibody 1 and Antibody 202.1 were titrated with IL-12p40, IL-12 or IL-23, Antibody 202.1 demonstrated titratable inhibition of cytokine binding to the IL-12Rβ1 Jurkat cell line (FIG. 7). In contrast, Antibody 1 did not appreciably neutralize binding of either IL-12, IL-23 or the IL-12p40 chain alone to the IL-12Rβ1 Jurkat cell line (FIG. 7). The mean fluorescence intensity of both IL-12 and IL-23 increased with increasing Antibody 1 concentration up to 1 µg/ml, reflecting the formation of antibody-cytokine-receptor complexes (FIG. 7).

Figure 8:
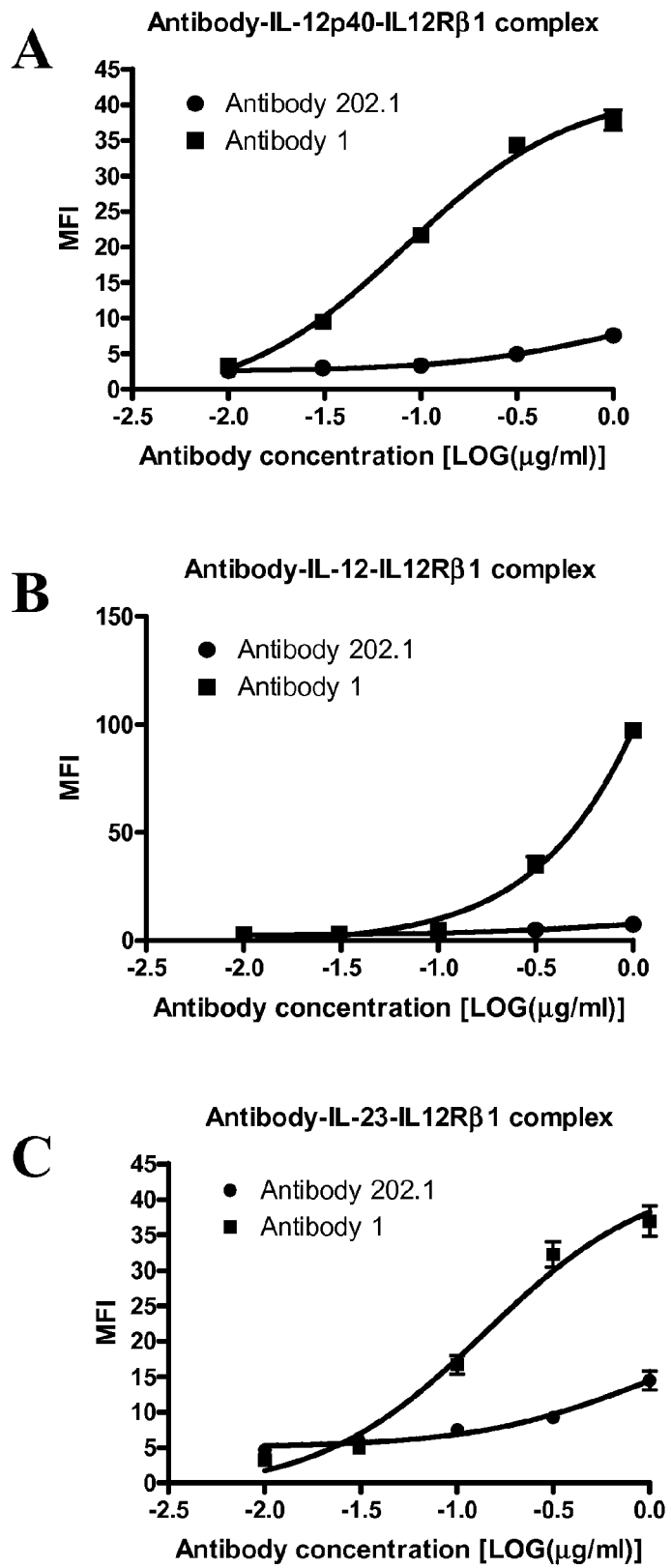
FIG. 8: Antibody 1 binds to IL-12p40 (A), IL-12 (B) and IL-23 (C) bound to IL-12Rβ1 stably transfected Jurkat cell lines, forming a complex. Positive control antibody 202.1 was not capable of forming such a complex.

2.5 Antibody 1 Forms a Complex with IL-12, IL-23 Bound to IL-12Rβ1 on Transfected Cell Lines Antibody 1 bound strongly to IL-12, IL-23 or the IL-12p40 chain bound to IL-12R131 on the surface of transfected cells (FIG. 8). It could be envisioned that this complex could occur in biological systems and present the antibody in such an orientation as to allow the Fc region of the antibody to interact with Fc binding receptors. Such receptors could be present on effector cells and induce ADCC and CDC activity thereby exhibiting cytotoxic effects on the target cell on which the antibody-cytokine-receptor complex is formed. In contrast, Antibody 202.1, showed negligible binding to cytokine-receptor complexes.

Example 3

3.1 Optimization of Antibody 1
3.1.1 W at Position 94 in the Light Chain

Figure 9:
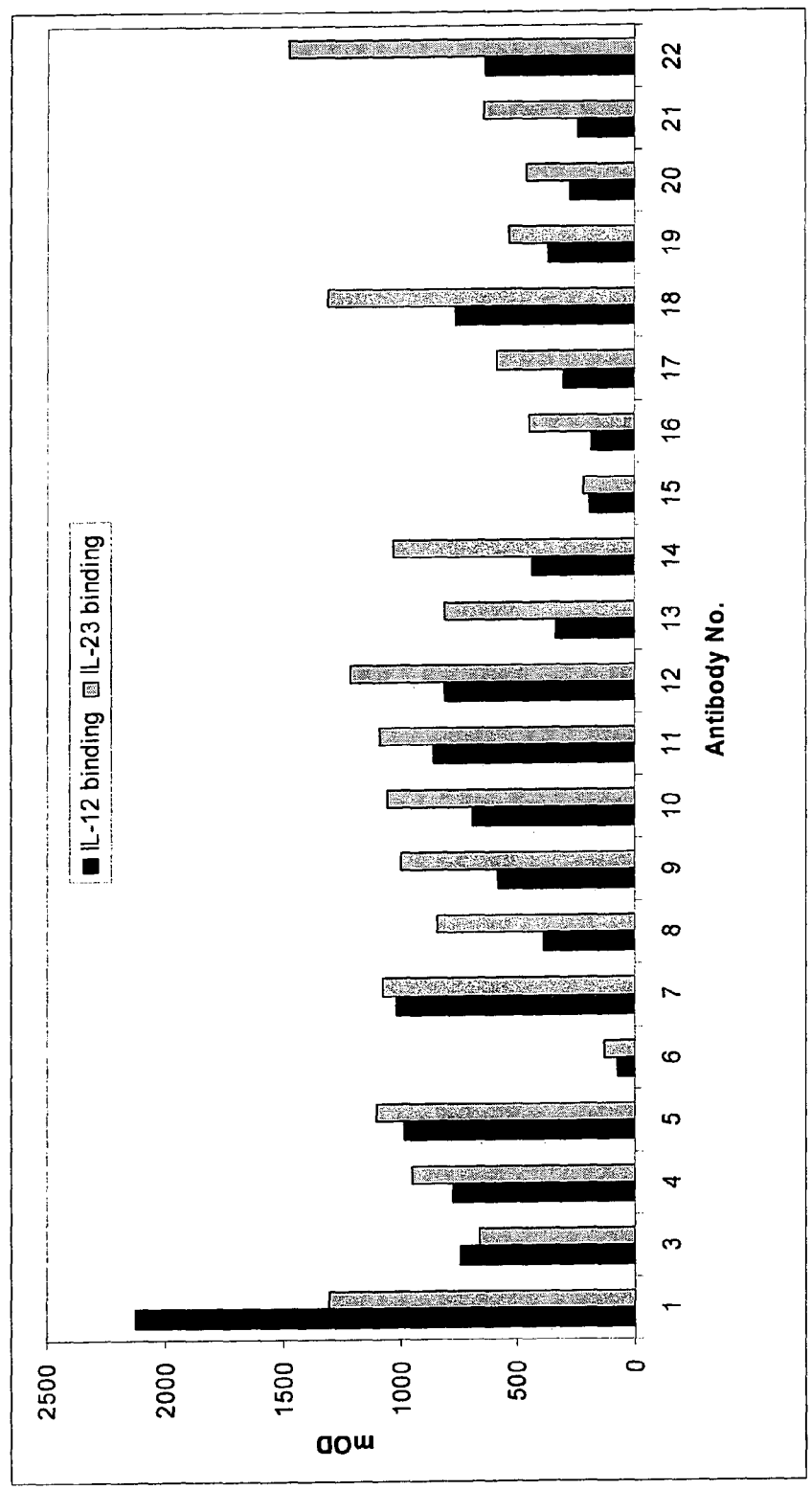
FIG. 9: ELISA data showing binding of various antibodies to IL-12 and IL-23.

Tryptophans can be oxidized during the antibody purification process leading to an oxidized and unoxidized species that causes problems during the HPLC analysis of the protein as seen by Yang et al. 2007 J Chromatogr A 1156 174-82. To avoid this a conservative substitution of Trp to Phe at position 94 in the light chain was made. This antibody named Antibody 3 was produced via gene synthesis, expressed and screened in ELISA (FIG. 9). In SPR screen this antibody dissociated from IL-12 and IL-23 faster than Antibody 1 (TABLE 2).

TABLE 2

SPR data for Antibodies 1, 3, 4 and 7.

| Antibody No. | IL-12 binding | | | IL-23 binding | | |
|---|---|---|---|---|---|---|
| | ka (1/Ms) | kd (1/s) | KD pM | ka (1/Ms) | kd (1/s) | KD pM |
| 1 | $1.67 \times 10^6$ | $1.32 \times 10^{-4}$ | 79.5 | $2.85 \times 10^6$ | $1.46 \times 10^{-4}$ | 51.3 |
| 3 | $2.15 \times 10^6$ | $9.39 \times 10^{-5}$ | 43.8 | $1.24 \times 10^6$ | $1.11 \times 10^{-4}$ | 89.6 |
| 4 | $1.54 \times 10^6$ | $2.04 \times 10^{-4}$ | 133.0 | $1.25 \times 10^6$ | $1.58 \times 10^{-4}$ | 127.0 |
| 7 | $1.82 \times 10^6$ | $1.67 \times 10^{-4}$ | 91.8 | $2.03 \times 10^6$ | $1.47 \times 10^{-4}$ | 72.2 |

3.1.2 M at Position 34 of the Heavy Chain

It has been shown that Met can be oxidized during purification and storage of antibodies. A BLAST search of human antibody sequences identified that Leu is common at this position. A M34L substitution was made and the construct named Antibody 4. The gene was synthesied, expressed and the antibody screened using SPR and ELISA (FIG. 9). Antibody 4 suffered a small loss in affinity for both IL-12 and IL-23 compared to Antibody 1 (TABLE 2).

3.1.3 Cysteine at Position 95 in the Heavy Chain

A problematic residue was observed in the heavy chain of Antibody 1 at position 95. This cysteine at the start of CDR3 could be oxidized, causing heterogeneity in any resulting antibody product. It could also form complexes by disulphide bond formation. Therefore, each of the other 18 (the exceptions being the original Cys and Trp) amino acids was substituted in this position using gene synthesis, and the antibodies were expressed transiently (Antibodies 5, 6, 7, 8, 9, 10, 11, 12, 13, 14, 15, 16, 17, 18, 19, 20, 21, 22). An ELISA was performed on these antibodies (FIG. 9). Some of the antibodies retained binding activity for both IL-12 and IL-23, others only for one cytokine or the other, while others minimally bound to either cytokine. SPR was performed on the samples and from this data the off-rate of the constructs were analysed. From this data Antibody 7 which had a C95N substitution displayed the closest affinity to that of Antibody 1 (TABLE 2).

Figure 10:
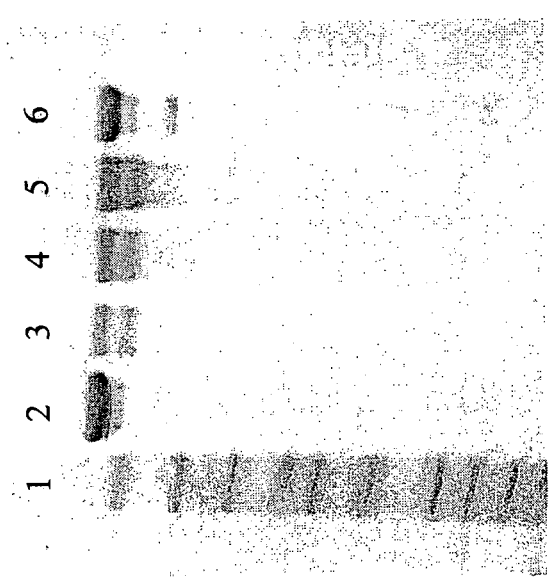
FIG. 10: SDS-PAGE gel of Antibodies 1, 3, 4, 7 and comparator antibody, demonstrating different band patterns.

Unexpectedly this substitution dramatically improved the homogenitiy of the product as seen by SDS-PAGE. Antibody 7 displayed a size pattern with one major species which is similar to that seen for a comparator antibody of known molecular weight (FIG. 10). This was compared to Antibody 1 which displayed two major species (FIG. 10).

The 3 substitutions were then combined into a single antibody which was called Antibody 50 which had the following heavy and light chain variable regions:

Antibody 50 VH domain
(SEQ ID NO: 112)
EVQLQQSGADLVRSGASIKLSCTASGFNIK<u>DYYLH</u>WVKQRPEQGLEWI G<u>WIDPENGDTEYAPKFQG</u>KATMTADTSSNTAYLQLSSLTSEDTAVYYC NA<u>NKELRYFDV</u>WGAGTTVTVSS Antibody 50 VL domain
(SEQ ID NO: 169)
DIVLTQSPATLSVTPGDSVSLSC<u>RASQSISINLH</u>WYQQKSHESPRLLI K<u>FASQSISGI</u>PSRFSGYGSGTDFTLSINSVETEDFGRYFC<u>QQSNSFPL</u>

<u>T</u>FGAGTKLELKR

Figure 11:
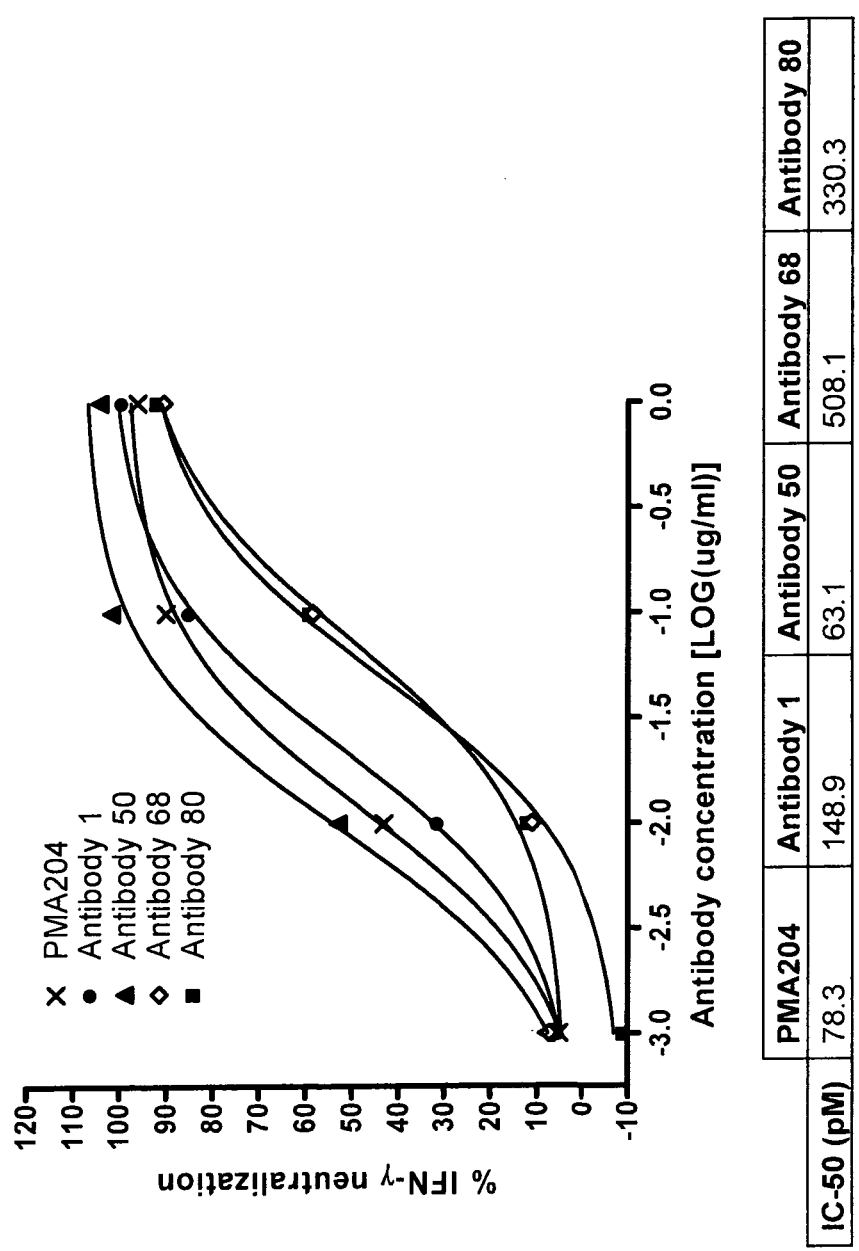
FIG. 11: PMA204, Antibody 1, Antibody 50, Antibody 68 and Antibody 80 demonstrating inhibition of IL-12 induced IFN-γ release by NK-92 cells.

This antibody retained high affinity for IL-12 and IL-23 as measured by ELISA, SPR and in cell based assays (FIG. 11).

Example 4

4.1 Superhumanization of PMA204

Superhumanization of PMA204 was performed in accordance with the method taught in US publication number US 2003/039649 (Foote) and PCT publication number WO 04/006955 (Foote) and as further explained by Tan et al. (2002) and by Hwang et al. (2005).

First, canonical structures for the CDRs of the heavy and light chains were determined (listed below) according to the method taught in the U.S. patent application Ser. No. 10/194,975 and U.S. Pat. No. 6,881,557 and as further explained by Tan et al (2002. J. Immunol. 169(2): 1119-25), by Hwang et al (2005) and in this application (see above). They were as follows:

TABLE 3

Canonical Structure pattern of the CDRs of PMA204

| CDR | Canonical Structure |
|---|---|
| Heavy Chain CDR1 | 1 |
| Heavy Chain CDR2 | 2 |
| Light Chain CDR1 | 2 |
| Light Chain CDR2 | 1 |
| Light Chain CDR3 | 1 |

Human germline VH region sequences (Hwang et al, 2005) that have a similar canonical structure pattern to PMA204 were selected as acceptors. These were the following germline sequences (Note: All germline sequences taken from IMGT database, Giudicelli, V. et al. Nucleic Acids Res., 33: D256-D261 (2005); Note some residues in the these germline sequences are hypervariable and are not listed in the sequence):

```
IGHV1-f*01
                                       (SEQ ID NO: 17)
EVQLVQSGAEVKKPGATVKISCKVSGYTFTDYYMHWVQQAPGKGLEWMG

LVDPEDGETIYAEKFQGRVTITADTSTDTAYMELSSLRSEDTAVYYCAT

IGHV1-24*01
                                       (SEQ ID NO: 18)
QVQLVQSGAEVKKPGASVKVSCKVSGYTLTELSMHWVRQAPGKGLEWMG

GFDPEDGETIYAQKFQGRVTMTEDTSTDTAYMELSSLRSEDTAVYYCAT

IGHV1-18*01
                                       (SEQ ID NO: 19)
QVQLVQSGAEVKKPGASVKVSCKASGYTFTSYGISWVRQAPGQGLEWMG

WISAYNGNTNYAQKLQGRVTMTTDTSTSTAYMELRSLRSDDTAVYYCAR
```

Any of the germline sequences shown (SEQ ID NO: 17, SEQ ID NO: 18, SEQ ID NO:19) in combination with any of the six known human germline JH sequences could supply the framework regions for making a humanized heavy chain. The following JH region sequence was chosen based on primary sequence similiarity:

```
        JH3   AFDVWGQGTMVTVSS    (SEQ ID NO: 20)
```

Human germline VL region sequences (Hwang et al, 2005) that have a similar canonical structure pattern to PMA204 were selected as acceptor sequences. These were the following germline sequences:

```
IGKV6D-21*01
                                       (SEQ ID NO: 21)
EIVLTQSPDFQSVTPKEKVTITCRASQSIGSSLHWYQQKPDQSPKLLI

KYASQSFSGVPSRFSGSGSGTDFTLTINSLEAEDAATYYCHQSSSLP

IGKV3-15*01
                                       (SEQ ID NO: 22)
EIVMTQSPATLSVSPGERATLSCRASQSVSSNLAWYQQKPGQAPRLLI

YGASTRATGIPARFSGSGSGTEFTLTISSLQSEDFAVYYCQQYNNWP

IGKV3-11*01
                                       (SEQ ID NO: 23)
EIVLTQSPATLSLSPGERATLSCRASQSVSSYLAWYQQKPGQAPRLLI

YDASNRATGIPARFSGSGSGTDFTLTISSLEPEDFAVYYCQQRSNWP
```

Any of the germline sequences shown (SEQ ID NO: 21, SEQ ID NO: 22, SEQ ID NO: 23) in combination with any of the 5 possible Jκ sequences could supply the framework regions for making a humanized light chain. The following Jκ region sequence was chosen based on primary sequence similiarity:

```
        Jκ4   LTFGGGTKVEIKR      (SEQ ID NO: 24)
```

Figure 12:
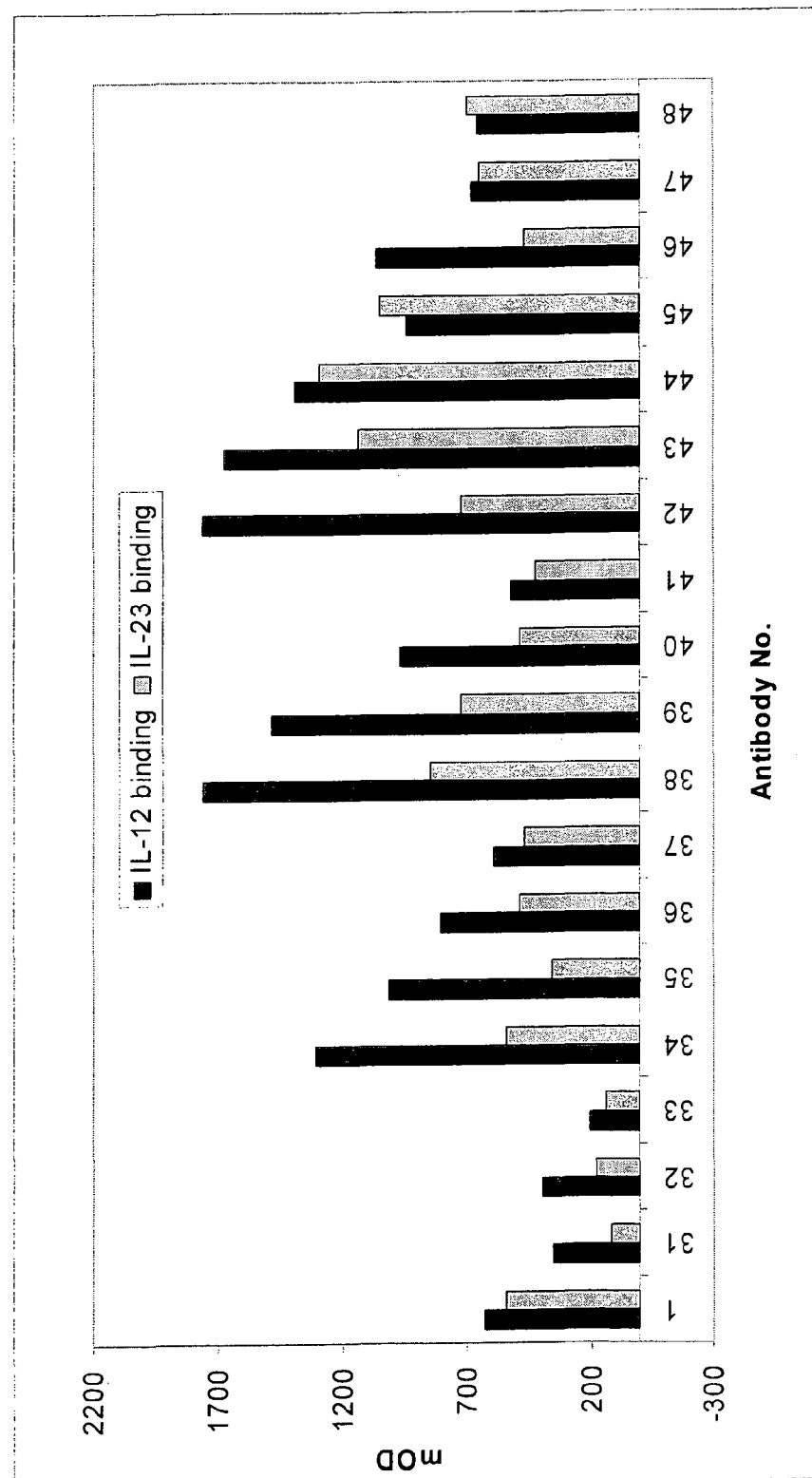
FIG. 12: ELISA data showing binding of various antibodies to IL-12 and IL-23

The CDRs of the acceptors were replaced with the corresponding CDRs from PMA204. The genes were created using gene synthesis, and different combinations of Superhumanized heavy and light chains were transfected (Antibodies 40, 41, 42, 43, 44, 45, 46, 47, 48). All of these expressed antibodies retained binding activity for both IL-12 and IL-23 (FIG. 12).

Two rare amino acids in the heavy chain of PMA204 were identified. An Ala at position 93 and Asn at position 94. These amino acids were introduced as backmutations into the heavy chain Superhumanized variants. The genes were created using gene synthesis, and different combinations of these backmutated Superhumanized heavy chains and the Superhumanized light chains were transfected (Antibodies 31, 32, 33, 34, 35, 36, 37, 38, 39). Some of the expressed antibodies retained binding activity for both IL-12 and IL-23, some antibodies bound only to one cytokine or the other, while other antibodies showed minimal binding to either cytokine (FIG. 12).

Figure 13:
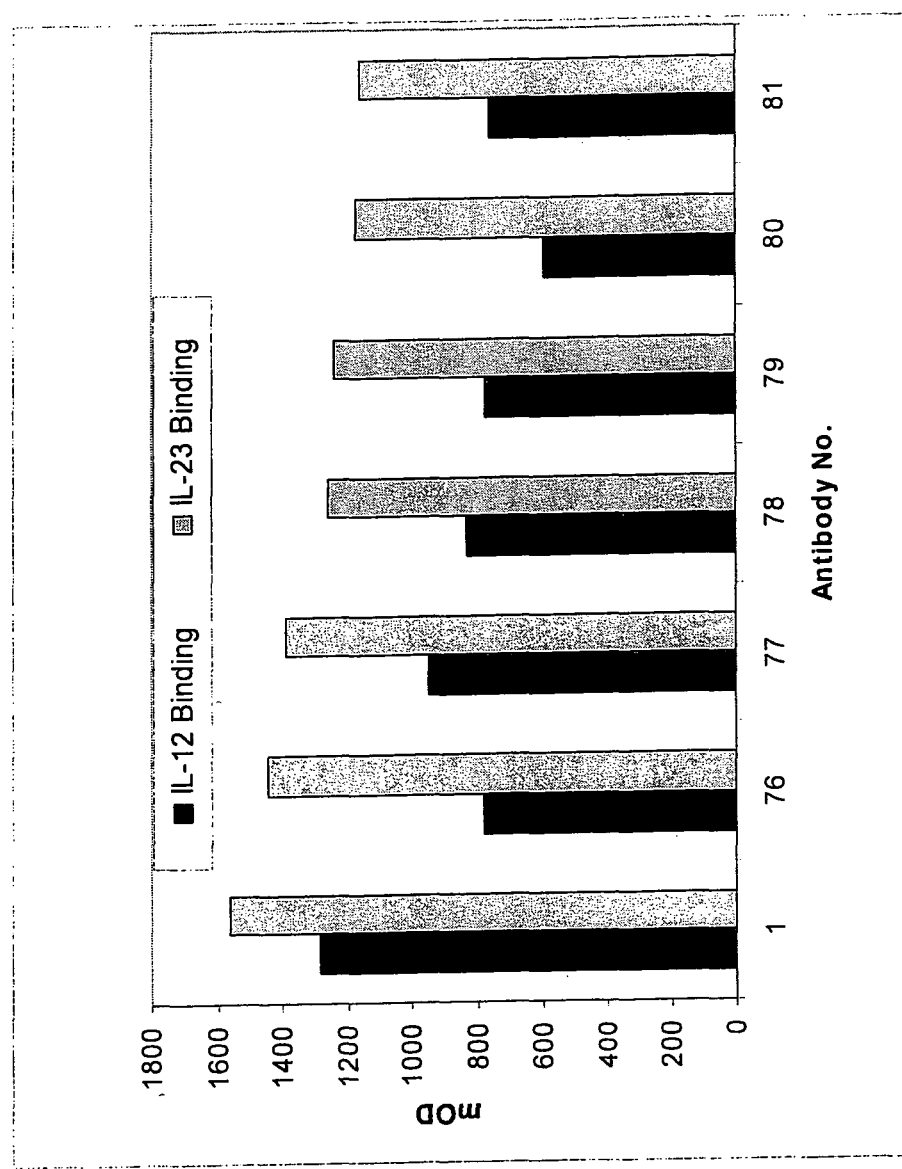
FIG. 13: ELISA data showing binding of various antibodies to IL-12 and IL-23
Figure 14:
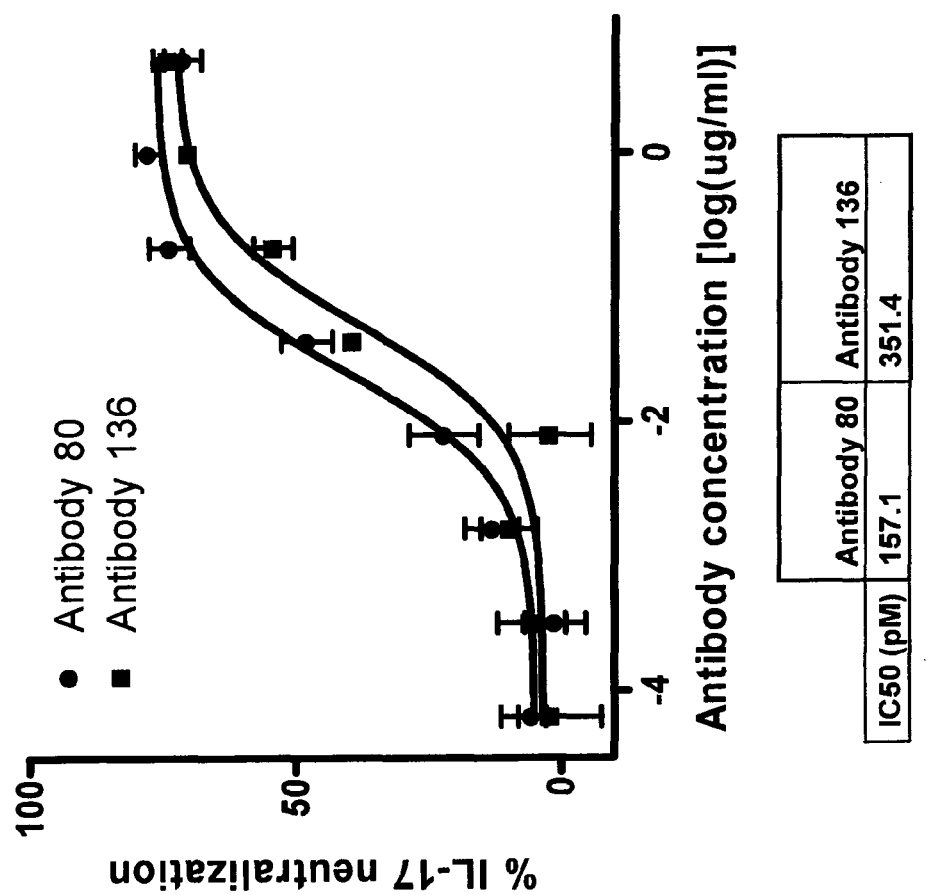
FIG. 14: Antibody 80 and Antibody 136 demonstrate inhibition of IL-23 induced IL-17 secretion by murine splenocytes.
Figure 17:
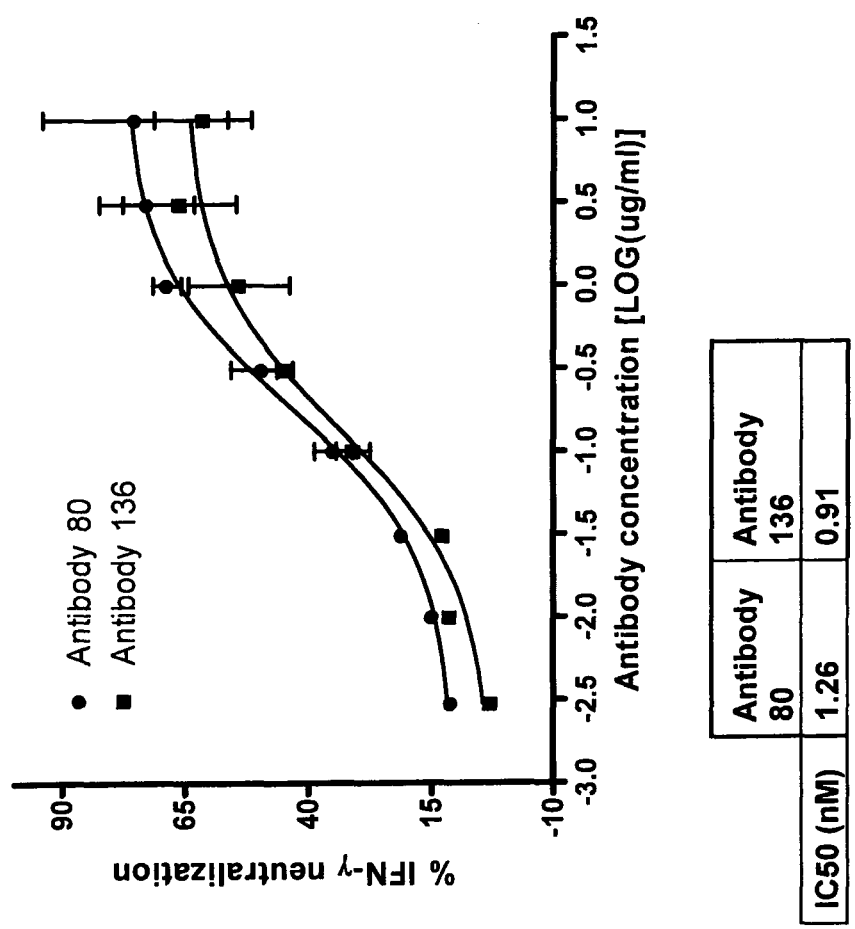
FIG. 17: Antibody 80 and Antibody 136 demonstrate inhibition of IL-12 induced IFN-γ release by human PBMCs.

From these combinations of antibodies, several antibodies displayed consistant and strong binding to their antigen in ELISA and SPR assays. Three antibodies were selected Antibodies 37, 39 and 44. Based on the optimization of Antibody 1, the 3 point mutations that enhanced the biophysical properties of Antibody 1 (Light Chain W94F, Heavy Chain M34L, Heavy Chain C95N) were introduced into Antibodies 37, 39 and 44. A combination approach mixing the heavy chains and light chains of the optimized variants was performed generating a panel of antibodies (Antibodies 76, 77, 78, 79, 80, 81). Of these antibodies all bound to IL-12 and IL-23 in ELISA (FIG. 13). Antibody 80 displayed strong binding to IL-12 as measured via SPR and was chosen for further analysis using the NK92 cell based assay (FIG. 11) and the human PBMC IL-12 induced IFN-γ assay (FIG. 17) and the murine splenocyte assay (FIG. 14). The construct Antibody 80 demonstrated strong inhibition of IL-12 induced IFN-γ secretion in NK-92 assay and IL-23 induced IL-17 secretion in the murine splenocyte assay.

Example 5

5.1 Humanization of PMA204

PMA204 was also humanized using human framework sequences that are closely homologous in linear peptide sequence to framework sequences of the original mouse antibody.

A BLAST search of the PBD database (http://www.pdb.org/pdb/home/home.do) was performed using the heavy and light chains of PMA204 as query sequences.

A close human homologue to the heavy chain variable region of PMA204 (SEO ID NO: 6) was 1RZ7HC variable region (SEQ ID NO: 25) as shown below:

```
PMA204HC    EVQLQQSGADLVRSGASIKLSCTASGFNIKDYYMHWVKQR        40

1RZ7HC      ....V....EVKKP..TV.I...K...YTFS.F...Y..R.A      40

PMA204HC    PEQGLEWIGWIDPENGDTEYAPKFQGKATMTADTSSNTAY        80

1RZ7HC      .GK....M.L....DA..M..E..R.RV.I.....TD.G.        80

PMA204HC    LQLSSLTSEDTAVYYCNACK-ELRYFDVWGAGTTVTVSS         118

1RZ7HC      .E....R.........A.DPW...NA.N...Q..L.S...        119
```

There are 31 amino acid differences between the two sequences outside of the CDR regions.

The light chains homology was also high between the light chain variable region of PMA204 (SEQ ID NO: 7) and 1RZ7LC variable region (SEQ ID NO: 26) as shown below:

```
PMA204LC    DIVLTQSPATLSVTPGDSVSLSCRASQSISINLHWYQQKS         40

1RZ7LC      D.QM....SSV.ASV..R.TIT.....D..TW.A.....P         40

PMA204LC    HESPRLLIKFASQSISGIPSRFSGYGSGTDFTLSINSVET         80

1RZ7LC      GKA.K...YA..TLQ..V......S.......S.T...LQP        80

PMA204LC    EDFGRYFCQQSNSWPLTFGAGTKLELKR                    107

1RZ7LC      ...AT.Y...A..F-F...G...V.I..                    107
```

There are 31 amino acid differences between the two sequences outside of the CDR regions.

Using 3D-modeling software (Accelrys, Modeller), 3D models of heavy and light chain of PMA204 were built using as templates the 10 most homologous antibodies, based on primary sequence, found during the BLAST search of the PBD database and where each template antibody had a published high resolution crystal structure. Aligning the model of PMA204 and 1RZ7 demonstrated a reasonable fit (RMSD heavy chains=1.53 and RMSD light chains=0.6) between the frameworks of the two antibodies. Therefore 1RZ7 was chosen as the acceptor framework into which the donor CDRs from PMA204 were grafted onto generating a CDR-grafted antibody.

A closer examination of the model of PMA204 identified critical framework residues that could influence the binding of the CDR-grafted antibody to the antigen. These were as follows:
Heavy Chain
ARG40—Hydrogen Bonds to another residue and stabilises a CDR loop structure
GLU42—Difference in secondary structure compared between donor and acceptor
LYS66—Hydrogen Bonds to 3 different residues and stabilises a CDR loop structure
Light Chain
LYS49—H-Bonds to the heavy chain CDR3 residues
TYR65—RARE residue non-conservative
ARG85—RARE residue non-conservative Each of these amino acids were introduced as backmutations into the CDR-grafted antibody. Based on the optimization of Antibody 1, the 3 point mutations that enhanced the biophysical properties of Antibody 1 (Light Chain W94F, Heavy Chain M34L, Heavy Chain C95N) were introduced into all the humanized variants.

Figure 15:
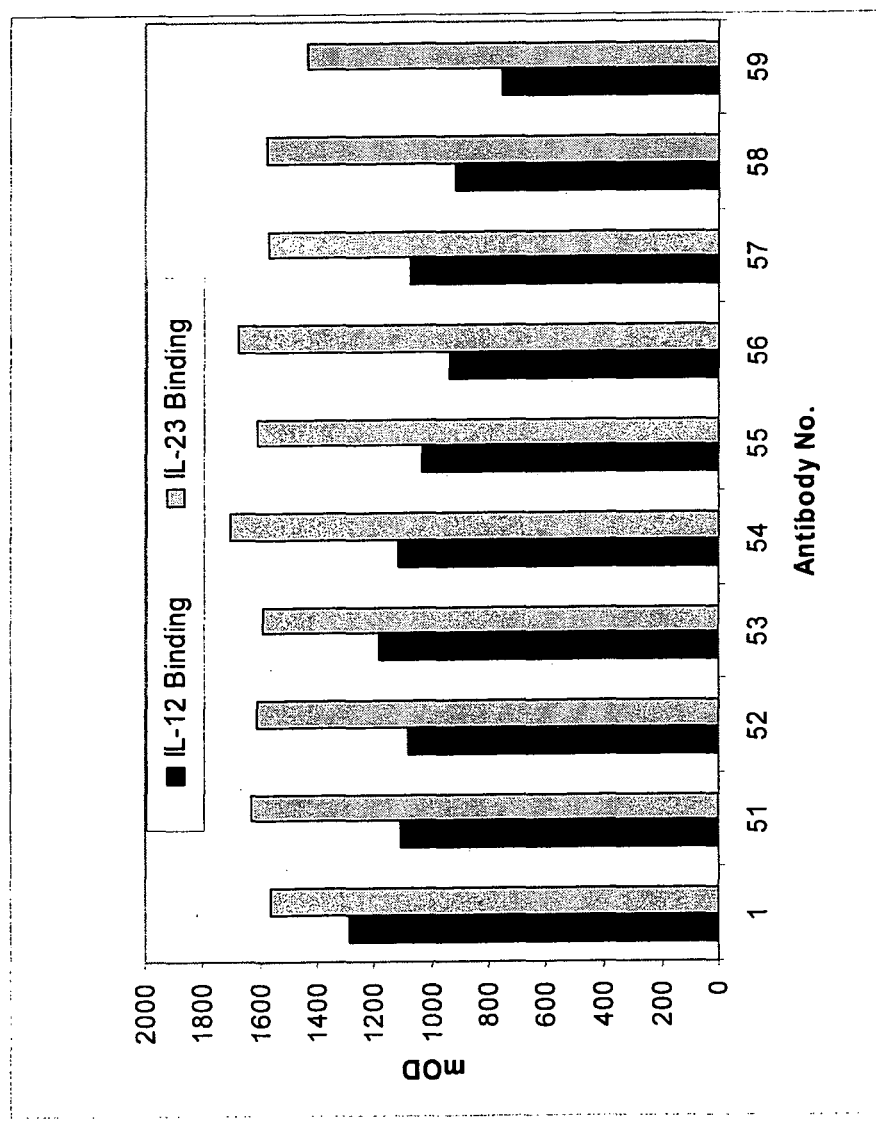
FIG. 15: ELISA data showing binding of various antibodies to IL-12 and IL-23.
Figure 16:
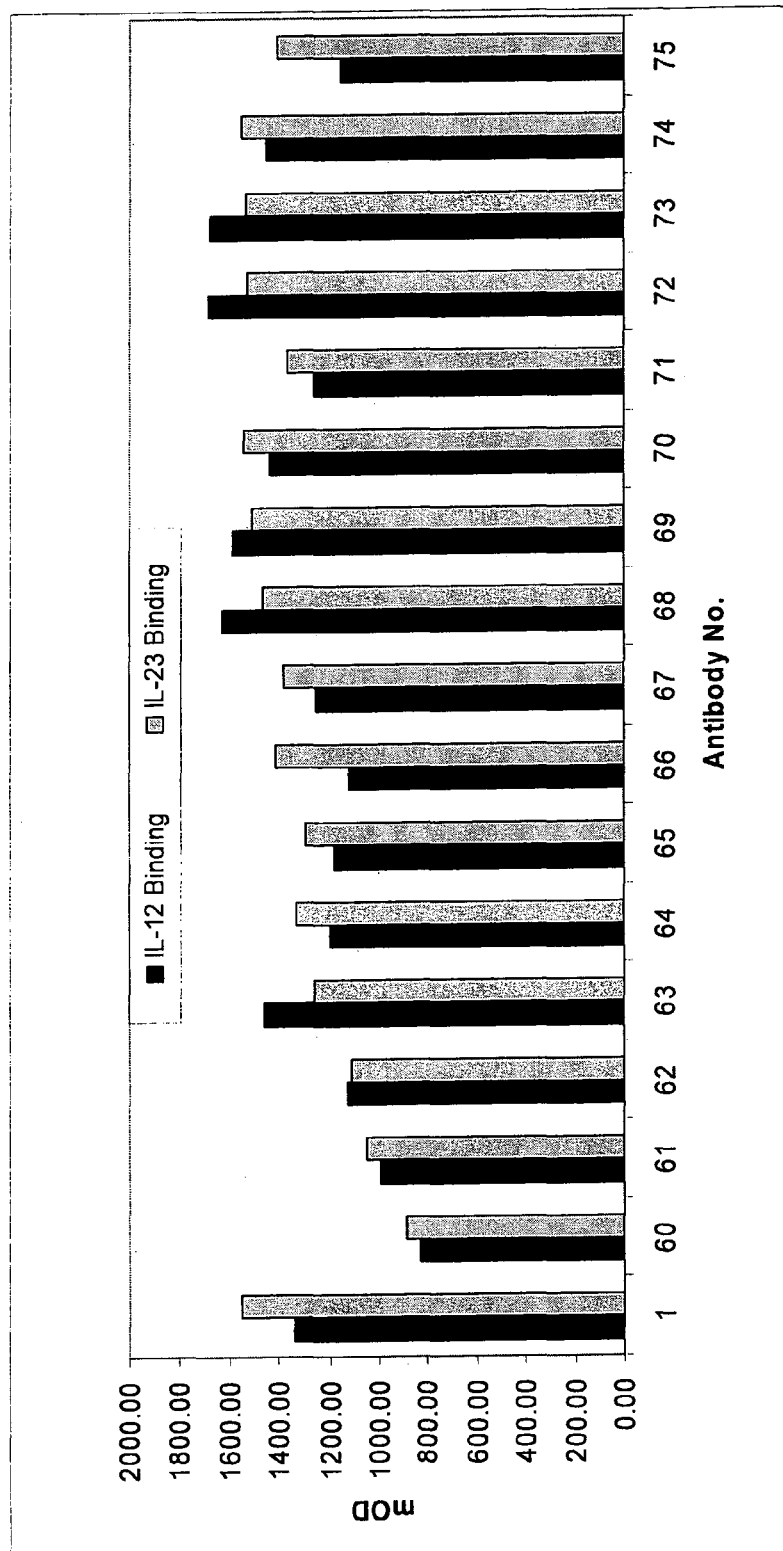
FIG. 16: ELISA data showing binding of various antibodies to IL-12 and IL-23.

After gene synthesis of all the humanized variants, combinations of the straight CDR-grafted antibody chains and the backmutated chains were expressed together generating a panel of humanized antibodies (Antibodies 51, 52, 53, 54, 55, 56, 57, 58, 59, 60, 61, 62, 63, 64, 65, 66, 67, 68, 69, 70, 71, 72, 73, 74, 75). An ELISA was performed on these antibodies. All of the antibodies retained binding activity for both IL-12 and IL-23 (FIG. 15, FIG. 16). Antibody 68 displayed strong binding to IL-23 as measured via SPR and was chosen for further analysis using the NK92 cell based assay (FIG. 11). Antibody 68 demonstrated strong inhibition of IL-12 induced IFN-γ secretion in NK-92 assay.

Figure 18:
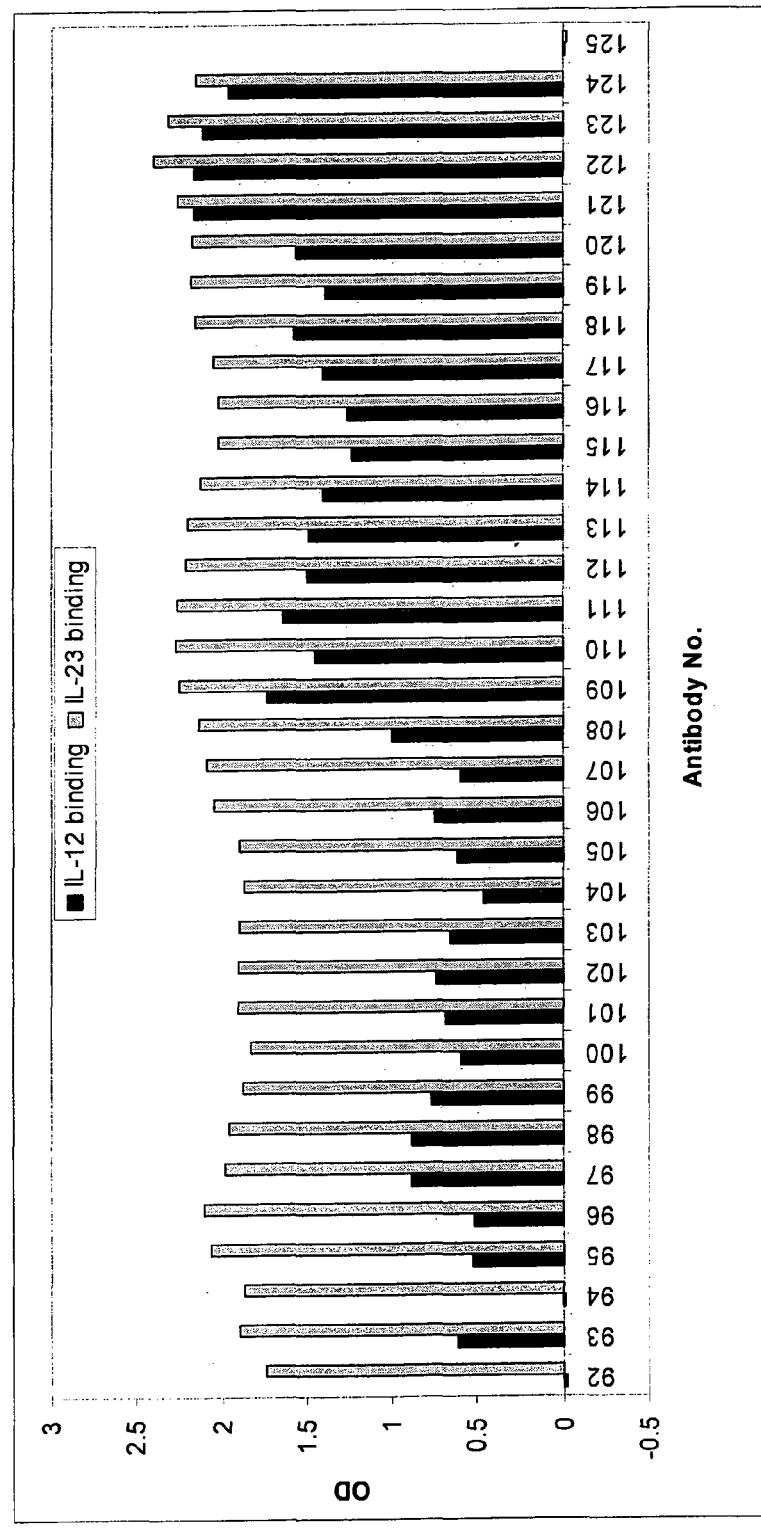
FIG. 18: ELISA data showing binding of various antibodies to IL-12 and IL-23.

To explore whether other backmutations could enhance the affinity and potency of the antibody, the heavy chain variable region of Antibody 68 was aligned with the heavy chain variable region of the optimized chimeric antibody Antibody 50. At each position in which Antibody 68 differed from Antibody 50 the residue from Antibody 50 at that position was introduced into Antibody 68. These variants were gene synthesized, paired with Antibody 68 light chain, and expressed (Antibodies 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125). An ELISA was performed on all the heavy chain and light chain antibodies. Some retained binding activity for both IL-12 and IL-23, others only for one cytokine or the other, while others showed no binding to either cytokine (FIG. 18).

Figure 19:
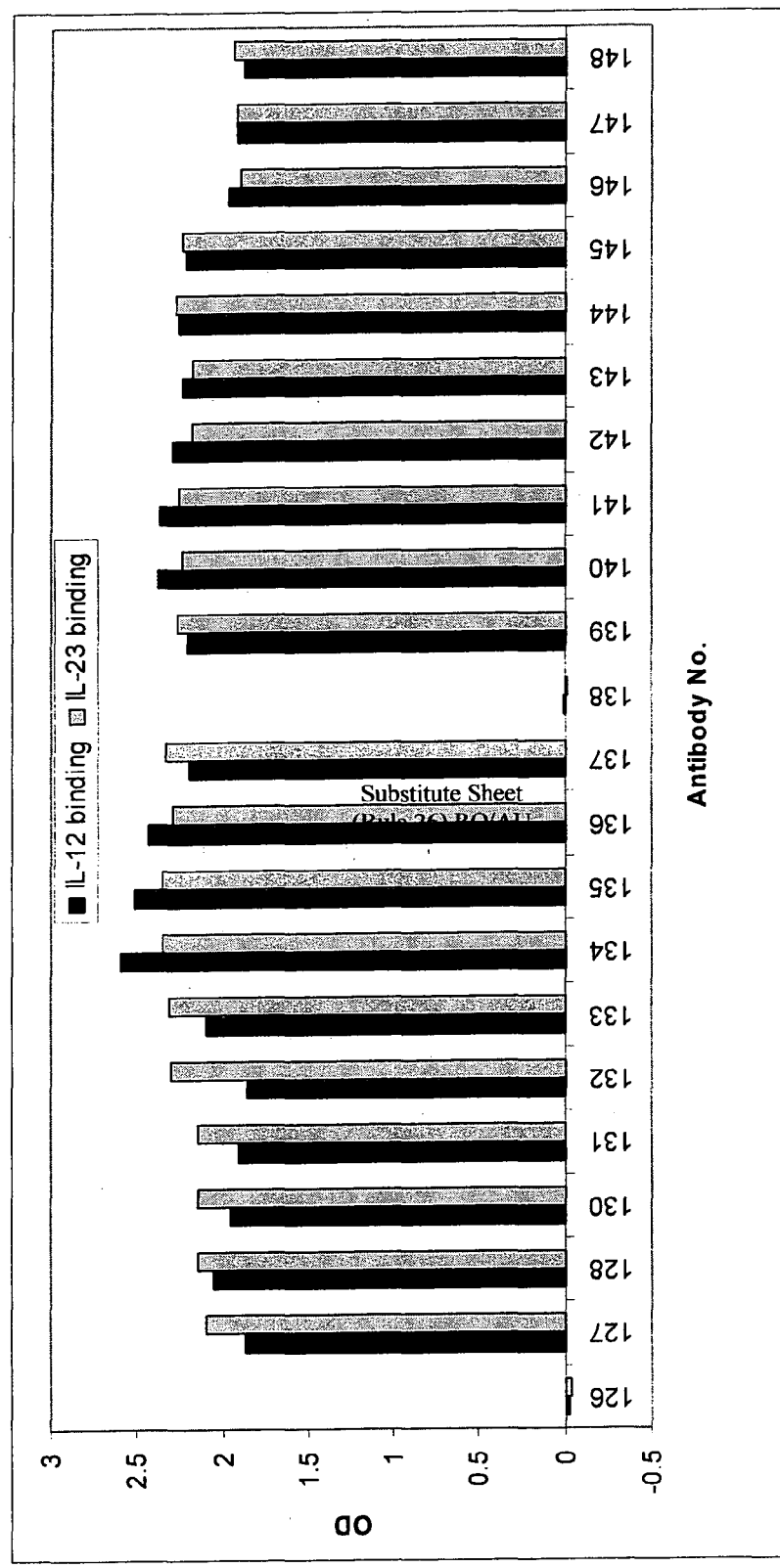
FIG. 19: ELISA data showing binding of various antibodies to IL-12 and IL-23.

To see whether other backmutations could enhance the affinity and potency of the antibody, the light chain variable region of Antibody 68 was aligned with the light chain variable region of the optimized chimeric Antibody 50. At each position in which Antibody 68 differed from Antibody 50 the residue from Antibody 50 at that position was introduced into Antibody 68. These variants were gene synthesized, paired with Antibody 68 heavy chain and expressed (Antibodies 126, 127, 128, 130, 131, 132, 133, 134, 135, 136, 137, 138, 139, 140, 141, 142, 143, 144, 145, 146, 147, 148). An ELISA was performed on all the heavy chain and light chain antibodies. Some retained binding activity for both IL-12 and IL-23, while others showed no binding to either cytokine (FIG. 19).

Antibodies 127, 130, 136, 140, 146, 147 and 148 were selected based on their strong binding to IL-12 and IL-23 to be screened in the cell based assays. Antibody 136 displayed strong inhibition of IL-12 human PBMC IL-12 induced IFN-γ assay (FIG. 17) and IL-23 induced IL-17 secretion in the murine splenocyte assay (FIG. 14).

Example 6

6.1 Affinity Maturation of Antibody 80
6.1.1 Preparation of Materials for Ribosome Display Antibody 80 was reformatted for expression as a scFv (scFv-80) (SEQ ID NO: 27) and sub-cloned into the pEGX448 expression vector. The scFv was expressed with a FLAG tag to allow for affinity purification. The scFv was then expressed in *E. coli* and purified by affinity-chromatography and gel filtration. Expression was confirmed by SDS-PAGE and immunoblotting. The scFv retained binding activity against both IL-12 and IL-23 with similar kinetics to the parental IgG, as confirmed by SPR.

The coding sequence for scFv-80 was sub-cloned into the pEGX412 mutagenesis/ribosome display vector and random mutations were introduced into the scFv sequence using Q-Beta replicase (Kopsidas et al., 2007, BMC Biotechnology, 7: 18). The resulting pool of DNA constructs encoding mutant scFv-80 variants was transcribed to single-stranded mRNA in a T7 RNA polymerase reaction and then used to conduct ribosome display.

A commercial preparation of IL-23 was biotinylated for use in ribosome display experiments. An SPR experiment was performed to confirm that biotinylated IL-23 bound well to streptavidin and retained binding against scFv-80 within minimal loss in binding affinity.

6.1.2 Enrichment of IL-23 Binding Variants Using Ribosome Display

The mRNA pool encoding the scFv-80 variants was translated using an in vitro expression system and the resulting scFv library was panned for IL-23 binders using the ribosome display protocol described by Kopsidas et al. (2007). The selective pressure of the system was adjusted to bias for binders with low dissociation constants ($k_d$). Once a single round of ribosome display process was complete, the coding sequences for the enriched scFvs were amplified by PCR and sub-cloned into the pEGX448 expression vector. Twenty random clones from the sub-cloned scFv pool were sequenced to confirm their identity as variants of scFv-80. The remaining clones were subjected to high throughput screening against IL-23.

6.1.3 High-Throughput Screening of scFv-80 Variants Recovered by Ribosome Display Approximately 6500 individual scFvs recovered from the ribosome display reactions were expressed and screened for binding against IL-23 using a high-throughout SPR assay. The variants were ranked according to the $k_d$ and the best variants were sequenced at the nucleic acid level. This process identified 22 novel scFv variants (TABLE 4), each exhibiting an IL-23 binding affinity (based on the $k_d$) equal to or better than the parental scFv-80.

TABLE 4

Sequence summary for unique scFv-80 variants identified through SPR screening.

| scFv name | VH domain | | | VL domain | | | $k_d$ (1/s) vs. IL-23 |
|---|---|---|---|---|---|---|---|
| | SEQ ID NO: Protein | Mutation* | SEQ ID NO: DNA | SEQ ID NO: Protein | Mutation* | SEQ ID NO: DNA | |
| scFv-80** | 119 | . | 286 | 179 | . | 348 | $6.5 \times 10^{-4}$ |
| AZ-D8 | 28 | Y27C | 217 | 179 | . | 348 | $4.3 \times 10^{-5}$ |
| AY-B2 | 29 | M69V | 218 | 179 | . | 348 | $1.0 \times 10^{-4}$ |
| AY-G7 | 119 | . | 286 | 46 | Y86H | 235 | $1.2 \times 10^{-4}$ |
| CL-G7 | 30 | E10Q | 219 | 179 | . | 348 | $1.2 \times 10^{-4}$ |
| CW-H1 | 119 | . | 286 | 47 | S52R*** | 236 | $1.6 \times 10^{-4}$ |
| CU-A6 | 31 | F29L, T107A | 220 | 32 | S63F | 221 | $1.9 \times 10^{-4}$ |
| CP-A6 | 33 | Y59H*** | 222 | 179 | . | 348 | $1.9 \times 10^{-4}$ |
| AW-F2 | 34 | Y59S*** | 223 | 179 | . | 348 | $2.5 \times 10^{-4}$ |
| CR-B1 | 35 | D85E | 224 | 179 | . | 348 | $2.6 \times 10^{-4}$ |
| CW-H7 | 119 | . | 286 | 48 | V13M | 237 | $2.78 \times 10^{-4}$ |
| AV-F11 | 36 | S112P | 225 | 37 | I75T | 226 | $2.8 \times 10^{-4}$ |
| CE-B1 | 38 | F29L | 227 | 179 | . | 348 | $2.8 \times 10^{-4}$ |
| BV-B2 | 119 | . | 286 | 49 | D82G | 238 | $2.9 \times 10^{-4}$ |
| BU-B1 | 39 | L34M*** | 228 | 179 | . | 348 | $2.9 \times 10^{-4}$ |
| AQ-G10 | 40 | K12E, R66G | 229 | 179 | . | 348 | $2.9 \times 10^{-4}$ |
| AU-G9 | 41 | Q43R | 230 | 42 | I55T*** | 231 | $3.1 \times 10^{-4}$ |
| CE-G10 | 43 | V5L | 232 | 179 | . | 348 | $3.1 \times 10^{-4}$ |
| BY-B4 | 44 | T28A | 233 | 179 | . | 348 | $3.3 \times 10^{-4}$ |
| CE-A6 | 119 | . | 286 | 50 | G64S | 239 | $3.3 \times 10^{-4}$ |
| AX-G4 | 119 | . | 286 | 51 | S26P*** | 240 | $3.6 \times 10^{-4}$ |
| BZ-G10 | 119 | . | 286 | 52 | Q27R*** | 241 | $3.6 \times 10^{-4}$ |
| BB-A9 | 45 | T28A, T68S | 234 | 179 | . | 348 | $4.5 \times 10^{-4}$ |

*All mutations are reported relative to the wild-type scFv-80 sequence
**This is the average $k_d$ for scFv-80 established across entire screening experiment (n = 110).
***Mutations in the CDR region of the variable regions

6.1.4 Full Kinetic Characterization of Unique ScFv-80 Variants

A number of the scFv variants presented in TABLE 4 were selected for full characterization of binding kinetics, encompassing a broad range of mutation profiles and binding affinities. Large-scale protein expressions were carried out for each scFv. The expressed scFvs were purified as monomeric proteins and tested for binding against IL-12 and IL-23 by SPR (TABLE 5). These results confirmed that all variants isolated via ribosome display and screening bound to both antigens, with some exhibiting affinity improvements of up to 5-fold compared to parental scFv-80.

TABLE 5

Full kinetic characterization of selected scFv-80 variants.

| | IL-12 binding | | | IL-23 binding | | |
|---|---|---|---|---|---|---|
| scFv name | ka (1/Ms) | kd (1/s) | KD (pM) | ka (1/Ms) | kd (1/S) | KD (pM) |
| scFv-80 | $2.0 \times 10^6$ | $4.5 \times 10^{-4}$ | 230 | $3.1 \times 10^5$ | $6.1 \times 10^{-5}$ | 200 |
| CU-A6 | $2.0 \times 10^6$ | $9.7 \times 10^{-5}$ | 48 | $3.0 \times 10^5$ | <LOD* | <LOD* |
| AW-F2 | $2.2 \times 10^6$ | $1.0 \times 10^{-4}$ | 46 | $3.5 \times 10^5$ | <LOD* | <LOD* |
| CP-A6 | $2.0 \times 10^6$ | $1.2 \times 10^{-4}$ | 61 | $3.1 \times 10^5$ | <LOD* | <LOD* |
| CE-B1 | $2.0 \times 10^6$ | $1.8 \times 10^{-4}$ | 89 | $3.1 \times 10^5$ | $3.0 \times 10^{-5}$ | 98 |
| BU-B1 | $2.0 \times 10^6$ | $2.4 \times 10^{-4}$ | 120 | $3.0 \times 10^5$ | $3.7 \times 10^{-5}$ | 120 |
| AU-G9 | $2.1 \times 10^6$ | $2.4 \times 10^{-4}$ | 110 | $3.4 \times 10^5$ | $4.4 \times 10^{-5}$ | 130 |
| BB-A9 | $2.0 \times 10^6$ | $2.3 \times 10^{-4}$ | 120 | $3.1 \times 10^5$ | $4.4 \times 10^{-5}$ | 160 |
| AX-G4 | $2.3 \times 10^6$ | $3.1 \times 10^{-4}$ | 140 | $3.6 \times 10^5$ | $5.5 \times 10^{-5}$ | 150 |
| AV-F11 | $1.6 \times 10^6$ | $3.3 \times 10^{-4}$ | 200 | $2.7 \times 10^5$ | $2.5 \times 10^{-5}$ | 93 |
| CR-B1 | $1.9 \times 10^6$ | $4.4 \times 10^{-4}$ | 230 | $3.2 \times 10^5$ | $4.1 \times 10^{-5}$ | 130 |
| AQ-G10 | $1.5 \times 10^6$ | $5.2 \times 10^{-4}$ | 350 | $2.8 \times 10^5$ | $4.9 \times 10^{-5}$ | 170 |

**$k_d$ for this these variants were below the limit of detection (LOD) of the BIAcoreT100 using this assay format. The LOD was estimated to be $1 \times 10^{-5}$ s$^{-1}$.

6.1.5 Conversion of scFv Variants to the IgG Format

The three scFvs that showed the highest binding affinities in SPR assays (AW-F2, CU-A6 and CP-A6) were reformatted for IgG expression by subcloning the $V_H$ and $V_L$ domains into separate mammalian expression vectors (i.e. one construct for the antibody heavy chain, one for the light chain). CU-A6 was converted to Antibody 183, CP-A6 was converted to Antibody 184 and AW-F2 was converted to Antibody 207 by addition of a human heavy chain Fc region (SEQ ID NO: 8) and a constant kappa light chain region (SEQ ID NO: 9). IgG molecules were expressed by co-transfecting the heavy and light chain construct for each antibody into HEK 293E cultures. The expressed IgGs were purified by affinity chromatography and gel exclusion and the resulting monomeric molecules were tested for IL-12 and IL-23 binding by SPR (TABLE 6). All three IgG variants retained binding activity against both analytes with a visible improvement in $k_d$ compared to the parental wild-type IgG. Based on this, it is reasonable to expect that scFv variants described in TABLE 4 could be converted to the IgG format and retain improved binding characteristics against IL-12 and IL-23.

TABLE 6

Full kinetic characterization of scFv variants after reformatting and expression as full-length IgGs.

| Antibody No. | scFv name | IL-12 binding | | | IL-23 binding | | |
|---|---|---|---|---|---|---|---|
| | | ka (1/Ms) | kd (1/s) | KD pM | ka (1/Ms) | kd (1/s) | KD pM |
| 80 | n/a | $4.3 \times 10^6$ | $1.3 \times 10^{-3}$ | 292 | $4.1 \times 10^5$ | $1.1 \times 10^{-4}$ | 280 |
| 183 | CU-A6 | $4.1 \times 10^6$ | $2.7 \times 10^{-4}$ | 65 | $4.0 \times 10^5$ | <L.O.D.* | 2.7 |
| 184 | CP-A6 | $4.2 \times 10^6$ | $5.4 \times 10^{-4}$ | 127 | $4.1 \times 10^5$ | $4.2 \times 10^{-5}$ | 104 |
| 207 | AW-F2 | $3.7 \times 10^6$ | $6.3 \times 10^{-4}$ | 167 | $3.7 \times 10^5$ | $6.5 \times 10^{-5}$ | 176 |

*$k_d$ for this variant was below the limit of detection (LOD) of the SPR T100 using this assay format. The LOD was estimated to be $1 \times 10^{-5}$ s$^{-1}$.

6.1.6 Combination of Mutations Identified Through Ribosome Display and Screening A series of additional scFv variants were created by combination of various mutations described above (TABLE 4). These scFvs derived by weighting the various mutations based on a) number of times observed in the screening runs b) affinity of the scFv associated with the mutation. The highest weighted combinations (TABLE 7) were added to scFv-80 using site-directed mutagenesis. All of these combination scFvs were then expressed on a small scale and then partially purified using affinity chromatography and a desalting column. Each new scFv was tested for binding against IL-12 and IL-23 by SPR using a medium-throughput analysis protocol with a single concentration of analyte (TABLE 7). The data showed that all of these variants retained IL-12 or IL-23 binding. In most cases, the dissociation rate of the new variant was at least equal to the parental variants. Two mutation combinations (T28A in the VH domain plus S26P in the VL domain, F29L in the VH domain plus S26P in the VL domain) showed improvement in affinity compared to the parental variants. Therefore, it is reasonable to expect that scFvs carrying new combinations of the mutations listed in TABLE 4 could bind to IL-12 and IL-23 with equal if not better affinity than the parental mutants and indeed wild-type scFv-80.

TABLE 7

Single concentration kinetic analysis of scFvs carrying mutation combinations.

| | VH domain | | | VL domain | | | | Binding Kinetics | | | |
|---|---|---|---|---|---|---|---|---|---|---|---|
| scFv combo. # | SEQ ID NO: Protein | Mutation* | SEQ ID NO: DNA | SEQ ID NO: Protein | Mutation* | SEQ ID NO: DNA | Analyte | $k_a$ (1/Ms) | $k_d$ (1/s) | $K_D$ pM | Effect |
| scFv-80 | | nil. | | | | | IL-23 | $3.0 \times 10^5$ | $3.1 \times 10^{-5}$ | 104 | n/a |
| scFv-80 | | nil. | | | | | IL-12 | $1.6 \times 10^6$ | $2.5 \times 10^{-4}$ | 156 | n/a |
| 1 | 53 | Q43R, Y59H | 242 | 42 | I55T | 231 | IL-23 | $2.3 \times 10^5$ | <LOD** | 32 | ++ |
| 2 | 54 | T28A, Y59S | 243 | 179 | . | 348 | IL-23 | $2.3 \times 10^5$ | <LOD** | 34 | ++ |
| 3 | 44 | T28A | 233 | 51 | S26P | 240 | IL-12 | $1.6 \times 10^6$ | $4.5 \times 10^{-5}$ | 29 | ++ |

TABLE 7-continued

Single concentration kinetic analysis of scFvs carrying mutation combinations.

| | VH domain | | | VL domain | | | Binding Kinetics | | | |
|---|---|---|---|---|---|---|---|---|---|---|
| scFv combo. # | SEQ ID NO: Protein | Muta-tion* | SEQ ID NO: DNA | SEQ ID NO: Protein | Muta-tion* | SEQ ID NO: DNA | Analyte | $k_a$ (1/Ms) | $k_d$ (1/s) | $K_D$ pM | Effect |
| 4 | 38 | F29L | 227 | 51 | S26P | 240 | IL-12 | $1.8 \times 10^6$ | $4.8 \times 10^{-5}$ | 27 | ++ |
| 5 | 44 | T28A | 233 | 32 | S63F | 221 | IL-12 | $1.7 \times 10^6$ | $6.5 \times 10^{-5}$ | 38 | ++ |
| 6 | 55 | T28A, Y59H, T68S | 244 | 179 | . | 348 | IL-23 | $2.3 \times 10^5$ | <LOD** | 41 | + |
| 7 | 56 | F29L, Y59H | 245 | 179 | . | 348 | IL-23 | $2.0 \times 10^5$ | <LOD** | 3.3 | + |
| 8 | 57 | F29L, Y59S | 246 | 179 | . | 348 | IL-23 | $2.0 \times 10^5$ | <LOD** | 7.5 | + |
| 9 | 58 | Q43R, Y59S | 247 | 42 | I55T | 231 | IL-23 | $2.2 \times 10^5$ | <LOD** | 27 | + |
| 10 | 59 | T28A, Y59H | 248 | 179 | . | 348 | IL-23 | $2.2 \times 10^5$ | <LOD** | 13 | + |
| 11 | 34 | Y59S | 223 | 51 | S26P | 240 | IL-23 | $2.2 \times 10^5$ | <LOD** | 27 | + |
| 12 | 60 | T28A, Y59S, T68S | 249 | 179 | . | 348 | IL-23 | $2.2 \times 10^5$ | <LOD** | 16 | + |
| 13 | 61 | T28A, Q43R | 250 | 42 | I55T | 231 | IL-23 | $2.5 \times 10^5$ | $1.3 \times 10^{-5}$ | 51 | + |
| 14 | 62 | F29L, Q43R | 251 | 42 | I55T | 231 | IL-23 | $2.7 \times 10^5$ | $2.1 \times 10^{-5}$ | 79 | + |
| 15 | 38 | F29L | 224 | 32 | S63F | 221 | IL-12 | $1.7 \times 10^6$ | $6.4 \times 10^{-5}$ | 39 | + |
| 16 | 38 | F29L | 224 | 47 | S52R | 236 | IL-12 | $1.5 \times 10^6$ | $7.5 \times 10^{-5}$ | 50 | + |

*All mutations are reported relative to the wild-type scFv-80 sequence.
**$k_d$ for this variant was below the limit of detection (LOD) of the BIAcore T100 in this assay format. The The lower LOD was estimated to be approximately $1 \times 10^{-5}$ s$^{-1}$.
+ Mutation combination resulted in a $k_d$ rate at least equal to parent variants.
++ Mutation combination resulted in an improved $k_d$ compared to parent variants.
− Mutation showed reduced affinity.

Example 7

7.1 Further Maturation of Humanized antibodies

7.1.1 Introduction of Affinity Improved Mutations into Antibody 136

Figure 20:
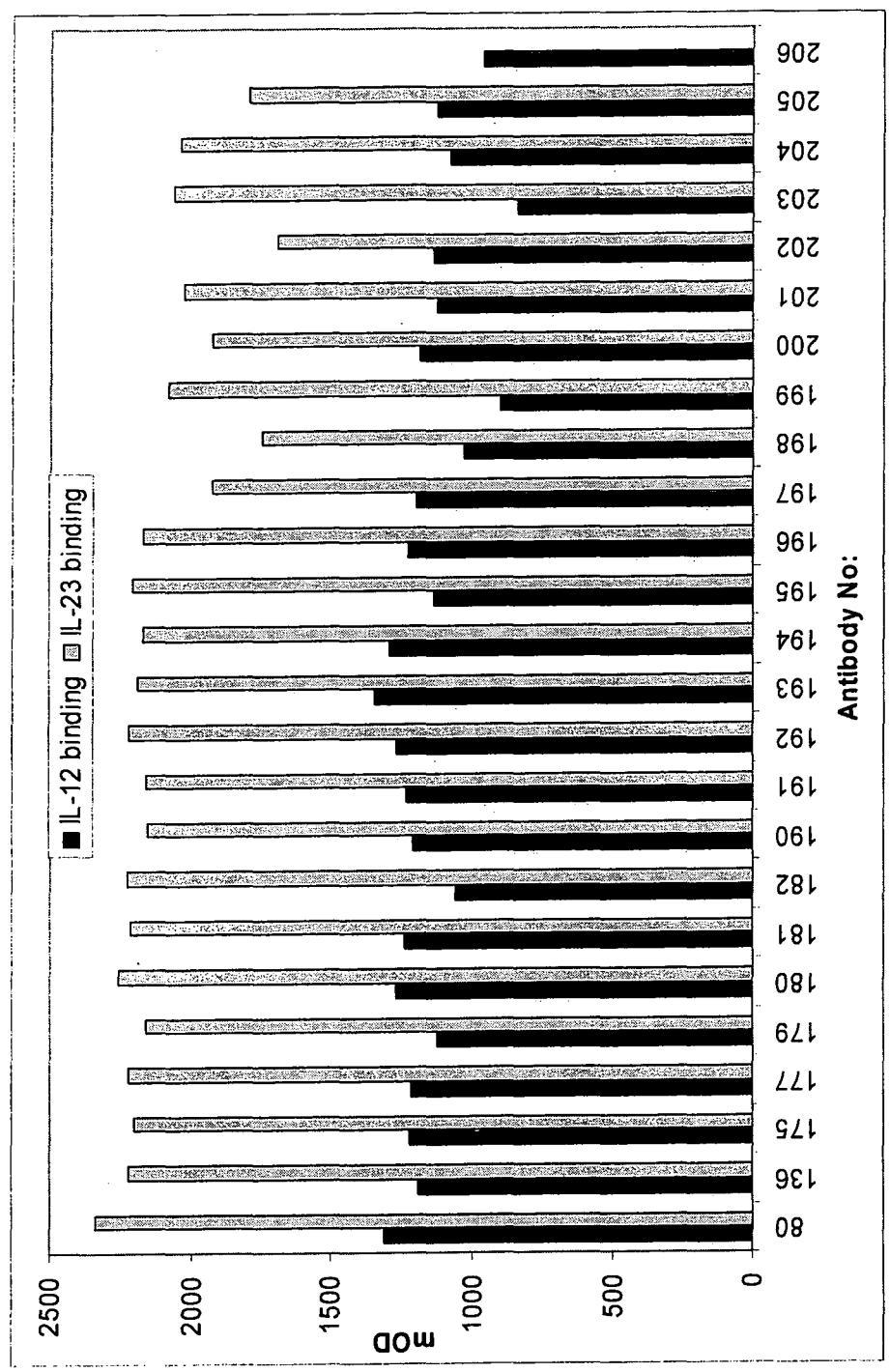
FIG. 20: ELISA data showing binding of various antibodies to IL-12 and IL-23.

Based on the affinity maturation of Antibody 80 several key mutations in the heavy chain variable region (Y59S, Y59H and F29L) that enhanced affinity to IL-12 and IL-23 were introduced into Antibody 136 (Antibodies 175, 176, 177, 178, 179, 180, 181, 182). These were expressed and screened in ELISA (FIG. 20). All antibodies showed binding to IL-12 and IL-23.

7.1.2 Other Combinations of Antibodies

Affinity matured variants of Antibody 80 heavy chain containing a substitution at position 93 (N93A) were paired with their corresponding light chains (Antibodies 199, 200, 201, 202, 203, 204, 205, 206) (FIG. 20). This substitution was introduced to return position 93 back to the human germline which most frequently contains an Ala at this position. Affinity matured variants of Antibody 80 heavy chain containing the N93A substitution were also expressed with Antibody 136 light chain in order to identify higher affinity variants (Antibodies 190, 191, 192, 193, 194, 195, 196, 197, 198) (FIG. 20).

7.2 Binding Affinity Measurements

Using SPR technology the $k_a$ and $k_d$ and the $K_D$ of various humanized antibodies was determined. These affinities are listed in TABLE 8. In all cases antibodies that contained a Y59S or Y59H substitution, independent of the framework of the antibody, displayed an improvement in binding affinity to IL-12 and IL-23.

TABLE 8

SPR data for various humanized antibodies.

| | IL-23 binding | | | IL-12 binding | | |
|---|---|---|---|---|---|---|
| Antibody | ka 1/Ms | kd 1/s | KD pM | ka 1/Ms | kd 1/s | KD pM |
| 80 | 6.25E+06 | 3.34E−04 | 53.5 | 4.88E+06 | 5.39E−04 | 110.0 |
| 136 | 7.55E+06 | 7.95E−04 | 105.3 | 5.05E+06 | 9.97E−04 | 197.0 |
| 177 | 3.43E+06 | 1.28E−04 | 37.3 | 4.61E+06 | 2.12E−04 | 46.0 |
| 180 | 3.12E+06 | 9.27E−05 | 29.7 | 5.31E+06 | 1.73E−04 | 32.5 |
| 181 | 4.09E+06 | 1.73E−04 | 42.4 | 3.57E+06 | 2.44E−04 | 68.1 |
| 182 | 5.27E+06 | 1.29E−04 | 24.6 | 6.23E+06 | 2.14E−04 | 34.4 |
| 190 | 4.28E+06 | 6.09E−04 | 142.0 | 3.86E+06 | 8.40E−04 | 217.0 |
| 192 | 2.66E+06 | 2.11E−04 | 79.4 | 4.16E+06 | 3.56E−04 | 85.5 |
| 193 | N/D | N/D | N/D | 2.60E+06 | 2.06E−04 | 79.4 |
| 194 | 2.99E+06 | 1.22E−04 | 41.0 | 2.09E+06 | 1.94E−04 | 92.7 |
| 195 | 4.03E+06 | 2.02E−04 | 50.0 | 2.65E+06 | 2.74E−04 | 103.0 |
| 198 | 4.65E+06 | 4.09E−04 | 87.7 | 3.75E+06 | 5.94E−04 | 158.0 |
| 205 | 4.81E+06 | 4.15E−04 | 86.2 | 3.70E+06 | 5.81E−04 | 157.0 |

Example 8

8.1 Further Characterisation of Various Antibodies

8.1.1 Competition Experiments-Spr

Figure 21:
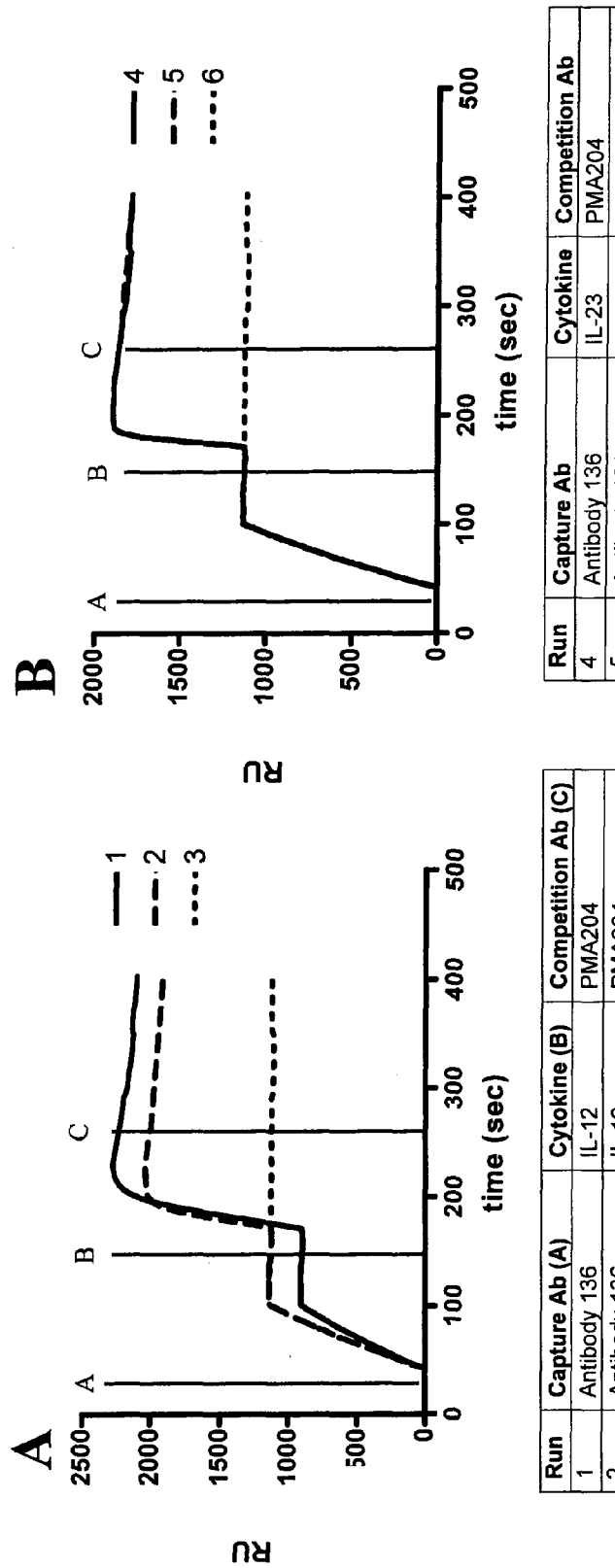
FIG. 21: Competition SPR experiments demonstrating that Antibody 136 and PMA204 compete for binding to IL-12 (A) and IL-23 (B).

A competition assay was established using SPR to verify that the chimeric and humanized antibodies described above maintained the same binding specificity as PMA204. In the SPR experiment Antibody 136 was captured on a Protein A coated surface leading to an increase in the response units (RU) and then loaded with IL-12 or IL-23 (leading to another increase in response units). PMA204 was then loaded but did not bind to the surface IL-12 or IL-23-Antibody 136 complex (FIG. 21) (no increase in response units). This indicates that Antibody 136 binds IL-12 and IL-23 in such as way as to prevent PMA204 binding and that the two antibodies share an overlapping epitope on IL-12 and IL-23.

Figure 22:
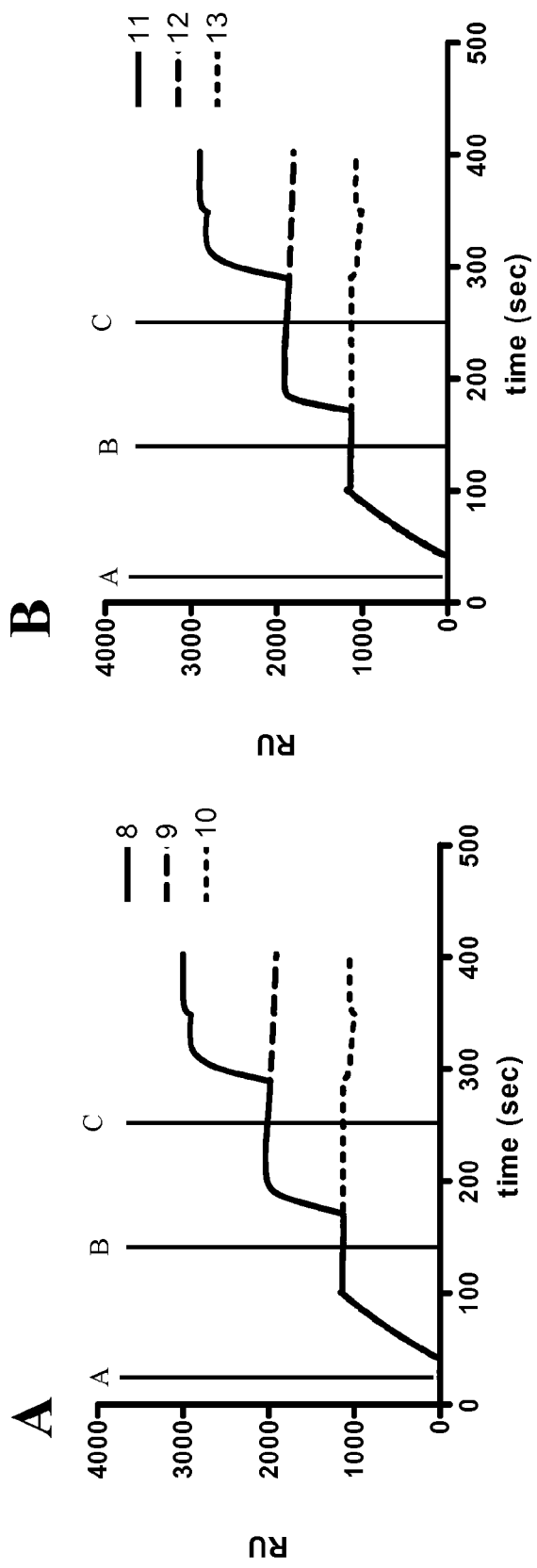
FIG. 22: Competition SPR experiments demonstrating that Antibody 136 and PMA202 do not compete for binding to IL-12 (A) and IL-23 (B).

In a control experiment Antibody 136 was captured on a Protein A coated surface leading to an increase in the response units and loaded with IL-12 or IL-23 (leading to another increase in response units). PMA202 was then loaded and demonstrated an increase in response units indicating binding to the complex. PMA202 and Antibody 1 can form a complex sandwiching IL-12 or IL-23 thus indicating they bind to IL-12 or IL-23 in different locations on the molecule (FIG. 22).

It could be envisaged that a similar competition ELISA could be performed using other combinations of capture antibody, IL-12 or IL-23 and competition antibody.

8.1.2 Competition Experiments-ELISA

A competition assay was established using ELISA methodology to verify that

Figure 23:
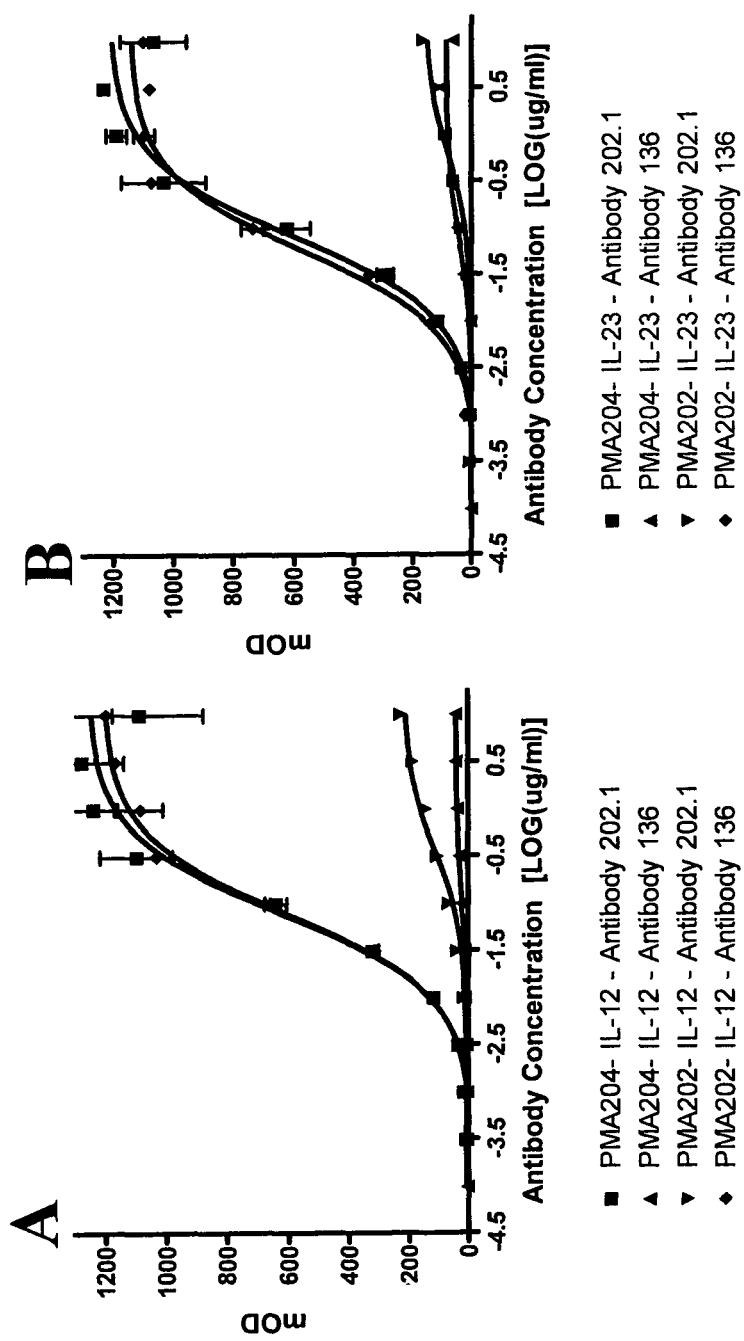
FIG. 23: Competition ELISA experiments demonstrating that PMA204 and Antibody 202.1 do not compete for binding to IL-12 or IL-23. PMA204 and Antibody 136 compete for binding to IL-12 and IL-23.

Antibody 136 maintained the same binding specificity as PMA204. When PMA204 was coated on an ELISA plate, then IL-12 or IL-23 was added, followed by Antibody 136, no binding of Antibody 136 could be detected (FIG. 23A). This indicated that Antibody 136 and PMA204 compete for binding to IL-12 or IL-23. When a control antibody PMA202 was coated and a pre-incubated mixture of Antibody 136 and IL-12p40 was added, binding of Antibody 136 could be detected (FIG. 23B). This indicated that Antibody 1 and PMA202 do not compete for binding to IL-12. Antibody 202.1 was used as a positive binding control for the first experiment (FIG. 23A) and a negative control for the second experiment (FIG. 23B).

Figure 24:
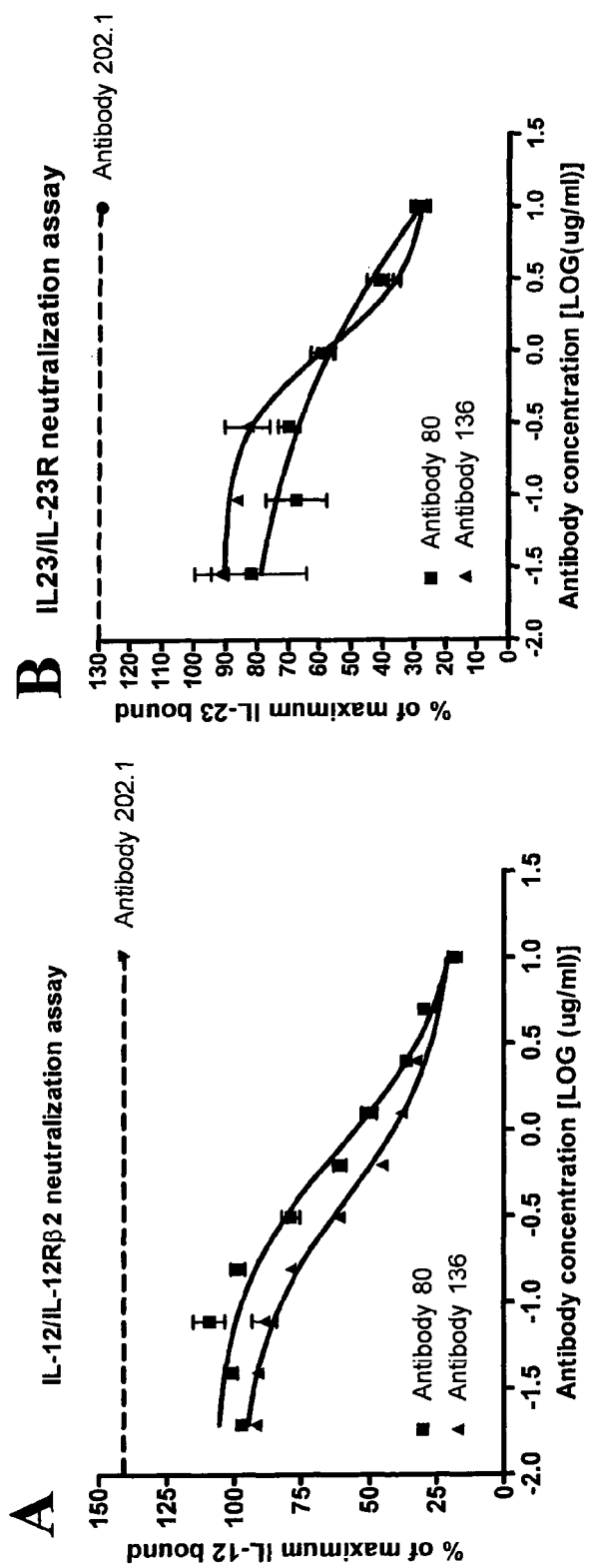
FIG. 24: Antibody 80 and Antibody 136 neutralize the binding of IL-12 to IL-12Rβ2 (A) and IL-23 to IL-23R (B), compared to Antibody 202.1 which demonstrates no inhibition at the highest concentration of antibody tested.

8.1.3 Receptor Neutralization Assays 8.1.3.1 Antibody 80 and Antibody 136 Neutralize IL-12 Binding to IL-12Rβ2 and IL-23 Binding to IL-23R Using receptor neutralization assays it was demonstrated that Antibody 80 and Antibody 136 neutralized the binding of IL-12 to IL-12Rβ2 (FIG. 24A) and the binding of IL-23 to IL-23R (FIG. 24B). The control Antibody 202.1 displayed no inhibition of IL-12 binding to IL-12Rβ2 or IL-23 binding to IL-23R.

8.1.3.2 Antibody 80 and Antibody 136 do not Neutralize IL-12 or IL-23 Binding to IL-12Rβ1

Figure 25:
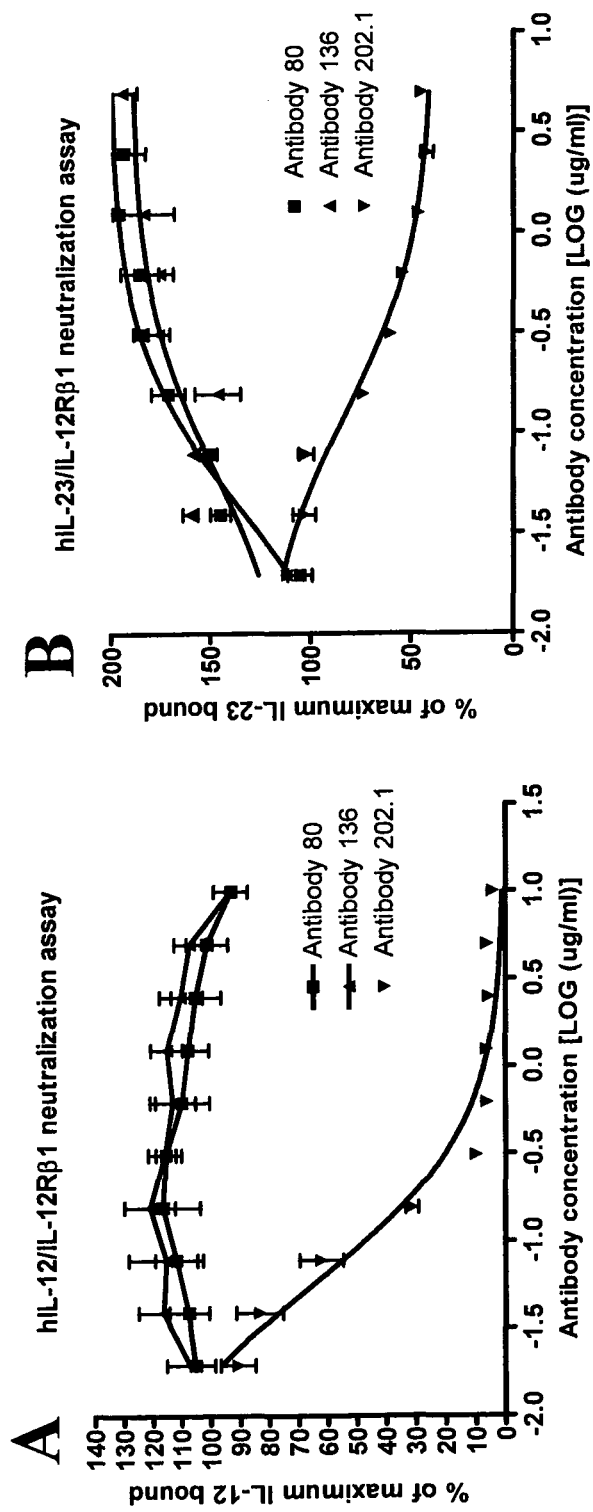
FIG. 25: PMA204 and Antibody 1 do not neutralize the binding of IL-12 to IL-12Rβ1 (A) and IL-23 to IL-12Rβ1 (B). Antibody 202.1 displayed dose dependant inhibition of IL-12 binding to IL-12Rβ1 (A) and IL-23 binding to IL-12Rβ1 (B).

Antibody 80 and Antibody 136 did not neutralize the binding of IL-12 to IL-12Rβ1 (FIG. 25A). IL-23 binding to IL-12Rβ1 was not inhibited by Antibody 80 and Antibody 136 (FIG. 25B) but rather complex formation occurred as evidenced by the increase in the bound IL-23 above that of just IL-23 and receptor alone. The control Antibody 202.1 inhibited the binding IL-12 and IL-23 to IL-12Rβ1.

Example 9

Figure 26:
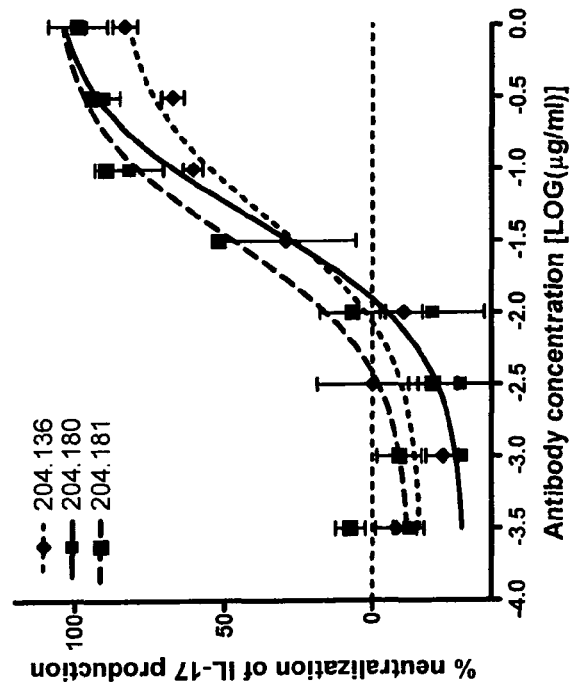
FIG. 26: Various humanized and affinity matured antibodies inhibited IL-23 induced IL-17 release from murine splenocytes. Shown are two groups of affinity matured humanized lead antibodies, those based on Antibody 80 (A) and those based on Antibody 136 (B).
Figure 26:
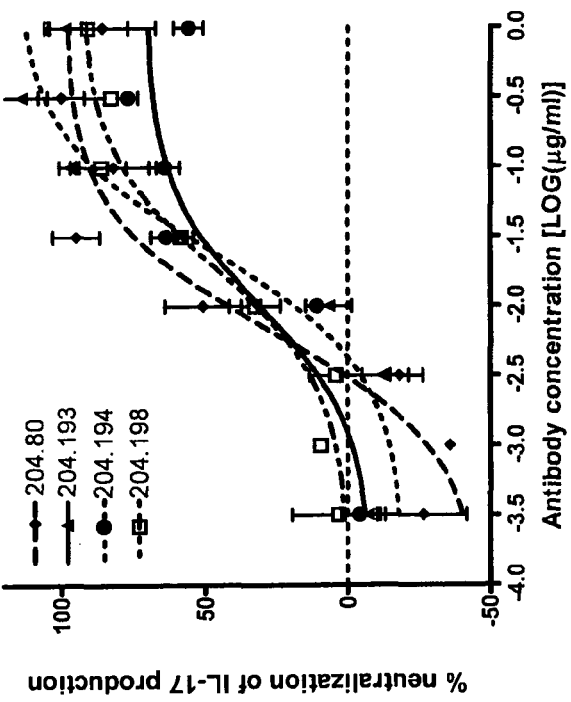

9.1 Amelioration of Skin Inflammation Induced by Intradermal IL-23 Administration After observing that several of the lead antibodies were capable of inhibiting IL-23 induced release of IL-17 on murine splenocytes (FIG. 26) further work was performed to design an animal model in which human IL-23 could be used as an inducer of disease. Treatment of C57B1/6J mice with IL-23 intradermally to the back for 6 days induced a localized inflammatory response characterized by erythema and induration, with histological evidence of epidermal hyperplasia, parakeratosis, and localized inflammatory infiltrate. Antibodies were tested for their ability to decrease the inflammatory response at a single dose on the day before cytokine treatment commenced. Both groups that received Antibody 80 and Antibody 136 had a reduced clinical score, from day 5 onwards, relative to an isotype control, demonstrating efficacy of the antibodies in this study (FIG. 27A).

Figure 27:
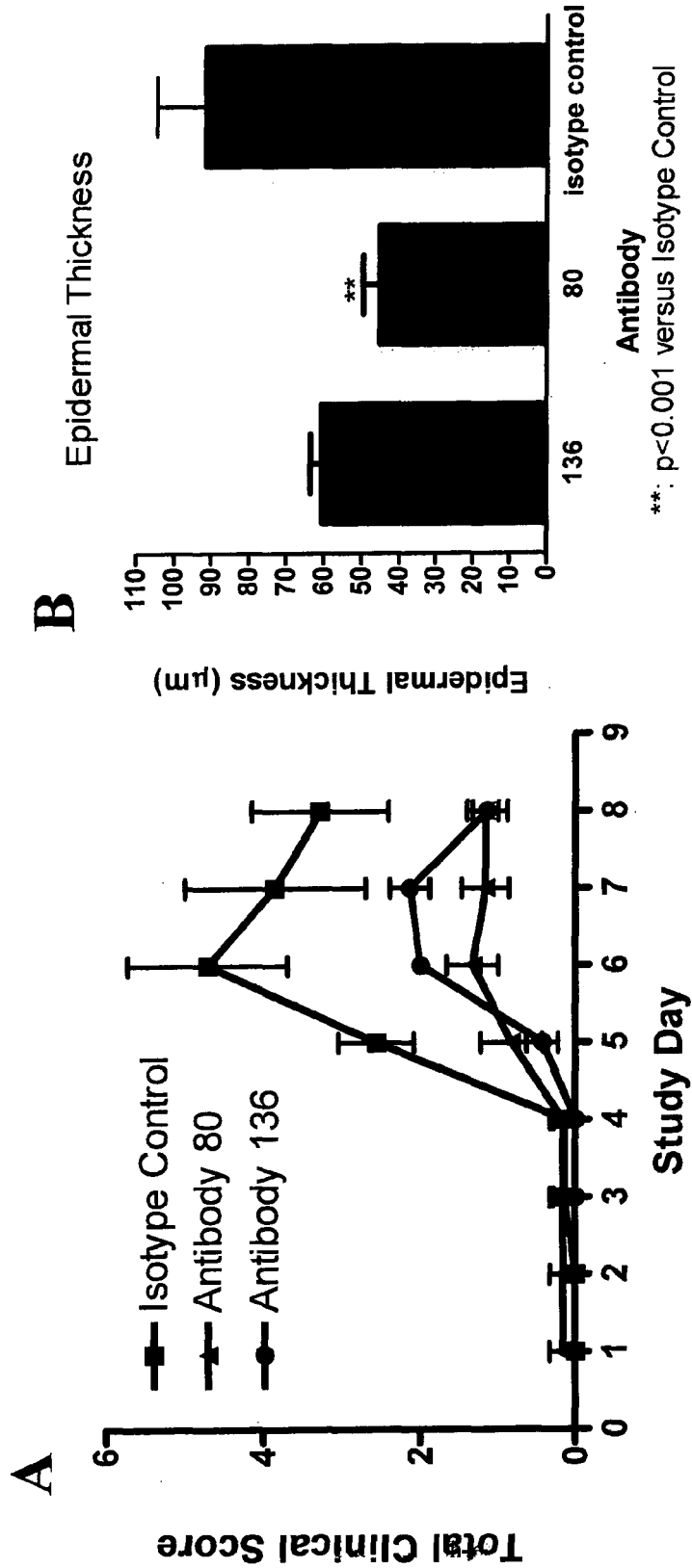
FIG. 27: After 6 days of IL-23 intradermal administration to mice they develop skin inflammation resembling psoriasis. A) Administration of an isotype control did not prevent skin inflammation, however Antibody 80 and Antibody 136 reduced inflammation in this model as evidenced by the lower clinical score. B) At the histological level, epidermal thickening occurs after IL-23 intradermal administration over 6 days. Treatment with Antibody 80 and Antibody 136 ameliorated this epidermal thickening, but treatment with the isotype control antibody did not.

Although Antibody 136 showed a trend towards decreased epidermal thickness as compared to isotype control, only Antibody 80 caused a statistically significant decrease in epidermal thickness (FIG. 27B). This correlates well with the clinical scoring, where although both Antibody 136 and Antibody 80 significantly reduced erythema and induration caused by IL-23, Antibody 80 was more effective.

Example 10

10.1 Neutralisation of IFN-γ Induced by Chimeric IL-12 on Murine Splenocytes

It was found that human IL-12 is weakly reactive with murine splenocytes to induce IFN-γ production. However a chimeric molecule consisting of a human p40 and a murine p35 (SEQ ID NO: 63) was capable of inducing a IFN-γ response from murine splenocytes at levels similar to that seen for murine IL-12. Several lead antibodies (Antibody No's: 36, 80, 180, 181, 193, 194, 198) where then added to this assay with the aim of inhibiting chimeric IL-12 from inducing a IFN-γ response on murine splenocytes. All the antibodies demonstrated neutralisation in this assay (FIG. 28).

10.2 Neutralization of Serum INTERFERON-γ (IFN-γ) Response to Chimeric IL-12 (IL-12) in Normal Inbred Mice Treatment of C57B1/6J mice with 0.1 mg/kg chimeric IL-12 (human IL-12p40 chain with mouse IL-12 p35 chain (SEQ ID NO: 63) for five consecutive days induced a robust serum IFN-γ response with no apparent toxicity. Antibodies were tested for their ability to neutralize the chimeric IL-12 and hence abrogate the IFNγ response at a dose of 5 mg/kg with either a single dose on the first day of cytokine treatment or three doses on alternate days concurrent with cytokine treatment. Both antibodies tested showed neutralization capabilities and a single dose of Antibody 80 at 5 mg/kg was sufficient to reduce serum IFN-γ to baseline detectable levels (FIG. 29).

Example 11

11.1 Stimulation of PBMC to Produce IL-23 Diagnostic Detection with Antibody 80

Humanized antibodies against IL-12 and IL-23 can be used as diagnostic reagents for the detection of IL-12 and IL-23 in biological samples. An ELISA was developed to detect recombinant human IL-23. In this assay, an anti-human p19 antibody was used as the capture antibody and Antibody 80 was used as the detection antibody. Antibody 80 was able to detect recombinant human IL-23 in this sandwich ELISA format (FIG. 30A).

Treatment with *Staphylococcus aureus* Cowan 1 (SAC) induced the secretion of IL-23 by human peripheral blood cells (PBMC). Antibody 80 was able to detect endogenous native human IL-23 secreted by SAC stimulated PBMCs in this sandwich ELISA format (FIG. 30B).

Example 12

12.1 Epitope Mapping by H/D Exchange

In the first experiment, the hydrogens on IL-12p40 was exchanged with deutrons in solution, then bound to Antibody 80 immobilized on a column, and then exchanged back again in $H_2O$ while still bound to the antibody column, resulting in the epitope being protected. Thus the epitope is labelled with deuterons. In the second experiment, the IL-12p40 was bound to the antibody column, then labelled with deuterons and then exchange back into H₂O while still bound to the column. After each experiment the IL-12p40 was eluted from the column using low pH aggressively reduced and passed over a pepsin column which digested the protein. The peptic fragments were then loaded onto an LC:MS. The difference in deuteration levels between the two experiments is a measure of the retardation of the exchange when bound to the antibody.

In this study IL-12p40 was used as given in SEQ ID NO: 64. The only region to show a significant perturbation in the rate of H/D exchange was between amino acids 253 to 286 which corresponds to the sequence VQVQGK-SKREKKDRVFTDKTSATVICRKNASISV (SEQ ID NO: 65) as shown in TABLE 9.

TABLE 9

Percentage difference in deuteration levels in each segment of IL-12p40 after on/off exchange experiments at pH 7 at 3° C. An average percentage difference greater then 10% corresponds to a region that is significantly protected during the exchange reation.

| Residue start | Residue end | Peptide charge | Time (sec) 500 | 1,500 | 5,000 | Average |
|---|---|---|---|---|---|---|
| 3 | 9 | 1 | 6% | 3% | 8% | 5% |
| 3 | 12 | 2 | 11% | 2% | 5% | 6% |
| 15 | 23 | 1 | 10% | 6% | 11% | 9% |
| 16 | 23 | 1 | 10% | 6% | 12% | 9% |
| 38 | 40 | 1 | -2% | 2% | 4% | 2% |
| 57 | 65 | 1 | 2% | 6% | 6% | 5% |
| 57 | 80 | 2 | 2% | 3% | 8% | 4% |
| 68 | 80 | 2 | 9% | 3% | 0% | 4% |
| 83 | 90 | 1 | 10% | 9% | 6% | 8% |
| 83 | 95 | 2 | 12% | 2% | 8% | 7% |
| 93 | 95 | 1 | 2% | 8% | 7% | 6% |
| 93 | 109 | 2 | 8% | -3% | 2% | 2% |
| 93 | 125 | 3 | 6% | 0% | 4% | 3% |
| 93 | 129 | 3 | 4% | -2% | 1% | 1% |
| 128 | 132 | 1 | 5% | 5% | 7% | 6% |
| 131 | 132 | 1 | 4% | 2% | -2% | 1% |
| 135 | 153 | 2 | 5% | 5% | 2% | 4% |
| 156 | 166 | 2 | 1% | 0% | 2% | 1% |
| 158 | 168 | 2 | 3% | 0% | 3% | 2% |
| 173 | 181 | 1 | 5% | -7% | 2% | 0% |
| 184 | 187 | 1 | 6% | 4% | 5% | 5% |
| 184 | 189 | 1 | 4% | 1% | 3% | 2% |
| 208 | 231 | 3 | 7% | 5% | 9% | 7% |
| 212 | 231 | 3 | 9% | 5% | 9% | 8% |
| 234 | 246 | 2 | 6% | 1% | 1% | 3% |
| 236 | 246 | 2 | 9% | 3% | 9% | 7% |
| 249 | 250 | 1 | 4% | -2% | -1% | 1% |
| 249 | 251 | 1 | 1% | -2% | 1% | 0% |
| 253 | 274 | 3 | 27% | 28% | 30% | 28% |
| 253 | 275 | 3 | 28% | 25% | 29% | 27% |
| 254 | 275 | 3 | 33% | 27% | 31% | 30% |
| 277 | 286 | 2 | 10% | 16% | 25% | 17% |
| 295 | 299 | 1 | 1% | 1% | 7% | 3% |
| 302 | 306 | 1 | 2% | 0% | -1% | 0% |

Note
residue numbers correspond to IL-12p40 as given in SEQ ID NO: 64.

12.2 Analysis of Binding of Mutant IL-23 to Antibody 80

Based on the results from the H/D exchange experiments targeted mutations were introduced into IL-23 in the region identified. To further narrow down the number of mutations that needed to be screened human IL-12p40 (SEO ID NO: 65) was aligned with murine IL-12p40 (SEO ID NO: 378) (Uni-Prot No: P43432; http://www.uniprot.org) at this location.

```
human p40
VQVQGKSKREK--------KDRVFTDKTSATVICRKNASISV murine p40
.RI.R.KEKM.ETEEGCNQ.GAFLVE...TE.Q.-.GGNVC.
```

Based on the observation that Antibody 80 binds to human IL-23 but not murine IL-23 only residues that differ between the two species were selected for targeted mutation. The mutations that were introduced are summarized in the following alignment of amino acids 253-297 taken from the SEQ ID Numbers listed.

```
IL-23WT  CVQVQGKSKREKKDRVFTDKTSATVICRKNASISVR (SEQ ID NO: 66)

Q254A    ..A................................ (SEQ ID NO: 67)

V255A    ...A............................... (SEQ ID NO: 68)

G257A    .....A............................. (SEQ ID NO: 69)

S259A    .......A........................... (SEQ ID NO: 70)

K260A    ........A.......................... (SEQ ID NO: 71)

R261A    .........A......................... (SEQ ID NO: 72)

E262A    ..........A........................ (SEQ ID NO: 73)

K264A    ............A...................... (SEQ ID NO: 74)

D265A    .............A..................... (SEQ ID NO: 75)

R266A    ..............A.................... (SEQ ID NO: 76)

V267A    ...............A................... (SEQ ID NO: 77)

F268A    ................A.................. (SEQ ID NO: 78)
```

```
-continued
T269A           ................A................. (SEQ ID NO: 79)

D270A           .................A................ (SEQ ID NO: 80)

T275A           ......................A........... (SEQ ID NO: 81)

I277A           ..........................A....... (SEQ ID NO: 82)

R279A           ............................A..... (SEQ ID NO: 83)

N281A           ..............................A... (SEQ ID NO: 84)

S283A           ................................A. (SEQ ID NO: 85)

S285A           ..................................A (SEQ ID NO: 86)
```

After transfecting each of the mutants into HEK-293E cells the supernatants from these transfections were screened via SPR against Antibody 80. All the constructs showed levels of binding similiar to Antibody 80 except for the mutants D265A and R266A. The $k_d$ of several of the mutants was appreciably lower than that of IL-23 wild-type indicating that residues in this region of IL-12p40 contribute to the interaction of IL-12p40 with Antibody 80.

D265A and R266A were further analysed in an ELISA in which Antibody 80, Antibody 202.1 or IL-12Rβ1 and IL-23R was coated on the plate and transfection supernatants containing IL-23 wild-type (IL-23WT), D265A and R266A were titrated across the plate. The mutant, D265A, displayed background levels of binding to Antibody 80 (FIG. 31), thus identifying D265 as an important residue on IL-12p40 to which Antibody 80 binds. D265A bound Antibody 202.1, IL-12Rβ1 and IL-23R at comparable levels to that of IL-23 wildtype, indicating it had folded correctly and was capable of functional binding. The mutant R266A displayed low levels of binding to IL-12Rβ1, IL-23R, Antibody 80 and Antibody 202.1 indicating that mis-folding of the mutant protein had occurred (FIG. 31).

List of Antibodies

TABLE 10

List of antibody numbers and corresponding sequence identification numbers. Except for Antibody 1 all sequences listed in this table are the variable regions of the antibodies. All variable regions listed in this table form part of antibodies that contain a human heavy chain $IgG_1$ Fc region (SEQ ID NO: 8) and a light chain kappa constant region (SEQ ID NO: 9).

| Antibody | VH domain | | VL domain | |
|---|---|---|---|---|
| Number | Protein | DNA | Protein | DNA |
| 1 | SEQ ID NO: 12 | SEQ ID NO: 252 | SEQ ID NO: 13 | SEQ ID NO: 336 |
| 3 | SEQ ID NO: 6 | SEQ ID NO: 252 | SEQ ID NO: 169 | SEQ ID NO: 338 |
| 4 | SEQ ID NO: 87 | SEQ ID NO: 254 | SEQ ID NO: 7 | SEQ ID NO: 336 |
| 5 | SEQ ID NO: 88 | SEQ ID NO: 255 | SEQ ID NO: 7 | SEQ ID NO: 336 |
| 6 | SEQ ID NO: 89 | SEQ ID NO: 256 | SEQ ID NO: 7 | SEQ ID NO: 336 |
| 7 | SEQ ID NO: 90 | SEQ ID NO: 257 | SEQ ID NO: 7 | SEQ ID NO: 336 |
| 8 | SEQ ID NO: 91 | SEQ ID NO: 258 | SEQ ID NO: 7 | SEQ ID NO: 336 |
| 9 | SEQ ID NO: 92 | SEQ ID NO: 259 | SEQ ID NO: 7 | SEQ ID NO: 336 |
| 10 | SEQ ID NO: 93 | SEQ ID NO: 260 | SEQ ID NO: 7 | SEQ ID NO: 336 |
| 11 | SEQ ID NO: 94 | SEQ ID NO: 261 | SEQ ID NO: 7 | SEQ ID NO: 336 |
| 12 | SEQ ID NO: 95 | SEQ ID NO: 262 | SEQ ID NO: 7 | SEQ ID NO: 336 |
| 13 | SEQ ID NO: 96 | SEQ ID NO: 263 | SEQ ID NO: 7 | SEQ ID NO: 336 |
| 14 | SEQ ID NO: 97 | SEQ ID NO: 264 | SEQ ID NO: 7 | SEQ ID NO: 336 |
| 15 | SEQ ID NO: 98 | SEQ ID NO: 265 | SEQ ID NO: 7 | SEQ ID NO: 336 |
| 16 | SEQ ID NO: 99 | SEQ ID NO: 266 | SEQ ID NO: 7 | SEQ ID NO: 336 |
| 17 | SEQ ID NO: 100 | SEQ ID NO: 267 | SEQ ID NO: 7 | SEQ ID NO: 336 |
| 18 | SEQ ID NO: 101 | SEQ ID NO: 268 | SEQ ID NO: 7 | SEQ ID NO: 336 |
| 19 | SEQ ID NO: 102 | SEQ ID NO: 269 | SEQ ID NO: 7 | SEQ ID NO: 336 |
| 20 | SEQ ID NO: 103 | SEQ ID NO: 270 | SEQ ID NO: 7 | SEQ ID NO: 336 |
| 21 | SEQ ID NO: 104 | SEQ ID NO: 271 | SEQ ID NO: 7 | SEQ ID NO: 336 |
| 22 | SEQ ID NO: 105 | SEQ ID NO: 272 | SEQ ID NO: 7 | SEQ ID NO: 336 |
| 31 | SEQ ID NO: 106 | SEQ ID NO: 273 | SEQ ID NO: 170 | SEQ ID NO: 339 |
| 32 | SEQ ID NO: 107 | SEQ ID NO: 274 | SEQ ID NO: 170 | SEQ ID NO: 339 |
| 33 | SEQ ID NO: 108 | SEQ ID NO: 275 | SEQ ID NO: 170 | SEQ ID NO: 339 |
| 34 | SEQ ID NO: 106 | SEQ ID NO: 273 | SEQ ID NO: 171 | SEQ ID NO: 340 |
| 35 | SEQ ID NO: 107 | SEQ ID NO: 274 | SEQ ID NO: 171 | SEQ ID NO: 340 |
| 36 | SEQ ID NO: 108 | SEQ ID NO: 275 | SEQ ID NO: 171 | SEQ ID NO: 340 |
| 37 | SEQ ID NO: 106 | SEQ ID NO: 273 | SEQ ID NO: 172 | SEQ ID NO: 341 |
| 38 | SEQ ID NO: 107 | SEQ ID NO: 274 | SEQ ID NO: 172 | SEQ ID NO: 341 |
| 39 | SEQ ID NO: 108 | SEQ ID NO: 275 | SEQ ID NO: 172 | SEQ ID NO: 341 |
| 40 | SEQ ID NO: 109 | SEQ ID NO: 276 | SEQ ID NO: 170 | SEQ ID NO: 339 |
| 43 | SEQ ID NO: 110 | SEQ ID NO: 277 | SEQ ID NO: 171 | SEQ ID NO: 340 |
| 46 | SEQ ID NO: 111 | SEQ ID NO: 278 | SEQ ID NO: 172 | SEQ ID NO: 341 |
| 50 | SEQ ID NO: 112 | SEQ ID NO: 279 | SEQ ID NO: 169 | SEQ ID NO: 338 |

TABLE 10-continued

List of antibody numbers and corresponding sequence identification numbers. Except for Antibody 1 all sequences listed in this table are the variable regions of the antibodies. All variable regions listed in this table form part of antibodies that contain a human heavy chain IgG$_1$ Fc region (SEQ ID NO: 8) and a light chain kappa constant region (SEQ ID NO: 9).

| Antibody Number | VH domain Protein | VH domain DNA | VL domain Protein | VL domain DNA |
| --- | --- | --- | --- | --- |
| 51 | SEQ ID NO: 113 | SEQ ID NO: 280 | SEQ ID NO: 173 | SEQ ID NO: 342 |
| 52 | SEQ ID NO: 114 | SEQ ID NO: 281 | SEQ ID NO: 173 | SEQ ID NO: 342 |
| 53 | SEQ ID NO: 115 | SEQ ID NO: 282 | SEQ ID NO: 173 | SEQ ID NO: 342 |
| 54 | SEQ ID NO: 116 | SEQ ID NO: 283 | SEQ ID NO: 173 | SEQ ID NO: 342 |
| 55 | SEQ ID NO: 117 | SEQ ID NO: 284 | SEQ ID NO: 173 | SEQ ID NO: 342 |
| 56 | SEQ ID NO: 113 | SEQ ID NO: 280 | SEQ ID NO: 174 | SEQ ID NO: 343 |
| 57 | SEQ ID NO: 114 | SEQ ID NO: 281 | SEQ ID NO: 174 | SEQ ID NO: 343 |
| 58 | SEQ ID NO: 115 | SEQ ID NO: 282 | SEQ ID NO: 174 | SEQ ID NO: 343 |
| 59 | SEQ ID NO: 116 | SEQ ID NO: 283 | SEQ ID NO: 174 | SEQ ID NO: 343 |
| 60 | SEQ ID NO: 117 | SEQ ID NO: 284 | SEQ ID NO: 174 | SEQ ID NO: 343 |
| 61 | SEQ ID NO: 113 | SEQ ID NO: 280 | SEQ ID NO: 175 | SEQ ID NO: 344 |
| 62 | SEQ ID NO: 114 | SEQ ID NO: 281 | SEQ ID NO: 175 | SEQ ID NO: 344 |
| 63 | SEQ ID NO: 115 | SEQ ID NO: 282 | SEQ ID NO: 175 | SEQ ID NO: 344 |
| 64 | SEQ ID NO: 116 | SEQ ID NO: 283 | SEQ ID NO: 175 | SEQ ID NO: 344 |
| 65 | SEQ ID NO: 117 | SEQ ID NO: 284 | SEQ ID NO: 175 | SEQ ID NO: 344 |
| 66 | SEQ ID NO: 113 | SEQ ID NO: 280 | SEQ ID NO: 176 | SEQ ID NO: 345 |
| 67 | SEQ ID NO: 114 | SEQ ID NO: 281 | SEQ ID NO: 176 | SEQ ID NO: 345 |
| 68 | SEQ ID NO: 115 | SEQ ID NO: 282 | SEQ ID NO: 176 | SEQ ID NO: 345 |
| 69 | SEQ ID NO: 116 | SEQ ID NO: 283 | SEQ ID NO: 176 | SEQ ID NO: 345 |
| 70 | SEQ ID NO: 117 | SEQ ID NO: 284 | SEQ ID NO: 176 | SEQ ID NO: 345 |
| 71 | SEQ ID NO: 113 | SEQ ID NO: 280 | SEQ ID NO: 177 | SEQ ID NO: 346 |
| 72 | SEQ ID NO: 114 | SEQ ID NO: 281 | SEQ ID NO: 177 | SEQ ID NO: 346 |
| 73 | SEQ ID NO: 115 | SEQ ID NO: 282 | SEQ ID NO: 177 | SEQ ID NO: 346 |
| 74 | SEQ ID NO: 116 | SEQ ID NO: 283 | SEQ ID NO: 177 | SEQ ID NO: 346 |
| 75 | SEQ ID NO: 117 | SEQ ID NO: 284 | SEQ ID NO: 177 | SEQ ID NO: 346 |
| 76 | SEQ ID NO: 118 | SEQ ID NO: 285 | SEQ ID NO: 178 | SEQ ID NO: 347 |
| 77 | SEQ ID NO: 119 | SEQ ID NO: 286 | SEQ ID NO: 178 | SEQ ID NO: 347 |
| 78 | SEQ ID NO: 120 | SEQ ID NO: 287 | SEQ ID NO: 178 | SEQ ID NO: 347 |
| 79 | SEQ ID NO: 118 | SEQ ID NO: 285 | SEQ ID NO: 179 | SEQ ID NO: 348 |
| 80 | SEQ ID NO: 119 | SEQ ID NO: 286 | SEQ ID NO: 179 | SEQ ID NO: 348 |
| 81 | SEQ ID NO: 120 | SEQ ID NO: 287 | SEQ ID NO: 179 | SEQ ID NO: 348 |
| 92 | SEQ ID NO: 121 | SEQ ID NO: 288 | SEQ ID NO: 176 | SEQ ID NO: 345 |
| 93 | SEQ ID NO: 122 | SEQ ID NO: 289 | SEQ ID NO: 176 | SEQ ID NO: 345 |
| 94 | SEQ ID NO: 123 | SEQ ID NO: 290 | SEQ ID NO: 176 | SEQ ID NO: 345 |
| 95 | SEQ ID NO: 124 | SEQ ID NO: 291 | SEQ ID NO: 176 | SEQ ID NO: 345 |
| 96 | SEQ ID NO: 125 | SEQ ID NO: 292 | SEQ ID NO: 176 | SEQ ID NO: 345 |
| 97 | SEQ ID NO: 126 | SEQ ID NO: 293 | SEQ ID NO: 176 | SEQ ID NO: 345 |
| 98 | SEQ ID NO: 127 | SEQ ID NO: 294 | SEQ ID NO: 176 | SEQ ID NO: 345 |
| 99 | SEQ ID NO: 128 | SEQ ID NO: 295 | SEQ ID NO: 176 | SEQ ID NO: 345 |
| 100 | SEQ ID NO: 129 | SEQ ID NO: 296 | SEQ ID NO: 176 | SEQ ID NO: 345 |
| 101 | SEQ ID NO: 130 | SEQ ID NO: 297 | SEQ ID NO: 176 | SEQ ID NO: 345 |
| 102 | SEQ ID NO: 131 | SEQ ID NO: 298 | SEQ ID NO: 176 | SEQ ID NO: 345 |
| 103 | SEQ ID NO: 132 | SEQ ID NO: 299 | SEQ ID NO: 176 | SEQ ID NO: 345 |
| 104 | SEQ ID NO: 133 | SEQ ID NO: 300 | SEQ ID NO: 176 | SEQ ID NO: 345 |
| 105 | SEQ ID NO: 134 | SEQ ID NO: 301 | SEQ ID NO: 176 | SEQ ID NO: 345 |
| 106 | SEQ ID NO: 135 | SEQ ID NO: 302 | SEQ ID NO: 176 | SEQ ID NO: 345 |
| 107 | SEQ ID NO: 136 | SEQ ID NO: 303 | SEQ ID NO: 176 | SEQ ID NO: 345 |
| 108 | SEQ ID NO: 137 | SEQ ID NO: 304 | SEQ ID NO: 176 | SEQ ID NO: 345 |
| 109 | SEQ ID NO: 138 | SEQ ID NO: 305 | SEQ ID NO: 176 | SEQ ID NO: 345 |
| 110 | SEQ ID NO: 139 | SEQ ID NO: 306 | SEQ ID NO: 176 | SEQ ID NO: 345 |
| 111 | SEQ ID NO: 113 | SEQ ID NO: 280 | SEQ ID NO: 176 | SEQ ID NO: 345 |
| 112 | SEQ ID NO: 140 | SEQ ID NO: 307 | SEQ ID NO: 176 | SEQ ID NO: 345 |
| 113 | SEQ ID NO: 141 | SEQ ID NO: 308 | SEQ ID NO: 176 | SEQ ID NO: 345 |
| 114 | SEQ ID NO: 142 | SEQ ID NO: 309 | SEQ ID NO: 176 | SEQ ID NO: 345 |
| 115 | SEQ ID NO: 143 | SEQ ID NO: 310 | SEQ ID NO: 176 | SEQ ID NO: 345 |
| 116 | SEQ ID NO: 144 | SEQ ID NO: 311 | SEQ ID NO: 176 | SEQ ID NO: 345 |
| 117 | SEQ ID NO: 145 | SEQ ID NO: 312 | SEQ ID NO: 176 | SEQ ID NO: 345 |
| 118 | SEQ ID NO: 146 | SEQ ID NO: 313 | SEQ ID NO: 176 | SEQ ID NO: 345 |
| 119 | SEQ ID NO: 147 | SEQ ID NO: 314 | SEQ ID NO: 176 | SEQ ID NO: 345 |
| 120 | SEQ ID NO: 148 | SEQ ID NO: 315 | SEQ ID NO: 176 | SEQ ID NO: 345 |
| 121 | SEQ ID NO: 149 | SEQ ID NO: 316 | SEQ ID NO: 176 | SEQ ID NO: 345 |
| 122 | SEQ ID NO: 150 | SEQ ID NO: 317 | SEQ ID NO: 176 | SEQ ID NO: 345 |
| 123 | SEQ ID NO: 151 | SEQ ID NO: 318 | SEQ ID NO: 176 | SEQ ID NO: 345 |
| 124 | SEQ ID NO: 152 | SEQ ID NO: 319 | SEQ ID NO: 176 | SEQ ID NO: 345 |
| 125 | SEQ ID NO: 115 | SEQ ID NO: 282 | SEQ ID NO: 176 | SEQ ID NO: 345 |

TABLE 10-continued

List of antibody numbers and corresponding sequence identification numbers. Except for Antibody 1 all sequences listed in this table are the variable regions of the antibodies. All variable regions listed in this table form part of antibodies that contain a human heavy chain IgG$_1$ Fc region (SEQ ID NO: 8) and a light chain kappa constant region (SEQ ID NO: 9).

| Antibody Number | VH domain Protein | VH domain DNA | VL domain Protein | VL domain DNA |
|---|---|---|---|---|
| 126 | SEQ ID NO: 115 | SEQ ID NO: 282 | SEQ ID NO: 180 | SEQ ID NO: 349 |
| 127 | SEQ ID NO: 115 | SEQ ID NO: 282 | SEQ ID NO: 181 | SEQ ID NO: 350 |
| 128 | SEQ ID NO: 115 | SEQ ID NO: 282 | SEQ ID NO: 182 | SEQ ID NO: 351 |
| 130 | SEQ ID NO: 115 | SEQ ID NO: 282 | SEQ ID NO: 183 | SEQ ID NO: 352 |
| 131 | SEQ ID NO: 115 | SEQ ID NO: 282 | SEQ ID NO: 184 | SEQ ID NO: 353 |
| 132 | SEQ ID NO: 115 | SEQ ID NO: 282 | SEQ ID NO: 185 | SEQ ID NO: 354 |
| 133 | SEQ ID NO: 115 | SEQ ID NO: 282 | SEQ ID NO: 186 | SEQ ID NO: 355 |
| 134 | SEQ ID NO: 115 | SEQ ID NO: 282 | SEQ ID NO: 187 | SEQ ID NO: 356 |
| 135 | SEQ ID NO: 115 | SEQ ID NO: 282 | SEQ ID NO: 188 | SEQ ID NO: 357 |
| 136 | SEQ ID NO: 115 | SEQ ID NO: 282 | SEQ ID NO: 189 | SEQ ID NO: 358 |
| 137 | SEQ ID NO: 115 | SEQ ID NO: 282 | SEQ ID NO: 190 | SEQ ID NO: 359 |
| 138 | SEQ ID NO: 115 | SEQ ID NO: 282 | SEQ ID NO: 191 | SEQ ID NO: 360 |
| 139 | SEQ ID NO: 115 | SEQ ID NO: 282 | SEQ ID NO: 192 | SEQ ID NO: 361 |
| 140 | SEQ ID NO: 115 | SEQ ID NO: 282 | SEQ ID NO: 193 | SEQ ID NO: 362 |
| 141 | SEQ ID NO: 115 | SEQ ID NO: 282 | SEQ ID NO: 194 | SEQ ID NO: 363 |
| 142 | SEQ ID NO: 115 | SEQ ID NO: 282 | SEQ ID NO: 195 | SEQ ID NO: 364 |
| 143 | SEQ ID NO: 115 | SEQ ID NO: 282 | SEQ ID NO: 196 | SEQ ID NO: 365 |
| 144 | SEQ ID NO: 115 | SEQ ID NO: 282 | SEQ ID NO: 197 | SEQ ID NO: 366 |
| 145 | SEQ ID NO: 115 | SEQ ID NO: 282 | SEQ ID NO: 198 | SEQ ID NO: 367 |
| 146 | SEQ ID NO: 115 | SEQ ID NO: 282 | SEQ ID NO: 199 | SEQ ID NO: 368 |
| 147 | SEQ ID NO: 115 | SEQ ID NO: 282 | SEQ ID NO: 200 | SEQ ID NO: 369 |
| 148 | SEQ ID NO: 115 | SEQ ID NO: 282 | SEQ ID NO: 201 | SEQ ID NO: 370 |
| 175 | SEQ ID NO: 153 | SEQ ID NO: 320 | SEQ ID NO: 189 | SEQ ID NO: 358 |
| 176 | SEQ ID NO: 154 | SEQ ID NO: 321 | SEQ ID NO: 189 | SEQ ID NO: 358 |
| 177 | SEQ ID NO: 155 | SEQ ID NO: 322 | SEQ ID NO: 189 | SEQ ID NO: 358 |
| 178 | SEQ ID NO: 156 | SEQ ID NO: 323 | SEQ ID NO: 189 | SEQ ID NO: 358 |
| 179 | SEQ ID NO: 157 | SEQ ID NO: 324 | SEQ ID NO: 189 | SEQ ID NO: 358 |
| 180 | SEQ ID NO: 158 | SEQ ID NO: 325 | SEQ ID NO: 189 | SEQ ID NO: 358 |
| 181 | SEQ ID NO: 159 | SEQ ID NO: 326 | SEQ ID NO: 189 | SEQ ID NO: 358 |
| 182 | SEQ ID NO: 160 | SEQ ID NO: 327 | SEQ ID NO: 189 | SEQ ID NO: 358 |
| 183 | SEQ ID NO: 31 | SEQ ID NO: 220 | SEQ ID NO: 32 | SEQ ID NO: 221 |
| 184 | SEQ ID NO: 33 | SEQ ID NO: 222 | SEQ ID NO: 179 | SEQ ID NO: 348 |
| 185 | SEQ ID NO: 45 | SEQ ID NO: 234 | SEQ ID NO: 179 | SEQ ID NO: 348 |
| 186 | SEQ ID NO: 119 | SEQ ID NO: 286 | SEQ ID NO: 51 | SEQ ID NO: 240 |
| 190 | SEQ ID NO: 119 | SEQ ID NO: 286 | SEQ ID NO: 189 | SEQ ID NO: 358 |
| 191 | SEQ ID NO: 161 | SEQ ID NO: 328 | SEQ ID NO: 189 | SEQ ID NO: 358 |
| 192 | SEQ ID NO: 162 | SEQ ID NO: 329 | SEQ ID NO: 189 | SEQ ID NO: 358 |
| 193 | SEQ ID NO: 163 | SEQ ID NO: 330 | SEQ ID NO: 189 | SEQ ID NO: 358 |
| 194 | SEQ ID NO: 164 | SEQ ID NO: 331 | SEQ ID NO: 189 | SEQ ID NO: 358 |
| 195 | SEQ ID NO: 165 | SEQ ID NO: 332 | SEQ ID NO: 189 | SEQ ID NO: 358 |
| 196 | SEQ ID NO: 166 | SEQ ID NO: 333 | SEQ ID NO: 189 | SEQ ID NO: 358 |
| 197 | SEQ ID NO: 167 | SEQ ID NO: 334 | SEQ ID NO: 189 | SEQ ID NO: 358 |
| 198 | SEQ ID NO: 168 | SEQ ID NO: 335 | SEQ ID NO: 189 | SEQ ID NO: 358 |
| 199 | SEQ ID NO: 161 | SEQ ID NO: 328 | SEQ ID NO: 179 | SEQ ID NO: 348 |
| 200 | SEQ ID NO: 162 | SEQ ID NO: 329 | SEQ ID NO: 179 | SEQ ID NO: 348 |
| 201 | SEQ ID NO: 163 | SEQ ID NO: 330 | SEQ ID NO: 179 | SEQ ID NO: 348 |
| 202 | SEQ ID NO: 164 | SEQ ID NO: 331 | SEQ ID NO: 179 | SEQ ID NO: 348 |
| 203 | SEQ ID NO: 165 | SEQ ID NO: 332 | SEQ ID NO: 179 | SEQ ID NO: 348 |
| 204 | SEQ ID NO: 166 | SEQ ID NO: 333 | SEQ ID NO: 179 | SEQ ID NO: 348 |
| 205 | SEQ ID NO: 167 | SEQ ID NO: 334 | SEQ ID NO: 179 | SEQ ID NO: 348 |
| 206 | SEQ ID NO: 168 | SEQ ID NO: 335 | SEQ ID NO: 179 | SEQ ID NO: 348 |

Methods:

Creation, Isolation, Expression of Antibodies in Mammalian Cells

Generation of Hybridoma Cell Lines, Expression and Purification

5 BALB/C mice were immunized with human IL-12 (Peprotech) in Complete Freund's adjuvant each, followed by a boost of human IL-12 in Incomplete Freund's adjuvant on day 14, 35 and 70. On day 74, mouse spleens were harvested and mouse splenocytes obtained. A fusion was performed between these cells and myeloma cell line SP2/0 Ag-14 and cells were deposited in 96-well tissue culture plates. Anti-IL-12, Anti-IL-12p40 and Anti-IL-23 ELISAs (see below) were performed on the supernatant for each well of the 96 well plates. Supernatants that tested positive for all three ELISAs were carried forward and cloned by limiting dilution. Clones that tested positive in downstream ELISAs were culture up to 500 mL scale and antibody purification performed (see below). The antibody purified from this method was dialysed against 1×PBS and the concentration determined via BCA® assay kit (Pierce®).

DNA Sequencing

RNA was isolated from the hybridoma cells, using TR1 reagent (Sigma-Aldrich®) according to the manufacturer's protocol. cDNA was synthesized from 10-200 ng RNA, using the AccuScript® High Fidelity 1st Strand cDNA Synthesis Kit (Stratagene®), then used as a template in the following PCR reaction. Primers from the Novagen Murine IgG Primer Set for heavy-chain and for light-chain respectively were mixed together with cDNA and Pfu II Mastermix® (Stratagene®) then run in a Thermocyler (Eppendorf Mastercycler®) according to the following conditions:

| °C. | Time | cycles |
|---|---|---|
| 94 | 2 min | 1 |
| 94 | 30 sec | 30 |
| 60 | 30 sec | 30 |
| 72 | 45 sec | 30 |
| 94 | 5 min | 1 |

The PCR product was gel purified with the DNA Gel Extraction Kit (QIAgen®), A-tagged [dATPs and Taq-polymerase (Invitrogen™) at 72° C. for 15 minutes adds an A-overhang to the PCR-product], ligated into pGEM-T-Vector System (Promega®) and transformed into TOP10 competent cells (Invitrogen™). Clones were screened for a 500 bp insert. From positive clones the plasmids were isolated (Miniprep, QIAgen®) and sequenced at a conventional sequencing facility. The nucleotide sequence was then translated into primary amino acid sequence.

Construction of Vectors Expressing Chimeric Antibodies

The VH domains determined via DNA sequencing from the hybridoma cells, PMA202 and PMA204, were expressed with a human constant region (human IgG1 heavy chain CH1, hinge, CH2 & CH3 domains). This was achieved by back translation of amino acid sequences into DNA sequences which were optimized for mammalian cell expression using GeneOptimizer technology and synthesized de novo by assembly of synthetic oligonucleotides (GeneArt, Germany). Following gene synthesis the whole sequence was subcloned into the multiple cloning site of the pTT5 heavy chain vector (Durocher et al. 2002 Nucleic Acids Res 30 E9). The VL amino acid chain discovered via DNA sequencing from the hybridoma cells, PMA202 and PMA204, were expressed with a human kappa light chain constant region by subcloning the sequence into the multiple cloning site of the pTT5 light chain vector. The resulting PMA202 murine-human chimeric antibody was designated Antibody 202.1. The resulting PMA204 murine-human chimeric antibody was designated Antibody 1. All antibodies were produced using this methodology with the candidate protein sequence being back-translated into DNA sequence, optimized and synthesis de novo by assembly of synthetic oligonucleotides. All antibodies contained a human heavy chain Fc region and a human light chain kappa constant region. All genes encoding antibody varible regions were then cloned into the pTT5 vector for expression.

Expression of Recombinant Antibodies Via Transient Transfection

For all antibodies expressed transiently the following method was used. Briefly, HEK293E cells were cultured in complete cell growth media (1 L of F17 medium (Invitrogen™), 9 mL of Pluronic F68 (Invitrogen™), 2 mM Glutamine containing 20% (w/v) Tryptone NI (Organotechnie®) with Geneticin (50 mg/mL, Invitrogen™) at 50 µl/100 mL culture). At the day before transfection, the cells were harvested by centrifugation and resuspended in fresh media (without Geneticin). The next day heavy and light chain DNA was mixed with FuGENE® (Roche) transfection reagent and the DNA transfection mix added to the culture drop-wise. The culture was incubated overnight at 37° C., 5% $CO_2$ and 120 rpm without Geneticin. The next day 12.5 mL of Tryptone was added along with 250 µl of Geneticin per 500 mL culture. The culture was incubated at 37° C., 5% $CO_2$ and 120 rpm. After 7 days the supernatant was harvested by centrifugation, ready for purification.

Purification of Antibodies Via Affinity Chromatography

The supernatant derived from the above transfections were adjusted to pH 7.4 before being loaded onto a HiTrap® Protein A column (5 mL, GE Healthcare). The column was washed with 50 mL of 1×PBS (pH 7.4). Elution was performed using 0.1M citric acid pH 2.5. The eluted antibody was desalted using Zeba® Desalting columns (Pierce®) into 1×PBS (pH 7.4). The integrity of the antibody was analysed using SDS-PAGE and gel filtration HPLC. The concentration of the antibody was determined using the BCA® assay kit (Pierce®).

Characterization of Anti-IL-12/23 Antibodies

Anti-IL-12/23 ELISA

IL-12 (Peprotech), IL-23 (Ebioscience™), IL-12p40 (Ebioscience™) or IL-12p80 (Peprotech), was diluted to 1 µg/mL in carbonate coating buffer (35 mM sodium carbonate, 15 mM sodium hydrogen carbonate pH 9.6) and coated onto a 96 well plate (Nunc™, Maxisorp™) overnight at 4° C. The plate was then washed three times with wash buffer (0.01M PBS pH 7.2, 0.05% Tween-20) and then three times with 0.01M PBS pH 7.2. The wells were then blocked by adding 200 µl of blocking buffer (1% w/v BSA in 0.01 M PBS pH 7.2) to each well and incubating the plate at 25° C. for 1 hour. The antibody was diluted in antibody diluent (1% w/v BSA, 0.05% Tween-20 in 0.01M PBS pH 7.2) sufficient to generate a titration curve. The wells were incubated with the antibody for 1 hour at 25° C. The plate was then washed as previously described. Goat anti-human immunoglobulin G (H+L) antibody HRP conjugate (Zymed®) at 1:2000 in antibody diluent was used to detect bound primary antibody. Goat anti-murine immunoglobulin antibody HRP conjugate (Dako) at 1:2000 in antibody diluent was used to detect bound murine antibody. After incubation at 25° C. for 1 hour the plate was washed again as previously described. TMB substrate solution (Zymed®) was added to each well and the colour allowed to develop; the reaction was terminated by adding 1M HCl to the wells. The absorbance of each well was determined at 450 nm (ref. 620 nm).

IL-12/IL-12Rβ1 Neutralization Assay

IL-12Rβ1/Fc Chimera (R&D Systems®) was diluted to 1 µg/mL in carbonate coating buffer and added to each well of a 96 well plate and incubated at 4° C. overnight. The plate was then washed three times with wash buffer and then three times with 0.01M PBS pH 7.2. The wells were then blocked by adding 200 µl of blocking buffer to each well and incubating the plate at 25° C. for 1 hour. The antibody was diluted in antibody diluent sufficient to generate a titration curve. IL-12 (Peprotech) was diluted to 300 ng/mL in antibody diluent. IL-12 was preincubated with the antibody in a deep well container for 2 hours. Then the plate was washed as previously described and wells were incubated with the antibody/IL-12 solution for 1 hour at 25° C. The plate was then washed as previously described and 100 µl of biotinylated anti-human IL-12 antibody (Peprotech) at 0.5 µg/mL in antibody diluent was used to detect bound antibody for 1 hour at 25° C. The plate was washed as previously described. 100 µl of Streptavidin HRP (Zymed®) at 1:1000 in antibody diluent was used to detect bound biotinylated antibody. After incubation at 25° C. for 1 hour the plate was washed again as previously described. 100 µl TMB substrate solution (Zymed®) was added to each well and the colour allowed to develop for 5 minutes. 100 µl of 1M HCl was added to terminate the colour development reaction and absorbance was determined at 450 nm (ref. 620 nm).

IL-12p80/IL-12Rβ1 Neutralization Assay

This assay was performed as described above for the IL-12/IL-12Rβ1 neutralization assay but with the following alterations:

IL-12 was Replaced with IL-12p80 (Peprotech)

IL-12/IL-12Rβ2 Neutralization Assay

This assay was performed as described above for the IL-12/IL-12Rβ1 neutralization assay but with the following alterations: IL-12Rβ1/Fc Chimera was replaced with IL-12Rβ2/Fc Chimera (R&D Sytsems®) and was diluted to 5 ug/ml instead of 1 ug/ml. The plate was washed three times with wash buffer without extra PBS washes. IL-12 (Peprotech) was replaced by biotinylated IL-12 (Peprotech). The wells with antibody/IL-12 solution were incubated for 2 hours at 25° C. No biotinylated anti-human IL-12 antibody was added to the wells. 100u1 of 1:1000 Streptavidin HRP (Zymed®) was replaced by 100 ul of 1:5000 Streptavidin HRP (Sigma-Aldrich°). 100u1 TMB substrate solution (Zymed®) was replaced by 100 ul TMB substrate solution (Sigma-Aldrich®).

IL-23/IL-23R Neutralization Assay

IL-23/Fc Chimera (R&D Systems®) was diluted to 1 μg/mL in carbonate coating buffer and added to each well of a 96 well plate and incubated at 4° C. overnight. The plate was then washed three times with wash buffer and then three times with 0.01M PBS pH 7.2. The wells were then blocked by adding 200 μl of blocking buffer to each well and incubating the plate at 25° C. for 1 hour. The antibody was diluted in antibody diluent sufficient to generate a titration curve. IL-23 (Ebioscience™) was diluted to 300 ng/mL in antibody diluent. IL-23 was preincubated with the antibody in a deep well container for 2 hours. Then the plate was washed as previously described and wells were incubated with the antibody/IL-23 solution for 1 hour at 25° C. The plate was then washed as previously described and 100 μl of biotinylated anti-human IL-12 antibody (Peprotech) at 0.5 μg/mL in antibody diluent was used to detect bound antibody for 1 hour at 25° C. The plate was washed as previously described. 100 μl of Strepdavidin HRP (Zymed®) at 1:1000 in antibody diluent was used to detect bound biotinylated antibody. After incubation at 25° C. for 1 hour the plate was washed again as previously described. 100 μl TMB substrate solution (Zymed®) was added to each well and the colour allowed to develop for 5 minutes. 100 μl of 1M HCl was added to terminate the colour development reaction and absorbance was determined at 450 nm (ref. 620 nm).

This assay was also performed as described above for the IL-23/IL-23R neutralization assay but with the following alterations: IL-23/Fc Chimera (R&D Systems®) was replaced with internal produced IL-23R-HIS, dervied from HEK-293E cells and purified using affinity chromatography. The plate was washed three times with wash buffer without extra PBS washes. IL-23 (Ebioscience™) was replaced by biotinylated IL-23 (Ebioscience™). IL-23 was diluted to 50 ng/ml instead of 300 ng/ml in antibody diluent. The wells with antibody/IL-23 solution were incubated for 2 hours at 25° C. No biotinylated anti-human IL-12 antibody was added to the wells. 100u1 of 1:1000 Streptavidin HRP (Zymed®) was replaced by 100u1 of 1:5000 Streptavidin HRP (Sigma-Aldrich®). 100u1 TMB substrate solution (Zymed®) was replaced by 100 ul TMB substrate solution (Sigma-Aldrich®). Colour was allowed to develop for 15 minutes instead of 5 minutes.

Competition Binding Experiments

IL-12/23 Competition ELISA

PMA204 or PMA202 was diluted to 1 μg/mL in carbonate coating buffer (35 mM sodium carbonate, 15 mM sodium hydrogen carbonate pH 9.6) and coated onto a 96 well plate (Nunc™, Maxisorp™) overnight at 4° C. The plate was then washed three times with wash buffer (0.01M PBS pH 7.2, 0.05% Tween-20) and then three times with 0.01M PBS pH 7.2. The wells were then blocked by adding 200 μl of blocking buffer (1% w/v BSA in 0.01 M PBS pH 7.2) to each well and incubating the plate at 25° C. for 1 hour. IL-12 (Peprotech) or IL-12 (Ebioscience™) was diluted to 0.5 μg/ml in antibody diluent (1% w/v BSA, 0.05% Tween-20 in 0.01M PBS pH 7.2) and 100 μl added to each well followed by incubation for 1 hour at 25° C. The plate was then washed as previously described. Serial half log dilutions of the competition antibodies were performed and 100 μl added to each well. Final protein concentrations were sufficient to generate a titration curve. The plates were incubated for 1 hour at 25° C. and then washed as described previously. Goat anti-human immunoglobulin G (Fc specific)-HRP conjugate (Sigma-Aldrich®) at 1:2000 in antibody diluent was used to detect bound competition antibody. After incubation at 25° C. for 1 hour the plate was washed again as previously described. For horse-radish-peroxidase (HRP)-labelled detection reagents, enzymatic reactions were developed in the dark with 100 μl/well tetramethylbenzidine (Zymed®) substrate at room temperature. The reaction was stopped with 100 μl of 1 M HCl and the optical density measured at 450 nm (ref. 620 nm).

SPR Competition Assay

Protein A (Thermo) was immobilized onto a CM5 sensor chip using a BIAcore 3000. Chimeric or humanized antibody at 5 ug/mL in HBS-P (GE Healthcare) was then injected for 1 min at a flow rate of 20 ul/min. IL-12 or IL-23 was then injected over the surface at 5 ug/mL in HBS-P for 1 min at a flow rate of 20 ul/min. Murine antibody was then injected at 5 ug/mL in HBS-P for 1 min at a flow rate of 20 ul/min. Controls in which IL-12 or IL-23 was replaced with HBS-P, and in which the murine antibody was replaced with HBS-P were also performed. All data was substrated from a control run in which IL-12 or IL-23 or the murine antibody was tested for background binding to the Protein A surface.

Generation of a Stably Transfected Cell Line Expressing the Il-12Rβ1 Chain

The amino acid sequence of IL-12Rβ1 was back translated into DNA sequences which were optimized for mammalian cell expression using GeneOptimizer technology and synthesized de novo by assembly of synthetic oligonucleotides (GeneArt, Germany). The DNA sequence encoding IL-12Rβ1 was subcloned into pcDNADEST-40 and then transformed into Top-10 chemically competent E. coli cells. Plasmid DNA was recovered from cell culture using a HiSpeed Plasmid Maxi Kit (QIAgen®), and linearized by restriction enzyme digest with ScaI (Promega®). Plasmids were transfected into Jurkat 6E cells (ATCC) and surface expression determined by staining with anti-receptor chain antibodies to IL-12R131 (R&D Systems®)

Detection of IL-12p40, IL-12 and IL-23 binding to an IL-12Rβ1 Expressed Cell Line FLAG-tagged IL-12 or HIS-tagged IL-23 or IL-12p40 was co-incubated with IL-12-Rβ1-expressing cells ($10^6$/ml) at concentrations ranging from 1000 to 0.01 ng/ml by serial half log dilution for 2 hours at 37° C. Binding of cytokine to cells was detected with phycoerythrin-conjugated mouse anti-6× HIS tag antibody (Abcam®) or FITC-conjugated anti-FLAG (Sigma-Aldrich®). Sample data were acquired on a Beckman-Coulter Quanta®.

Detection of Inhibiton of IL-12p40, IL-12 and IL-23 Binding to an IL-12Rβ1 Expressing Cell Line FLAG-tagged IL-12 or HIS-tagged IL-23 or IL-12p40 at a concentration of 250 ng/ml was co-incubated with antibody at concentrations ranging from 10 to 0.01 µg/ml by serial half-log dilution for one hour at 37° C., then IL-12Rβ1-expressing cells as described above were added at $10^6$/ml and incubated for a further hour. Cells were washed thoroughly in PBS/10% FBS and cell-bound cytokine was detected with phycoerythrin-conjugated mouse anti-6×HIS tag antibody (Abcam®) or FITC-conjugated anti-FLAG antibody (Sigma-Aldrich®). Sample data were acquired on a Beckman-Coulter Quanta.

Detection of Antibod-Cytokine Complexes on the Surface of an IL-12Rβ1 Expressing Cell Line FLAG-tagged IL-12 or HIS-tagged IL-23 or IL-12p40 was co-incubated with IL-12Rβ1-expressing cells as described above at a concentration of 250 ng/ml. After 2 hours incubation, antibody was added at concentrations ranging from 10 to 0.01 µg/ml by serial half-log dilution and incubated for a further hour. Cells were washed thoroughly in PBS/10% FBS and antibody bound to cell-bound cytokine was detected with FITC-conjugated Rabbit anti-human IgG (Dako). Sample data were acquired on a Beckman-Coulter Quanta®.

Affinity Maturation

Methods

Assembly of the scFv-80 Coding Sequence from the Antibody 80 $V_H$ and $V_L$ Domains A single-chain antibody fragment (scFv-80) was derived from antibody 80 by designing a polypeptide that comprised the variable domain of the heavy chain (VL) joined to the variable domain of the light chain (VL) by a 15 amino acid linker of the sequence $(Gly_4Ser)_3$ (SEQ ID NO: 379)(scFv-80, SEQ ID NO: 27). The VH and VL sequences were oriented at the N and C-terminal ends of the polypeptide (respectively). The amino acid sequence was then back-translated to a DNA sequence that was optimized for mammalian expression using GeneOptimizer technology. The entire gene was then synthesized de novo by assembly of synthetic oligonucleotides (GeneArt). The final sequence also included 5' NcoI and 3' NotI sites to facilitate further sub-cloning.

The recombinant gene encoding the scFv-80 protein was sub-cloned into the NcoI and NotI sites of the pEGX448 expression vector. pEGX448 is designed such that any scFv sub-cloned into the NcoI and NotI sites is automatically fused a proprietary 'FLAG' affinity tag at the C-terminus.

The scFv-80 gene was similarly sub-cloned into the pEGX412 vector for RNA production, mutagenesis and ribosome display. This vector was identical to pEGX253 plasmid described by Kopsidas et al. (2007), except that pEGX412 uses the gene III protein sequence to link the scFv to the ribosome instead of the $C_L$ sequence used in pEGX253.

RNA Production and Mutagenesis

The pEGX412-scFv80 construct described above was used to produce a pool of RNA encoding mutant variants of scFv-80. To achieve this, the plasmid was linearized with SmaI and used directly as the template for single-stranded RNA (ssRNA) production using a T7 RNA polymerase kit (Promega®) as per manufacturer's instructions. The resulting single-stranded RNA molecule was used as the template for error-prone replication using Q-Beta replicase (Epicentre® Biotechnologies). To achieve this, 200 ng of RNA was mixed with 33 mM Tris-acetate (pH 7.8), 66 mM potassium acetate, 10 mM magnesium acetate, 0.5 mM dithiothreitol (DTT), 5 mM rATP, 5 mM rUTP, 10 mM rCTP, 10 mM rGTP, 0.1 U/µL of Q-Beta Replicase and $H_2O$ to a final volume of 20 µL. The reaction was incubated at 45° C. for ~16 hours.

The Q-Beta replicase reaction generated a library of double-stranded RNA (dsRNA) molecules encoding a pool of mutants of the parental scFv-80 with 1-2 point mutations per mutant. The dsRNA library was converted to a pool of DNA fragments using reverse-transcriptase PCR (RT-PCR). The RT-PCR product was purified by agarose gel electrophoresis and gel extraction, before forming the template for a final T7 RNA polymerase reaction. The product of all reactions described above were tested by agarose gel electrophoresis.

Enrichment of IL-23 Binders from the Library of ScFv-80 Variants

The scFv library described above was expressed from the pEGX412 vector to produce scFv-ribosome complexes that were then panned against IL-23 following the ribosome display protocol described by Kopsidas et al. (2007). Briefly, the scFv-ribosome complexes (which also included scFv-encoding ssRNA) were incubated with biotinylated IL-23 to a final concentration of 1 nM for 24 hrs on ice. Selective pressure was then added to bias the panning experiment towards enrichment of IL-23 binders with low dissociation constants. This was achieved by adding an 800-fold excess of non-biotinylated IL-23 and continuing the panning reaction for a further 5 days. ScFv-ribosome complexes that remained bound to biotinylated IL-23 at the end of the panning period were recovered with streptavidin-coated magnetic beads. The beads were then washed three times with PBS containing 0.05% Tween20 and 5 mM MgC12 and twice with PBS containing 5 mM MgC12. Finally, ssRNA was eluted from the recovered scFv-ribosome complexes and the encoded scFv pool was amplified by RT-PCR using a Superscript III One-Step RT-PCR system (Invitrogen™) as per manufacturer's instructions, but with 8 µL of recovered RNA as the reaction template and the scFv-specific oligonucleotide primers listed below. Note that these oligonucleotides also added 5' NcoI and 3' NotI sites to facilitate sub-cloning.

```
                                     (SEQ ID NO: 380)
Forward: 5'-CCATGGCCCAGGTGCAGCTG-3'

(SEQ ID NO: 381)
Reverse: 5'-GCGGCCGCTGTCGTACGC-3'
```

High Throughput Screening Protocol for Identifying IL-23 Binders

The pools of RT-PCR products amplified at the end of ribosome display experiments (above) were sub-cloned into the NcoI and NotI sites of the pEGX448 expression vector, transformed into One-Step Competent KRX *E. coli* (Stratagene®) and grown on solid culture media. The resulting bacterial colonies were individually inoculated into 200 µL liquid growth cultures in 96-well plates, which were grown to an OD at 600 nm ($OD^{600\ nm}$) of 0.8 and then induced for protein expression with 0.5 mM isopropyl-beta-D-thiogalactopyranoside (IPTG). The 200 µL expression cultures were incubated overnight at 20° C. and then used to produce crude bacterial lysates by adding 40 µL of lysis buffer (2 M Sucrose; 0.25M Tris pH 7; 0.2M EDTA pH 8) and agitating the plates at 900 RPM for 30 mins. The lysates were then cleared by centrifugation and passed through a 10 000 molecular weight cut-off filter plate (Millipore). This method was used to prepare approximately 6500 scFv samples that were screened for IL-23 binding using the high-throughput SPR protocol detailed below.

High-throughput SPR screening was conducted using a BIAcore A100 biosensor (GE Healthcare). Approximately 10 000 RU of the proprietary FLAG-specific capture molecule was immobilized on a CM5 Series S Sensor chip, using standard amine coupling chemistry on Spots 1 & 5 (outer spots) and 3,000RU to Spots 2 & 4 (inner spots) in each of the four flow cells of the BIAcore A100 Biosensor. The running buffer used was HBS-EP+ (BIAcore) and all interactions measured at 25° C. Crude periplasmic preparations of FLAG-tagged scFvs (prepared as described in the previous paragraph), were diluted two-fold in running buffer before capturing at a flow rate of 5ul/min for 60 sec. Approx. 100RU (on outer spots) and 50RU (on inner spots) of tagged scFv was captured. Following a 2 min stabilization period, IL-23 was passed over all spots of all four flow cells simultaneously at a flow rate of 30u1/min for 120 sec and dissociation monitored for 200 sec. Generated sensorgrams were referenced against the unmodified spot 3 of each flow cell, and fitted using a 1:1 Langmuir equation with R1 set to local to account for varying ligand densities to generate the $k_a$, $k_d$ and KD values.

The data from the SPR screening process was used to select potential improved binders. The $k_d$ vs. IL-23 of each individual scFv was compared to the value recorded for the wild-type scFv-80 control included on each plate. Any scFv variant with a $k_d$ that was at least 1.5-fold improved (i.e. lower) than the control was designated as a potential improved binder. Each of these variants was then submitted for DNA sequence analysis and any scFv that carried a novel amino acid sequence was carried forward for further characterization.

Full Kinetic Characterization of Highly Purified Scfvs

This protocol was used for full kinetic characterization of scFv variants identified directly from ribosome display and screening experiments. First, the pEGX448 construct encoding the relevant scFv was transformed into HB2151 E. coli. Recombinant scFvs were then expressed into the bacterial periplasm by growing 500 mL cultures to an $OD^{600}$ of 0.8, then inducing protein expression with 0.5 mM of IPTG. The cells were harvested by centrifugation and the periplasmic fraction was extracted by osmotic shock as described by Minsky et al. (1986, Proc. Natl. Acad. Sci., Vol. 83, 4180-4184). ScFvs were purified from the periplasmic fraction using 1 mL column of sepharose resin conjugated to an antibody that specifically recognises the C-terminal FLAG tag. The affinity purified protein was concentrated to a final volume of 200 μL and subjected to gel-filtration chromatography on a Superdex 200 column (GE Healthcare) equilibrated in PBS and the peak protein fraction corresponding to monomeric scFv (~32 kDa) was collected for functional characterization (see below).

Purified scFvs were subjected to full kinetic characterization using a BIAcore T100 biosensor (GE Healthcare). Approximately 10,000 RU of the proprietry FLAG-specific capture molecule was immobilized on a CM5 Series S Sensor chip, using standard amine coupling chemistry in flow cells (FC) 1 and FC2 (or alternatively FC3 and FC4) of the BIAcore T100 Biosensor. The running buffer used was HBS-EP+ (BIAcore) and interactions measured at 30° C. or 35° C. to promote differentiation of scFvs with very similiar $k_d$ values. Peak purified FLAG-tagged scFvs (prepared as described in the previous paragraph) were diluted to 10 nM in running buffer, and captured on FC2 at a flow rate of 10 μl/min in order to capture 50 RU of scFv (typically 60 sec was sufficient to capture this level of tagged scFv). After an appropriate stabilization period, the target, IL-12 or IL-23, were passed over FC1 and FC2 at a flow rate of 60 μl/min at concentrations ranging from 81 nM to 0.13 nM (using a five-fold dilution of IL-12) and 81 nM to 1 nM (using a three-fold dilution of IL-23). The contact time for association was 180 sec and dissociation measured for 10 mins for the highest concentration and 300 sec for all other concentrations in the series. The sensorgram data from FC2 was subtracted from FC1 and a buffer only control. The curves were fitted using a 1:1 Langmuir equation to generate the $k_a$, $k_d$ and KD values.

Combination of Mutations Identified Through Ribosome Display and Screening

Additional scfv-80 variants were derived by combining the mutations discovered through ribosome display and screening. It is important to note that these mutation combinations did not arise as a result of one round of ribosome display, where the mutagenesis level is intrinsically set to create one mutation (on average) per scFv sequence. These combinations were instead derived by design. Combinations were chosen by weighting each individual mutation according to TABLE 11.

TABLE 11

Mutation weighting strategy for design of additional scFv-80 variants.

| Mutation* | Weighting |
|---|---|
| $V_H$: F29L | 7 |
| $V_H$: Y59S | 3 |
| $V_H$: Y59H | 3 |
| $V_H$: T07A | 3 |
| $V_L$: S63F | 3 |
| $V_H$: T28A | 2 |
| $V_H$: T68S | 1 |
| $V_H$: Q43R | 1 |
| $V_L$: I55T | 1 |
| $V_L$: S26P | 1 |
| $V_L$: Q27R | 1 |
| $V_L$: S52R | 1 |

*All mutations are reported relative to the wild-type scFv-80 sequence
Weighting key

| Times observed during screening | Resulting fold-improvement in $k_d$* | | |
|---|---|---|---|
| | Up to 2-fold | 2-fold plus | 3.5-fold plus |
| Once | 1 | 2 | 3 |
| Twice | 2 | 4 | 5 |
| 3 times | 3 | 5 | 6 |
| 4 times | 4 | 6 | 7 |

*Where $k_d$ was measured using purified, monomeric scFv proteins (see TABLE 5).

Nucleotide sequences encoding scFvs with the combinations of the highest-weighted mutations were produced by site-directed mutagenesis with scFv-80 as the template, using a Quikchange Lightning kit (Stratagene®) according to manufacturer's instructions. The mutagenesis primers used to add each specific mutation are listed below. The full range of scFvs are listed in TABLE 4×with cross-references to amino acid sequences.

$V_H$ mutation Y59S (SEQ ID NO: 382)
Sense:     5'-gaacggcgataccgagtccgcccccaa-3'

(SEQ ID NO: 383)
Antisense:5'-ttgggggcggactcggtatcgccgttc-3'

$V_H$ mutation Y59H (SEQ ID NO: 384)
Sense:     5'-cggcgataccgagcacgcccccaagtt-3'

(SEQ ID NO: 385)
Antisense:5'-aacttggggcgtgctcggtatcgccg-3'

$V_H$ mutation T28A (SEQ ID NO: 386)
Sense:     5'-ggccagcggctacgccttcaccgacta-3'

(SEQ ID NO: 387)
Antisense:5'-tagtcggtgaaggcgtagccgctggcc-3'

$V_H$ mutation F29L (SEQ ID NO: 388)
Sense:     5'-gccagcggctacaccctcaccgactactatc-3'

(SEQ ID NO: 389)
Antisense:5'-gatagtagtcggtgagggtgtagccgctggc-3'

-continued

V<sub>L</sub> mutation S26P (SEQ ID NO: 390)
Sense:     5'-tgtcctgtagagcccccagagcatcagc-3'

(SEQ ID NO: 391)
Antisense:5'-gctgatgctctgggggctctacaggaca-3'

V<sub>L</sub> mutation S52R (SEQ ID NO: 392)
Sense:     5'-gatctacttcgccagacagtccatcagcggc-3'

(SEQ ID NO: 393)
Antisense:5'-gccgctgatggactgtctggcgaagtagatc-3'

V<sub>L</sub> mutation Q27R (SEQ ID NO: 394)
Sense:     5'-cctgtagagcctcccggagcatcagcatcaa-3'

(SEQ ID NO: 395)
Antisense:5'-ttgatgctgatgctccgggaggctctacagg-3'

Note that no primers were designed to add heavy chain mutation Q43R or light chain mutation I55T. Instead, other mutations introduced directly into a construct that already carried R43 and T55 in the $V_H$ and $V_L$, respectively (SEQ ID NO: 230 and SEQ ID NO: 231).

Medium Throughput Kinetic Analysis of ScFvs with Mutation Combinations

This protocol was used to study IL-12 and IL-23 binding of scFv-80 variants carrying mutation combinations. Small-scale HB2151 E. coli cultures were used to produce partially purified scFvs for medium throughput SPR analyses (see below). The recombinant scFvs were expressed into the periplasm and then extracted and purified using an anti-FLAG antibody-sepharose column as described above. The scFv samples were then buffer-exchanged into PBS using a PD10 desalting column (GE Healthcare) and concentrated to a final volume of 200 μL. This material was subjected to SPR analysis with no further purification.

These scFvs with combined heavy and light chain mutations were analysed using similar methodology to that used for full characterization of highly purified scFvs (see above) except that a single double referenced concentration of 81 nM of either IL-12 or IL-23 was used and dissociation measured for 3000s.

Surface Plasmon Resonance Binding Experiments on IgG

Using a SPR 3000, Protein A was immobilized onto FC1 and FC2 (or alternatively FC3 and FC4) of a CM5 research grade sensor chip using amine coupling, giving approximately 200 μl RU. FC1 was used a blank throughout the experiments. The experiments were run in HBS-P buffer (SPR). At a flow rate of 20 μl/min, 20 μl of 5 μg/mL of antibody was passed over FC2. IL-12, IL-23 or IL-12p40 (Peprotech) were passed over the surface of FC1 and FC2 at concentrations ranging from 66 nM to 2 nM. Regeneration of the surface was performed using 10 mM Glycine, pH 1.0. The sensorgram data from FC2 was subtracted from FC1 and a buffer only control. The curves were fitted using a 1:1 Langmuir equation to generate the kd, ka and KD values. All curves were fitted with a $\chi^2$ of less then 2.0 where possible.

In Vitro Efficacy Studies
In Vitro Murine Splenocyte Assay

Single cell suspensions were obtained from mouse spleens by disruption and passing through a 100 μm sieve. Red blood cells were lysed by the water method, in which the cell suspension was centrifuged and resuspended in 9 ml of sterile water. 1 ml of 10×PBS was then immediately added and mixed in. Cells were washed and counted then resuspended in RPMI (with 2 mM l-glutamine, 100 U/ml Pen/Strep, 10% FBS) at a concentration of $10^7$ cells/ml.

Cells were plated out into 96-well flat-bottom tissue culture plates at $10^6$ cells/well in 100 μl. Concanavalin A and rhIL-23 was added to a final concentration of 1 μg/ml and 25 ng/ml respectively. Test antibodies were titrated across samples. A typical assay had 3-5 biological replicates per test antibody, and a starting test antibody concentration of 1-10 μg/ml. Each assay plate contained replicate samples that have Con A+IL-23 but no antibody and Con A alone. Plates were incubated at 37° C., 5% $CO_2$ for 3 days then supernatants were collected for IL-17 ELISA. IL-17 was assayed using an IL-17 ELISA kit (R&D Systems®) as per manufacturer's instructions. Concentrations were determined by the standard curve method.

NK92 IFN-γ Release Assay

NK92 cells (ATCC, CRL-2407) were cultured in RPMI1640, 2 mM L-Glutamine, 100U Pen/Strep, 10% FBS and supplemented with 200 U/ml of human IL-2 (Peprotech Asia) and 10 ng/ml of human IL-15 (Ebioscience™). Cells were starved from human IL-2 and human IL-15 prior to assay. The antibody was diluted in culture media sufficient to generate a titration curve. IL-12 (Peprotech) was added to the plate and incubated at 37° C. with 5% $CO_2$ for 2 hours. The cells were harvested and added to the wells giving a cell concentration of $1 \times 10^5$ cells/mL in a total volume of 2000/well. Cultures were incubated at 37° C. with 5% $CO_2$ for 24 hours. Supernatants were harvested at the end of incubation and a Duoset ELISA human IFN-γ kit (R&D Systems®) was used to detect human IFN-γ produced.

Human PBMC IL-12 Induced IFN-γ Assay

Human PBMC were harvested from human buffy coat using lymphoprep separation and cultured at $1 \times 10^7$ cells/mL in culture media (50% DMEM, 50% RPMI, 0.045% D(+) glucose, 2 mM L-Glutamine, 5% foetal bovine serum (FBS), 10 mM HEPES). PHA-P (Sigma-Aldrich®) was added at 10 ug/mL and incubated at 37° C. with 5% $CO_2$ with for 3 days. Human IL-2 (R&D Systems®) was then added at 50 U/mL. The culture was incubated at 37° C. with 5% $CO_2$ for 1 day. The antibody was diluted in culture media sufficient to generate a titration curve covering the ranges from 10 μg/mL to 0.001 μg/mL across a 96-well plate. 1 ng/mL of human IL-12 (Peprotech) was added to the plate and incubated at 37° C. with 5% $CO_2$ for 2 hours. 1 ng/mL of hIL-2 (R&D Systems®) was added to each well. The cells were harvested and added to the wells giving a cell concentration of $2 \times 10^5$ cells/mL in a total volume of 200 μl/well. Cultures were incubated at 37° C. with 5% $CO_2$ with for 2 days. Supernatants were harvested at the end of incubation and a Duoset ELISA human IFN-γ kit (R&D Systems®) was used to detect human IFN-γ produced.

Amelioration of Skin Inflammation Induced by Intradermal IL-23 Administration

Pilot Range-Finding and Kinetic Studies

Male C57B1/6J mice were depilated on a test area of the back two days prior to the commencement of injections, then given daily intradermal injections of either PBS or rhIL-23 in two locations on the back to a total of 3 or 10 μg/mouse/day. Both regimes gave some indication of inflammation but the dose of 10 μg/day gave a robust response with high levels of erythema. In a later study, mice were given 10 μg of rhIL-23/day for a total of 10 days to determine the full kinetics of the inflammatory response. The response was detectable from the third day of treatment, peaked at days 6-7 then started to resolve.

Antibody Testing In Vivo

Male C57B1/6J mice were treated with 10 μg/day of rhIL-23 as described above for 6 days. One day before the start of cytokine injection they were given a single intraperitoneal injection of Antibody 80, Antibody 136 or an isotype control antibody at a dose of 10 mg/kg. Mice were scored daily erythema and induration in the test area. All treatments and observations were performed blinded. At the termination of the study, skin samples were collected from each mouse and fixed for histological processing and Haematoxylin and Eosin (H&E) staining by standard protocols.

Values for epidermal thickness were determined by printing off a paper copy of the lower power images of the sections of skin from each mouse. The skin section on each image was divided into four quadrants by the use of three vertical lines. The epidermal thickness was then measured at the point of intersection for the three lines used to delineate the quadrants, i.e. three thickness measurements per photograph. The actual distances in mm were then converted to microns using the scale on each image. In those instances where the measuring point intersected a region considered to be non-representative of epidermal thickness such as a hair follicle or sweat gland the location of the measuring point was adjusted to an adjacent section of skin. Measurements were done blinded by two independent observers.

Neutralization of Serum Interferon-γ (IFN-γ) Response to Chimeric IL-12 (IL-12) in Normal Inbred Mice Chimeric IL-12

Chimeric IL-12 was produced that contained human IL-12p40 and murine IL-12p35 (SEQ ID NO: 63). The protein was backtranslated into a gene sequence, optimized, synthesized and subcloned into the pTT5 vector. Chimeric IL-12 was expressed in HEK-293E cells and purified via HIS tag affinity purification columns. Responsiveness of mouse T cells to the chimeric IL-12 was tested in vitro. Mouse splenocytes ($10^7$/ml) were cultured overnight in RPMI supplemented with 2 mM 1-glutamine and 10% fetal bovine serum plus chimeric, recombinant mouse or recombinant human IL-12 (0-20 ng/ml). Supernatants were collected and assayed for IFN-γ by enzyme-linked immunosorbent assay (ELISA), using an IFN-γ ELISA kit (R&D systems®) as per manufacturer's instructions. Chimeric IL-12 was capable of inducing IFN-γ secretion from mouse splenocytes over a range of concentrations. Human IL-12 was inactive except at the highest concentrations tested.

Antibody Inhibition of Chimeric IL-12 Induced IFN-γ Release by Murine Splenocytes Single cell suspensions were obtained from mouse spleens by disruption and passing through a 100 μm sieve. Red blood cells were lysed by the water method in which the cell suspension was spun down and resuspended in 9 ml of sterile water with 1 ml of 10×PBS immediately added and mixed in. Cells were washed and counted then resuspended in RPMI+2 mM 1-glutamine+100 U/ml pen/strep+10% FBS at a concentration of $5 \times 10^6$/ml.

Cells were plated out into 96-well flat-bottom tissue culture plates at $5 \times 10^5$ cells/well in 100 μl. Concanavalin A and chimeric IL-12 were added to a final concentration of 0.5 μg/ml and 20 ng/ml respectively. Test antibodies were titrated across samples. A typical assay will have 3-5 biological replicates per test antibody, and a starting test antibody concentration of 1-10 μg/ml. Each assay plate should contain replicate samples that have Con A+IL-12 but no antibody and Con A alone. Plates were incubated at 37° C., 5% $CO_2$ for 24 hours then supernatants were collected for IFN-γ ELISA. IFN-γ was assayed using an IFN-γ ELISA kit (R&D systems®) as per manufacturer's instructions. Concentrations were determined by the standard curve method. If the background IFN-γ production (as determined from Con A-only samples) was high, this background is subtracted from the IL-12 treated sample values to give the IFN-γ concentrations directly attributable to IL-12.

Pilot Range-Finding Study

Male C57B1/6J mice were treated with either PBS, mouse IL-12 (IL-12) at 0.03 mg/kg, or chimeric IL-12 at 0.03, 0.1 or 0.3 mg/kg by intraperitoneal injection for five days. On the sixth day, terminal blood samples were collected for production of serum. IFN-γ concentrations in sera were determined using a high-sensitivity IFN-γ ELISA kit (Ebioscience™) as per manufacturer's instructions.

IFN-γ was not detected in the PBS treated control mice but was detected in all groups treated with mouse or chimeric IL-12. Chimeric IL-12 treatment resulted in a robust dose-dependent induction of serum IFN-γ. 0.1 mg/kg was selected as the ideal dose to measure a change in serum IFN-γ response.

Antibody Testing In Vivo

Male C57B1/6J mice were treated with chimeric IL-12 at 0.1 mg/kg by intraperitoneal injection for five days. They were also treated with a single dose of either Antibody 80 or Antibody 136, 5 mg/kg on day 1 of cytokine injection 30 minutes before dosing with chimeric IL-12, or with three doses of Antibody 80, Antibody 136 or an isotype control on days 1, 3 and 5 of cytokine injection 30 minutes before dosing with chimeric IL-12. On the sixth day terminal blood samples were collected and serum IFN-γ determined as described above.

Stimulation of PBMC to Produce IL-23: Diagnostic Detection with Antibody 80

ELISA Development 96-well flat-bottom ELISA plates (Nunc Maxisorp) were coated with mouse anti-human IL-23p19 (Ebioscience™) at 0.5 μg/ml in PBS overnight at 4° C. Plates were washed (all washing is performed three times), then blocked for 1 hr with PBS/10% FBS. Plates were washed, then recombinant IL-23 was added at concentrations ranging between 1000 and 0.003 ng/ml by half-log dilution. Plates were incubated for 2 hours at room temperature. Plates were washed, then cytokines were detected with Antibody 80 at 0.5 ug/ml. Plates were incubated a further 2 hr at room temperature, washed, then mouse adsorbed anti-human IgG, horseradish peroxidase-conjugated (Invitrogen™) was added. After a further 30' incubation, plates were washed six times, TMB substrate was added (Sigma-Aldrich®), and colour allowed to develop for 5-10 minutes. The reaction was stopped with 1M HCl and plates read at 450 nm absorbance. All washes were performed in PBS+0.1% Tween using a Biotek® ELx405 plate washer.

Stimulation of Human PBMC to Produce IL-23

PBMC were obtained from a single buffy coat by centrifugation over a Lymphoprep gradient (Axis-shield®). They were plated out at $10^5$/well in 96 well flat-bottom plates. *Staphylococcus aureus* Cowan 1 (SAC) (Sigma-Aldrich®) was prepared as follows: From a stock solution of 10% w/v, the appropriate volume was removed and centrifuged to pellet cells. These were washed×2 in X-Vivo 15 medium (Biowhittaker™) then resuspended at the starting concentration for titration. SAC was added to PBMC at concentrations ranging between 1% w/v and 0.0001% w/v in serial half-log dilution. Plates were incubated for 72 hr then supernatants collected for ELISA. ELISAs for detection of IL-23 were performed as described above.

H/D Exchange Experiments

IL-12p40 was used at 1 mg/mL in PBS. Antibody 80 was used at 2.0 mg/mL in PBS. The antibody was coupled to POROS AL resin (Applied Biosystems) according to the manufacture's instructions. A mab column was packed with 600 uL of the Antibody 80-POROS AL resin and stored at 4° C.

The column was washed with PBS in 87.5% $D_2O$. 5 uL of 1 mg/mL IL-12p40 was mixed with 35 uL of ice chilled PBS buffer (pH 7.0) in 100% $D_2O$. The IL-12p40 mixture was incubated for 500, 1500, 5000s (in separated runs) before being injected onto the antibody column. The column was washed with 200 uL of chilled PBS (with $H_2O$). The column was allowed to stand at 3° C. for 250, 750 or 2500s (in separate runs). 80 uL of chilled 0.8% formic acid was injected onto the column. A further 40 uL of chilled 0.8% formic acid was used to elute the antigen from the antibody column. This 40 uL sample was collected and to it 20 uL of chilled 2 M urea, 1 M TCEP, pH 3.0 was added. 55 uL was then injected onto a column contain pepsin to digest the protein into peptides that were separated by rpHPLC using a 13-40% gradient of elution buffer (95% acetonitrile, 5% water, 0.0025% TFA) over 23 mins. Eluates were analysed by mass spectroscopy in MS1: Profile and MS2: DDA modes. The SEQUEST software program (Thermo) was used to identify the sequence of the parent peptide ions.

The effects of the antibody on the rate of exchange of different parts of IL-12p40 was performed essentially the same as above with the following exceptions: 5 uL of IL-12p40 was diluted with 35 uL of ice chilled PBS buffer (pH 7.0) in $H_2O$, then injected onto the column which had been prepared with PBS in $H_2O$. After binding the column was washed with 100 uL of PBS in $H_2O$. The on-exchange reaction was initiate by passing 200 uL of PBS, pH 7.0 in 87.5% $D_2O$ over the column. The column was incubated at 3° C. for 500, 1500 and 5000s in separate runs.

Creation of Mutant IL-23 Constructs

A gene was synthesized encoding wild-type IL-23 containing a linker between subunits and a C-terminal FLAG tag. After analysis of the X-ray crystal structures of IL-23 (e.g. 3D85) animo acids with exposed side chains were selected for mutation to an ala residue. This was performed using site-directed mutagenesis on the wild-type IL-23 gene. All genes were cloned into the pTT5 vector.

Transfection of Mutant IL-23 Constructs

HEK293E cells were cultured in F17 media (Invitrogen™) with Geneticin (Invitrogen™) and transfected without Geneticin at $1\times10^6$ cells/ml. 5 ml transfection culture was set up for each construct. 7.5 ug of DNA was transfected using Opti-MEM® I (Invitrogen™) and Fugene® HD transfection reagent (Roche). Tryptone (BD®) and Geneticin were added to the culture the day after transfection. The cultures were grown for 6 days and supernatant was harvested and filtered for analysis.

ELISA Screening Mutant IL-23 Constructs

IL 12Rβ1/Fc Chimera (R&D Systems®), IL-23/Fc Chimera (R&D Systems®), Antibody 202.1 and Antibody 80 were diluted to 1 μg/mL in carbonate coating buffer and added to each well of a 96 well plate and incubated at 4° C. overnight. The plate was then washed three times with wash buffer. The wells were then blocked by adding 200 μl of blocking buffer to each well and incubating the plate at 25° C. for 1 hour. The supernatant was diluted in antibody diluent sufficient to generate a titration curve and 100u1 was added to wells then incubated for 1 hour at 25° C. The plate was then washed as previously described and 100 μl of Monoclonal Anti-FLAG® M2-HRP (Sigma-Aldrich®) at 1:1000 in antibody diluent was used to detect bound cytokine. After incubation at 25° C. for 1 hour the plate was washed again as previously described. 100 μl TMB substrate solution (Sigma-Aldrich®) was added to each well and the colour allowed to develop for 5 minutes. 100 μl of 1M HCl was added to terminate the colour development reaction and absorbance was determined at 450 nm (ref. 620 nm).

REFERENCES

Journal Articles

Azzazy, H. M. and W. E. Highsmith, Jr. (2002). Clin Biochem 35(6): 425-45.

Babcook, J. S., K. B. Leslie, O. A. Olsen, R. A. Salmon and J. W. Schrader (1996). Proc Natl Acad Sci USA 93(15): 7843-8.

Bird, R. E., et al. (1988). Science 242(4877): 423-6.

Brown, P. S., Jr., et al. (1991). Proc Natl Acad Sci USA 88(7): 2663-7.

Camoglio, L., N. P. Juffermans, M. Peppelenbosch, A. A. to Velde, F. J. ten Kate, S. J. van Deventer and M. Kopf (2002). Eur J Immunol 32(1): 261-9.

Capellas, M., G. Caminal, G. Gonzalez, J. Lopez-Santin and P. Clapes (1997). Biotechnol Bioeng 56(4): 456-63.

Carter, P., et al. (1992). Proc Natl Acad Sci USA 89(10): 4285-9.

Carter, P. J. (2006). Nat Rev Immunol 6(5): 343-57.

Caspary, F., G. Elliott, B. T. Nave, P. Verzaal, M. Rohrbach, P. K. Das, L. Nagelkerken and J. D. Nieland (2005). Br J Dermatol 153(5): 937-44.

Chen, Z., C. M. Tato, L. Muul, A. Laurence and J. J. O'Shea (2007). Arthritis Rheum 56(9): 2936-46.

Chizzonite, R., T. Truitt, B. B. Desai, P. Nunes, F. J. Podlaski, A. S. Stern and M. K. Gately (1992). J Immunol 148(10): 3117-24.

Chothia, C. and A. M. Lesk (1987). J Mol Biol 196(4): 901-17.

Chothia, C., A. M. Lesk, E. Gherardi, I. M. Tomlinson, G. Walter, J. D. Marks, M. B. Llewelyn and G. Winter (1992). J Mol Biol 227(3): 799-817.

Chothia, C., et al. (1989). Nature 342(6252): 877-83.

Chua, A. O., et al. (1994). J Immunol 153(1): 128-36.

Clackson, T., H. R. Hoogenboom, A. D. Griffiths and G. Winter (1991). Nature 352(6336): 624-8.

Conrad, U. and U. Fiedler (1998). Plant Mol Biol 38(1-2): 101-9.

Cooper, A. M. and S. A. Khader (2007). Trends Immunol 28(1): 33-8.

Corcoran, A. E., K. Barrett, M. Turner, A. Brown, A. M. Kissonerghis, M. Gadnell, P. W. Gray, Y. Chemajovsky and M. Feldmann (1994). Eur J Biochem 223(3): 831-40.

Cramer, C. L., J. G. Boothe and K. K. Oishi (1999). Curr Top Microbiol Immunol 240: 95-118.

Cua, D. J., et al. (2003). Nature 421(6924): 744-8.

Cunningham, B. C. and J. A. Wells (1989). Science 244 (4908): 1081-5.

D'Andrea, A., et al. (1992). J Exp Med 176(5): 1387-98.

de Rie, M. A. (1999). Dermatology 199(2): 101.

de Vos, A. M., M. Ultsch and A. A. Kossiakoff (1992). Science 255(5042): 306-12.

Devergne, O., A. Coulomb-L'Hermine, F. Capel, M. Moussa and F. Capron (2001). Am J Pathol 159(5): 1763-76.

Ding, C., J. Xu and J. Li (2008). Curr Opin Investig Drugs 9(5): 515-22.

Dong, C. (2008). Nat Rev Immunol 8(5): 337-48.

Durocher, Y., S. Perret and A. Kamen (2002). Nucleic Acids Res 30(2): E9.

Elliott, M. J., R. N. Maini, M. Feldmann, A. Long-Fox, P. Charles, H. Bijl and J. N. Woody (1994). Lancet 344(8930): 1125-7.

Engelmann, H., D. Novick and D. Wallach (1990). J Biol Chem 265(3): 1531-6.

Fassbender, K., A. Ragoschke, S. Rossol, A. Schwartz, O. Mielke, A. Paulig and M. Hennerici (1998). Neurology 51(3): 753-8.

Fisch, I., G. Kunzi, K. Rose and R. E. Offord (1992). Bioconjug Chem 3(2): 147-53.
Fishwild, D. M., et al. (1996). Nat Biotechnol 14(7): 845-51.
Foote, J. and G. Winter (1992). J Mol Biol 224(2): 487-99.
Galfre, G., S. C. Howe, C. Milstein, G. W. Butcher and J. C. Howard (1977). Nature 266(5602): 550-2.
Gately, M. K., et al. (1996). Ann NY Acad Sci 795: 1-12.
Gavilondo, J. V. and J. W. Larrick (2000). Biotechniques 29(1): 128-32, 134-6, 138 passim.
Gillessen, S., et al. (1995). Eur J Immunol 25(1): 200-6.
Giudicelli, V. et al. Nucleic Acids Res., 33: D256-D261 (2005)
Gordon, J. N., A. Di Sabatino and T. T. Macdonald (2005). Curr Opin Gastroenterol 21(4): 431-7.
Gray, F., J. S. Kenney and J. F. Dunne (1995). J Immunol Methods 182(2): 155-63.
Green, L. L., et al. (1994). Nat Genet. 7(1): 13-21.
Griffiths, A. D., et al. (1993). Embo J 12(2): 725-34.
Gustafsson, B., M. Jondal and V. A. Sundqvist (1991). Hum Antibodies Hybridomas 2(1): 26-32.
Hanes, J., L. Jermutus, S. Weber-Bornhauser, H. R. Bosshard and A. Pluckthun (1998). Proc Natl Acad Sci USA 95(24): 14130-5.
Hanes, J. and A. Pluckthun (1997). Proc Natl Acad Sci USA 94(10): 4937-42.
Holliger, P., T. Prospero and G. Winter (1993). Proc Natl Acad Sci USA 90(14): 6444-8.
Hood, E. E., A. Kusnadi, Z. Nikolov and J. A. Howard (1999). Adv Exp Med Biol 464: 127-47.
Hoogenboom, H. R. (1997). Trends Biotechnol 15(2): 62-70.
Hoogenboom, H. R. and P. Chames (2000). Immunol Today 21(8): 371-8.
Huston, J. S., et al. (1988). Proc Natl Acad Sci USA 85(16): 5879-83.
Hwang, W. Y., J. C. Almagro, T. N. Buss, P. Tan and J. Foote (2005). Methods 36(1): 35-42.
Johnson, K. S. (1993). Current Opinions in Structural Biology 3: 564-571.
Jones, P. T., P. H. Dear, J. Foote, M. S, Neuberger and G. Winter (1986). Nature 321(6069): 522-5.
Junghans, R. P., T. A. Waldmann, N. F. Landolfi, N. M. Avdalovic, W. P. Schneider and C. Queen (1990). Cancer Res 50(5): 1495-502.
Kabat, E. A. and T. T. Wu (1971). Ann NY Acad Sci 190: 382-93.
Kaplan, M. H., Y. L. Sun, T. Hoey and M. J. Grusby (1996). Nature 382(6587): 174-7.
Katsube, Y., H. Suzuki, T. Muryoi and T. Sasaki (1998). Int J Mol Med 1(5): 863-8.
Kenney, J. S., F. Gray, M. H. Ancel and J. F. Dunne (1995). Biotechnology (NY) 13(8): 787-90.
Khader, S. A., et al. (2006). J Exp Med 203(7): 1805-15.
Kim, W., S. Min, M. Cho, J. Youn, J. Min, S. Lee, S. Park, C. Cho and H. Kim (2000). Clin Exp Immunol 119(1): 175-81.
Kipriyanov, S. M., F. Breitling, M. Little and S. Dubel (1995). Hum Antibodies Hybridomas 6(3): 93-101.
Kipriyanov, S. M., S. Dubel, F. Breitling, R. E. Kontermann and M. Little (1994). Mol Immunol 31(14): 1047-58.
Knorre, D. G., V. V. Vlassov and V. F. Zarytova (1985). Biochimie 67(7-8): 785-9.
Kohler, G. and C. Milstein (1975). Nature 256(5517): 495-7.
Kohler, G. and C. Milstein (1976). Eur J Immunol 6(7): 511-9.
Kumaran, S., D. Datta and R. P. Roy (1997). Protein Sci 6(10): 2233-41.
Laman, J. D., M. van Meurs, M. M. Schellekens, M. de Boer, B. Melchers, L. Massacesi, H. Lassmann, E. Claassen and B. A. Hart (1998). J Neuroimmunol 86(1): 30-45.
Lazar, G. A., et al. (2006). Proc Natl Acad Sci USA 103(11): 4005-10.
Lee, B. L., A. Murakami, K. R. Blake, S. B. Lin and P. S. Miller (1988). Biochemistry 27(9): 3197-203.
Lee, E., W. L. Trepicchio, J. L. Oestreicher, D. Pittman, F. Wang, F. Chamian, M. Dhodapkar and J. G. Krueger (2004). J Exp Med 199(1): 125-30.
Leonard, J. P., K. E. Waldburger, R. G. Schaub, T. Smith, A. K. Hewson, M. L. Cuzner and S. J. Goldman (1997). Crit. Rev Immunol 17(5-6): 545-53.
Leung, B. P., I. B. McInnes, E. Esfandiari, X. Q. Wei and F. Y. Liew (2000). J Immunol 164(12): 6495-502.
Li, H., et al. (2006). Nat Biotechnol 24(2): 210-5.
Little, M., S. M. Kipriyanov, F. Le Gall and G. Moldenhauer (2000). Immunol Today 21(8): 364-70.
Loetscher, H., Y. C. Pan, H. W. Lahm, R. Gentz, M. Brockhaus, H. Tabuchi and W. Lesslauer (1990). Cell 61(2): 351-9.
Lonberg, N. and D. Huszar (1995). Int Rev Immunol 13(1): 65-93.
Lonberg, N., et al. (1994). Nature 368(6474): 856-9.
Ma, J. K. and M. B. Hein (1995). Trends Biotechnol 13(12): 522-7.
Ma, J. K. and M. B. Hein (1995). Plant Physiol 109(2): 341-6.
Marchalonis, J. J., M. K. Adelman, B. J. Zeitler, P. M. Sarazin, P. M. Jaqua and S. F. Schluter (2001). Adv Exp Med Biol 484: 13-30.
Marks, J. D., A. D. Griffiths, M. Malmqvist, T. P. Clackson, J. M. Bye and G. Winter (1992). Biotechnology (NY) 10(7): 779-83.
Marks, J. D., H. R. Hoogenboom, T. P. Bonnert, J. McCafferty, A. D. Griffiths and G. Winter (1991). J Mol Biol 222(3): 581-97.
Mattner, F., S. Fischer, S. Guckes, S. Jin, H. Kaulen, E. Schmitt, E. Rude and T. Germann (1993). Eur J Immunol 23(9): 2202-8.
Mattner, F., L. Ozmen, F. J. Podlaski, V. L. Wilkinson, D. H. Presky, M. K. Gately and G. Alber (1997). Infect Immun 65(11): 4734-7.
Mendez, M. J., et al. (1997). Nat Genet. 15(2): 146-56.
Meyers, F. J., S. J. Denardo, D. Macey, R. D. White and M. Unger (1989). Prostate 14(3): 209-20.
Milstein, C. and A. C. Cuello (1983). Nature 305(5934): 537-40.
Neurath, M. F. (2007). Nat Med 13(1): 26-8.
Neurath, M. F., I. Fuss, B. L. Kelsall, E. Stuber and W. Strober (1995). J Exp Med 182(5): 1281-90.
Nguyen, H., J. Sandhu and N. Hozumi (1997). Microbiol Immunol 41(12): 901-7.
Niedbala, W., X. Q. Wei, B. Cai, A. J. Hueber, B. P. Leung, I. B. McInnes and F. Y. Liew (2007). Eur J Immunol 37(11): 3021-9.
Niedbala, W. G. and D. I. Stott (1998). Hybridoma 17(3): 299-304.
Oppmann, B., et al. (2000). Immunity 13(5): 715-25.
Papp, K. A., et al. (2008). Lancet 371(9625): 1675-84.
Parham, C., et al. (2002). J Immunol 168(11): 5699-708.
Powell, K. T. and J. C. Weaver (1990). Biotechnology (NY) 8(4): 333-7.
Presky, D. H., L. J. Minetti, S. Gillessen, U. Gubler, R. Chizzonite, A. S. Stern and M. K. Gately (1996). Ann NY Acad Sci 795: 390-3.

Presky, D. H., H. Yang, L. J. Minetti, A. O. Chua, N. Nabavi, C. Y. Wu, M. K. Gately and U. Gubler (1996). Proc Natl Acad Sci USA 93(24): 14002-7.

Presta, L. G. (2006). Adv Drug Deliv Rev 58(5-6): 640-56.

Presta, L. G., S. J. Lahr, R. L. Shields, J. P. Porter, C. M. Gorman, B. M. Fendly and P. M. Jardieu (1993). J Immunol 151(5): 2623-32.

Qiu, X. Q., H. Wang, B. Cai, L. L. Wang and S. T. Yue (2007). Nat Biotechnol 25(8): 921-9.

Quinones, M., S. K. Ahuja, P. C. Melby, L. Pate, R. L. Reddick and S. S. Ahuja (2000). J Exp Med 192(4): 507-16.

Riechmann, L., M. Clark, H. Waldmann and G. Winter (1988). Nature 332(6162): 323-7.

Rogge, L., L. Barberis-Maino, M. Biffi, N. Passini, D. H. Presky, U. Gubler and F. Sinigaglia (1997). J Exp Med 185(5): 825-31.

Russell, T. D., Q. Yan, G. Fan, A. P. Khalifah, D. K. Bishop, S. L. Brody and M. J. Walter (2003). J Immunol 171(12): 6866-74.

Sandhu, J. S., E. Boynton, R. Gorczynski and N. Hozumi (1996). Crit. Rev Biotechnol 16(1): 95-118.

Schall, T. J., et al. (1990). Cell 61(2): 361-70.

Schuster, M., et al. (2007). Biotechnol J 2(6): 700-8.

Shaker, O. G., W. Moustafa, S. Essmat, M. Abdel-Halim and M. El-Komy (2006). Clin Biochem 39(2): 119-25.

Shapiro, G. S, and L. J. Wysocki (2002). Crit. Rev Immunol 22(3): 183-200.

Shields, R. L., et al. (2001). J Biol Chem 276(9): 6591-604.

Shimozato, 0., S. Ugai, M. Chiyo, H. Takenobu, H. Nagakawa, A. Wada, K. Kawamura, H. Yamamoto and M. Tagawa (2006). Immunology 117(1): 22-8.

Simpson, S. J., S. Shah, M. Comiskey, Y. P. de Jong, B. Wang, E. Mizoguchi, A. K. Bhan and C. Terhorst (1998). J Exp Med 187(8): 1225-34.

Sims, M. J., et al. (1993). J Immunol 151(4): 2296-308.

Smith, L. J., C. Redfield, J. Boyd, G. M. Lawrence, R. G. Edwards, R. A. Smith and C. M. Dobson (1992). J Mol Biol 224(4): 899-904.

Sprague, J., J. H. Condra, H. Arnheiter and R. A. Lazzarini (1983). J Virol 45(2): 773-81.

Steenbakkers, P. G., H. A. Hubers and A. W. Rijnders (1994). Mol Biol Rep 19(2): 125-34.

Suresh, M. R., A. C. Cuello and C. Milstein (1986). Methods Enzymol 121: 210-28.

Taylor, L. D., et al. (1994). Int Immunol 6(4): 579-91.

Taylor, L. D., C. E. Carmack, S. R. Schramm, R. Mashayekh, K. M. Higgins, C. C. Kuo, C. Woodhouse, R. M. Kay and N. Lonberg (1992). Nucleic Acids Res 20(23): 6287-95.

Torti, D. C. and S. R. Feldman (2007). J Am Acad Dermatol 57(6): 1059-68.

Traunecker, A., A. Lanzavecchia and K. Karjalainen (1991). Embo J 10(12): 3655-9.

Trinchieri, G. (2003). Nat Rev Immunol 3(2): 133-46.

Trinchieri, G., S. Pflanz and R. A. Kastelein (2003). Immunity 19(5): 641-4.

Tuaillon, N., L. D. Taylor, N. Lonberg, P. W. Tucker and J. D. Capra (1993). Proc Natl Acad Sci USA 90(8): 3720-4.

Verhoeyen, M., C. Milstein and G. Winter (1988). Science 239(4847): 1534-6.

Verreck, F. A., et al. (2004). Proc Natl Acad Sci USA 101(13): 4560-5.

Vlassov, V. V., V. F. Zarytova, I. V. Kutiavin, S. V. Mamaev and M. A. Podyminogin (1986). Nucleic Acids Res 14(10): 4065-76.

Vogel, L. A., L. C. Showe, T. L. Lester, R. M. McNutt, V. H. Van Cleave and D. W. Metzger (1996). Int Immunol 8(12): 1955-62.

Wang, X., V. L. Wilkinson, F. J. Podlaski, C. Wu, A. S. Stern, D. H. Presky and J. Magram (1999). Eur J Immunol 29(6): 2007-13.

Ward, E. S., D. Gussow, A. D. Griffiths, P. T. Jones and G. Winter (1989). Nature 341(6242): 544-6.

Waterhouse, P., A. D. Griffiths, K. S. Johnson and G. Winter (1993). Nucleic Acids Res 21(9): 2265-6.

Watford, W. T., B. D. Hissong, J. H. Bream, Y. Kanno, L. Muul and J. J. O'Shea (2004). Immunol Rev 202: 139-56.

Webb, T. R. and M. D. Matteucci (1986). Nucleic Acids Res 14(19): 7661-74.

Wen, L., M. Hanvanich, C. Werner-Favre, N. Brouwers, L. H. Perrin and R. H. Zubler (1987). Eur J Immunol 17(6): 887-92.

Werlen, R. C., M. Lankinen, K. Rose, D. Blakey, H. Shuttleworth, R. Melton and R. E. Offord (1994). Bioconjug Chem 5(5): 411-7.

Whitelam, G. C., W. Cockburn and M. R. Owen (1994). Biochem Soc Trans 22(4): 940-4.

Wrone-Smith, T. and B. J. Nickoloff (1996). J Clin Invest 98(8): 1878-87.

Yamane-Ohnuki, N., et al. (2004). Biotechnol Bioeng 87(5): 614-22.

Yao, B. B., P. Niu, C. S. Surowy and C. R. Faltynek (1999). Arch Biochem Biophys 368(1): 147-55.

Yawalkar, N., S. Karlen, R. Hunger, C. U. Brand and L. R. Braathen (1998). J Invest Dermatol 111(6): 1053-7.

Yoon, C., S. C. Johnston, J. Tang, M. Stahl, J. F. Tobin and W. S. Somers (2000). Embo J 19(14): 3530-41.

Zanella, I., R. Verardi, R. Negrini, C. Poiesi, S. Ghielmi and A. Albertini (1992). J Immunol Methods 156(2): 205-15.

Zhou, L., Ivanov, I I, R. Spolski, R. Min, K. Shenderov, T. Egawa, D. E. Levy, W. J. Leonard and D. R. Littman (2007). Nat Immunol 8(9): 967-74.

Zou, J., D. H. Presky, C. Y. Wu and U. Gubler (1997). J Biol Chem 272(9): 6073-7.

Thie H, Voedisch B, Diibel S, Hust M, Schirrmann T 2009 Methods Mol. Biol. 525:309-22

Kolkman J A, Stemmer W P 2001 Nat. Biotechnol. May; 19(5):423-8

Greener, A., Callahan, M. and Jerpseth, B. (1996) In Vitro Mutagenesis Protocols. Humana press, NJ Peled J U, Kuang F L, Iglesias-Ussel M D, Roa S, Kalis S L, Goodman M F, Scharff M D 2008 Annu Rev Immunol. 26:481-511

Kopsidas G, Roberts A S, Coia G, Streltsov V A, Nuttall S D. 2006 Immunol Lett. 2006 Nov. 15; 107(2):163-8. Epub 2006 October 16

Kopsidas et al., 2007, BMC Biotechnology, 7: 18

Benhar I 2007 Expert Opin Biol Ther. May; 7(5):763-79

Queen C, Schneider W P, Selick H E, Payne P W, Landolfi N F, Duncan J F, Avdalovic N M, Levitt M, Junghans R P, Waldmann T A 1989 Proc Natl Acad Sci USA. December; 86(24):10029-33

Morrison S L 1985 Science. September 20; 229(4719):1202-7

Oi 1986 BioTechniques 4:214

Gillies S D, Lo K M, Wesolowski J 1989 J Immunol Methods. December 20; 125(1-2):191-202

Davies D R, Padlan E A, Sheriff S 1990 Annu Rev Biochem.; 59:439-73

Jones P T, Dear P H, Foote J, Neuberger M S, Winter G 1986 Nature. May 29-June 4; 321(6069):522-5

Riechmann L, Clark M, Waldmann H, Winter G 1988 Nature. March 24; 332(6162):323-7

Verhoeyen M, Milstein C, Winter G 1988 Science. March 25; 239(4847):1534-6

Padlan EA 1991 Mol. Immunol. April-May; 28(4-5):489-98

Studnicka G M, Soares S, Better M, Williams R E, Nadell R, Horwitz AH 1994 Protein Eng. June; 7(6):805-14

Roguska M A, Pedersen J T, Keddy C A, Henry A H, Searle S J, Lambert J M, Goldmacher V S, Blättler W A, Rees A R, Guild B C 1994 Proc Natl Acad Sci USA. February 1; 91(3):969-73

Riechmann L, Clark M, Waldmann H, Winter G 1988 Nature. March 24; 332(6162):323-7

Tan P, Mitchell D A, Buss T N, Holmes M A, Anasetti C, Foote J 2002 J. Immunol. July 15; 169(2):1119-25

Jones P T, Dear P H, Foote J, Neuberger M S, Winter G 1986 Nature. May 29-June 4; 321(6069):522-5

Riechmann L, Clark M, Waldmann H, Winter G 1988 Nature. March 24; 332(6162):323-7

Presta 1992. Curr Opin Struct Biol. 2:593-596.

Jespers et al. 1988. Bio/technology 12:899-903

Lonberg N, Huszar D 1995 Int Rev Immunol. 1995; 13(1): 65-93

J. Immunol. Dall'Acqua W F, Woods R M, Ward E S, Palaszynski S R, Patel N K, Brewah Y A, Wu H, Kiener P A, Langermann S 2002 J. Immunol. November 1; 169(9):5171-80

Dall'Acqua W F, Kiener P A, Wu H 2006 J Biol. Chem. August 18; 281(33):23514-24. Epub 2006 June Hinton P R, Johlfs M G, Xiong J M, Hanestad K, Ong K C, Bullock C, Keller S, Tang M T, Tso J Y, Vásquez M, Tsurushita N 2004 J Biol. Chem. February 20; 279(8):6213-6. Epub 2003 December 29

Hinton P R, Xiong J M, Johlfs M G, Tang M T, Keller S, Tsurushita N 2006 J. Immunol. January 1; 176(1):346-56

Petkova S B, Akilesh S, Sproule T J, Christianson G J, Al Khabbaz H, Brown A C, Presta L G, Meng Y G, Roopenian D C 2006 Int Immunol. December; 18(12):1759-69. Epub 2006 October 31

Shields R L, Namenuk A K, Hong K, Meng Y G, Rae J, Briggs J, Xie D, Lai J, Stadlen A, L1 B, Fox J A, Presta L G 2001 J Biol. Chem. March 2; 276(9):6591-604. Epub 2000 November 28

Kaneko Y, Nimmerjahn F, Ravetch J V 2006 Science. August 4; 313(5787):670-3

Jones A J, Papac D I, Chin E H, Keck R, Baughman S A, Lin Y S, Kneer J, Battersby J E 2007 Glycobiology. May; 17(5):529-40. Epub 2007 March 1

Kanda Y, Yamada T, Mori K, Okazaki A, Inoue M, Kitajima-Miyama K, Kuni-Kamochi R, Nakano R, Yano K, Kakita S, Shitara K, Satoh M 2007 Glycobiology. January; 17(1): 104-18. Epub 2006 September 29

Fishburn C S 2008 J Pharm Sci. October; 97(10):4167-83

Books

Alberts, B., et al., Molecular Biology of The Cell, Third Ed., Garland Publishing, Inc., New York, 1994

Ausubel, F. M. et al, Current Protocols In Molecular Biology, Vol. 2 (e.g., Supplement 27, Summer '94), Eds., John Wiley & Sons: New York, N.Y.

Berzofsky, et al., "Antibody-Antigen Interactions," In Fundamental Immunology, Paul, W. E., Ed., Raven Press: New York, N.Y. (1984);

Brodeur et al., Monoclonal Antibody Production Techniques and Applications, pp. 51-63 (Marcel Dekker, Inc., New York, 1987)

Colligan, Current Protocols in Immunology, or Current Protocols in Protein Science, John Wiley & Sons, NY, N.Y., (1997-2003)

Gennaro, Ed., Remington's Pharmaceutical Sciences, 18$^{th}$ Edition, Mack Publishing Co. (Easton, Pa.) 1990

Health Professional's Drug Guide 2001, ed., Shannon, Wilson, Stang, Prentice-Hall, Inc, Upper Saddle River, N.J.;

Hermanson, G. T., Bioconjugate Techniques, Academic Press: San Diego, Calif. (1996)

Nursing 2001 Handbook of Drugs, 21$^{st}$ edition, Springhouse Corp., Springhouse, Pa., 2001;

Innis, et al., PCR Protocols A Guide to Methods and Applications, Eds., Academic Press Inc., San Diego, Calif. (1990)

Jonak et al., Progress Biotech, Vol. 5, In Vitro Immunization in Hybridoma Technology, Borrebaeck, ed., Elsevier Science Publishers B.V., Amsterdam, Netherlands (1988)

Junginger, et al. In "Drug Permeation Enhancement"; Hsieh, D. S., Eds., pp. 59-90 (Marcel Dekker, Inc. New York 1994

Kabat, E. A., et atl. (1991) Sequences of Proteins of Immunological Interest, Fifth Edition, U.S. Department of Health and Human Services, NIH Publication No. 91-3242

Kontermann and Dubel eds., Antibody Engineering (2001) Springer-Verlag. New York.

Koprowski et al., U.S. Pat. No. 4,172,124; Harlow, E. and D. Lane, 1988, Using Antibodies: A Laboratory Manual, Cold Spring Harbor Laboratory: Cold Spring Harbor, N.Y.

Kuby, Janis, Immunology, W.H. Freeman and Company: New York, N.Y. (1992)

PDR Pharmacopoeia, Tarascon Pocket Pharmacopoeia 2000, Deluxe Edition, Tarascon Publishing, Loma Linda, Calif. (2000)

Sustained and Controlled Release Drug Delivery Systems", J. R. Robinson ed., Marcel Dekker, Inc., N.Y., 1978)

Wells et al., eds., Pharmacotherapy Handbook, 2nd Edition, Appleton and Lange, Stamford, Conn. (2000)

PATENT REFERENCES

WO 97/15327
WO9937682 A2
WO2002097048A2
U.S. Pat. No. 5,225,539
U.S. Pat. No. 5,693,761
WO 2007/005608
U.S. Pat. No. 7,306,907
U.S. Pat. No. 5,969,108
U.S. Pat. No. 7,041,870
U.S. Pat. No. 5,939,598
U.S. Pat. No. 6,9141,28
WO2006/069036
WO2007/027714
U.S. Pat. No. 7,247,711
U.S. Pat. No. 4,172,124
EP 368,684
PCT/GB91/01134
PCT/GB92/01755
PCT/GB92/002240
PCT/GB92/00883
PCT/GB93/00605
US 2003/039649
WO 04/006955
U.S. Ser. No. 08/350,260
PCT/GB94/01422
PCT/GB94/02662
PCT/GB97/01835
WO90/14443
WO90/14424
WO90/14430
PCT/US594/1234
WO92/18619

WO96/07754
WO96/13583
WO97/08320
WO95/16027
WO88/06630
WO90/3809
U.S. Pat. No. 4,704,692
PCT/US91/02989
WO89/06283
EP 371 998
EP 550 400
EP 229 046
PCT/US91/07149
U.S. Pat. No. 5,723,323
U.S. Pat. No. 5,763,192
U.S. Pat. No. 5,814,476
U.S. Pat. No. 5,817,483
U.S. Pat. No. 5,824,514
U.S. Pat. No. 5,976,862
WO 86/05803
EP 590 689
U.S. Pat. No. 5,627,052
PCT WO 93/06213
WO 93/08829
U.S. Pat. No. 4,676,980
WO 91/00360
WO 92/00373
EP 03089
U.S. Pat. No. 4,676,980
U.S. Pat. No. 5,770,428
U.S. Pat. No. 5,569,825
U.S. Pat. No. 5,545,806
U.S. Pat. No. 5,625,126
U.S. Pat. No. 5,625,825
U.S. Pat. No. 5,633,425
U.S. Pat. No. 5,661,016
U.S. Pat. No. 5,789,650
WO 98/50433
WO 98/24893
WO 98/24884
WO 97/13852
WO 94/25585
WO 96/34096
EP 0463 151 B1
EP 0710 719 A1
U.S. Pat. No. 5,545,807
WO 90/04036
EP 0438 474 B1
EP 0814 259 A2
GB 2 272 440 A
PCT 91/17271
PCT 91/18980
PCT 91/19818
PCT 93/08278
PCT 92/05258
PCT 92/14843
PCT 96/19256
U.S. Pat. No. 5,658,754
U.S. Pat. No. 5,643,768
U.S. Pat. No. 4,704,692
U.S. Pat. No. 4,939,666
U.S. Pat. No. 4,946,778
U.S. Pat. No. 5,260,203
U.S. Pat. No. 5,455,030
U.S. Pat. No. 5,518,889
U.S. Pat. No. 5,534,621
U.S. Pat. No. 5,656,730
U.S. Pat. No. 5,763,733
U.S. Pat. No. 5,767,260
U.S. Pat. No. 5,856,456
U.S. Pat. No. 5,223,409
U.S. Pat. No. 5,403,484
U.S. Pat. No. 5,571,698
U.S. Pat. No. 5,837,500
U.S. Pat. No. 5,427,908
U.S. Pat. No. 5,580,717
U.S. Pat. No. 5,885,793
U.S. Pat. No. 5,750,373
U.S. Pat. No. 5,618,920
U.S. Pat. No. 5,595,898
U.S. Pat. No. 5,576,195
U.S. Pat. No. 5,698,435
U.S. Pat. No. 5,693,493
U.S. Pat. No. 5,698,417
U.S. Pat. No. 5,827,690
U.S. Pat. No. 5,849,992
U.S. Pat. No. 4,873,316
U.S. Pat. No. 5,849,992
U.S. Pat. No. 5,994,616
U.S. Pat. No. 5,565,362
U.S. Pat. No. 5,304,489
U.S. Pat. No. 4,683,195
U.S. Pat. No. 4,683,202
U.S. Pat. No. 4,800,159
U.S. Pat. No. 4,965,188
U.S. Pat. No. 4,795,699
U.S. Pat. No. 4,921,794
U.S. Pat. No. 5,142,033
U.S. Pat. No. 5,122,464
U.S. Pat. No. 5,091,310
U.S. Pat. No. 5,066,584
U.S. Pat. No. 4,889,818
U.S. Pat. No. 4,994,370
U.S. Pat. No. 4,766,067
U.S. Pat. No. 4,656,134
U.S. Pat. No. 5,130,238
U.S. Pat. No. 4,683,202
U.S. Pat. No. 5,543,507
U.S. Pat. No. 5,672,593
U.S. Pat. No. 5,484,908
U.S. Pat. No. 5,256,648
U.S. Pat. No. 5,681,941
U.S. Pat. No. 4,399,216
U.S. Pat. No. 4,634,665
U.S. Pat. No. 4,656,134
U.S. Pat. No. 4,956,288
U.S. Pat. No. 5,149,636
U.S. Pat. No. 5,179,017
U.S. Pat. No. 5,122,464
U.S. Pat. No. 5,770,359
U.S. Pat. No. 5,827,739
U.S. Pat. No. 5,580,734
U.S. Pat. No. 5,641,670
U.S. Pat. No. 5,733,746
U.S. Pat. No. 5,733,761
U.S. Pat. No. 5,168,062
U.S. Pat. No. 5,385,839
U.S. Pat. No. 5,266,491
WO 92/16221
WO 92/07076
U.S. Pat. No. 5,851,198
U.S. Pat. No. 5,839,446
U.S. Pat. No. 4,309,989
U.S. Pat. No. 4,767,402

WO 94/16970
WO 98/35888
U.S. Pat. No. 4,668,218
EP 237507
WO 97/25086
WO 94/08552
U.S. Pat. No. 5,458,135
WO 94/06498
U.S. Pat. No. 5,404,871

WO 97/22376
U.S. Pat. No. 4,239,754
U.S. Pat. No. 4,925,673
U.S. Pat. No. 5,879,681
U.S. Pat. No. 5,871,753
U.S. Pat. No. 5,514,670
U.S. Pat. No. 5,849,695
U.S. Pat. No. 5,814,599
U.S. Pat. No. 5,770,222

The invention claimed is:

1. An isolated antibody which binds human IL-12p40, said antibody comprising an immunoglobulin heavy chain variable region selected from the group consisting of SEQ ID NO: 6, SEQ ID NO: 115, SEQ ID NO: 119, SEQ ID NO: 158, SEQ ID NO: 159, SEQ ID NO: 162, and SEQ ID NO: 112.

2. The antibody as claimed in claim 1 in which the antibody comprises a human or non-human primate heavy chain immunoglobulin constant region selected from a group consisting of IgG1, IgG2, IgG3, IgG4, IgM, IgE and IgA.

3. An isolated antibody which binds human IL-12p40, said antibody comprising an immunoglobulin light chain variable region selected from the group consisting of SEQ ID NO: 7, SEQ ID NO: 169, SEQ ID NO: 189, and SEQ ID NO: 179.

4. The antibody as claimed in claim 3 in which the antibody comprises a human or non-human primate light chain immunoglobulin constant region selected from a group consisting of kappa or lambda.

5. An isolated antibody which binds human IL-12p40, said antibody comprising two immunoglobulin variable regions, wherein said two immunoglobulin variable regions are selected from a group consisting of:
SEQ ID NO:6 and SEQ ID NO:7;
SEQ ID NO:119 and SEQ ID NO:179;
SEQ ID NO:112 and SEQ ID NO:169;
SEQ ID NO:158 and SEQ ID NO:189;
SEQ ID NO:159 and SEQ ID NO:189;
SEQ ID NO:162 and SEQ ID NO:189; and
SEQ ID NO:115 and SEQ ID NO:189.

6. The antibody as claimed in claim 5 in which the antibody comprises a human or non-human primate heavy chain immunoglobulin constant region selected from a group consisting of IgG1, IgG2, IgG3, IgG4, IgM, IgE and IgA.

7. The antibody as claimed in claim 5 in which the antibody comprises a human or non-human primate light chain immunoglobulin constant region selected from a group consisting of kappa or lambda.

8. The antibody as claimed in claim 5 in which the antibody is modified by the covalent attachment of an organic moiety.

9. The antibody as claimed in claim 8 in which the organic moiety is a linear or branched hydrophilic polymeric group, fatty acid group, or fatty acid ester group.

10. The antibody as claimed in claim 5 in which the antibody is modified to modulate a functional characteristic selected from the group consisting of antibody-dependent cellular cytotoxicity, complement-dependent cytotoxicity, serum half-life, biodistribution and binding to Fc receptors.

11. The antibody as claimed in claim 10 in which the modification is by protein engineering, glycoengineering or chemical methods.

* * * * *

UNITED STATES PATENT AND TRADEMARK OFFICE
CERTIFICATE OF CORRECTION

| | | |
|---|---|---|
| PATENT NO. | : 8,563,697 B2 | Page 1 of 1 |
| APPLICATION NO. | : 13/058914 | |
| DATED | : October 22, 2013 | |
| INVENTOR(S) | : Clarke et al. | |

It is certified that error appears in the above-identified patent and that said Letters Patent is hereby corrected as shown below:

Title Page Item (75) Inventors:

Please delete "Bernadette Wai" and insert -- Hoi Yi Wai -- therefor.

Signed and Sealed this
Thirty-first Day of March, 2015

Michelle K. Lee
*Director of the United States Patent and Trademark Office*